(12) United States Patent
Fiedler et al.

(10) Patent No.: US 10,934,340 B2
(45) Date of Patent: Mar. 2, 2021

(54) SEPARATION OF VWF AND VWF PROPEPTIDE BY CHROMATOGRAPHIC METHODS

(71) Applicants: Baxalta Incorporated, Bannockburn, IL (US); Baxalta GmbH, Glattpark (CH)

(72) Inventors: Christian Fiedler, Vienna (AT); Meinhard Hasslacher, Vienna (AT); Christa Mayer, Wolfsthal (AT)

(73) Assignees: Baxalta Incorporated, Bannockburn, IL (US); Baxalta GmbH, Glattpark (CH)

( * ) Notice: Subject to any disclaimer, the term of this patent is extended or adjusted under 35 U.S.C. 154(b) by 0 days.

(21) Appl. No.: 16/359,939

(22) Filed: Mar. 20, 2019

(65) Prior Publication Data
US 2019/0382467 A1 Dec. 19, 2019

Related U.S. Application Data

(60) Provisional application No. 62/646,109, filed on Mar. 21, 2018.

(51) Int. Cl.
| | | |
|---|---|---|
| *C07K 14/755* | (2006.01) | |
| *B01D 15/34* | (2006.01) | |
| *B01D 15/36* | (2006.01) | |
| *B01D 15/38* | (2006.01) | |
| *C07K 1/16* | (2006.01) | |
| *C07K 1/18* | (2006.01) | |
| *C07K 1/22* | (2006.01) | |
| *C07K 1/36* | (2006.01) | |
| *A61K 38/00* | (2006.01) | |

(52) U.S. Cl.
CPC ............ *C07K 14/755* (2013.01); *B01D 15/34* (2013.01); *B01D 15/362* (2013.01); *B01D 15/363* (2013.01); *B01D 15/3809* (2013.01); *C07K 1/16* (2013.01); *C07K 1/18* (2013.01); *C07K 1/22* (2013.01); *C07K 1/36* (2013.01); *A61K 38/00* (2013.01)

(58) Field of Classification Search
CPC .................................................. C07K 14/755
See application file for complete search history.

(56) References Cited

U.S. PATENT DOCUMENTS

| | | |
|---|---|---|
| 3,941,763 A | 3/1976 | Sarantakis |
| 4,179,337 A | 12/1979 | Davis et al. |
| 4,301,144 A | 11/1981 | Iwashita et al. |
| 4,361,509 A | 11/1982 | Zimmerman et al. |
| 4,496,689 A | 1/1985 | Mitra |
| 4,640,835 A | 2/1987 | Shimizu et al. |
| 4,670,417 A | 6/1987 | Nakagawa et al. |
| 4,791,192 A | 12/1988 | Nakagawa et al. |
| 6,190,609 B1 | 2/2001 | Chapman et al. |
| 6,465,624 B1 | 10/2002 | Fischer et al. |
| 6,579,723 B1 | 6/2003 | Mitterer et al. |
| 7,005,502 B1 | 2/2006 | Schwarz et al. |
| 7,559,509 B1 | 7/2009 | Taylor |
| 8,058,411 B2 * | 11/2011 | Mundt ...................... A61P 7/00 530/416 |
| 8,597,910 B1 | 12/2013 | Ginsburg et al. |
| 8,852,888 B2 | 8/2014 | Grillberger et al. |
| 9,315,560 B2 | 4/2016 | Mitterer et al. |
| 9,409,971 B2 | 8/2016 | Grillberger et al. |
| 2006/0094104 A1 | 5/2006 | Grillberger et al. |
| 2006/0160948 A1 | 7/2006 | Scheiflinger et al. |
| 2007/0212770 A1 | 9/2007 | Grillberger et al. |
| 2008/0009040 A1 | 1/2008 | Grillberger et al. |
| 2009/0029918 A1 * | 1/2009 | Mundt ...................... A61P 7/00 514/14.9 |
| 2011/0092681 A1 * | 4/2011 | Mitterer ............... C07K 14/755 530/416 |
| 2016/0024180 A1 | 1/2016 | Schroeder |
| 2016/0129090 A1 | 5/2016 | Schnecker et al. |
| 2017/0327559 A1 | 11/2017 | Felgenhauer et al. |

FOREIGN PATENT DOCUMENTS

| | | |
|---|---|---|
| WO | WO-86/06096 | 10/1986 |
| WO | WO-92/06999 | 4/1992 |
| WO | WO-2000/049047 | 8/2000 |
| WO | WO-2004/039337 | 5/2004 |
| WO | WO-2008/143977 | 11/2008 |

OTHER PUBLICATIONS

Weinstein, 1989, Immunoaffinity Purification of Factor VIII, Annals of Clinical and Laboratory Science, 19(2): 84-91.*
Acikara, 2013, Chapter 2: Ion-Exchange Chromatography and Its Applications, Column Chromatography, 31-58.*
Josic et al., 1994, Purification of factor VIII and von Willebrand factor from human plasma by anion-exchange chromatography, Journal of Chromatography, 662: 181-190.*
Havryliuk et al., 2017, The Simultaneous Human FVIII/vWF Purification and Virus Inactivation Combined in Chromatographic Column, Journal of Biomolecular Research & Therapeutics, 6(2): 9 pages.*
A. P. Mackenzie, Phil Trans R Soc London, Ser B, Biol 278:167 (1977).

(Continued)

*Primary Examiner* — Amber D Steele
(74) *Attorney, Agent, or Firm* — Morgan, Lewis & Bockius LLP

(57) ABSTRACT

The present invention relates to a method for separating a mature von Willebrand Factor (mat-VWF) from von Willebrand Factor pro-peptide (VWF-PP) by incubating a composition comprising inducing dissociation of mat-VWF and VWF-PP by disruption of the non-covalently associated mat-VWF and VWF-PP, wherein said dissociation is induced by: (i) addition of at least one chelating agent, or (ii) increasing the pH to a pH of at least 7, and then collecting said mat-VWF to obtain a high purity, propeptide depleted mature VWF (mat-VWF).

28 Claims, 95 Drawing Sheets

Specification includes a Sequence Listing.

(56) References Cited

OTHER PUBLICATIONS

Carpenter et al., Develop. Biol. Standard 74:225, (1991).
Chang, B, J. Pharm. Sci. 85:1325, (1996).
Chen B, et al., Pharm Sci., 88(4): 477-82 (1999).
Chen B, et al., Pharm Res., 20(12): 1952-60 (2003).
Chen, Drug Development and Industrial Pharmacy, 18:1311-1354 (1992).
Derrick TS, et al., /. Pharm. Sci., 93(10): 2549-57 (2004).
Eikenboom et al (1995) Haemophilia, 1, 77-90.
Erickson et al. (1976), The Proteins (3rd ed.) 2: 257-527.
Fatouros, A., et al., Int. J. Pharm., 155, 121-131 (1997).
Finn et al. (1976), The Proteins (3rd ed.) 2: 105-253.
Hollander-Rodriguez JC, et al., Am. Fam. Physician., 73(2): 283-90 (2006).
Kappelgaard A.M., Horm Res. 62 Suppl 3:98-103 (2004).
Lam XM, et al., J Pharm ScL, 86(11): 1250-5 (1997).
Laursen T, et al., Basic Clin Pharmacol Toxicol., 98(2): 218-21 (2006).
Merrifield (1963), J. Am. Chem. Soc. 85: 2149.
Merrifield (1973), Chem. Polypeptides, pp. 335-361 (Katsoyannis and Panayotis eds.).
Minogue SC, and Sun DA., AnesthAnalg., 100(3): 683-6 (2005).
Powell et al., Compendium of Excipients fir Parenteral Formulations (1998), PDA J. Pharm. Sci. Technology, 52:238-311.
Remmele R.L. Jr., et al., Biochemistry, 38(16): 5241-7 (1999).
Remmele RL Jr., et al., Pharm Res., 15(2): 200-8 (1998).
Roy S, et al., J Pharm ScL, 94(2): 382-96 (2005).
Saenko et al., Haemophilia 12:42-51, 2006.
Tomita M, et al., Biochemistry, 8(12): 5149-60 (1969).
Van Wezel, A. L., Nature, 1967, 216:64-5.
Schlokat U. et al (1996) Production of highly homogeneous and structurally intact recombinant von Willebrand factor multimers by furin-mediated propeptide removal in vitro Biotechnology Application Biochemistry. 24:257-267.
Preinger A. et al. Strategies for recombinant Furin employment in a biotechnological process: complete target protein precursor cleavage (1999) Cytotechnology 30: 1-15.
Lankhof et al., von Willebrand Factor without the A2 Domain Is Resistant to Proteolysis; Thromb. Haemost. 77: 1008-1013, 1997.
Pietu et al., Biochem. Biophys. Res. Commun. 164: 1339-1347, 1989.
Migneault et al., Biotechniques 37: 790-796, 2004.

Cumming et al., (J Clin Pathol.) Analysis of von Willebrand factor multimers using a commercially available enhanced chemiluminescence kit, May 1993; 46(5): 470-473.
Wen et al., Chemiluminographic detection of von Willebrand factor multimeric composition; J. Clin. Lab. Anal., 1993, 7: 317-323.
Favaloro et al., Pathology, 1997, 29(4): 341-456.
Sadler, JE, Biochemistry and genetics of von Willebrand factor. Annu Rev Biochem, 1998, 67:395-424.
Turecek et al., Structure and function of a recombinant von Willebrand factor drug candidate. Semin Thromb Hemost, 2010, 36:510-521.
Weiss et al., J. Clin. Invest., 1973, 52: 2708-2716.
Macfarlane et al., Thromb. Diath. Haemorrh., A method for assaying von Willebrand Factor (Ristocetin Cofactor). 1975, 34: 306-308.
Turecek, P., Hämostaseologie, (vol. 37): Supplement 1, 2017, pp. S15-S25.
Hermanson G., Bioconjugate Techniques 2nd Ed., Academic Press, Inc. 2008.
Jennings and Lugowski, J. Immunochemistry of groups A, B, and C meningococcal polysaccharide-tetanus toxoid conjugates. 1981; 127:1011-8.
Femandes and Gregonradis, "Polysialylated asparaginase: preparation, activity and pharmacokinetics" Biochim Biophys Acta. 1997; 1341; 26-34.
Brown and Bosak, Thromb. Res., An ELISA test for the binding of von Willebrand antigen to collagen. 1986, 43:303-311.
Favaloro, Thromb. Haemost., Collagen Binding Assay for von Willebrand Factor (VWF:CBA): Detection of von Willebrands Disease (VWD), and Discrimination of VWD Subtypes, Depends on Collagen Source 2000, 83 127-135.
Tang et al., Pharm Res. 2004, 21:191-200.
Chang et al., Pharm Res. Development of a stable freeze-dried formulation of recombinant human interleukin-1 receptor antagonist. 1996, 13:243-9.
Mayadas et al. "The Journal of Biological Chemistry by the American Society for Biochemistry and Molecular Biology, Inc. In Vitro Multimerization of Von Willebrand Factor Is Triggered by Low Ph Importance of the Propol Ypeptide and Free Sulfhydryls", Aug. 15, 1989 (Aug. 15, 1989), pp. 13497-13503.
Luke T Dang et al: "Phylogenetic and Functional Analysis of Histidine Residues Essential for Ph-Dependent Multimerization of Von Willebrand Factor", Journal of Biological Chemistry. (Microfilms), US, vol. 286, No. 29,Jul. 22, 2011 (Jul. 22, 2011), pp. 25763-25769.

* cited by examiner

FIG. 2

YIELD vWF AG ELISA (SOP: OR-13-00127)

| Sample Code | Amount [g] | Conc. [µg/mL] | Total [µg] | Yield LOAD [%] |
|---|---|---|---|---|
| LOAD | 817,10 | 77 | 62.916,70 | 100,0% |
| ELUATE Pool | 58,17 | 211,5 | 12.302,96 | 19,6% | vWF AG ELISA (continued, Total [U] column)

| Sample Code | Total [U] | Yield LOAD [%] |
|---|---|---|
| LOAD | 6.291,67 | 100,0% |
| ELUATE Pool | 1.230,30 | 19,6% | vWF-Risto (SOP: OR13-00497 (HN02 Standard))

| Sample Code | Risto [U/mL] | Total [U] | spec. Akt. [U Risto/U Ag] | Yield LOAD [%] |
|---|---|---|---|---|
| LOAD | 2,55 | 2083,81 | 0,33 | 100% |
| ELUATE Pool | 15,6 | 907,45 | 0,74 | 43,6% |

CHO AG ELISA (SOP: OR-13-00497)

| Sample Code | CHO-HCP [µg/ml] | Total [µg] | Purity [µg/1000U Risto] | Yield [%] |
|---|---|---|---|---|
| LOAD | 1,70 | 1391,223 | 667,7 | 100% |
| ELUATE Pool | 0,38 | 22,317 | 24,6 | 1,60% | vWF-propeptid AG ELISA (SOP: OR-13-00405)

| Sample Code | Conc [µg/mL] | Total [µg] | Yield [%] |
|---|---|---|---|
| LOAD | 12,098 | 9.885,28 | 100% |
| ELUATE Pool | 0,071 | 4,13 | 0,04% |

FIG. 6

BUFFER

| | |
|---|---|
| Na Citrate Dilution buffer<br>10mM Na Citrate<br>pH: 7.574 at 22.7°C<br>C: 2.56 mS/cm at 22.6°C<br>Lot.: Reag_RCF_14/047, 08.07.2014<br>Exp date: 08.07.2015 | TWA Puffer<br>2M NaCl<br>pH: 6.452 at 21.9°C<br>C: 158.6 mS/cm at 21.8°C<br>Lot.: Reag_RCF_14/052, 08.07.2014<br>Exp date: 08.07.2015 |
| Na Citrate Equilibrationbuffer<br>10mM NaCl, 30mM Na Citrate,<br>2mM Citric acid<br>pH: 7.559 at 22.9°C<br>C: 7.71 mS/cm at 22.9°C<br>Lot.: Reag_RCF_14/046, 08.07.2014<br>Exp date: 08.07.2015 | 1M NaOH<br>Lot.: ORMPSHD14504<br>Exp date: 31.08.2014 |
| Na Citrate Elution buffer<br>500mM NaCl, 30mM Na Citrate<br>pH: 7.593 at 21.9 °C<br>C: 51.0 mS/cm at 21.8°C<br>Lot.: Reag_RCF_14/048, 08.07.2014<br>Exp date: 08.07.2015 | 1M HAc<br>Lot.: ORMPESB14501<br>Exp date: 20.07.2014 |
| TQA Buffer (TQB 1:3 diluted with purified water):<br>10mM Tris, 100mM Na Acetate, 85mM NaCl<br>pH: 6.547 at 22.5°C<br>C: 15.84 mS/cm at 22.4°C<br>Lot.: Reag_RCF_14/051, 09.07.2014<br>Exp date: 08.07.2015 | 0.1M NaOH<br>Lot.: Reag_RCF_14/049<br>Exp date: 09.07.2015 |

YIELD

| Sample Code | Amount [g] | vWF AG ELISA SOP: OR-13-00127 ||| | vWF-Risto SOP: OR13-00407 |||
|---|---|---|---|---|---|---|---|---|
| | | Conc. [µg/mL] | Total [µg] | Total [U] | Yield LOAD [%] | Risto [U/mL] | Total [U] | spec. Akt. [U Risto/U Ag] |
| LOAD | 296,36 | 51 | 14.966,18 | 1.496,62 | 100,0% | | | |
| ELUAT (Pool) | 16,00 | 514,0 | 8.224,00 | 822,40 | 55,0% | 23,7 | 378,56 | 0,46 |

| Sample Code | Amount [g] | CHO AG ELISA SOP: OR-13-00497 |||| vWF-propeptid AG ELISA SOP: OR-13-00405 |||
|---|---|---|---|---|---|---|---|---|
| | | CHO-HCP [µg/ml] | Total [µg] | Purity [µg/1000U Risto] | Yield [%] | Conc. [µg/mL] | Total [µg] | Yield [%] |
| LOAD | 296,36 | 5,28 | 1563,406 | | 100% | 13,039 | 3.864,12 | 100% |
| ELUAT (Pool) | 16,00 | 1,33 | 21,200 | 56,003 | 1,36% | 0,564 | 9,02 | 0,23% |

FIG. 9

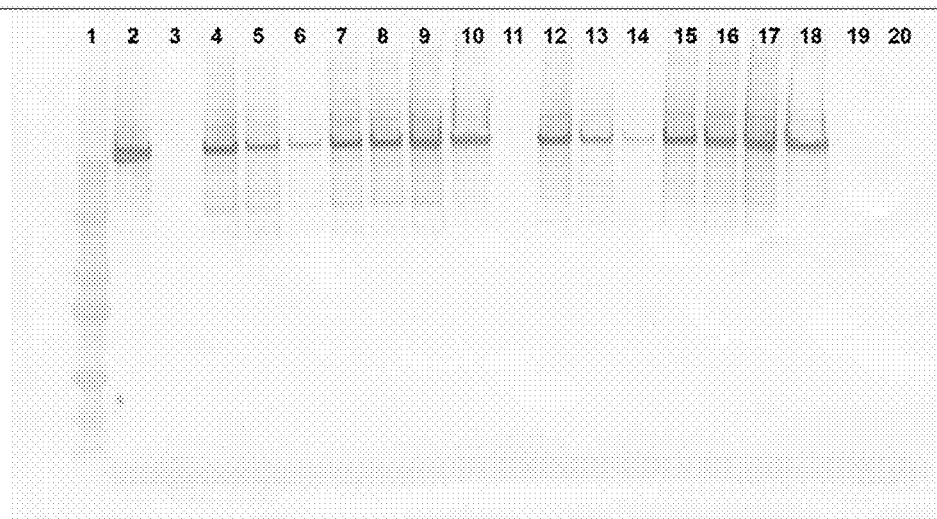

Example 2+3 : vWF_UNO-S_UPO_04 + vWF_UNO-S_UPO_05
Western Blot

1. Mol weight marker
2. Reference HN02R01
3. Blank
4. vWF_UNOS_UPO_04_LOAD
5. vWF_UNOS_UPO_04_ABS
6. vWF_UNOS_UPO_04_WASH
7. vWF_UNOS_UPO_04_ELUAT1
8. vWF_UNOS_UPO_04_ELUAT2
9. vWF_UNOS_UPO_04_ELUAT3
10. vWF_UNOS_UPO_04_NE
11. Blank
12. vWF_UNOS_UPO_05_LOAD
13. vWF_UNOS_UPO_05_ABS
14. vWF_UNOS_UPO_05_WASH
15. vWF_UNOS_UPO_05_ELUAT1
16. vWF_UNOS_UPO_05_ELUAT2
17. vWF_UNOS_UPO_05_ELUAT3
18. vWF_UNOS_UPO_05_NE
19. Blank
20. Blank
SDS-PAGE : DF.Nr.:2721/009

NuPAGE 3-8% TrisAcetate Midi Gel (20 well)
Invitrogen CatNo: WG1602BOX
Sample treatment with LDS Sample Buffer (Invitrogen Cat NP0007 ) 1h / 37°C blocked with Iodacetamide
1st Antibody : Rabbit anti vWF DAKO Cat. Nr A0082
2nd Antibody : Goat anti Rabbit IgG (H+L) AP Conjugate SIGMA Cat. Nr A8025
SDS-PAGE : DF.Nr.: 2721/010

FIG. 11

Example 4 : vWF_P_SEC_98
YIELD

| Sample Code | Amount [g] | vWF:Ag SOP: OR-13-00127 | | | | vWF-Risto (SHP Standard) SOP: OR-13-00407 | | | |
|---|---|---|---|---|---|---|---|---|---|
| | | Antigen [µg/mL] | Total [µg] | Total [U] | Yield [%] | RiCoF [U/mL] | Total [U] | spec. Act. [U Risto/U Ag] | Yield [%] |
| ORUFA12016RF | 6.60 | 2416.6667 | 15950.00 | 1595 | | 136.499 | 901 | 0.56 | |
| LOAD | 6.60 | 2350 | 15510 | 1551 | 100.0% | 140.097 | 925 | 0.60 | 100.0% |
| ELU1 A10-C1 | 12.94 | 290 | 3752.6 | 375.26 | 24.2% | 37.239 | 482 | 1.28 | 52.1% |
| ELU2 C2-D1 | 9.51 | 605 | 5753.55 | 575.355 | 37.1% | 31.639 | 301 | 0.52 | 32.5% |
| ELU3 D2-F6 | 23.77 | 185 | 4397.45 | 439.745 | 28.4% | 1.677 | 40 | 0.09 | 4.3% |
| ELU4 F11-I4 | 24.73 | 2.78 | 68.7494 | 6.87494 | 0.4% | <0.50 | <12.365 | <1.80 | <1.3% |

| Sample Code | Amount [g] | CHO Ag ELISA SOP: OR-13-00497 | | | | vWF propeptide ELISA SOP: OR-13-00405 | | | | |
|---|---|---|---|---|---|---|---|---|---|---|
| | | CHO [ng/ml] | Total [ng] | Yield [%] | Purity [µg/1000U Risto] | propeptide [µg/ml] | Total [µg] | Yield [%] | PP/vWF [µg/mg vWF] | µg/1000U Risto |
| ORUFA12016RF | 6.60 | | | | | | | | | |
| LOAD | 6.60 | 12753.46 | 84172.836 | 100% | 91.03 | 288.380 | 1903.308 | 100% | 122.715 | 2058.431 |
| ELU1 A10-C1 | 12.94 | 40.301 | 521.496 | 0.62% | 1.08 | <0.03125 | <0.404 | <0.02% | <0.108 | <0.839 |
| ELU2 C2-D1 | 9.51 | 167.03 | 1588.4553 | 2% | 5.28 | 0.04320 | 0.41 | 0.02% | 0.07 | 1.365 |
| ELU3 D2-F6 | 23.77 | 539.72 | 12829.1444 | 15% | 321.84 | 0.04320 | 1.026864 | 0.05% | 0.234 | 25.760 |
| ELU4 F11-I4 | 24.73 | 229.608 | 5678.20584 | 7% | 459.22 | 56.3080 | 1392.44738 | 73.18% | 20253.957 | 112612.000 |

FIG. 12

| Example 4: vWF_P_SEC_98 (DF: 2534/019) Silver Stain | Example 4: vWF_P_SEC_98 (DF: 2534/019) Western Blot |
|---|---|
| [Gel image with lanes 1-9] | [Gel image with lanes 1-9] |
| 1. Mol weight marker<br>2. Blank<br>3. r-vWF Reference (ORUFA12016RF)<br>4. Blank<br>5. r-vWF SEC LOAD<br>6. r-vWF SEC Pool 1<br>7. r-vWF SEC Pool 2<br>8. r-vWF SEC Pool 3<br>9. r-vWF SEC Pool 4 | 1. Mol weight marker<br>2. Blank<br>3. r-vWF Reference (ORUFA12016RF)<br>4. Blank<br>5. r-vWF SEC LOAD<br>6. r-vWF SEC Pool 1<br>7. r-vWF SEC Pool 2<br>8. r-vWF SEC Pool 3<br>9. r-vWF SEC Pool 4 |
| 8% Polyacrylamid gel<br>SB+DTT Incubation 5min / 100°C. 10min cool down Iodacetic amide treatment<br><br>SDS-PAGE : DF.Nr.: 2485/007 | 8% Polyacrylamid gel<br>SB+DTT Incubation 5min / 100°C. 10min cool down Iodacetic amide treatment Blocking agent : 3% Skim milk in TBS+Tween<br>1st Antibody : Rabbit anti vWF DAKO Cat. Nr A0082<br>2nd Antibody : Goat anti Rabbit IgG (H+L) AP Conjugate SIGMA Cat. Nr A8025<br>SDS-PAGE : DF.Nr.:2485/008 |

FIG. 14

| | | YIELD | | | | | | | | | | | |
|---|---|---|---|---|---|---|---|---|---|---|---|---|---|
| | | vWF:Ag SOP: OR-13-00127 | | | | vWF-Risto SOP: OR-13-00407 | | | | CHO Ag ELISA SOP: OR-13-00407 | | | |
| Proben Code | Menge [g] | Aktivität [µg/mL] | Gesamt [µg] | Gesamt [%] | Ausbeute [%] | Risto [µg/mL] | Gesamt [µg] | spez. Akt. U Risto/Ag | Ausbeute [%] | CHO [ng/mL] | Gesamt [ng] | Ausbeute [%] | pg/1000U Risto |
| OAC 11002 | 6,60 | 1803 | 9900 | 990 | 100,0% | 53,2 | 351 | 0,35 | 100,0% | 1411,4 | 9318,24 | 100% | 26,53 |
| ELU1 A12-C1 | 19,98 | 350 | 2054,94 | 205,494 | 20,8% | 15,90 | 174 | 0,85 | 49,5% | 31,290 | 1341,593 | 43,7% | 51,87 |
| ELU2 C2-C10 | 6,74 | 440 | 296,6 | 296,58 | 30,0% | 11,70 | 79 | 0,27 | 22,5% | 92,832 | 626,36168 | 7% | 7,84 |
| ELU3 C11-D6 | 7,86 | 184 | 1446,24 | 144,624 | 14,6% | 1,36 | 11 | 0,08 | 3,1% | 190,905 | 1453,4 | 16% | 139,71 |
| ELU4 D9-E10 | 12,60 | 87 | 1096,2 | 109,62 | 11,1% | 0,25 | 3 | 0,03 | 0,9% | 286,350 | 3608,01 | 39% | 1145,40 |
| ELU5 F1-8 | 34,77 | 1,95 | 67,8015 | 6,78015 | 0,7% | <0,15 | <7 | <1,03 | <2,0% | 84,306 | 2931,31962 | 31% | 443,72 |
| Wiederfindung | | | | | 77,2% | | | | 78,1% | | | 97% | |

| | | vWF propeptide ELISA SOP: OR-13-00405 | | | | | FS Ag ELISA SOP: OR-13-00409 | | | |
|---|---|---|---|---|---|---|---|---|---|---|---|
| Proben Code | Menge [g] | propeptide [µg/mL] | Gesamt [µg] | Ausbeute [%] | µg/mg vWF | µg/1000U Risto | FS [ng/mL] | Gesamt [ng] | FVIII:Ag Gehalt µg/1000U Risto | µg/mg vWF Ag |
| OAC 11002 | 6,60 | 187,204 | 1235,5434 | 100% | 124,843 | 3529,009 | | | | |
| ELU1 A12-C1 | 19,98 | 6,198 | 1,51 | 0,12% | 8,72 | 8,679 | 190,60 | 1973,998 | 11,36 | 0,96 |
| ELU2 C2-C10 | 6,74 | 2,768 | 18,66 | 1,51% | 6,29 | 236,581 | 250,58 | 1697,970 | 24,53 | 0,86 |
| ELU3 C11-D6 | 7,86 | 4,908 | 38,57838 | 3,12% | 26,674 | 3608,624 | | | | |
| ELU4 D9-E10 | 12,60 | 10,628 | 193,9128 | 15,63% | 122,183 | 42812,390 | | | | |
| ELU5 F1-8 | 34,77 | 15,391 | 533,73427 | 43,19% | 7872,388 | 80794,737 | | | | |
| Wiederfindung | | | | 59% | | | | | | |

Yellow marked: product containing fraction / No SDS-PAGE Available

FIG. 16

Example 6: vWF_P_UNOS_02 (DF2202/014)
CEX without Chelator

FIG. 18

Example 7: vWF_P_SEC_49 (DF: 2000/007)

YIELD

| Proben Code | Menge [g] | vWF:Ag SOP-QR-13-00127 | | | vWF-Risto SOP-QR-13-00107 | | | | CHO-Ag ELISA SOP-QR-13-00097 | | |
|---|---|---|---|---|---|---|---|---|---|---|---|
| | | Aktivität [µg/mL] | Gesamt [µg] | Ausbeute [%] | Risto [U/mL] | Gesamt [U] | spez. Akt. [U Risto/µg Ag] | Ausbeute [%] | CHO [ng/ml] | Gesamt [ng] | [µg/1000U Risto] |
| LOAD_11806 | 6.60 | 284.0 | 1874.4 | 100.0% | 123.2 | 813 | 0.43 | 100.0% | 118.5 | 78816.9 | 96.72 |
| ELU1_B3-C8 | 12.82 | 274.00 | 3512.68 | 187.4% | 24.70 | 317 | 0.09 | 39.0% | 32.258 | 414.060 | -1.308 |
| ELU2_C9-D10 | 9.35 | 675.00 | 6311.25 | 337.7% | 27.80 | 260 | 0.04 | 32.0% | 329.166 | 3077.8991 | 15.24 |
| ELU3_D11-E5 | 5.09 | 316.00 | 1608.44 | 85.8% | 2.17 | 11 | 0.01 | 1.4% | 795.285 | 4048.95155 | 365.50 |
| ELU4_E6-F12 | 13.74 | 158.00 | 2170.92 | 115.8% | 0.68 | 9 | 0.00 | 1.0% | 847.336 | 11642.3884 | 1313.40 |
| ELU5_G1-I2 | 26.21 | 4.14 | 108.5336 | 0.6% | 0.22 | 6 | 0.05 | 0.7% | 319.454 | 8382.47296 | 1452.08 |
| Wiederfindung | | | | 73.2% | | | | 66.9% | | | 36% |

| Proben Code | Menge [g] | vWF propeptide ELISA SOP-QR-13-00105 | | | | | F8 Ag ELISA SOP-QR-13-00108 | | |
|---|---|---|---|---|---|---|---|---|---|
| | | propeptide [µg/ml] | Gesamt [µg] | Ausbeute [%] | [µg/mg vWF] | [µg/1000U Risto] | F8 [ng/ml] | Gesamt [ng] | FVIII:Ag Gehalt [µg/1000U Risto] | [µg/mg vWF:Ag] |
| LOAD_11806 | 6.60 | 354.793 | 2341.6338 | 100% | 124.927 | 2879.813 | | | | |
| ELU1_B3-C8 | 12.82 | 0.457 | 5.86 | 0.25% | 1.67 | 18.500 | 511.80 | 6561.276 | 20.72 | 1.87 |
| ELU2_C9-D10 | 9.35 | 19.062 | 178.23 | 7.61% | 28.24 | 852.500 | 929.20 | 8631.920 | 42.71 | 1.37 |
| ELU3_D11-E5 | 5.09 | 21.875 | 111.34375 | 4.75% | 69.225 | 10089.645 | | | | |
| ELU4_E6-F12 | 13.74 | 26.718 | 367.10632 | 15.66% | 169.101 | 4770.714 | | | | |
| ELU5_G1-I2 | 26.21 | 19.364 | 507.5498 | 21.92% | 4725.604 | 86887.273 | | | | |
| Wiederfindung | | | | 50% | | | | | | |

Yellow marked: product containing fraction / No SDS-PAGE Available
The product containing fraction of example 7 results in low yield and vWF propeptide containing material

FIG. 20

YIELD

VW_USS_04 DF3350/002

| Code | Volumen [g] | vWF Antigengehalt OR-13-00726 | | Bestimmung der Ristocetin-Cofaktor-Aktivität des vWF OR-13-00407 | | Specific Activity |
|---|---|---|---|---|---|---|
| | | [µg/ml] | [%] | [IE/ml] | [IE] | U.RiCoF/mg.vWF:AG |
| L prior SD/VI | 240,22 | 100,00 | 100,00% | 8,347 | 2005,12 | 83,47 |
| FT | 595,63 | 23,50 | 58,3% | < 0,5 | --- | x |
| WASH | 56,75 | 27,20 | 6,4% | 1,636 | 92,84 | 60,1 |
| E1 | 56,87 | 39,50 | 9,4% | 5,673 | 322,62 | 143,6 |
| E2 | 27,59 | 70,60 | 8,1% | 12,431 | 342,97 | 176,1 |

VW_USS_04 DF3350/002

| Code | Volumen [g] | FVIII-Chromogen NE VN-13-45272TB | | Method ID1057 KVA_AG CHO / Elisa (new platform) | | Propeptid Elisa | | CHO / vWF:AG | | CHO / RiCoF | |
|---|---|---|---|---|---|---|---|---|---|---|---|
| | | [IU/ml] | [%] | [µg/ml] | [µg] | [ng/ml] | [ng] | [%] | | [µg/1000U] | |
| L prior SD/VI | 240,22 | 0,38 | 91,28 | 1,88 | 451,61 | 28687,10 | 6891215,16 | 100,00% | 0,02 | x | 225,23 |
| FT | 595,63 | < 0,2 | --- | 0,86 | 512,24 | 15320,80 | 9125528,10 | 132,4% | 0,04 | x | x |
| WASH | 56,75 | < 0,2 | --- | < 0,14 | --- | 658,10 | 37347,18 | 0,5% | 0,01 | v | 85,57 |
| E1 | 56,87 | < 0,2 | --- | < 0,14 | --- | 30,62 | 1741,36 | 0,0% | 0,00 | v | 24,68 |
| E2 | 27,59 | < 0,2 | --- | < 0,14 | --- | 23,77 | 655,81 | 0,0% | 0,00 | v | 11,26 |

FIG. 21

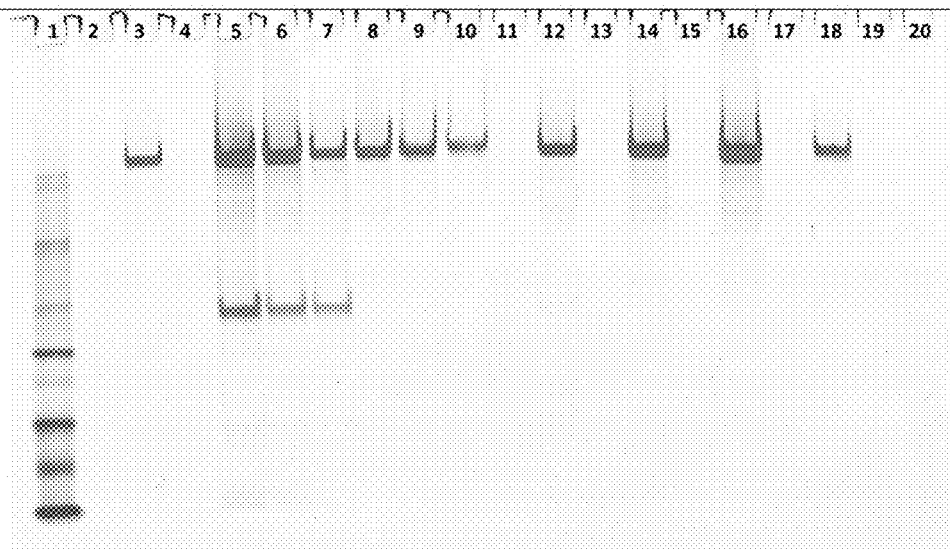

1. Mol weight marker
2. Blank
3. Reference HN02R01
4. Blank
5. MUQ_FT prior SD Treatment
6. CEX_LOAD
7. CEX_FT
8. CEX_VE*
9. CEX_NE*
10. CEX_PE*
11. Blank
12. CEX_WASH
13. Blank
14. CEX_Elution 1 (Product fraction)
15. Blank
16. CEX_Elution 2 (Product fraction)
17. Blank
18. VWF_SEC_Eluate (Reference)
19. Blank
20. Blank
.* Non product relevant samples to collect additional information NuPAGE 3-8% TrisAcetate Midi Gel (1,0 mm; 20 well, Invitrogen Cat.Nr WG1602BOX)
Sample treatment with LDS Sample Buffer (Invitrogen Cat NP0007) 1h / 37°C blocked with Iodacetamide
SDS-PAGE : DF.Nr.: 3314/016

FIG. 22

Example 8 : VW_USS_04 DF3350/002
SDS PAGE Multimere pattern 1% agarose Western Blot Lanes: 1 2 3 4 5 6 7 8 9 10 11 12 13 14 15

1. Blank
2. Reference HN02R01
3. Blank
4. MUQ_FT prior SD Treatment
5. CEX_LOAD
6. Blank
7. CEX_FT
8. CEX_WASH
9. CEX_Elution 1 (Product fraction)
10. CEX_VE*
11. CEX_Elution 2 (Product fraction)
12. CEX_NE*
13. Blank
14. VWF_SEC_Eluate (Reference)
15. Blank .* Non product relevant samples to collect additional information 1% Agarose gel according to SOP VV-0069924
All samples diluted and prepared to approx. 31.3ng vWF/Lane for Agarose gel electrophoresis including Iodacetic amide treatment to block free thiol groups
1st Antibody : Rabbit anti vWF DAKO Cat. Nr A0082  1:1000
2nd Antibody : Goat anti Rabbit IgG (H+L) AP Conjugate SIGMA Cat. Nr A8025 1: 2000

FIG. 25

YIELD

Example 9: VW_USS_05 DF.Nr.: 3350/003

| Code | Amount [g] | vWF Antigen OR-13-00726 | | | Ristocetin-Cofaktor-Activity vWF OR-13-00407 | | | Specific Activity |
|---|---|---|---|---|---|---|---|---|
| | | [µg/ml] | [µg] | [%] | [IE/ml] | [IE] | [%] | U RiCoF/mg vWF-AG |
| L prior SD | 364,03 | 121,00 | 44047,63 | 100,00% | 8,243 | 3000,70 | 100,00% | 68,12 |
| FT | 798,98 | 25,60 | 20453,89 | 46,4% | < 0,5 | --- | --- | x |
| E | 34,69 | 231,50 | 8030,74 | 18,2% | 19,696 | 683,25 | 22,8% | 85,1 |

Example 9: VW_USS_05 DF.Nr.: 3350/003

| Code | Amount [g] | FVIII Chromogen NE VN-13-46272TB | | | CHO HCP Elisa DF 3366/034 | | | CHO Protein Elisa OR-13-00407 | | Propeptid Elisa | |
|---|---|---|---|---|---|---|---|---|---|---|---|
| | | [U/ml] | [IU] | [%] | [µg/ml] | [µg] | [%] | [µg/ml] | [%] | [ng/ml] | [ng] |
| L prior SD | 364,03 | 0,56 | 203,86 | 100,00% | 1,22 | 444,12 | 100,00% | 2,39 | 100,00% | 36201,25 | 13178341,04 |
| FT | 798,98 | < 0,2 | --- | --- | 0,59 | 471,40 | 106,1% | --- | 88,0% | 14512,80 | 11595436,94 |
| E | 34,69 | 0,83 | 28,79 | 14,1% | 0,008 | 0,28 | 0,1% | <0,0625 | 0,0% | 142,60 | 4946,79 |

FIG. 26

| Analysis | Value |
|---|---|
| vWF: Antigen | 231,5μg /ml |
| RiCoF activity | 19,7U/ml |
| Specific activity RiCoF / Antigen | 85,1U/mg |
| Factor VIII activity (Chromogen) | 0,83U/ml |
| CHO-HCP | 0,008μg/ml |
| CHO-HCP / 1000U RiCoF activity | 0,41μg/1000U |
| r-vWF-Propeptide | 142ng/ml |
| Depletion factor CHO – HCP Load to Eluate | 1575 |
| Depletion factor vWF-Propeptide Load to Eluate | 2664 |
| Depletion factor FVIII- Chromogen activity Load to Eluate | 7,1 |

FIG. 28

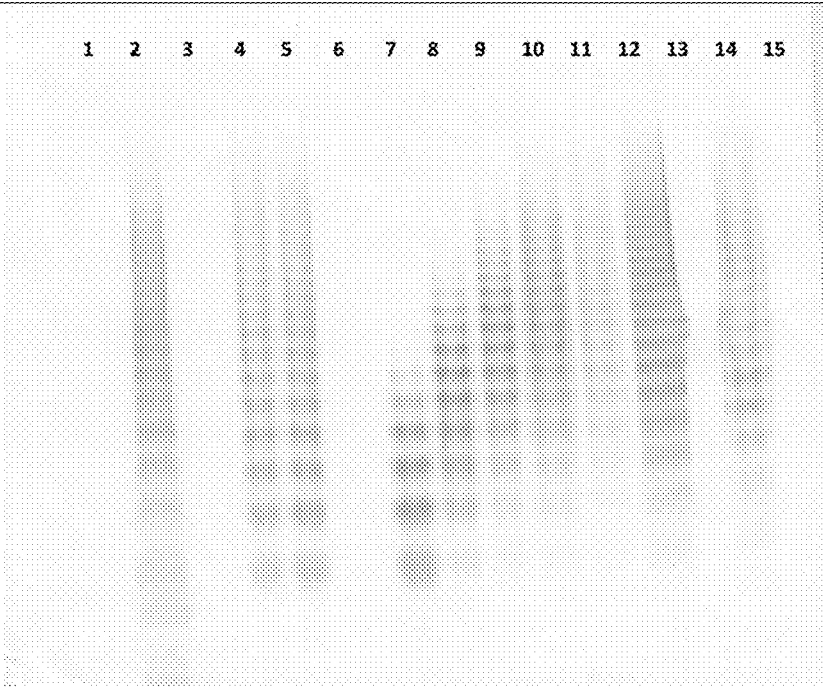

Example 9 : VW_USS_05 DF.Nr.: 3350/003
SDS PAGE Multimere pattern 1% agarose Western Blot 1. Blank
2. Reference HN02R01
3. Blank
4. MUQ_FT prior SD Treatment
5. CEX_LOAD
6. Blank
7. CEX_FT
8. CEX_WASH
9. CEX_VE*
10. CEX_Elution (Product fraction)
11. CEX_NE*
12. CEX_PE*
13. Blank
14. VWF_SEC_Eluate (Reference)
15. Blank
.* Non product relevant samples to collect additional information 1% Agarose gel according to SOP VV-0069924
All samples diluted and prepared to approx. 31.3ng vWF/Lane for Agarose gel electrophoresis including Iodacetic amide treatment to block free thiol groups
1st Antibody : Rabbit anti vWF  DAKO Cat. Nr A0082   1:1000
2nd Antibody : Goat anti Rabbit IgG (H+L) AP Conjugate SIGMA  Cat. Nr A8025 1: 2000

FIG. 30

| ID | Method | vWF-PP/vWF ng/µg Antigen/Antigen | vWF-PP/RiCoF µg/1000Units Antigen/Activity | CHO-HCP/vWF ng/µg Antigen/Antigen |
|---|---|---|---|---|
| Example 1 | Citrate buffer Version 1 | 0.34 | 4.55 | 1.814 |
| Example 2 | Citrate buffer Version 2 | 1.10 | 23.83 | 2.578 |
| Example 3 | Citrate buffer Version 2 | 0.94 | 21.14 | 1.704 |
| Example 6 | Without chelating agent | 163.3 | 3599 | 2.073 |
| Example 8 | Optimized Citrate buffer | E1  0.78<br>E2  0.34 | E1  5.4<br>E2  1.9 | E1  <5.15<br>E2  <1.98 |
| Example 9 | Optimized Citrate buffer protocol for manufacturing | E  0.62 | E  7.2 | E  0.035 |

FIG. 31

DEPLETION FACTOR of product related impurities

| ID | Method | Depletion factor vWF-Propeptide Load/Eluate | Depletion factor CHO-HCP Load/Eluate |
|---|---|---|---|
| Example 1 | Citrate buffer Version 1 | 2393 | 62.3 |
| Example 2 | Citrate buffer Version 2 | 428 | 73.7 |
| Example 3 | Citrate buffer Version 2 | 400 | 69.1 |
| Example 6 | Without chelating agent | 3.5 | 12.2 |
| Example 8** | Optimized Citrate buffer | E1  3957<br>E2  10508 | E1  >56.7<br>E2  >116.9 |
| Example 9 | Optimized Citrate buffer Protocol for manufacturing | E   2664 | E   1574 |

** two eluates E1 and E2 represent one final product after pooling

In Example 8 the CHO-HCP value was under the detection limit of 140ng/ml

FIG. 32

Enhanced Size Exclusion Chromatography (SEC)

| ID | Method | vWF-PP/vWF ng/µg Antigen/Antigen | vWF-PP/RiCoF µg/1000Units Antigen/Activity | CHO-HCP/vWF ng/µg Antigen/Antigen |
|---|---|---|---|---|
| Example 4 | Chelator Citrate | <0.11 | <0.84 | 0.14 |
| Example 5 | Elevated pH | 0.73 | 8.68 | <0.17 |

FIG. 33

DEPLETION FACTOR of product related impurities

| ID | Method | Depletion factor vWF-Propeptide Load/Eluate | Depletion factor CHO-HCP Load/Eluate |
|---|---|---|---|
| Example 4 | Chelator Citrate | >4710 | 84.3 |
| Example 5 | Elevated pH | 819 | >13.3 |

FIG. 34

Material

| SETUP | Detail | Remark |
|---|---|---|
| COLUMN | TMAE 4ml | ID 10mm / h = approx. 5cm |
| Buffer A | 50mM TrisHCl + 2mM EDTA + 0.1% Tween80 /pH 8.5 | - |
| Buffer B | 50mM TrisHCl + 2mM EDTA + 0.1% Tween80 /pH 8.5 +1000mM NaCl | - |
| Buffer C | 50mM TrisHCl + 2mM EDTA pH 8.5 + 16.6g/kg SD Reagent [10.54g Triton X100, 3.15g Polysorbate 80, 2.91g Tri-n-butyl phosphate] | Buffer for SD_VI Treatment "ON-COLUMN" |

FIG. 35

Conditioning of the LOAD

| Original | Conditioning | Remark |
|---|---|---|
| ORVW16102MUQ-E  25ml | r-vWF MUQ – FT diluted 1:4 in BUFFER A  50mM TrisHCl + 2mM EDTA + 0.1% Tween80 /pH 8.5 | Incubation > 120min |

FIG. 36

Chromatography

| Chromatography | Buffer | Buffer Details | CV | Flow rate | Fraction |
|---|---|---|---|---|---|
| 1. Activation | 2M NaCl | | 5 | 0.6ml/min | Waste |
| 2. Equilibration | Buffer A | 50mM TrisHCl + 2mM EDTA + 0.1% Tween80 /pH 8.5 | 8 | 0.6ml/min | Waste |
| 3. Loading | r-vWF MUQ – FT diluted 1:4 in Buffer A | 50mM TrisHCl + 2mM EDTA + 0.1% Tween80 /pH 8.5 | x | 0.6ml/min | FT |
| 4. Re-Equilibration | Buffer A | 50mM TrisHCl + 2mM EDTA + 0.1% Tween80 /pH 8.5 | 5 | 0.6ml/min | FT |
| 5. On Column SD_VI | Buffer C | 50mM TrisHCl + 2mM EDTA pH 8.5 + SD Reagent 16.6g/kg | 10 | 0.6ml/min | REG_W |
| 6. Re-Equilibration II | Buffer A | 50mM TrisHCl + 2mM EDTA + 0.1% Tween80 /pH 8.5 | 20 | 0.6ml/min | REG_W |
| 7. Elution | Gradient 0% Buffer A to 50% Buffer B In 20CV | 50mM TrisHCl + 2mM EDTA + 0.1% Tween80 /pH 8.5 +1000mM NaCl in 50mM TrisHCl + 2mM EDTA + 0.1% Tween80 /pH 8.5 | 20 | 0.6ml/min | Fraction - 1.5ml |
| 8. Post Elution | 50% Buffer B | 50mM TrisHCl + 2mM EDTA + 0.1% Tween80 /pH 8.5 +1000mM NaCl | 8 | 0.6ml/min | Fraction - 1.5ml |

CONDITIONS / PARAMETER
LOAD: rvWF_MUQ_FT – Furin processed r-vWF
Buffer + Split conditions: TrisHCl + elevated pH 8.5 + EDTA
Gradient counter: Chloride Cl⁻
SD_VI Treatment _ On Column post Wash 1 (Duration ca. 60min )

FIG. 40

| CAT Feature | CAT 1.0 | CAT 2.0 | Comment |
|---|---|---|---|
| Concentration of product | yes | yes | No change |
| Removal of host cell protein impurities | Yes, reduction factor of about 40 | Yes, reduction factor of > 1000 | Significant improvement |
| Host cell DNA removal | to be determined | to be determined | |
| VWF pro-peptide removal | no | Yes, reduction of > 2000 | Significant improvement |
| Residual FVIII removal | reduction factor of < 10 | reduction factor of < 10 | No improvement |
| Separation and pooling of VWF multimers | yes | Yes, replacing SEC | Significant improvement |

FIG. 42

| SEC Feature | SEC (SQA buffer) | Improved SEC (SQC buffer) | Comment |
|---|---|---|---|
| Removal of host cell protein impurities | Yes, reduction factor of approx. 100 | Yes, reduction factor of > approx. 100 | No improvement |
| VWF pro-peptide removal | Yes, but not robust (impurity levels ranging from 20 – 250 µg/1000 Units | Yes, very robust (impurity levels < 2 µg/1000 Units) | Significant improvement in terms of level and robustness |
| Residual FVIII removal | reduction factor of < 10 | reduction factor of < 10 | No improvement |
| Separation and pooling of VWF multimers | yes | yes | No improvement |

FIG. 44

| Column parameter | 1st generation MFG NE | 2nd generation small scale | Difference/ Rationale |
|---|---|---|---|
| Cation Exchange media | UNO_Sphere S (BioRad) | | No |
| Mean Pore size | 80 µm | | |
| Column | Pall Resolution | KronLab 10/250 | Yes / scale dependent |
| Bed height | 14 cm (15 – 18°cm) | 14.3 cm | No |
| Bed diameter | 120 cm | 1 cm | |
| Column volume | Approx. 170 – 204°L | 11.23°mL | |
| Frit material | Stainless steel 20 µm | 10 µm Polypropylene | |
| Plates/meter | ≥ 2500 | 1565 | |
| Asymmetry | 0.8 – 1.8 | 1.93 | |
| | Online filtration | Off line filtration in course of S/D treatment prior to CAT loading | Yes / scale dependent |
| filter | Sartoguard membrane or Pall Supor EAV | Pall Kleenpack; Supor membrane EA | |
| | 7.2 m² (3 x 30" cartridge) | 260 cm² | |
| | 0.2 µm | 0.2 µm | No |
| System parameter | | | |
| Chromatography system | Millipore | GE-Healthcare ÄKTA Pure 25 | Yes / scale dependent |

FIG. 45

| Run I.D. | Wash | | Elution | | 2M NaCl |
|---|---|---|---|---|---|
| 1st Gen process (MFG) | Wash buffer 100 cm/h; 10 - 11CV | | Elution buffer 65 cm/h; 3.3 – 3.6 CV | | 65 cm/h; 10 CV |
| VW_USS_01 | 100% A 100 cm/h; 10 CV | | 0%B – 100%B 65 cm/h; 12 CV | 100%B 65 cm/h; 3 CV | 65 cm/h; 5 CV |
| VW_USS_02 | 55% B; 65 cm/h; 10 CV | | 55%B – 100%B 65 cm/h; 6 CV | 100%B 65 cm/h; 2 CV | 65 cm/h; 5 CV |
| VW_USS_03 and VW_USS_04 | 40% B; 65 cm/h; 5 CV | 45% B; 65 cm/h; 5 CV | 45%B – 100%B 65 cm/h; 6 CV | 100%B 65 cm/h; 2 CV | 65 cm/h; 5 CV |
| VW_USS_05 | 36% B; 50 cm/h; 5 CV | | 36%B – 100%B 50 cm/h; 6 CV | 100%B 50 cm/h; 2 CV | 65 cm/h; 5 CV |

FIG. 46

| Step | | Buffer | 1st generation MFG NE | | 2nd generation small scale setting | | Difference / Rationale |
|---|---|---|---|---|---|---|---|
| | | | Amount [CV] | Flow rate [cm/h] | Amount [CV] | Flow rate [cm/h] | |
| 1 | Equilibration | TQA | 25 | 100 | ≥ 32 | 100 | Yes; improved impurity removal |
| 2 | Product load | S/D treated and diluted MUQ effluent | 16 – 19 | 100 | 38 – 66 | 100 | Yes; improved capacity and impurity removal |
| | | | in-line filtration 0.2°µm; Supor EAV, 70 L/h/m² | | - | | |
| | | | Load: 60 – 140 IU/ml resin | | Load 90 – 270 IU/ml resin | | |
| 3 | Wash | TQA | 10 – 11 | 100 | 5 – 20 | 100 | Yes; improved impurity removal |
| 4.1. | Elution | TEA | 3.3 – 3.6 | 65 | 8 - 18 | 65 | Yes; replacement of SEC |
| 4.2. | | Pool collection | when the UV signal rises ≥ 0.1 O.D. above baseline; Vol. collected: 3.3 – 3.6 CV | | to be explored | | |
| 5 | Wash 3 | 2 M NaCl | 10 – 11 | 100 | 5 | 65 | No |

All chromatographic steps were performed at room temperature at lab scale the specification for MFG is +18°C - +25°C.

FIG. 47

| Step | | Buffer | 1st generation MFG NE | | 2nd generation small scale setting | | Difference / Rationale |
|---|---|---|---|---|---|---|---|
| | | | Amount [CV] | Flow rate [cm/h] | Amount [CV] | Flow rate [cm/h] | |
| 1.1 | Reg 1 | 1 M NaOH | 5 – 5.5 | 65 | 10 | 65 | No |
| 1.2 | Flush | WFI | 0.5 | 65 | 10 | 65 | - |
| 2.1 | Reg 2 | 0.5 M acetic acid | 2 – 2.2 | 65 | 5 – 10 | 65 | No |
| 2.2 | Flush | WFI | - | - | 5 | 65 | Yes |
| 3 | Reg 3 Storage | 0.1 M NaOH | 3 – 3.3 | 65 | 10 | 65 | No |
| All steps are performed in reversed flow direction | | | | | | | |

FIG. 48

| Buffer ID | | 1st generation MFG NE | | 2nd generation small scale | | Difference / Rationale |
|---|---|---|---|---|---|---|
| Steps | Buffer | Composition | Conductivity [mS/cm] at +25°C | Composition | Conductivity [mS/cm] at +25°C | |
| S/D Dilution buffer | WFI | Inactivated MUQ-E is 1:2 diluted with WFI to reach a pH of 7.0 ± 0.5 | After dilution a conductivity of 13 - 17 mS/cm is reached | Inactivated MUQ-E is diluted 1:2 with 60mM Na-citrate buffer that will sets the CAT feed to a preferred pH of 7.5 – 8.0 (pH testing range 6.0 – 9.0) | After dilution a preferred conductivity of 10 – 30 mS/cm is reached (testing rage 5 – 40 mS/cm) | Yes / New buffer conditions to optimize the removal of product and process related impurities |
| CAT wash | TQA | 100 mM NaOAc, 10 mM Tris, 85 mM NaCl, pH= 6.5 ± 0.2 (RT) | 13 – 17 | 30 mM Na-Citrate, 2 mM Citric Acid, 10 mM NaCl; pH testing range 6.0 – 9.0 | testing rage 5 – 40 mS/cm | |
| CAT step Elution | CAT-Elu | 100 mM NaOAc, 100 mM Glycine, 500 mM NaCl, 3 mM CaCl2, pH= 7.5 ± 0.2 (RT) | 47 - 53 | - | - | |
| CAT Gradient Elution | CAT-Elu A | - | - | 30 mM Na-Citrate, 2 mM Citric Acid, 10 mM NaCl; pH testing range 6.0 – 9.0 | testing rage 5 – 40 mS/cm | |
| | CAT-Elu B | - | - | 30 mM Na-Citrate, 500 mM NaCl; pH testing range 6.0 – 9.0 | testing rage 5 – 40 mS/cm | | lanes 1, 2, 4, 7, 14: blank
lane 3: ref. Std. Human Plasma
lane 5: VW_USS_05 Load pre S/D
lane 6: VW_USS_05 Load after S/D
lane 8: VW_USS_05 FT
lane 9: VW_USS_05 Wash
lane 10: VW_USS_05 pre-elution
lane 11: VW_USS_05 Elution
lane 12: VW_USS_05 post-elution lane
13: VW_USS_05 high salt wash
lane 15: ORVWSEC16070F
    (530 µg/ml antigen)

FIG. 52

| Run I.D. | rVWF:Ag Yield % | | | | | | | comment |
|---|---|---|---|---|---|---|---|---|
| | FT | Wash(es) | pre-elu | elu | post-elu | High Salt | Total Rec | |
| VW_USS_01 | 2.30 | 0.20 | | 0.02 | 41.5 | 0.70 | 0.10 | 44.8 | --- |
| VW_USS_02 | 38.3 | 24.5 | | n.d. | 0.10 | n.d. | 0.05 | 63.0 | wash conductivity to high |
| VW_USS_03 | 46.8 | 15.2 | 11.2 | 0.70 | 7.20 | 0.50 | 0.30 | 82.0 | --- |
| VW_USS_04 | 58.3 | 6.43 | 9.35 | 0.50 | 8.10 | 0.60 | 0.10 | 83.4 | --- |
| VW_USS_05 | 46.4 | 7.20 | | 2.50 | 18.2 | 1.60 | 0.30 | 76.2 | --- |

FIG. 53

| Run I.D. | rVWF Risto Co Activity % | | | | | | | comment |
|---|---|---|---|---|---|---|---|---|
| | FT | Wash(es) | pre-elu | elu | post-elu | High Salt | Total Rec | |
| VW_USS_01 | n.d. | n.d. | | n.d. | 27.1 | n.d. | n.d. | 27.1 | --- |
| VW_USS_02 | n.d. | 52.5 | | n.d. | n.d. | n.d. | n.d. | 52.5 | wash conductivity to high |
| VW_USS_03 | n.d. | 10.4 | 18.4 | 1.10 | 12.9 | n.d. | n.d. | 43.2 | --- |
| VW_USS_04 | n.d. | 4.63 | 16.1 | n.d. | 17.1 | 1.30 | 6.00 | 45.1 | --- |
| VW_USS_05 | n.d. | 5.00 | | 2.40 | 22.8 | 1.60 | n.d. | 31.7 | --- |

FIG. 54

| Run I.D. | pro-peptide [µg/mg rVWF:Ag] | | | | | | |
|---|---|---|---|---|---|---|---|
| | Load | FT | Wash(es) | | pre-elu | elu | post-elu | High Salt |
| VW_USS_01 | n.d. | n.d. | n.d. | | n.d. | 0.10 | n.d. | n.d. |
| VW_USS_02 | 272 | 747 | 62.5 | | n.d. | 4.51 | n.d. | < 14.2 |
| VW_USS_03 | 388 | 722 | 184 | 2.35 | 0.95 | 0.60 | 2.67 | < 2.58 |
| VW_USS_04 | 287 | 652 | 24.2 | 0.78 | 0.41 | 0.34 | 7.12 | 24.5 |
| VW_USS_05 | 299 | 567 | 465 | | 4.29 | 0.62 | 2.46 | 19.3 |

FIG. 55

| Run I.D. | pro-peptide [µg PP /1000 U Risto] | | | | | | |
|---|---|---|---|---|---|---|---|
| | Load | FT | Wash(es) | | pre-elu | elu | post-elu | High Salt |
| VW_USS_01 | n.d. | n.d. | n.d. | | n.d. | 2.90 | n.d. | n.d. |
| VW_USS_02 | 3997 | 29150 | 429 | | n.d. | 14.8 | n.d. | < 6.25 |
| VW_USS_03 | 4794 | 30486 | 3306 | 17.3 | 7.89 | 4.14 | 14.6 | < 6.25 |
| VW_USS_04 | 3437 | 30642 | 40.0 | 5.40 | 9.02 | 1.91 | 35.98 | 7.15 |
| VW_USS_05 | 4392 | 29026 | 9927 | | 66.0 | 7.24 | 35.43 | 79.0 |

FIG. 56

| Run I.D. | Eluate Pools | | | | | |
|---|---|---|---|---|---|---|
| | VWF: Ag yield [%] | VWF Risto Act. yield [%] | Spec. act [RIU/IU:Ag] | CHO Ag / rVWF act. [µg/1000U Risto] | PP / rVWF act. [µg PP /1000U Risto] | FVIII act. / rVWF:Rco [IU/ IU] |
| VW_USS_01 | 41.5 | 27.1 | 0.44 | 66 | 2.90 | < 0.054 |
| VW_USS_02 | 0.10 | n.d. | n.d. | n.d. | 14.8 | n.d. |
| VW_USS_03 | 7.20 | 12.9 | 1.45 | < 7.7 | 4.14 | < 0.021 |
| VW_USS_04 | 8.10 | 17.1 | 1.76 | < 11.3 | 1.91 | < 0.016 |
| VW_USS_05 | 18.2 | 22.8 | 0.85 | < 0.41 | 7.24 | 0.042 |

FIG. 57

| Test | Acceptance criteria | Result run VW_USS_05 |
|---|---|---|
| Specific activity: ratio RCo Activity rVWF / rVWF:Ag (ELISA) / | 0.7 – 1.4 IU/IU | 0.85 |
| CHO impurity ratio: CHO-HCP (ELISA) / RCo Activity rVWF | ≤ 2 µg / 1000 IU | < 0.41 |
| FVIII impurity ratio: rFVIII:Ag (ELISA) / RCo Activity rVWF | ≤ 25 µg / 1000 IU | n.d. |
| pro-rVWF impurity ratio: pro-rVWF:Ag (ELISA) / RCo Activity rVWF | ≤ 50 µg / 1000 IU | n.d. |
| rVWF pro-peptide impurity ratio: rVWF pro-peptide:Ag (ELISA) / RCo Activity rVWF | ≤ 2 µg / 1000 IU | 7.24 (1.91 in run VW_USS_04) |
| N-Glycane Profile | Monosialo: 20 – 35% Area Disialo 35 – 50% Area N-glycan Index 150 - 175 | n.d. |
| Ratio Sialic Acid / Total Protein (BCA) | 60 – 150 nmol/mg | n.d. |
| Ratio FVIII Activity / rVWF:RCo | ≤ 0.04 IU / IU | 0.042 (< 0.016 in run VW_USS_04) |
| rVWF Multimer Analysis | ≥ 15 multimer bands ≤ 40% multimers larger than band 15 | ≥ 15 multimer bands ≤ 40% multimers larger than band 15 |
| Ratio CHO-DNA / rVWF:RCo Activity | ≤ 0.5°pg / IU | n.d. |

FIG. 58

| Unit operation | Mode of unit operation | Load | Wash | Elution | comment |
|---|---|---|---|---|---|
| AEX | Binding mode | no | no | Yes, Gradient<br>• high pH<br>• Chelat + neutral<br>• both | |
| | Flow through mode | Yes<br>• Low pH+chelat | no | no | |
| CEX | Binding mode | Yes<br>• high pH<br>• Chelate + neutral<br>• both | Yes<br>• high pH<br>• Chelate + neutral<br>• both | Yes, Gradient<br>• high pH<br>• Chelate + neutral<br>• both | |
| | Flow through mode | no | no | no | |
| SEC | | • high pH<br>• neutral+ chelat<br>• both | | | |

No/yes: is physical separation of matVWF and VWF-PP possible

FIG. 59
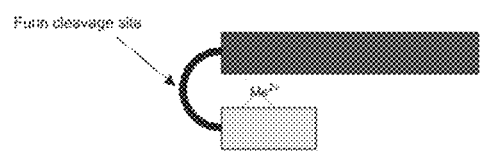  pro-VWF
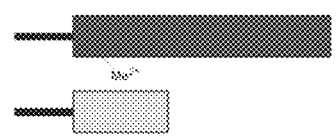  matVWF/ VWF-PP complex
  matVWF
  VWF-PP

FIG. 60A

SEQ ID NO:1

```
agctcacagc tattgtggtg ggaaagggag ggtggttggt ggatgtcaca gcttgggctt     60
tatctccccc agcagtgggg actccacagc ccctgggcta cataacagca agacagtccg    120
gagctgtagc agacctgatt gagcctttgc agcagctgag agcatggcct agggtgggcg    180
gcaccattgt ccagcagctg agtttcccag ggaccttgga gatagccgca gccctcattt    240
gcaggggaag atgattcctg ccagatttgc cggggtgctg cttgctctgg ccctcatttt    300
gccagggacc ctttgtgcag aaggaactcg cggcaggtca tccacggccc gatgcagcct    360
tttcggaagt gacttcgtca acacctttga tgggagcatg tacagctttg cgggatactg    420
cagttacctc ctggcagggg ctgccagaa cgctccttc tcgattattg ggacttcca      480
gaatggcaag agagtgagcc tctccgtgta tcttggggaa ttttttgaca tccatttgtt    540
tgtcaatggt accgtgacac aggggacca aagagtctcc atgccctatg cctccaaagg    600
gctgtatcta gaaactgagg ctgggtacta caagctgtcc ggtgaggcct atggctttgt    660
ggccaggatc gatggcagcg gcaactttca agtcctgctg tcagacagat acttcaacaa    720
gacctgcggg ctgtgtggca actttaacat ctttgctgaa gatgacttta tgacccaaga    780
agggaccttg acctcggacc cttatgactt tgccaactca tgggctctga gcagtggaga    840
acagtggtgt gaacgggcat ctcctcccag cagctcatgc aacatctcct ctggggaaat    900
gcagaagggc ctgtgggagc agtgccagct tctgaagagc acctcggtgt tgcccgctg     960
ccaccctctg gtggaccccg agccttttgt ggccctgtgt gagaagactt tgtgtgagtg   1020
tgctgggggg ctggagtgcg cctgccctgc cctcctggag tacgcccgga cctgtgccca   1080
ggagggaatg tgctgtacg gctggaccga ccacagcgcg tgcagcccag tgtgccctgc   1140
tggtatggag tataggcagt gtgtgtcccc ttgcgccagg acctgccaga gcctgcacat   1200
caatgaaatg tgtcaggagc gatgcgtgga tggctgcagc tgccctgagg acagctcct    1260
ggatgaaggc ctctgcgtgg agagcaccga gtgtcctgc gtgcattccg gaaagcgcta   1320
ccctccggc acctccctct ctcgagactg caacacctgc atttgccgaa acagccagtg   1380
gatctgcagc aatgaagaat gtccagggga gtgccttgtc acaggtcaat cacacttcaa   1440
gagctttgac aacagatact tcaccttcag tgggatctgc cagtacctgc tggcccggga   1500
ttgccaggac cactccttct ccattgtcat tgagactgtc cagtgtgctg atgaccgcga   1560
cgctgtgtgc accgctccg tcaccgtccg gctgcctggc ctgcacaaca gccttgtgaa   1620
actgaagcat ggggcaggag ttgccatgga tggccaggac gtccagctcc ccctcctgaa   1680
aggtgacctc gcatccagc atacagtgac ggcctccgtg cgcctcagct acggggagga   1740
cctgcagatg gactgggatg ccgcgggag gctgctggtg aagctgtccc cgtctatgc    1800
cgggaagacc tgcggcctgt gtgggaatta caatggcaac cagggcgacg acttccttac   1860
cccctctggg ctggcggagc cccgggtgga ggacttcggg aacgcctgga gctgcacgg   1920
ggactgccag gacctgcaga agcagcacag cgatccctgc gccctcaacc cgcgcatgac   1980
caggttctcc gaggaggcgt gcgcggtcct gacgtccccc acattcgagg cctgccatcg   2040
tgccgtcagc ccgctgccct acctgcggaa ctgccgctac gacgtgtgct cctgctcgga   2100
cggccgcgag tgcctgtgcg gcgccctggc cagctatgcc gcggcctgcg cggggagagg   2160
cgtgcgcgtc gcgtggcgcg agccaggccg ctgtgagctg aactgcccga aggccaggt   2220
gtacctgcag tgcgggaccc cctgcaacct gacctgccgc tctctctctt acccggatga   2280
ggaatgcaat gaggcctgcc tggagggctg cttctgcccc ccagggctct acatggatga   2340
gaggggggac tgcgtgccca aggccagtg ccctgttac tatgacggtg agatcttcca   2400
gccagaagac atcttctcag accatcacac catgtgctac tgtgaggatg cttcatgca   2460
ctgtaccatg agtggagtcc ccggaagctt gctgcctgac gctgtcctca gcagtccct   2520
gtctcatcgc agcaaaagga gcctatcctg tcggccccc atggtcaagc tggtgtgtcc   2580
cgctgacaac ctgcgggctg aagggtctga gtgtaccaaa cgtgccaga actatgacct   2640
ggagtgcatg agcatgggct gtgtctctgg ctgcctctgc cccgggca tggtccggca   2700
tgagaacaga tgtgtggccc tggaaggtg tccctgcttc catcagggca aggagtatgc   2760
ccctggagaa acagtgaaga ttggctgcaa cacttgtgtc tgtcgggacc ggaagtggaa   2820
ctgcacagac catgtgtgtg atgccacgtg ctccacgatc ggcatggccc actacctcac   2880
cttcgacggg ctcaaatacc tgttccccgg ggagtgccag tacgttctgg tgcaggatta   2940
ctgcggcagt aaccctggga cctttcggat cctagtgggg aataagggat gcagccaccc   3000
ctcagtgaaa tgcaagaaac gggtcaccat cctggtggag ggaggagaga ttgagctgtt   3060
tgacggggag gtgaatgtga agaggcccat gaaggatgag actcactttg aggtggtgga   3120
gtctggccgg tacatcattc tgctgctggg caaagccctc tccgtggtct gggaccgcca   3180
cctgagcatc tccgtggtcc tgaagcagac ataccaggag aaagtgtgtg gcctgtgtgg   3240
gaattttgat ggcatccaga acaatgacct caccagcagc aacctccaag tggaggaaga   3300
ccctgtggac tttgggaact cctgaaagt gagctcgcag tgtgctgaca cagaaaagt    3360
gcctctggac tcatccctg ccacctgcca taacaacatc atgaagcaga cgatggtgga   3420
ttcctcctgt agaatcctta ccagtgacgt cttccaggac tgcaacaagc tggtggaccc   3480
cgagccatat ctggatgtct gcatttacga cacctgctcc tgtgagtcca ttgggggactg   3540
```

FIG. 60B

```
cgcctgcttc tgcgacacca ttgctgccta tgcccacgtg tgtgcccagc atggcaaggt    3600
ggtgacctgg aggacggcca cattgtgccc ccagagctgc gaggagagga atctccggga    3660
gaacgggtat gagtgtgagt ggcgctataa cagctgtgca cctgcctgtc aagtcacgtg    3720
tcagcaccct gagccactgg cctgccctgt gcagtgtgtg gagggctgcc atgcccactg    3780
ccctccaggg aaaatcctgg atgagctttt gcagacctgc gttgaccctg aagactgtcc    3840
agtgtgtgag gtggctggcc ggcgttttgc ctcaggaaag aaagtcacct tgaatcccag    3900
tgaccctgag cactgccaga tttgccactg tgatgttgtc aacctcacct gtgaagcctg    3960
ccaggagccg ggaggcctgg tggtgcctcc cacagatgcc ccggtgagcc ccaccactct    4020
gtatgtggag gacatctcgg aaccgccgtt gcacgatttc tactgcagca ggctactgga    4080
cctggtcttc tgctggatg gctcctccag gctgtccgag gctgagtttg aagtgctgaa    4140
ggcctttgtg gtggacatga tggagcggct gcgcatctcc cagaagtggg tccgcgtggc    4200
cgtggtggag taccacgacg gctcccacgc ctacatcggg ctcaaggacc ggaagcgacc    4260
gtcagagctg cggcgcattg ccagccaggt gaagtatgcg ggcagccagg tggcctccac    4320
cagcgaggtc ttgaaataca cactgttcca aatcttcagc aagatcgacc gccctgaagc    4380
ctcccgcatc accctgctcc tgatggccag ccaggagccc aacggatgt cccggaactt    4440
tgtccgctac gtccagggcc tgaagaagaa gaaggtcatt gtgatcccgg tgggcattgg    4500
gccccatgcc aacctcaagc agatccgcct catcgagaag caggcccctg agaacaaggc    4560
cttcgtgctg agcagtgtgg atgagctgga gcagcaaagg gacgagatcg ttagctacct    4620
ctgtgacctt gcccctgaag ccctcctcc tactctgccc cccgacatgg cacaagtcac    4680
tgtgggcccg gggctcttgg gggtttcgac cctggggccc aagaggaact ccatggttct    4740
ggatgtggcg ttcgtcctgg aaggatcgga caaaattggt gaagccgact tcaacaggag    4800
caaggagttc atggaggagg tgattcagcg gatggatgtg ggccaggaca gcatccacgt    4860
cacggtgctg cagtactcct acatggtgac tgtggagtac cccttcagcg aggcacagtc    4920
caaaggggac atcctgcagc gggtgcgaga gatccgctac cagggcggca acaggaccaa    4980
cactgggctg gccctgcggt acctctctga ccacagcttc ttggtcagcc agggtgaccg    5040
ggagcaggcg cccaacctgg tctacatggt caccggaaat cctgcctctg atgagatcaa    5100
gaggctgcct ggagacatcc aggtggtgcc cattggagtg ggccctaatg ccaacgtgca    5160
ggagctggag aggattggct ggcccaatgc ccctatcctc atccaggact tgagacgct    5220
cccccgagag gctcctgacc tggtgctgca gaggtgctgc tccggagagg ggctgcagat    5280
cccacacctc tccctgcac ctgactgcag ccagccctg gacgtgatcc ttctcctgga    5340
tggctcctcc agtttcccag cttcttattt tgatgaaatg aagagtttcg ccaaggcttt    5400
catttcaaaa gccaatatag ggcctcgtct cactcaggtg tcagtgctgc agtatggaag    5460
catcaccacc attgacgtgc catggaacgt ggtcccggag aaagcccatt tgctgagcct    5520
tgtggacgtc atgcagcggg agggaggccc cagccaaatc ggggatgcct tgggctttgc    5580
tgtgcgatac ttgacttcag aaatgcatgg tgccaggccg ggagcctcaa aggcggtggt    5640
catcctggtc acggacgtct ctgtggattc agtggatgca gcagctgatg ccgccaggtc    5700
caacagagtg acagtgttcc ctattggaat tggagatcgc tacgatgcag cccagctacg    5760
gatcttggca ggccagcag gcgactccaa cgtggtgaag ctccagcgaa tgaagacct    5820
cctaccatg gtcaccttgg gcaattcctt cctccacaaa ctgtgctctg gatttgttag    5880
gatttgcatg gatgaggatg ggaatgagaa gaggcccggg acgtctgga ccttgccaga    5940
ccagtgccac accgtgactt gccagccaga tggccagacc ttgctgaaga gtcatcgggt    6000
caactgtgac cggggctga ggccttcgtg cccaacagc cagtcccctg ttaaagtgga    6060
agagacctgt ggctgccgct ggacctgccc ctgcgtgtgc acaggcagct ccactcggca    6120
catcgtgacc tttgatgggc agaatttcaa gctgactggc agctgttctt atgtcctatt    6180
tcaaaacaag gagcaggacc tggaggtgat tctccataat ggtgcctgca gccctggagc    6240
aaggcagggc tgcatgaaat ccatcgaggt gaagcacagt gccctctccg tcgagctgca    6300
cagtgacatg gaggtgacgg tgaatgggag actggtctct gttccttacg tgggtgggaa    6360
catggaagtc aacgttatg gtgccatcat gcatgaggtc agattcaatc accttggtca    6420
catcttcaca ttcactccac aaaacaatga gttccaactg cagctcagcc caagactt    6480
tgcttcaaag acgtatggtc tgtgtgggat ctgtgatgag aacggagcca atgacttcat    6540
gctgagggat ggcacagtca ccacagactg gaaaacactt gttcaggaat ggactgtgca    6600
gcggccaggg cagacgtgcc agcccatcct ggaggagcag tgtcttgtcc ccgacagctc    6660
ccactgccag gtcctcctct taccactgtt tgctgaatgc cacaaggtcc tggctccagc    6720
cacattctat gccatctgcc agcaggacag ttgccaccag gagcaagtgt gtgaggtgat    6780
cgcctcttat gcccacctct gtcggaccaa cggggtctgc gttgactgga ggacacctga    6840
tttctgtgct atgtcatgcc caccatctct ggtctacaac cactgtgagc atgctgtcc    6900
ccggcactgt gatggcaacg tgagctcctg tgggaccat cctccgaag gctgtttctg    6960
ccctccagat aaagtcatgt tggaaggcag ctgtgtccct gaagaggcct gcactcagtg    7020
cattggtgag gatggagtcc agcaccagtt cctggaagcc tgggtcccgg accaccagcc    7080
ctgtcagatc tgcacatgcc tcagcgggcg gaaggtcaac tgcacaacgc agcctgcc    7140
```

FIG. 60C

```
cacggccaaa gctcccacgt gtggcctgtg tgaagtagcc cgcctccgcc agaatgcaga   7200
ccagtgctgc cccgagtatg agtgtgtgtg tgacccagtg agctgtgacc tgcccccagt   7260
gcctcactgt gaacgtggcc tccagcccac actgaccaac cctggcgagt gcagacccaa   7320
cttcacctgc gcctgcagga aggaggagtg caaaagagtg tccccaccct cctgcccccc   7380
gcaccgtttg cccacccttc ggaagaccca gtgctgtgat gagtatgagt gtgcctgcaa   7440
ctgtgtcaac tccacagtga gctgtcccct tgggtacttg gcctcaactg ccaccaatga   7500
ctgtggctgt accacaacca cctgccttcc cgacaaggtg tgtgtccacc gaagcaccat   7560
ctaccctgtg ggccagttct gggaggaggg ctgcgatgtg tgcacctgca ccgacatgga   7620
ggatgccgtg atgggcctcc gcgtggccca gtgctcccag aagccctgtg aggacagctg   7680
tcggtcgggc ttcacttacg ttctgcatga aggcgagtgc tgtggaaggt gcctgccatc   7740
tgcctgtgag gtggtgactg gctcaccgcg gggggactcc cagtcttcct ggaagagtgt   7800
cggctcccag tgggcctccc cggagaaccc ctgcctcatc aatgagtgtg tccgagtgaa   7860
ggaggaggtc tttatacaac aaaggaacgt ctcctgcccc cagctggagg tccctgtctg   7920
cccctcgggc tttcagctga gctgtaagac ctcagcgtgc tgcccaagct gtcgctgtga   7980
gcgcatggag gcctgcatgc tcaatggcac tgtcattggg cccgggaaga ctgtgatgat   8040
cgatgtgtgc acgacctgcc gctgcatggt gcaggtgggg gtcatctctg gattcaagct   8100
ggagtgcagg aagaccacct gcaaccctg cccctgggt tacaaggaag aaaataacac   8160
aggtgaatgt tgtgggagat gtttgcctac ggcttgcacc attcagctaa gaggaggaca   8220
gatcatgaca ctgaagcgtg atgagacgct ccaggatggc tgtgatactc acttctgcaa   8280
ggtcaatgag agaggagagt acttctggga gaagagggtc acaggctgcc cacccttga   8340
tgaacacaag tgtctggctg agggaggtaa aattatgaaa attccaggca cctgctgtga   8400
cacatgtgag gagcctgagt gcaacgacat cactgccagg ctgcagtatg tcaaggtggg   8460
aagctgtaag tctgaagtag aggtggatat ccactactgc cagggcaaat gtgccagcaa   8520
agccatgtac tccattgaca tcaacgatgt gcaggaccag tgctcctgct gctctccgac   8580
acggacggag cccatgcagg tggccctgca ctgcaccaat ggctctgttg tgtaccatga   8640
ggttctcaat gccatggagt gcaaatgctc ccccaggaag tgcagcaagt gaggctgctg   8700
cagctgcatg ggtgcctgct gctgcctgcc ttggcctgat ggccaggcca gagtgctgcc   8760
agtcctctgc atgttctgct cttgtgccct tctgagccca caataaaggc tgagctctta   8820
tcttgcaaaa ggc                                                      8833
```

SEQ ID NO:2

```
Met Ile Pro Ala Arg Phe Ala Gly Val Leu Leu Ile Leu Pro Gly
1               5                   10                  15

Thr Leu Cys Ala Glu Gly Thr Arg Gly Arg Ser Ser Thr Ala Arg Cys
            20                  25                  30

Ser Leu Phe Gly Ser Asp Phe Val Asn Thr Phe Asp Gly Ser Met Tyr
            35                  40                  45

Ser Phe Ala Gly Tyr Cys Ser Tyr Leu Leu Ala Gly Gly Cys Gln Lys
        50                  55                  60

Arg Ser Phe Ser Ile Ile Gly Asp Phe Gln Asn Gly Lys Arg Val Ser
65                  70                  75                  80

Leu Ser Val Tyr Leu Gly Glu Phe Phe Asp Ile His Leu Phe Val Asn
                85                  90                  95

Gly Thr Val Thr Gln Gly Asp Gln Arg Val Ser Met Pro Tyr Ala Ser
            100                 105                 110

Lys Leu Glu Thr Glu Ala Gly Tyr Tyr Lys Leu Ser Gly Glu Ala Tyr
            115                 120                 125

Gly Phe Val Ala Arg Ile Asp Gly Ser Gly Asn Phe Gln Val Leu Leu
        130                 135                 140
```

FIG. 60D

Ser Asp Arg Tyr Phe Asn Lys Thr Cys Gly Leu Cys Gly Asn Phe Asn
145                 150                 155                 160

Ile Phe Ala Glu Asp Asp Phe Met Thr Gln Glu Gly Thr Leu Thr Ser
                165                 170                 175

Asp Pro Tyr Asp Phe Ala Asn Ser Trp Ala Leu Ser Ser Gly Glu Gln
            180                 185                 190

Trp Cys Glu Arg Pro Ser Ser Ser Cys Asn Ile Ser Ser Gly Glu Met
        195                 200                 205

Gln Lys Gly Leu Trp Glu Gln Cys Gln Leu Leu Lys Ser Thr Ser Val
    210                 215                 220

Phe Ala Arg Cys His Pro Leu Val Asp Pro Glu Pro Phe Cys Glu Lys
225                 230                 235                 240

Thr Leu Cys Glu Cys Ala Gly Gly Leu Glu Cys Ala Cys Pro Ala Leu
                245                 250                 255

Leu Glu Tyr Ala Arg Thr Cys Ala Gln Glu Gly Met Val Leu Tyr Gly
            260                 265                 270

Trp Thr Asp His Ser Ala Cys Ser Pro Val Cys Pro Ala Gly Met Glu
        275                 280                 285

Tyr Arg Gln Cys Val Ser Pro Cys Ala Arg Thr Cys Gln Ser Leu His
    290                 295                 300

Ile Asn Glu Met Cys Gln Glu Arg Cys Val Asp Gly Cys Ser Cys Pro
305                 310                 315                 320

Glu Gly Gln Leu Leu Asp Glu Gly Leu Cys Val Glu Ser Thr Glu Cys
                325                 330                 335

Pro Cys Val His Ser Gly Lys Arg Tyr Pro Pro Gly Thr Ser Leu Ser
            340                 345                 350

Arg Asp Cys Asn Thr Cys Ile Cys Arg Asn Ser Gln Trp Ile Cys Ser
        355                 360                 365

Asn Glu Glu Cys Pro Gly Glu Cys Leu Val Thr Gly Gln Ser His Phe
    370                 375                 380

Lys Ser Phe Asp Asn Arg Tyr Phe Thr Phe Ser Gly Ile Cys Gln Tyr
385                 390                 395                 400

Leu Leu Ala Arg Asp Cys Gln Asp His Ser Phe Ser Ile Val Ile Glu
                405                 410                 415

Thr Val Gln Cys Ala Asp Asp Arg Asp Ala Val Cys Thr Arg Ser Val
            420                 425                 430

Thr Val Arg Leu Pro Gly Leu His Asn Ser Leu Val Lys Leu Lys His
        435                 440                 445

Gly Ala Gly Val Ala Met Asp Gly Gln Asp Val Gln Leu Pro Leu Leu
450                 455                 460

FIG. 60E

```
Lys Gly Asp Leu Arg Ile Gln His Thr Val Thr Ala Ser Val Arg Leu
465                 470                 475                 480

Ser Tyr Gly Glu Asp Leu Gln Met Asp Trp Asp Gly Arg Gly Arg Leu
            485                 490                 495

Leu Val Lys Leu Ser Pro Val Tyr Ala Gly Lys Thr Cys Gly Leu Cys
            500                 505                 510

Gly Asn Tyr Asn Gly Asn Gln Gly Asp Asp Phe Leu Thr Pro Ser Gly
            515                 520                 525

Leu Ala Glu Pro Arg Val Glu Asp Phe Gly Asn Ala Trp Lys Leu His
        530                 535                 540

Gly Asp Cys Gln Asp Leu Gln Lys Gln His Ser Asp Pro Cys Ala Leu
545                 550                 555                 560

Asn Pro Arg Met Thr Arg Phe Ser Glu Glu Ala Cys Ala Val Leu Thr
                565                 570                 575

Ser Pro Thr Phe Glu Ala Cys His Arg Ala Val Ser Pro Leu Pro Tyr
            580                 585                 590

Leu Arg Asn Cys Arg Tyr Asp Val Cys Ser Cys Ser Asp Gly Arg Glu
        595                 600                 605

Cys Leu Cys Gly Ser Tyr Ala Ala Ala Cys Ala Gly Arg Gly Val Arg
    610                 615                 620

Val Ala Trp Arg Glu Pro Gly Arg Cys Glu Leu Asn Cys Pro Lys Gly
625                 630                 635                 640

Gln Val Tyr Leu Gln Cys Gly Thr Pro Cys Asn Leu Thr Cys Arg Ser
            645                 650                 655

Leu Ser Tyr Pro Asp Glu Glu Cys Asn Glu Ala Cys Leu Glu Gly Cys
            660                 665                 670

Phe Cys Pro Pro Met Asp Glu Arg Gly Asp Cys Val Pro Lys Ala Gln
        675                 680                 685

Cys Pro Cys Tyr Tyr Asp Gly Glu Ile Phe Gln Pro Glu Asp Ile Phe
    690                 695                 700

Ser Asp His His Thr Met Cys Tyr Cys Glu Asp Gly Phe Met His Cys
705                 710                 715                 720

Thr Met Ser Gly Val Pro Gly Ser Leu Leu Pro Asp Ala Val Leu Ser
                725                 730                 735

Ser Pro Leu Ser His Arg Ser Lys Arg Ser Leu Ser Cys Arg Pro Pro
            740                 745                 750

Met Val Lys Leu Val Cys Pro Ala Asp Asn Leu Arg Ala Glu Gly Leu
        755                 760                 765

Glu Cys Thr Lys Thr Cys Gln Asn Tyr Asp Leu Glu Cys Met Ser Met
    770                 775                 780
```

FIG. 60F

```
Gly Cys Val Ser Gly Cys Leu Cys Pro Pro Gly Met Val Arg His Glu
785             790             795                     800

Asn Arg Cys Glu Arg Cys Pro Cys Phe His Gln Gly Lys Glu Tyr Ala
            805             810                 815

Pro Gly Glu Thr Val Lys Ile Gly Cys Asn Thr Cys Val Cys Arg Asp
            820             825             830

Arg Lys Trp Asn Cys Thr Asp His Val Cys Asp Ala Thr Cys Ser Thr
        835             840                 845

Ile Gly Met Ala His Tyr Leu Thr Phe Asp Gly Leu Lys Tyr Leu Phe
    850             855             860

Pro Gly Glu Cys Gln Tyr Val Leu Val Gln Asp Tyr Cys Gly Ser Asn
865             870             875             880

Pro Gly Thr Phe Arg Ile Leu Val Gly Asn Lys Gly Cys Ser His Pro
            885             890             895

Ser Val Lys Cys Lys Lys Arg Val Thr Ile Leu Val Glu Gly Gly Glu
        900             905             910

Ile Glu Leu Phe Asp Gly Val Asn Val Lys Arg Pro Met Lys Asp
        915             920             925

Glu Thr His Phe Glu Val Val Glu Ser Gly Arg Tyr Ile Ile Leu Leu
    930             935             940

Leu Gly Lys Ala Leu Ser Val Val Trp Asp Arg His Leu Ser Ile Ser
945             950             955             960

Val Val Leu Lys Gln Thr Tyr Gln Glu Lys Val Cys Gly Leu Cys Gly
            965             970             975

Asn Phe Asp Gly Ile Gln Asn Asn Asp Leu Thr Ser Ser Asn Leu Gln
            980             985             990

Val Glu Glu Asp Pro Val Asp Phe Gly Asn Ser Trp Lys Val Ser Ser
        995             1000            1005

Gln Cys Ala Asp Thr Arg Lys Val Pro Leu Asp Ser Ser Pro Ala
    1010            1015           1020

Thr Cys His Asn Asn Ile Met Lys Gln Thr Met Val Asp Ser Ser
    1025            1030           1035

Cys Arg Ile Leu Thr Ser Asp Val Phe Gln Asp Cys Asn Lys Leu
    1040            1045           1050

Val Asp Pro Glu Pro Tyr Leu Asp Val Cys Ile Tyr Asp Thr Cys
    1055            1060           1065

Ser Cys Glu Ser Ile Gly Asp Cys Ala Cys Phe Cys Asp Thr Ile
    1070            1075           1080

Ala Ala Tyr Ala His Val Cys Ala Gln His Gly Lys Val Val Thr
    1085            1090           1095
```

FIG. 60G

Trp Arg Thr Ala Thr Leu Cys Pro Gln Ser Cys Glu Glu Arg Asn
    1100              1105              1110

Leu Arg Glu Asn Gly Tyr Glu Cys Glu Trp Arg Tyr Asn Ser Cys
    1115              1120              1125

Ala Pro Ala Cys Gln Val Thr Cys Gln His Pro Glu Pro Leu Ala
    1130              1135              1140

Cys Pro Val Gln Cys Val Glu Gly Cys His Ala His Cys Pro Pro
    1145              1150              1155

Gly Lys Ile Leu Asp Glu Leu Leu Gln Thr Cys Val Asp Pro Glu
    1160              1165              1170

Asp Cys Pro Val Cys Glu Val Ala Gly Arg Arg Phe Ala Ser Gly
    1175              1180              1185

Lys Lys Val Thr Leu Asn Pro Ser Asp Pro Glu His Cys Gln Ile
    1190              1195              1200

Cys His Cys Asp Val Val Asn Leu Thr Cys Glu Ala Cys Gln Glu
    1205              1210              1215

Pro Gly Gly Leu Val Val Pro Pro Thr Asp Ala Pro Val Ser Pro
    1220              1225              1230

Thr Thr Leu Tyr Val Glu Asp Ile Ser Glu Pro Pro Leu His Asp
    1235              1240              1245

Phe Tyr Cys Ser Arg Leu Leu Asp Leu Val Phe Leu Leu Asp Gly
    1250              1255              1260

Ser Ser Arg Leu Ser Glu Ala Glu Phe Glu Val Leu Lys Ala Phe
    1265              1270              1275

Val Val Asp Met Met Glu Arg Leu Arg Ile Ser Gln Lys Trp Val
    1280              1285              1290

Arg Val Ala Val Val Glu Tyr His Asp Gly Ser His Ala Tyr Ile
    1295              1300              1305

Gly Leu Lys Asp Arg Lys Arg Pro Ser Glu Leu Arg Arg Ile Ala
    1310              1315              1320

Ser Gln Val Lys Tyr Ala Gly Ser Gln Val Ala Ser Thr Ser Glu
    1325              1330              1335

Val Leu Lys Tyr Thr Leu Phe Gln Ile Phe Ser Lys Ile Asp Arg
    1340              1345              1350

Pro Glu Ala Ser Arg Ile Thr Leu Leu Leu Met Ala Ser Gln Glu
    1355              1360              1365

Pro Gln Arg Met Ser Arg Asn Phe Val Arg Tyr Val Gln Gly Leu
    1370              1375              1380

Lys Lys Lys Lys Val Ile Val Ile Pro Val Gly Ile Gly Pro His
    1385              1390              1395

FIG. 60H

Ala Asn Leu Lys Gln Ile Arg Leu Ile Glu Lys Gln Ala Pro Glu
1400                1405                1410

Asn Lys Ala Phe Val Leu Ser Ser Val Asp Glu Leu Glu Gln Gln
1415                1420                1425

Arg Asp Glu Ile Val Ser Tyr Leu Cys Asp Leu Ala Pro Glu Ala
1430                1435                1440

Pro Pro Pro Thr Leu Pro Pro Asp Met Ala Gln Val Thr Val Gly
1445                1450                1455

Pro Gly Leu Leu Gly Val Ser Thr Leu Gly Pro Lys Arg Asn Ser
1460                1465                1470

Met Val Leu Asp Val Ala Phe Val Leu Glu Gly Ser Asp Lys Ile
1475                1480                1485

Gly Glu Ala Asp Phe Asn Arg Ser Lys Glu Phe Met Glu Glu Val
1490                1495                1500

Ile Gln Arg Met Asp Val Gly Gln Asp Ser Ile His Val Thr Val
1505                1510                1515

Leu Gln Tyr Ser Tyr Met Val Thr Val Glu Tyr Pro Phe Ser Glu
1520                1525                1530

Ala Gln Ser Lys Gly Asp Ile Leu Gln Arg Val Arg Glu Ile Arg
1535                1540                1545

Tyr Gln Gly Gly Asn Arg Thr Asn Thr Gly Leu Ala Leu Arg Tyr
1550                1555                1560

Leu Ser Asp His Ser Phe Leu Val Ser Gln Gly Asp Arg Glu Gln
1565                1570                1575

Ala Pro Asn Leu Val Tyr Met Val Thr Gly Asn Pro Ala Ser Asp
1580                1585                1590

Glu Ile Lys Arg Leu Pro Gly Asp Ile Gln Val Val Pro Ile Gly
1595                1600                1605

Val Gly Pro Asn Ala Asn Val Gln Glu Leu Glu Arg Ile Gly Trp
1610                1615                1620

Pro Asn Ala Pro Ile Leu Ile Gln Asp Phe Glu Thr Leu Pro Arg
1625                1630                1635

Glu Ala Pro Asp Leu Val Leu Gln Arg Cys Cys Ser Gly Glu Gly
1640                1645                1650

Leu Gln Ile Pro Thr Leu Ser Pro Ala Pro Asp Cys Ser Gln Pro
1655                1660                1665

Leu Asp Val Ile Leu Leu Leu Asp Gly Ser Ser Ser Phe Pro Ala
1670                1675                1680

Ser Tyr Phe Asp Glu Met Lys Ser Phe Ala Lys Ala Phe Ile Ser
1685                1690                1695

FIG. 60I

Lys Ala Asn Ile Gly Pro Arg Leu Thr Gln Val Ser Val Leu Gln
    1700                    1705                  1710

Tyr Gly Ser Ile Thr Thr Ile Asp Val Pro Trp Asn Val Val Pro
    1715                    1720                  1725

Glu Lys Ala His Leu Leu Ser Leu Val Asp Val Met Gln Arg Glu
    1730                    1735                  1740

Gly Gly Pro Ser Gln Ile Gly Asp Ala Leu Gly Phe Ala Val Arg
    1745                    1750                  1755

Tyr Leu Thr Ser Glu Met His Gly Ala Arg Pro Gly Ala Ser Lys
    1760                    1765                  1770

Ala Val Val Ile Leu Val Thr Asp Val Ser Val Asp Ser Val Asp
    1775                    1780                  1785

Ala Ala Ala Asp Ala Ala Arg Ser Asn Arg Val Thr Val Phe Pro
    1790                    1795                  1800

Ile Gly Ile Gly Asp Arg Tyr Asp Ala Ala Gln Leu Arg Ile Leu
    1805                    1810                  1815

Ala Gly Pro Ala Gly Asp Ser Asn Val Val Lys Leu Gln Arg Ile
    1820                    1825                  1830

Glu Asp Leu Pro Thr Met Val Thr Leu Gly Asn Ser Phe Leu His
    1835                    1840                  1845

Lys Leu Cys Ser Gly Phe Val Arg Ile Cys Met Asp Glu Asp Gly
    1850                    1855                  1860

Asn Glu Lys Arg Pro Gly Asp Val Trp Thr Leu Pro Asp Gln Cys
    1865                    1870                  1875

His Thr Val Thr Cys Gln Pro Asp Gly Gln Thr Leu Leu Lys Ser
    1880                    1885                  1890

His Arg Val Asn Cys Asp Arg Gly Leu Arg Pro Ser Cys Pro Asn
    1895                    1900                  1905

Ser Gln Ser Pro Val Lys Val Glu Glu Thr Cys Gly Cys Arg Trp
    1910                    1915                  1920

Thr Cys Pro Cys Val Cys Thr Gly Ser Ser Thr Arg His Ile Val
    1925                    1930                  1935

Thr Phe Asp Gly Gln Asn Phe Lys Leu Thr Gly Ser Cys Ser Tyr
    1940                    1945                  1950

Val Leu Phe Gln Asn Lys Glu Gln Asp Leu Glu Val Ile Leu His
    1955                    1960                  1965

Asn Gly Ala Cys Ser Pro Gly Ala Arg Gln Gly Cys Met Lys Ser
    1970                    1975                  1980

Ile Glu Val Lys His Ser Ala Leu Ser Val Glu Leu His Ser Asp
    1985                    1990                  1995

FIG. 60J

```
Met Glu Val Thr Val Asn Gly Arg Leu Val Ser Val Pro Tyr Val
    2000                2005            2010
Gly Gly Asn Met Glu Val Asn Val Tyr Gly Ala Ile Met His Glu
    2015                2020            2025
Val Arg Phe Asn His Leu Gly His Ile Phe Thr Phe Thr Pro Gln
    2030                2035            2040
Asn Asn Glu Phe Gln Leu Gln Leu Ser Pro Lys Thr Phe Ala Ser
    2045                2050            2055
Lys Thr Tyr Gly Leu Cys Gly Ile Cys Asp Glu Asn Gly Ala Asn
    2060                2065            2070
Asp Phe Met Leu Arg Asp Gly Thr Val Thr Thr Asp Trp Lys Thr
    2075                2080            2085
Leu Val Gln Glu Trp Thr Val Gln Arg Pro Gly Gln Thr Cys Gln
    2090                2095            2100
Pro Glu Gln Cys Leu Val Pro Asp Ser Ser His Cys Gln Val Leu
    2105                2110            2115
Leu Leu Pro Leu Phe Ala Glu Cys His Lys Val Leu Ala Pro Ala
    2120                2125            2130
Thr Phe Tyr Ala Ile Cys Gln Gln Asp Ser Cys His Gln Glu Gln
    2135                2140            2145
Val Cys Glu Val Ile Ala Ser Tyr Ala His Leu Cys Arg Thr Asn
    2150                2155            2160
Gly Val Cys Val Asp Trp Arg Thr Pro Asp Phe Cys Ala Met Ser
    2165                2170            2175
Cys Pro Pro Ser Leu Val Tyr Asn His Cys Glu His Gly Cys Pro
    2180                2185            2190
Arg His Cys Asp Gly Asn Val Ser Ser Cys Gly Asp His Pro Ser
    2195                2200            2205
Glu Gly Cys Phe Cys Pro Pro Asp Lys Val Met Leu Glu Gly Ser
    2210                2215            2220
Cys Val Pro Glu Glu Ala Cys Thr Gln Cys Ile Gly Glu Asp Gly
    2225                2230            2235
Val Gln His Gln Phe Leu Glu Ala Trp Val Pro Asp His Gln Pro
    2240                2245            2250
Cys Gln Ile Cys Thr Cys Leu Ser Gly Arg Lys Val Asn Cys Thr
    2255                2260            2265
Thr Gln Pro Cys Pro Thr Ala Lys Ala Pro Thr Cys Gly Leu Cys
    2270                2275            2280
Glu Val Ala Arg Leu Arg Gln Asn Ala Asp Gln Cys Cys Pro Glu
    2285                2290            2295
```

FIG. 60K

```
Tyr Glu Cys Val Cys Asp Pro Val Ser Cys Asp Leu Pro Pro Val
    2300            2305            2310

Pro His Cys Glu Arg Gly Leu Gln Pro Thr Leu Thr Asn Pro Gly
    2315            2320            2325

Glu Cys Arg Pro Asn Phe Thr Cys Ala Cys Arg Lys Glu Glu Cys
    2330            2335            2340

Lys Arg Val Ser Pro Pro Ser Cys Pro Pro His Arg Leu Pro Thr
    2345            2350            2355

Leu Arg Lys Thr Gln Cys Cys Asp Glu Tyr Glu Cys Ala Cys Asn
    2360            2365            2370

Cys Val Asn Ser Thr Val Ser Cys Pro Leu Gly Tyr Leu Ala Ser
    2375            2380            2385

Thr Ala Thr Asn Asp Cys Gly Cys Thr Thr Thr Cys Leu Pro
    2390            2395            2400

Asp Lys Val Cys Val His Arg Ser Thr Ile Tyr Pro Val Gly Gln
    2405            2410            2415

Phe Trp Glu Glu Gly Cys Asp Val Cys Thr Cys Thr Asp Met Glu
    2420            2425            2430

Asp Ala Val Met Gly Leu Arg Val Ala Gln Cys Ser Gln Lys Pro
    2435            2440            2445

Cys Glu Asp Ser Cys Arg Ser Gly Phe Thr Tyr Val Leu His Glu
    2450            2455            2460

Gly Glu Cys Cys Gly Arg Cys Leu Pro Ser Ala Cys Glu Val Val
    2465            2470            2475

Thr Gly Ser Pro Arg Gly Asp Ser Gln Ser Ser Trp Lys Ser Val
    2480            2485            2490

Gly Ser Gln Trp Glu Asn Pro Cys Leu Ile Asn Glu Cys Val Arg
    2495            2500            2505

Val Lys Glu Glu Val Phe Ile Gln Gln Arg Asn Val Ser Cys Pro
    2510            2515            2520

Gln Leu Glu Val Pro Val Cys Pro Ser Gly Phe Gln Leu Ser Cys
    2525            2530            2535

Lys Thr Ser Ala Cys Cys Pro Ser Cys Arg Cys Glu Arg Met Glu
    2540            2545            2550

Ala Cys Met Leu Asn Gly Thr Val Ile Gly Pro Gly Lys Thr Val
    2555            2560            2565

Met Ile Asp Val Cys Thr Thr Cys Arg Cys Met Val Gln Val Gly
    2570            2575            2580

Val Ile Ser Gly Phe Lys Leu Glu Cys Arg Lys Thr Thr Cys Asn
    2585            2590            2595
```

FIG. 60L

```
Pro Cys Pro Leu Gly Tyr Lys Glu Glu Asn Asn Thr Gly Glu Cys
    2600              2605                2610

Cys Gly Arg Cys Leu Pro Thr Ala Cys Thr Ile Gln Leu Arg Gly
    2615              2620                2625

Gly Gln Ile Met Thr Leu Lys Arg Asp Glu Thr Leu Gln Asp Gly
    2630              2635                2640

Cys Asp Thr His Phe Cys Lys Val Asn Glu Arg Gly Glu Tyr Phe
    2645              2650                2655

Trp Glu Lys Arg Val Thr Gly Cys Pro Pro Phe Asp Glu His Lys
    2660              2665                2670

Cys Leu Ala Glu Gly Gly Lys Ile Met Lys Ile Pro Gly Thr Cys
    2675              2680                2685

Cys Asp Thr Cys Glu Glu Pro Glu Cys Asn Asp Ile Thr Ala Arg
    2690              2695                2700

Leu Gln Tyr Val Lys Val Gly Ser Cys Lys Ser Glu Val Glu Val
    2705              2710                2715

Asp Ile His Tyr Cys Gln Gly Lys Cys Ala Ser Lys Ala Met Tyr
    2720              2725                2730

Ser Ile Asp Ile Asn Asp Val Gln Asp Gln Cys Ser Cys Cys Ser
    2735              2740                2745

Pro Thr Arg Thr Glu Pro Met Gln His Cys Thr Asn Gly Ser Val
    2750              2755                2760

Val Tyr His Glu Val Leu Asn Ala Met Glu Cys Lys Cys Ser Pro
    2765              2770                2775

Arg Lys Cys Ser Lys
    2780
```

SEQ ID NO:3

```
Ser Leu Ser Cys Arg Pro Pro Met Val Lys Leu Val Cys Pro Ala Asp
1           5               10              15

Asn Leu Arg Ala Glu Gly Leu Glu Cys Thr Lys Thr Cys Gln Asn Tyr
            20              25                      30

Asp Leu Glu Cys Met Ser Met Gly Cys Val Ser Gly Cys Leu Cys Pro
            35                      40                      45

Pro Gly Met Val Arg His Glu Asn Arg Cys Val Ala Leu Glu Arg Cys
    50                      55                      60

Pro Cys Phe His Gln Gly Lys Glu Tyr Ala Pro Gly Glu Thr Val Lys
65                      70                      75                      80
```

FIG. 60M

```
Ile Gly Cys Asn Thr Cys Val Cys Arg Asp Arg Lys Trp Asn Cys Thr
                85              90                  95
Asp His Val Cys Asp Ala Thr Cys Ser Thr Ile Gly Met Ala His Tyr
            100                 105                 110
Leu Thr Phe Asp Gly Leu Lys Tyr Leu Phe Pro Gly Glu Cys Gln Tyr
            115                 120                 125
Val Leu Val Gln Asp Tyr Cys Gly Ser Asn Pro Gly Thr Phe Arg Ile
        130                 135                 140
Leu Val Gly Asn Lys Gly Cys Ser His Pro Ser Val Lys Cys Lys Lys
145                 150                 155                 160
Arg Val Thr Ile Leu Val Glu Gly Gly Glu Ile Glu Leu Phe Asp Gly
                165                 170                 175
Glu Val Asn Val Lys Arg Pro Met Lys Asp Glu Thr His Phe Glu Val
            180                 185                 190
Val Glu Ser Gly Arg Tyr Ile Ile Leu Leu Leu Gly Lys Ala Leu Ser
            195                 200                 205
Val Val Trp Asp Arg His Leu Ser Ile Ser Val Val Leu Lys Gln Thr
        210                 215                 220
Tyr Gln Glu Lys Val Cys Gly Leu Cys Gly Asn Phe Asp Gly Ile Gln
225                 230                 235                 240
Asn Asn Asp Leu Thr Ser Ser Asn Leu Gln Val Glu Glu Asp Pro Val
                245                 250                 255
Asp Phe Gly Asn Ser Trp Lys Val Ser Ser Gln Cys Ala Asp Thr Arg
            260                 265                 270
Lys Val Pro Leu Asp Ser Ser Pro Ala Thr Cys His Asn Asn Ile Met
            275                 280                 285
Lys Gln Thr Met Val Asp Ser Ser Cys Arg Ile Leu Thr Ser Asp Val
            290                 295                 300
Phe Gln Asp Cys Asn Lys Leu Val Asp Pro Glu Pro Tyr Leu Asp Val
305                 310                 315                 320
Cys Ile Tyr Asp Thr Cys Ser Cys Glu Ser Ile Gly Asp Cys Ala Cys
                325                 330                 335
Phe Cys Asp Thr Ile Ala Ala Tyr Ala His Val Cys Ala Gln His Gly
            340                 345                 350
Lys Val Val Thr Trp Arg Thr Ala Thr Leu Cys Pro Gln Ser Cys Glu
            355                 360                 365
Glu Arg Asn Leu Arg Glu Asn Gly Tyr Glu Cys Glu Trp Arg Tyr Asn
        370                 375                 380
Ser Cys Ala Pro Ala Cys Gln Val Thr Cys Gln His Pro Glu Pro Leu
385                 390                 395                 400
```

FIG. 60N

```
Ala Cys Pro Val Gln Cys Val Glu Gly Cys His Ala His Cys Pro Pro
            405                 410                 415
Gly Lys Ile Leu Asp Glu Leu Leu Gln Thr Cys Val Asp Pro Glu Asp
            420                 425                 430
Cys Pro Val Cys Glu Val Ala Gly Arg Arg Phe Ala Ser Gly Lys Lys
            435                 440                 445
Val Thr Leu Asn Pro Ser Asp Pro Glu His Cys Gln Ile Cys His Cys
450             455                 460
Asp Val Val Asn Leu Thr Cys Glu Ala Cys Gln Glu Pro Gly Gly Leu
465             470                 475                         480
Val Val Pro Pro Thr Asp Ala Pro Val Ser Pro Thr Thr Leu Tyr Val
            485                 490                 495
Glu Asp Ile Ser Glu Pro Pro Leu His Asp Phe Tyr Cys Ser Arg Leu
            500                 505                 510
Leu Asp Leu Val Phe Leu Leu Asp Gly Ser Ser Arg Leu Ser Glu Ala
            515                 520                 525
Glu Phe Glu Val Leu Lys Ala Phe Val Val Asp Met Met Glu Arg Leu
            530                 535                 540
Arg Ile Ser Gln Lys Trp Val Arg Val Ala Val Val Glu Tyr His Asp
545                 550                 555                 560
Gly Ser His Ala Tyr Ile Gly Leu Lys Asp Arg Lys Arg Pro Ser Glu
                565                 570                 575
Leu Arg Arg Ile Ala Ser Gln Val Lys Tyr Ala Gly Ser Gln Val Ala
                580                 585                 590
Ser Thr Ser Glu Val Leu Lys Tyr Thr Leu Phe Gln Ile Phe Ser Lys
            595                 600                 605
Ile Asp Arg Pro Glu Ala Ser Arg Ile Thr Leu Leu Leu Met Ala Ser
    610                 615                 620
Gln Glu Pro Gln Arg Met Ser Arg Asn Phe Val Arg Tyr Val Gln Gly
625                 630                 635                 640
Leu Lys Lys Lys Lys Val Ile Val Ile Pro Val Gly Ile Gly Pro His
                645                 650                 655
Ala Asn Leu Lys Gln Ile Arg Leu Ile Glu Lys Gln Ala Pro Glu Asn
                660                 665                 670
Lys Ala Phe Val Leu Ser Ser Val Asp Glu Leu Glu Gln Gln Arg Asp
            675                 680                 685
Glu Ile Val Ser Tyr Leu Cys Asp Leu Ala Pro Glu Ala Pro Pro Pro
            690                 695                 700
Thr Leu Pro Pro Asp Met Ala Gln Val Thr Val Gly Pro Gly Leu Leu
705                 710                 715                 720
```

FIG. 60O

```
Gly Val Ser Thr Leu Gly Pro Lys Arg Asn Ser Met Val Leu Asp Val
            725                 730                 735
Ala Phe Val Leu Glu Gly Ser Asp Lys Ile Gly Glu Ala Asp Phe Asn
            740                 745                 750
Arg Ser Lys Glu Phe Met Glu Val Ile Gln Arg Met Asp Val Gly
            755                 760                 765
Gln Asp Ser Ile His Val Thr Val Leu Gln Tyr Ser Tyr Met Val Thr
770                 775                 780
Val Glu Tyr Pro Phe Ser Glu Ala Gln Ser Lys Gly Asp Ile Leu Gln
785                 790                 795                 800
Arg Val Arg Glu Ile Arg Tyr Gln Gly Gly Asn Arg Thr Asn Thr Gly
            805                 810                 815
Leu Ala Leu Arg Tyr Leu Ser Asp His Ser Phe Leu Val Ser Gln Gly
            820                 825                 830
Asp Arg Glu Gln Ala Pro Asn Leu Val Tyr Met Val Thr Gly Asn Pro
            835                 840                 845
Ala Ser Asp Glu Ile Lys Arg Leu Pro Gly Asp Ile Gln Val Val Pro
850                 855                 860
Ile Gly Val Gly Pro Asn Ala Asn Val Gln Glu Leu Glu Arg Ile Gly
865                 870                 875                 880
Trp Pro Asn Ala Pro Ile Leu Ile Gln Asp Phe Glu Thr Leu Pro Arg
                    885                 890                 895
Glu Ala Pro Asp Leu Val Leu Gln Arg Cys Cys Ser Gly Glu Gly Leu
            900                 905                 910
Gln Ile Pro Thr Leu Ser Pro Ala Pro Asp Cys Ser Gln Pro Leu Asp
            915                 920                 925
Val Ile Leu Leu Leu Asp Gly Ser Ser Ser Phe Pro Ala Ser Tyr Phe
930                 935                 940
Asp Glu Met Lys Ser Phe Ala Lys Ala Phe Ile Ser Lys Ala Asn Ile
945                 950                 955                 960
Gly Pro Arg Leu Thr Gln Val Ser Val Leu Gln Tyr Gly Ser Ile Thr
            965                 970                 975
Thr Ile Asp Val Pro Trp Asn Val Val Pro Glu Lys Ala His Leu Leu
            980                 985                 990
Ser Leu Val Asp Val Met Gln Arg Glu Gly Gly Pro Ser Gln Ile Gly
            995                 1000                1005
Asp Ala  Leu Gly Phe Ala Val Arg Tyr Leu Thr  Ser Glu Met His
    1010                1015                    1020
Gly Ala  Arg Pro Gly Ala Ser  Lys Ala Val Val Ile  Leu Val Thr
    1025                1030                     1035
```

FIG. 60P

```
Asp Val Ser Val Asp Ser Val Asp Ala Ala Ala Asp Ala Ala Arg
    1040            1045            1050

Ser Asn Arg Val Thr Val Phe Pro Ile Gly Ile Gly Asp Arg Tyr
    1055            1060            1065

Asp Ala Ala Gln Leu Arg Ile Leu Ala Gly Pro Ala Gly Asp Ser
    1070            1075            1080

Asn Val Val Lys Leu Gln Arg Ile Glu Asp Leu Pro Thr Met Val
    1085            1090            1095

Thr Leu Gly Asn Ser Phe Leu His Lys Leu Cys Ser Gly Phe Val
    1100            1105            1110

Arg Ile Cys Met Asp Glu Asp Gly Asn Glu Lys Arg Pro Gly Asp
    1115            1120            1125

Val Trp Thr Leu Pro Asp Gln Cys His Thr Val Thr Cys Gln Pro
    1130            1135            1140

Asp Gly Gln Thr Leu Leu Lys Ser His Arg Val Asn Cys Asp Arg
    1145            1150            1155

Gly Leu Arg Pro Ser Cys Pro Asn Ser Gln Ser Pro Val Lys Val
    1160            1165            1170

Glu Glu Thr Cys Gly Cys Arg Trp Thr Cys Pro Cys Val Cys Thr
    1175            1180            1185

Gly Ser Ser Thr Arg His Ile Val Thr Phe Asp Gly Gln Asn Phe
    1190            1195            1200

Lys Leu Thr Gly Ser Cys Ser Tyr Val Leu Phe Gln Asn Lys Glu
    1205            1210            1215

Gln Asp Leu Glu Val Ile Leu His Asn Gly Ala Cys Ser Pro Gly
    1220            1225            1230

Ala Arg Gln Gly Cys Met Lys Ser Ile Glu Val Lys His Ser Ala
    1235            1240            1245

Leu Ser Val Glu Leu His Ser Asp Met Glu Val Thr Val Asn Gly
    1250            1255            1260

Arg Leu Val Ser Val Pro Tyr Val Gly Gly Asn Met Glu Val Asn
    1265            1270            1275

Val Tyr Gly Ala Ile Met His Glu Val Arg Phe Asn His Leu Gly
    1280            1285            1290

His Ile Phe Thr Phe Thr Pro Gln Asn Asn Glu Phe Gln Leu Gln
    1295            1300            1305

Leu Ser Pro Lys Thr Phe Ala Ser Lys Thr Tyr Gly Leu Cys Gly
    1310            1315            1320

Ile Cys Asp Glu Asn Gly Ala Asn Asp Phe Met Leu Arg Asp Gly
    1325            1330            1335
```

FIG. 60Q

```
Thr Val Thr Thr Asp Trp Lys Thr Leu Val Gln Glu Trp Thr Val
    1340            1345            1350

Gln Arg Pro Gly Gln Thr Cys Gln Pro Ile Leu Glu Glu Gln Cys
    1355            1360            1365

Leu Val Pro Asp Ser Ser His Cys Gln Val Leu Leu Leu Pro Leu
    1370            1375            1380

Phe Ala Glu Cys His Lys Val Leu Ala Pro Ala Thr Phe Tyr Ala
    1385            1390            1395

Ile Cys Gln Gln Asp Ser Cys His Gln Glu Gln Val Cys Glu Val
    1400            1405            1410

Ile Ala Ser Tyr Ala His Leu Cys Arg Thr Asn Gly Val Cys Val
    1415            1420            1425

Asp Trp Arg Thr Pro Asp Phe Cys Ala Met Ser Cys Pro Pro Ser
    1430            1435            1440

Leu Val Tyr Asn His Cys Glu His Gly Cys Pro Arg His Cys Asp
    1445            1450            1455

Gly Asn Val Ser Ser Cys Gly Asp His Pro Ser Glu Gly Cys Phe
    1460            1465            1470

Cys Pro Pro Asp Lys Val Met Leu Glu Gly Ser Cys Val Pro Glu
    1475            1480            1485

Glu Ala Cys Thr Gln Cys Ile Gly Glu Asp Gly Val Gln His Gln
    1490            1495            1500

Phe Leu Glu Ala Trp Val Pro Asp His Gln Pro Cys Gln Ile Cys
    1505            1510            1515

Thr Cys Leu Ser Gly Arg Lys Val Asn Cys Thr Thr Gln Pro Cys
    1520            1525            1530

Pro Thr Ala Lys Ala Pro Thr Cys Gly Leu Cys Glu Val Ala Arg
    1535            1540            1545

Leu Arg Gln Asn Ala Asp Gln Cys Cys Pro Glu Tyr Glu Cys Val
    1550            1555            1560

Cys Asp Pro Val Ser Cys Asp Leu Pro Pro Val Pro His Cys Glu
    1565            1570            1575

Arg Gly Leu Gln Pro Thr Leu Thr Asn Pro Gly Glu Cys Arg Pro
    1580            1585            1590

Asn Phe Thr Cys Ala Cys Arg Lys Glu Glu Cys Lys Arg Val Ser
    1595            1600            1605

Pro Pro Ser Cys Pro Pro His Arg Leu Pro Thr Leu Arg Lys Thr
    1610            1615            1620

Gln Cys Cys Asp Glu Tyr Glu Cys Ala Cys Asn Cys Val Asn Ser
    1625            1630            1635
```

FIG. 60R

```
Thr Val Ser Cys Pro Leu Gly Tyr Leu Ala Ser Thr Ala Thr Asn
    1640            1645            1650

Asp Cys Gly Cys Thr Thr Thr Cys Leu Pro Asp Lys Val Cys
    1655            1660            1665

Val His Arg Ser Thr Ile Tyr Pro Val Gly Gln Phe Trp Glu Glu
    1670            1675            1680

Gly Cys Asp Val Cys Thr Cys Thr Asp Met Glu Asp Ala Val Met
    1685            1690            1695

Gly Leu Arg Val Ala Gln Cys Ser Gln Lys Pro Cys Glu Asp Ser
    1700            1705            1710

Cys Arg Ser Gly Phe Thr Tyr Val Leu His Glu Gly Glu Cys Cys
    1715            1720            1725

Gly Arg Cys Leu Pro Ser Ala Cys Glu Val Val Thr Gly Ser Pro
    1730            1735            1740

Arg Gly Asp Ser Gln Ser Ser Trp Lys Ser Val Gly Ser Gln Trp
    1745            1750            1755

Ala Ser Pro Glu Asn Pro Cys Leu Ile Asn Glu Cys Val Arg Val
    1760            1765            1770

Lys Glu Glu Val Phe Ile Gln Gln Arg Asn Val Ser Cys Pro Gln
    1775            1780            1785

Leu Glu Val Pro Val Cys Pro Ser Gly Phe Gln Leu Ser Cys Lys
    1790            1795            1800

Thr Ser Ala Cys Cys Pro Ser Cys Arg Cys Glu Arg Met Glu Ala
    1805            1810            1815

Cys Met Leu Asn Gly Thr Val Ile Gly Pro Gly Lys Thr Val Met
    1820            1825            1830

Ile Asp Val Cys Thr Thr Cys Arg Cys Met Val Gln Val Gly Val
    1835            1840            1845

Ile Ser Gly Phe Lys Leu Glu Cys Arg Lys Thr Thr Cys Asn Pro
    1850            1855            1860

Cys Pro Leu Gly Tyr Lys Glu Glu Asn Asn Thr Gly Glu Cys Cys
    1865            1870            1875

Gly Arg Cys Leu Pro Thr Ala Cys Thr Ile Gln Leu Arg Gly Gly
    1880            1885            1890

Gln Ile Met Thr Leu Lys Arg Asp Glu Thr Leu Gln Asp Gly Cys
    1895            1900            1905

Asp Thr His Phe Cys Lys Val Asn Glu Arg Gly Glu Tyr Phe Trp
    1910            1915            1920

Glu Lys Arg Val Thr Gly Cys Pro Pro Phe Asp Glu His Lys Cys
    1925            1930            1935
```

FIG. 60S

Leu Ala Glu Gly Gly Lys Ile Met Lys Ile Pro Gly Thr Cys Cys
    1940            1945            1950

Asp Thr Cys Glu Glu Pro Glu Cys Asn Asp Ile Thr Ala Arg Leu
    1955            1960            1965

Gln Tyr Val Lys Val Gly Ser Cys Lys Ser Glu Val Glu Val Asp
    1970            1975            1980

Ile His Tyr Cys Gln Gly Lys Cys Ala Ser Lys Ala Met Tyr Ser
    1985            1990            1995

Ile Asp Ile Asn Asp Val Gln Asp Gln Cys Ser Cys Cys Ser Pro
    2000            2005            2010

Thr Arg Thr Glu Pro Met Gln Val Ala Leu His Cys Thr Asn Gly
    2015            2020            2025

Ser Val Val Tyr His Glu Val Leu Asn Ala Met Glu Cys Lys Cys
    2030            2035            2040

Ser Pro Arg Lys Cys Ser Lys
    2045            2050

FIG. 61
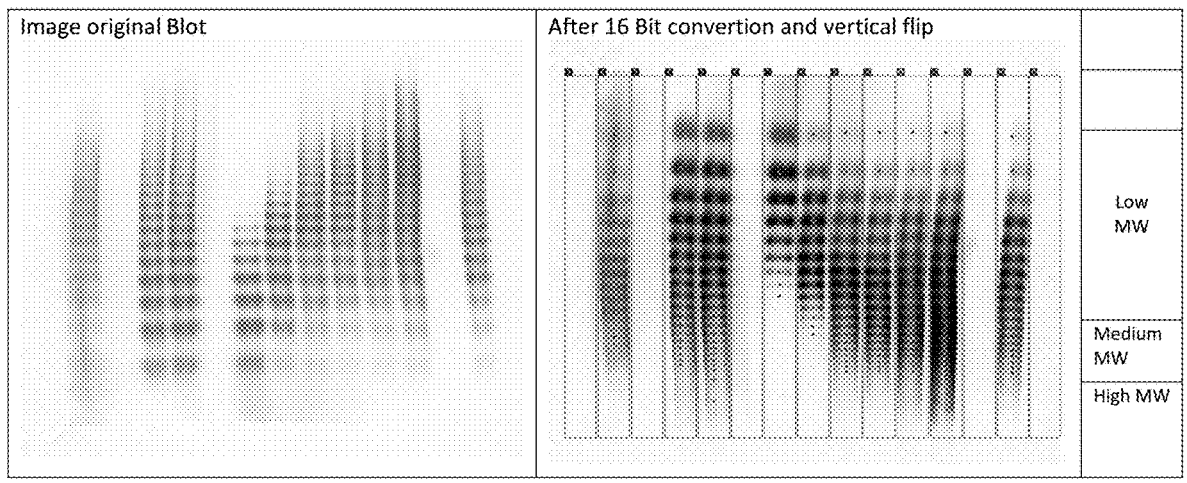
Order of samples per lane
| LANE | SAMPLE | Step | Overlay Lane 11+12 + 14 |
|---|---|---|---|
| 1 | SB | | |
| 2 | Control: Standard Human Plasma Dade Behring | | 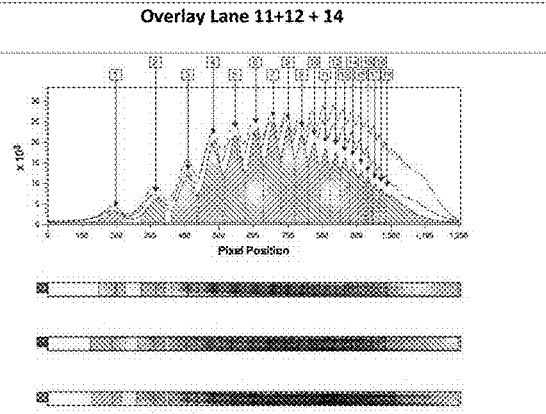 |
| 3 | SB | | |
| 4 | VW_USS_04 L prior SD treatment | | |
| 5 | VW_USS_04 L | | |
| 6 | SB | | |
| 7 | VW_USS_04 FT | | |
| 8 | VW_USS_04 W1 | | |
| 9 | VW_USS_04 W2 | | |
| 10 | VW_USS_04 VE | | |
| 11 | VW_USS_04 E | | |
| 12 | VW_USS_04 NE | | |
| 13 | SB | | |
| 14 | ORVWSEC16070F (530 µg/ml Antigen content) | Pos. Control | |
| 15 | SB | | |

FIG. 62
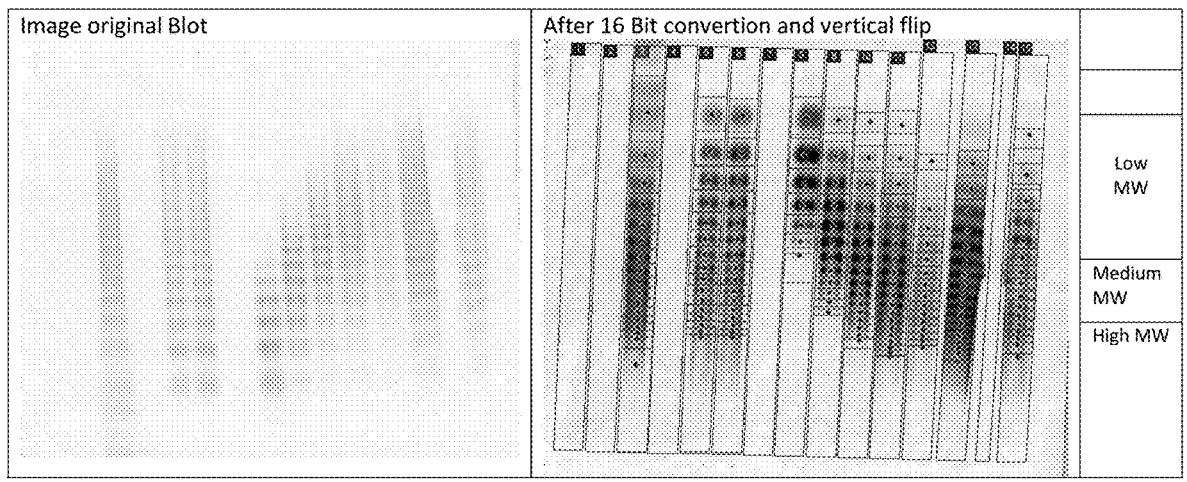
Order of samples per lane
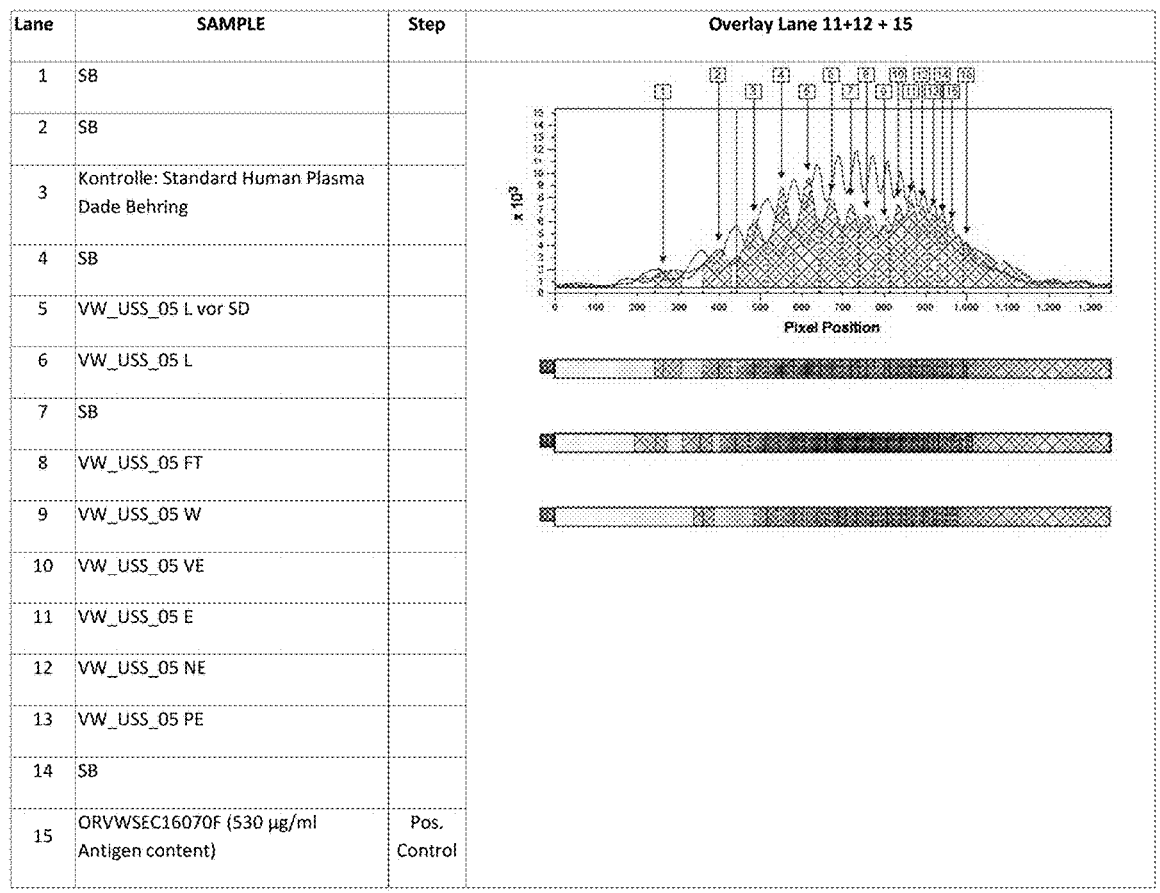
| Lane | SAMPLE | Step |
|---|---|---|
| 1 | SB | |
| 2 | SB | |
| 3 | Kontrolle: Standard Human Plasma Dade Behring | |
| 4 | SB | |
| 5 | VW_USS_05 L vor SD | |
| 6 | VW_USS_05 L | |
| 7 | SB | |
| 8 | VW_USS_05 FT | |
| 9 | VW_USS_05 W | |
| 10 | VW_USS_05 VE | |
| 11 | VW_USS_05 E | |
| 12 | VW_USS_05 NE | |
| 13 | VW_USS_05 PE | |
| 14 | SB | |
| 15 | ORVWSEC16070F (530 µg/ml Antigen content) | Pos. Control |

FIG. 63

RESULTS: EVALUATION

| | | VW_USS_04 E | VW_USS_04 NE | ORVWSEC16070F Positiv control |
|---|---|---|---|---|
| Lane Profiles: | | 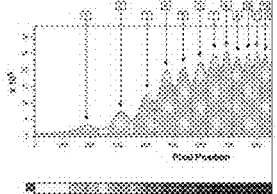 | 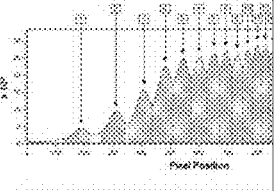 | 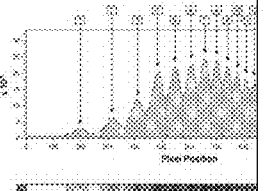 |
| | | Lane 11 | Lane 12 | Lane 14 |
| | | Band % | Band % | Band % |
| SUM Band 1-6 | Low MW | 34,91 | 32,93 | 40,86 |
| SUM Band 7-12 | Medium MW | 39 | 33,81 | 40,27 |
| SUM Band >12 | High MW | 26,08 | 33,24 | 18,87 |

DF3362/023

| | | VW_USS_05 E | VW_USS_05 NE | ORVWSEC16070F Positive control |
|---|---|---|---|---|
| Lane Profiles: | | 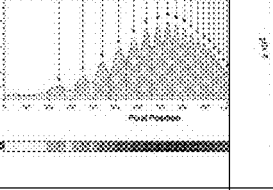 | 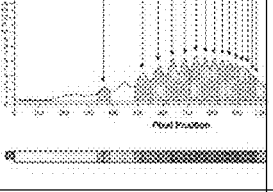 | 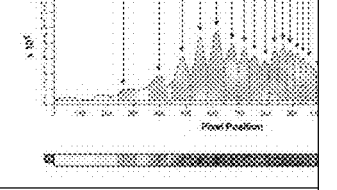 |
| | | Lane 11 | Lane 12 | Lane 15 |
| | | Band % | Band % | Band % |
| SUM Band 1-6 | Low MW | 38,39 | 29,65 | 37,21 |
| SUM Band 7-12 | Medium MW | 36,87 | 36,97 | 29,51 |
| SUM Band >12 | High MW | 24,74 | 33,38 | 33,27 |
| Data of ORVWSEC16070F Positivkontrol are not valid due deformation of the blot (see image on Original Blot and Lane Profile) Remark : Usually lane 15 is not used because the border zone is not easy to handle | | | | |

FIG. 64A

A VWF – FVIII FUSION PROTEIN WHEREIN AN ACTIVE FVIII IS EMBEDDED IN AN VWF MOTIV vWF 764 to 1336 – FVIII heavy chain 24 to 760 – vWF 2218 to 2593 – FVIII light chain 1333 to 2351- vWF 2620 to 2813

Number of amino acid is count from 1 – include signal and or propeptide (Source Uniprot)

VWF 2218 to 2593 is a glycosylation rich part with

2223 N-linked (GlcNAc...) asparagine

2290 N-linked (GlcNAc...) asparagine

2298 O-linked (GalNAc...) threonine

2357 N-linked (GlcNAc...) asparagine

2400 N-linked (GlcNAc...) asparagine

2546 N-linked (GlcNAc...) asparagine

2585 N-linked (GlcNAc...) asparagine

VWF⇨ SEQ ID NO: 4

```
764   770            780            790            800
SLSCRPP     MVKLVCPADN   LRAEGLECTK   TCQNYDLECM
            810         820          830          840          850
SMGCVSGCLC  PPGMVRHENR  CVALERCPCF   HQGKEYAPGE   TVKIGCNTCV
            860         870          880          890          900
CQDRKWNCTD  HVCDATCSTI  GMAHYLTFDG   LKYLFPGECQ   YVLVQDYCGS
            910         920          930          940          950
NPGTFRILVG  NKGCSHPSVK  CKKRVTILVE   GGEIELFDGE   VNVKRPMKDE
            960         970          980          990          1000
THFEVVESGR  YIILLLGKAL  SVVWDRHLSI   SVVLKQTYQE   KVCGLCGNFD
            1010        1020         1030         1040         1050
GIQNNDLTSS  NLQVEEDPVD  FGNSWKVSSQ   CADTRKVPLD   SSPATCHNNI
            1060        1070         1080         1090         1100
MKQTMVDSSC  RILTSDVFQD  CNKLVDPEPY   LDVCIYDTCS   CESIGDCACF
            1110        1120         1130         1140         1150
CDTIAAYAHV  CAQHGKVVTW  RTATLCPQSC   EERNLRENGY   ECEWRYNSCA
            1160        1170         1180         1190         1200
PACQVTCQHP  EPLACPVQCV  EGCHAHCPPG   KILDELLQTC   VDPEDCPVCE
            1210        1220         1230         1240         1250
VAGRRFASGK  KVTLNPSDPE  HCQICHCDVV   NLTCEACQEP   GGLVVPPTDA
            1260        1270         1280         1290         1300
PVSPTTLYVE  DISEPPLHDF  YCSRLLDLVF   LLDGSSRLSE   AEFEVLKAFV
            1310        1320         1330   ⇦vWF1336 FVIII⇨ 24-30 (heavy chain) 40    50
VDMMERLRIS  QKWVRVAVVE  YHDGSHAYIG   LKDRKR       YYLGAVE     LSWDYMQSDL  GELPVDARFP
            60          70           80           90           100
PRVPKSFPFN  TSVVYKKTLF  VEFTDHLFNI   AKPRPPWMGL   LGPTIQAEVY
            110         120          130          140          150
DTVVITLKNM  ASHPVSLHAV  GVSYWKASEG   AEYDDQTSQR   EKEDDKVFPG
            160         170          180          190          200
GSHTYVWQVL  KENGPMASDP  LCLTYSYLSH   VDLVKDLNSG   LIGALLVCRE
            210         220          230          240          250
GSLAKEKTQT  HKFILLFAV   FDEGKSWHSE   TKNSLMQDRD   AASARAWPKM
            260         270          280          290          300
HTVNGYVNRS  LPGLIGCHRK  SVYWHVIGMG   TTPEVHSIFL   EGHTFLVRNH
            310         320          330          340          350
RQASLEISPI  TFLTAQTLLM  DLGQFLLFCH   ISSHQHDGME   AYVKVDSCPE
            360         370          380          390          400
```

FIG. 64B

```
EPQLRMKNNE  EAEDYDDDLT  DSEMDVVRFD  DDNSPSFIQI  RSVAKKHPKT
    410         420         430         440         450
WVHYIAAEEE  DWDYAPLVLA  PDDRSYKSQY  LNNGPQRIGR  KYKKVRFMAY
    460         470         480         490         500
TDETFKTREA  IQHESGILGP  LLYGEVGDTL  LIIFKNQASR  PYNIYPHGIT
    510         520         530         540         550
DVRPLYSRRL  PKGVKHLKDF  PILPGEIFKY  KWTVTVEDGP  TKSDPRCLTR
    560         570         580         590         600
YYSSFVNMER  DLASGLIGPL  LICYKESVDQ  RGNQIMSDKR  NVILFSVFDE
    610         620         630         640         650
NRSWYLTENI  QRFLPNPAGV  QLEDPEFQAS  NIMHSINGYV  FDSLQLSVCL
    660         670         680         690         700
HEVAYWYILS  IGAQTDFLSV  FFSGYTFKHK  MVYEDTLTLF  PFSGETVFMS
    710         720         730         740         750
MENPGLWILG  CHNSDFRNRG  MTALLKVSSC  DKNTGDYYED  SYEDISAYLL
⇐FVIII  760  VWF⇒(2218)  VWF2230     VWF2240     VWF2250
SKNNAIEPRS  RHC  DGNVSSCGDH  PSEGCFCPPD    KVMLEGSCVP
      VWF2260             VWF2270         VWF2280     VWF2290     VWF2300

EEACTQCIGE        DGVQHQFLEA        WVPDHQPCQI  CTCLSGRKVN  CTTQPCPTAK
      VWF2310            VWF2320          VWF2330     VWF2340     VWF2350
APTCGLCEVA        RLRQNADQCC        PEYECVCDPV  SCDLPPVPHC  ERGLQPTLTN
      VWF2360            VWF2370          VWF2380     VWF2390     VWF2400
PGECRPNFTC        ACRKEECKRV        SPPSCPPHRL  PTLRKTQCCD  EYECACNCVN
      VWF2410            VWF2420          VWF2430     VWF2440     VWF2450
STVSCPLGYL        ASTATNDCGC        TTTTCLPDKV  CVHRSTIYPV  GQFWEEGCDV
      VWF2460            VWF2470          VWF2480     VWF2490     VWF2500
CTCTDMEDAV        MGLRVAQCSQ        KPCEDSCRSG  FTYVLHEGEC  CGRCLPSACE
      VWF2510            VWF2520          VWF2530     VWF2540     VWF2550
VVTGSPRGDS        QSSWKSVGSQ        WASPENPCLI  NECVRVKEEV  FIQQRNVSCP
      VWF2560            VWF2570          VWF2580     VWF2590     VWF2593
QLEVPVCPSG        FQLSCKTSAC        CPSCRCERME  ACMLNGTVIG  PGK
  FVIII ⇒(LIGHT CHAIN)
1333    1340        1350
ALKQFRLP    LEETELEKRI
        1360        1370        1380        1390        1400
IVDDTSTQWS  KNMKHLTPST  LTQIDYNEKE  KGAITQSPLS  DCLTRSHSIP
        1410        1420        1430        1440        1450
QANRSPLPIA  KVSSFPSIRP  IYLTRVLFQD  NSSHLPAASY  RKKDSGVQES
        1460        1470        1480        1490        1500
SHFLQGAKKN  NLSLAILTLE  MTGDQREVGS  LGTSATNSVT  YKKVENTVLP
        1510        1520        1530        1540        1550
KPDLPKTSGK  VELLPKVHIY  QKDLFPTETS  NGSPGHLDLV  EGSLLQGTEG
        1560        1570        1580        1590        1600
AIKWNEANRP  GKVPFLRVAT  ESSAKTPSKL  LDPLAWDNHY  GTQIPKEEWK
        1610        1620        1630        1640        1650
SQEKSPEKTA  FKKKDTILSL  NACESNHAIA  AINEGQNKPE  IEVTWAKQGR
        1660        1670        1680        1690        1700
TERLCSQNPP  VLKRHQREIT  RTTLQSDQEE  IDYDDTISVE  MKKEDFDIYD
        1710        1720        1730        1740        1750
EDENQSPRSF  QKKTRHYFIA  AVERLWDYGM  SSSPHVLRNR  AQSGSVPQFK
        1760        1770        1780        1790        1800
KVVFQEFTDG  SFTQPLYRGE  LNEHLGLLGP  YIRAEVEDNI  MVTFRNQASR
```

FIG. 64C

|      |      |      |      |      |
|------|------|------|------|------|
| 1810 | 1820 | 1830 | 1840 | 1850 |
| PYSFYSSLIS | YEEDQRQGAE | PRKNFVKPNE | TKTYFWKVQH | HMAPTKDEFD |
| 1860 | 1870 | 1880 | 1890 | 1900 |
| CKAWAYFSDV | DLEKDVHSGL | IGPLLVCHTN | TLNPAHGRQV | TVQEFALFFT |
| 1910 | 1920 | 1930 | 1940 | 1950 |
| IFDETKSWYF | TENMERNCRA | PCNIQMEDPT | FKENYRFHAI | NGYIMDTLPG |
| 1960 | 1970 | 1980 | 1990 | 2000 |
| LVMAQDQRIR | WYLLSMGSNE | NIHSIHFSGH | VFTVRKKEEY | KMALYNLYPG |
| 2010 | 2020 | 2030 | 2040 | 2050 |
| VFETVEMLPSK | AGIWRVECL | IGEHLHAGMS | TLFLVYSNKC | QTPLGMASGH |
| 2060 | 2070 | 2080 | 2090 | 2100 |
| IRDFQITASG | QYGQWAPKLA | RLHYSGSINA | WSTKEPFSWI | KVDLLAPMII |
| 2110 | 2120 | 2130 | 2140 | 2150 |
| HGIKTQGARQ | KFSSLYISQF | IIMYSLDGKK | WQTYRGNSTG | TLMVFFGNVD |
| 2160 | 2170 | 2180 | 2190 | 2200 |
| SSGIKHNIFN | PPIIARYIRL | HPTHYSIRST | LRMELMGCDL | NSCSMPLGME |
| 2210 | 2220 | 2230 | 2240 | 2250 |
| SKAISDAQIT | ASSYFTNMFA | TWSPSKARLH | LQGRSNAWRP | QVNNPKEWLQ |
| 2260 | 2270 | 2280 | 2290 | 2300 |
| VDFQKTMKVT | GVTTQGVKSL | LTSMYVKEFL | ISSSQDGHQW | TLFFQNGKVK |
| 2310 | 2320 | 2330 | 2340 | 2350 |
| VFQGNQDSFT | PVVNSLDPPL | LTRYLRIHPQ | SWVHQIALRM | EVLGCEAQDL |

2351 ⇐FVIII  VWF⇒2620

|      |      |      |      |      |
|------|------|------|------|------|
| Y    |      | R    | KTTCNPCPLG | YKEENNTGEC | CGRCLPTACT |
| 2660 | 2670 | 2680 | 2690 | 2700 |
| IQLRGGQIMT | LKRDETLQDG | CDTHFCKVNE | RGEYFWEKRV | TGCPPFDEHK |
| 2710 | 2720 | 2730 | 2740 | 2750 |
| CLAEGGKIMK | IPGTCCDTCE | EPECNDITAR | LQYVKVGSCK | SEVEVDIHYC |
| 2760 | 2770 | 2780 | 2790 | 2800 |
| QGKCASKAMY | SIDINDVQDQ | CSCCSPTRTE | PMQVALHCTN | GSVVYHEVLN |
| 2810 |      |      |      |      |
| AMECKCSPRK | CSK |      |      |      |

FIG. 65A

A VWF-FVIII FUSION PROTEIN WHEREIN THE N-GLYCOSYLATION RICH DOMAIN REPLACES THE FVIII-B-DOMAIN

FVIII heavy chain 19 to 760 – vWF 2218 to 2593 – FVIII light chain 1333 to 2351

REMARK 1-19 SIGNAL PEPTIDE SEQ ID NO: 5

```
              10         20         30         40         50
       MQIELSTCFF LCLLRFCFS A TRRYYLGAVE LSWDYMQSDL GELPVDARFP
              60         70         80         90        100
       PRVPKSFPFN TSVVYKKTLF VEFTDHLFNI AKPRPPWMGL LGPTIQAEVY
             110        120        130        140        150
       DTVVITLKNM ASHPVSLHAV GVSYWKASEG AEYDDQTSQR EKEDDKVFPG
             160        170        180        190        200
       GSHTYVWQVL KENGPMASDP LCLTYSYLSH VDLVKDLNSG LIGALLVCRE
             210        220        230        240        250
       GSLAKEKTQT HKFILLFAV  FDEGKSWHSE TKNSLMQDRD AASARAWPKM
             260        270        280        290        300
       HTVNGYVNRS LPGLIGCHRK SVYWHVIGMG TTPEVHSIFL EGHTFLVRNH
             310        320        330        340        350
       RQASLEISPI TFLTAQTLLM DLGQFLLFCH ISSHQHDGME AYVKVDSCPE
             360        370        380        390        400
       EPQLRMKNNE EAEDYDDDLT DSEMDVVRFD DDNSPSFIQI RSVAKKHPKT
             410        420        430        440        450
       WVHYIAAEEE DWDYAPLVLA PDDRSYKSQY LNNGPQRIGR KYKKVRFMAY
             460        470        480        490        500
       TDETFKTREA IQHESGILGP LLYGEVGDTL LIIFKNQASR PYNIYPHGIT
             510        520        530        540        550
       DVRPLYSRRL PKGVKHLKDF PILPGEIFKY KWTVTVEDGP TKSDPRCLTR
             560        570        580        590        600
       YYSSFVNMER DLASGLIGPL LICYKESVDQ RGNQIMSDKR NVILFSVFDE
             610        620        630        640        650
       NRSWYLTENI QRFLPNPAGV QLEDPEFQAS NIMHSINGYV FDSLQLSVCL
             660        670        680        690        700
       HEVAYWYILS IGAQTDFLSV FFSGYTFKHK MVYEDTLTLF PFSGETVFMS
             710        720        730        740        750
       MENPGLWILG CHNSDFRNRG MTALLKVSSC DKNTGDYYED SYEDISAYLL
       ⇐FVIII 760  VWF⇒(2218) VWF2230    VWF2240          VWF2250
       SKNNAIEPRS RHC DGNVSSCGDH PSEGCFCPPD     KVMLEGSCVP
          VWF2260           VWF2270          VWF2280    VWF2290    VWF2300
```

FIG. 65B

| | | | | |
|---|---|---|---|---|
| EEACTQCIGE | DGVQHQFLEA | WVPDHQPCQI | CTCLSGRKVN | CTTQPCPTAK |
| VWF2310 | VWF2320 | VWF2330 | VWF2340 | VWF2350 |
| APTCGLCEVA | RLRQNADQCC | PEYECVCDPV | SCDLPPVPHC | ERGLQPTLTN |
| VWF2360 | VWF2370 | VWF2380 | VWF2390 | VWF2400 |
| PGECRPNFTC | ACRKEECKRV | SPPSCPPHRL | PTLRKTQCCD | EYECACNCVN |
| VWF2410 | VWF2420 | VWF2430 | VWF2440 | VWF2450 |
| STVSCPLGYL | ASTATNDCGC | TTTTCLPDKV | CVHRSTIYPV | GQFWEEGCDV |
| VWF2460 | VWF2470 | VWF2480 | VWF2490 | VWF2500 |
| CTCTDMEDAV | MGLRVAQCSQ | KPCEDSCRSG | FTYVLHEGEC | CGRCLPSACE |
| VWF2510 | VWF2520 | VWF2530 | VWF2540 | VWF2550 |
| VVTGSPRGDS | QSSWKSVGSQ | WASPENPCLI | NECVRVKEEV | FIQQRNVSCP |
| VWF2560 | VWF2570 | VWF2580 | VWF2590 | |
| VWF2593⇐VWF | | | | |

QLEVPVCPSG    FQLSCKTSAC    CPSCRCERME  ACMLNGTVIG   PGK

FVIII ⇒

1333    1340        1350
ALKQFRLP   LEETELEKRI
         1360        1370        1380        1390        1400
IVDDTSTQWS  KNMKHLTPST  LTQIDYNEKE  KGAITQSPLS  DCLTRSHSIP
         1410        1420        1430        1440        1450
QANRSPLPIA  KVSSFPSIRP  IYLTRVLFQD  NSSHLPAASY  RKKDSGVQES
         1460        1470        1480        1490        1500
SHFLQGAKKN  NLSLAILTLE  MTGDQREVGS  LGTSATNSVT  YKKVENTVLP
         1510        1520        1530        1540        1550
KPDLPKTSGK  VELLPKVHIY  QKDLFPTETS  NGSPGHLDLV  EGSLLQGTEG
         1560        1570        1580        1590        1600
AIKWNEANRP  GKVPFLRVAT  ESSAKTPSKL  LDPLAWDNHY  GTQIPKEEWK
         1610        1620        1630        1640        1650
SQEKSPEKTA  FKKKDTILSL  NACESNHAIA  AINEGQNKPE  IEVTWAKQGR
         1660        1670        1680        1690        1700
TERLCSQNPP  VLKRHQREIT  RTTLQSDQEE  IDYDDTISVE  MKKEDFDIYD
         1710        1720        1730        1740        1750
EDENQSPRSF  QKKTRHYFIA  AVERLWDYGM  SSSPHVLRNR  AQSGSVPQFK
         1760        1770        1780        1790        1800
KVVFQEFTDG  SFTQPLYRGE  LNEHLGLLGP  YIRAEVEDNI  MVTFRNQASR
         1810        1820        1830        1840        1850
PYSFYSSLIS  YEEDQRQGAE  PRKNFVKPNE  TKTYFWKVQH  HMAPTKDEFD
         1860        1870        1880        1890        1900
CKAWAYFSDV  DLEKDVHSGL  IGPLLVCHTN  TLNPAHGRQV  TVQEFALFFT
         1910        1920        1930        1940        1950
IFDETKSWYF  TENMERNCRA  PCNIQMEDPT  FKENYRFHAI  NGYIMDTLPG
         1960        1970        1980        1990        2000
LVMAQDQRIR  WYLLSMGSNE  NIHSIHFSGH  VFTVRKKEEY  KMALYNLYPG

FIG. 65C

|      | 2010       | 2020       | 2030       | 2040       | 2050       |
|------|------------|------------|------------|------------|------------|
|      | VFETVEMLPSK | AGIWRVECL  | IGEHLHAGMS | TLFLVYSNKC | QTPLGMASGH |
|      | 2060       | 2070       | 2080       | 2090       | 2100       |
|      | IRDFQITASG | QYGQWAPKLA | RLHYSGSINA | WSTKEPFSWI | KVDLLAPMII |
|      | 2110       | 2120       | 2130       | 2140       | 2150       |
|      | HGIKTQGARQ | KFSSLYISQF | IIMYSLDGKK | WQTYRGNSTG | TLMVFFGNVD |
|      | 2160       | 2170       | 2180       | 2190       | 2200       |
|      | SSGIKHNIFN | PPIIARYIRL | HPTHYSIRST | LRMELMGCDL | NSCSMPLGME |
|      | 2210       | 2220       | 2230       | 2240       | 2250       |
|      | SKAISDAQIT | ASSYFTNMFA | TWSPSKARLH | LQGRSNAWRP | QVNNPKEWLQ |
|      | 2260       | 2270       | 2280       | 2290       | 2300       |
|      | VDFQKTMKVT | GVTTQGVKSL | LTSMYVKEFL | ISSSQDGHQW | TLFFQNGKVK |
|      | 2310       | 2320       | 2330       | 2340       | 2350       |
|      | VFQGNQDSFT | PVVNSLDPPL | LTRYLRIHPQ | SWVHQIALRM | EVLGCEAQDL |

2351 ⇐FVIII
Y

FIG. 66

| Nr: | Composition | pH | Purpose / Remark |
|---|---|---|---|
| 1. | 50mM NaCitrate | 7.6 ±0.2 | Dilution buffer |
| 2. | 30mM Na-Citrat, 180mM NaCl | 7.5 ±0.2 | Equilibration and wash buffer for r-vWF-Propeptide depletion |
| 3. | 30mM Na-Citrat, 180mM NaCl + SD_VI On column 25g/kg 10.0g Polysorbate 80 3.5g DMSO 3.5g TnBP | 7.5 ±0.2 | WSD_Buffer Potential buffer for inactivation of lipid enveloped viruses on column/on resin |
| 4. | 50mM Glycine 10mM Taurine 10% Sucrose 0.1% Polysorbate 80 | 5.5 ±0.2 | Buffer exchange equilibration buffer |
| 5. | 50mM Glycine 10mM Taurine 5% (w/w)Sucrose 5%(w/w) D-Mannitol 0.1% Polysorbate 80 2mM CaCl2 150mM NaCl | 7.4 ±0.2 | Pre_formulation_Buffer + FVIII Con buffer (addition) |
| 6. | 50mM Glycine 10mM Taurine 5% (w/w)Sucrose 5%(w/w) D-Mannitol 0.1% Polysorbate 80 2mM CaCl2 600mM NaCl | 7.4 ±0.2 | Elution buffer |
| 7. | 50mM Glycine 10mM Taurine 5% (w/w)Sucrose 5%(w/w) D-Mannitol 0.1% Polysorbate 80 2mM CaCl2 | 7.4 ±0.2 | Formulation Adjustment buffer |

FIG. 68

| Step | Amount | vWF:AG [µg/ml] | Total vWF Antigen [µg] | % vWF Antigen | FVIII:C [U/ml] | Total FVIII:C [U] | % FVIII:C |
|---|---|---|---|---|---|---|---|
| LOAD | 231.64 | 55.2 | 12786.5 | 100.0% | <0.2 | <46.33 | - |
| FT / WASH 1 | 248.95 | 19.5 | 4854.5 | 38.0% | <0.2 | <49.79 | - |
| Elution | 28.88 | 80.5 | 2324.84 | 18.2% | 34.28 | 990.01 | 100.0% |
| BDS | 119.23 | 20.2 | 2408.44 | 18.8% | 8.14 | 970.53 | 98.0% |

| Step | Amount | vWF-PP [µg/ml] | Total vWF Propeptide [µg] | % vWF Propeptide | CHO HCP [ng/ml] | Total CHO-HCP [µg] | % CHO-HCP |
|---|---|---|---|---|---|---|---|
| LOAD | 231.64 | 16.44 | 3807.74 | 100.0% | 930 | 215.43 | 100.0% |
| FT / WASH 1 | 248.95 | 9.18 | 2284.41 | 60.0% | 711 | 177.00 | 82.2% |
| Elution | 28.88 | 0.089 | 2.59 | 0.07% | 40 | 1.10 | 0.5% |
| BDS | 119.23 | 0.014 | 2.88 | 0.08% | <30 | <1 | <0.5% |

| Step | Amount | RiCoF [U/ml] | Total RiCoF [U] | % RiCoF | Ratio RiCoF/mg vWF:AG | Ratio FVIII:C/mg vWF:AG |
|---|---|---|---|---|---|---|
| LOAD | 231.64 | 4.38 | 1014.58 | 100.0% | 43.80 | <3.6U/mg |
| FT / WASH 1 | 248.95 | 0.23 | 57.26 | 5.6% | 11.79 | <10.3U/mg |
| Elution | 28.88 | 7.37 | 212.85 | 21.0% | 91.55 | 425.8U/mg |
| BDS | 119.23 | 1.77 | 211.04 | 20.8% | 87.62 | 403.0U/mg |

FIG. 70

| Nr: | Composition | pH | Purpose / Remark |
|---|---|---|---|
| 1. | 60mM NaCitrate | 7.6 ±0.2 | Dilution buffer |
| 2. | 30mM Na-Citrat 180mM NaCl | 7.5 ±0.2 | Equilibration and wash buffer for r-vWF-Propeptide depletion |
| 3. | 11mg CMP_NANA C8271-25mg Lot.Nr.: SLBV 7777 dissolved in 154.29g 30mM Na-Citrat, 180mM NaCl | 7.5 ±0.2 | Cytidine-5′-monophospho-N-acetylneuraminic acid sodium salt Reagent A |
| 4. | 0.5U alpha 2,6 Sialyltransferase in 30mM Na-Citrat, 180mM NaCl | 7.5 ±0.2 | alpha 2,6 Sialyltransferase Reagent B |
| 5. | 50mM HEPES 150mM NaCl | 6.0 ±0.2 | Pre_elution_ buffer |
| 6. | 50mM HEPES 500mM NaCl | 7.5 ±0.2 | Elution_ buffer |

FIG. 72

| YIELD | | | | | | | |
|---|---|---|---|---|---|---|---|
| Step | Amount | vWF-Ag [µg/ml] | Total vWF Antigen [µg] | % vWF Antigen | vWF-PP [µg/ml] | Total vWF Propeptide [µg] | % vWF Propeptide |
| LOAD | 226.02 | 50.6 | 11437 | 100% | 13.96 | 3156.14 | 100% |
| E | 34.84 | 46.4 | 1617 | 14.1% | <0.006 | <217.75 | <0.01% |

YIELD SIALYLATION

| STEP | Amount | 2,3 Sialylation | 2,6 Sialylation |
|---|---|---|---|
| LOAD | 226.02 | x | x |
| E | 34.84 | x | x |

FIG. 74

| Nr: | Composition | pH | Purpose / Remark |
|---|---|---|---|
| 1. | 60mM NaCitrate | 7.6 ±0.2 | Dilution buffer |
| 2. | 30mM Na-Citrat 180mM NaCl | 7.5 ±0.2 | Equilibration and wash buffer for r-vWF-Propeptide depletion |
| 3. | 14mg CMP_NANA C8271-25mg Lot Nr : SLBV 7777 dissolved in 121.57g 30mM Na-Citrat, 180mM NaCl | 7.5 ±0.2 | Cytidine-5'-monophospho-N-acetylneuraminic acid sodium salt Reagent A |
| 4. | 1.0U alpha 2,6 Sialyltransferase in 121.10g 30mM Na-Citrat, 180mM NaCl | 7.5 ±0.2 | alpha 2,6 Sialyltransferase Reagent B |
| 5. | 50mM HEPES 150mM NaCl | 6.0 ±0.2 | Pre_elution_ buffer |
| 6. | 50mM HEPES 500mM NaCl | 7.5 ±0.2 | Elution_ buffer |

FIG. 76

| YIELD | | | | | | | |
|---|---|---|---|---|---|---|---|
| Step | Amount | vWF:AG (IU/ml) | Total vWF Antigen (IU) | % vWF Antigen | vWF PP (IU/ml) | Total vWF Propeptide (IU) | % vWF Propeptide |
| LOAD | 312.15 | 57.40 | 17917.41 | 100% | 13.96 | 3156.14 | 100% |
| E | 56.85 | 1.70 | 96.65 | 0.5% | <0.086 | <217.75 | <0.01% |

YIELD SIALYLATION

| STEP | Amount | 2,3 Sialylation | 2,6 Sialylation |
|---|---|---|---|
| LOAD | 312.15 | x | x |
| E | 56.85 | x | x |

FIG. 78
Run Nr. VW_USS_08
Emf-File
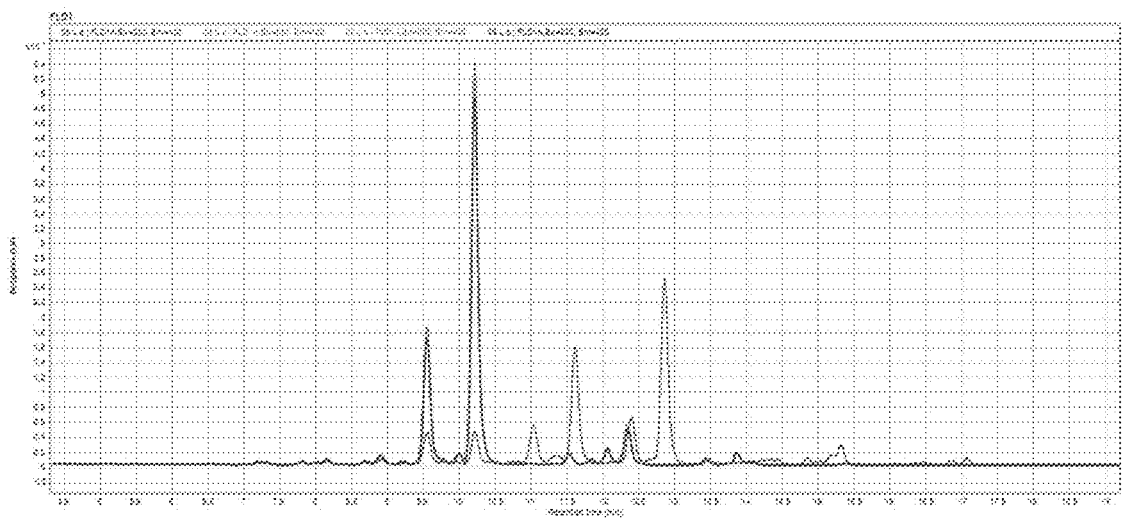
Run Nr. VW_USS_06
Emf-File
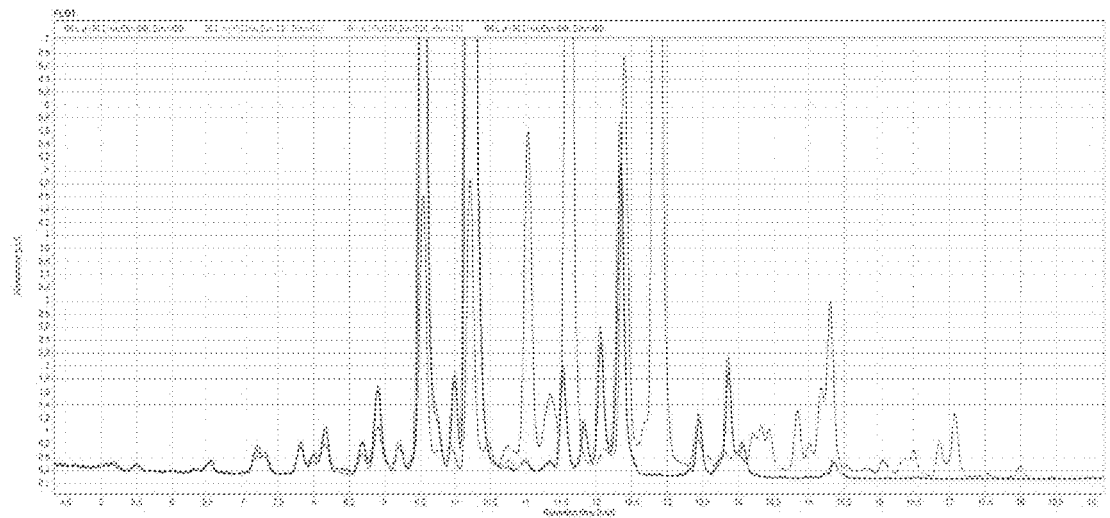

SEQUENCE LISTING

<160> NUMBER OF SEQ ID NOS: 5

<210> SEQ ID NO 1
<211> LENGTH: 8833
<212> TYPE: DNA
<213> ORGANISM: Artificial Sequence
<220> FEATURE:
<223> OTHER INFORMATION: VWF nucleic acid

<400> SEQUENCE: 1

```
agctcacagc tattgtggtg ggaaagggag ggtggttggt ggatgtcaca gcttgggctt        60
tatctccccc agcagtgggg actccacagc ccctgggcta cataacagca agacagtccg       120
gagctgtagc agacctgatt gagcctttgc agcagctgag agcatggcct agggtgggcg       180
gcaccattgt ccagcagctg agtttcccag ggaccttgga gatagccgca gccctcattt       240 gcagggaag atgattcctg ccagatttgc cggggtgctg cttgctctgg ccctcatttt        300
gccagggacc ctttgtgcag aaggaactcg cggcaggtca tccacggccc gatgcagcct       360
tttcggaagt gacttcgtca acacctttga tgggagcatg tacagctttg cgggatactg       420
cagttacctc ctggcagggg gctgccagaa acgctccttc tcgattattg gggacttcca       480
gaatggcaag agagtgagcc tctccgtgta tcttggggaa ttttttgaca tccatttgtt       540
tgtcaatggt accgtgacac aggggggacca aagagtctcc atgccctatg cctccaaagg      600
gctgtatcta gaaactgagg ctgggtacta caagctgtcc ggtgaggcct atggctttgt       660
ggccaggatc gatggcagcg gcaacttcca agtcctgctg tcagacagat acttcaacaa       720
gacctgcggg ctgtgtggca ctttaacat ctttgctgaa gatgactta tgacccaaga         780 agggaccttg acctcggacc cttatgactt tgccaactca tgggctctga gcagtggaga       840
acagtggtgt gaacgggcat ctcctcccag cagctcatgc aacatctcct ctggggaaat       900
gcagaagggc ctgtgggagc agtgccagct tctgaagagc acctcggtgt ttgcccgctg       960 ccacccctctg gtggacccg agcctttgt ggccctgtgt gagaagactt tgtgtgagtg        1020 tgctggggg ctggagtgcg cctgccctgc cctcctggag tacgcccgga cctgtgccca       1080
ggagggaatg gtgctgtacg gctggaccga ccacagcgcg tgcagcccag tgtgccctgc      1140
tggtatggag tataggcagt gtgtgtcccc ttgcgccagg acctgccaga gcctgcacat      1200
caatgaaatg tgtcaggagc gatgcgtgga tggctgcagc tgccctgagg gacagctcct      1260
ggatgaaggc ctctgcgtgg agagcaccga gtgtccctgc gtgcattccg gaaagcgcta      1320
ccctcccggc acctccctct ctcgagactg caacacctgc atttgccgaa acagccagtg     1380
gatctgcagc aatgaagaat gtccagggga gtgccttgtc acaggtcaat cacacttcaa     1440
gagctttgac aacagatact tcaccttcag tgggatctgc cagtacctgc tggcccggga     1500
```

```
ttgccaggac cactccttct ccattgtcat tgagactgtc cagtgtgctg atgaccgcga   1560
cgctgtgtgc acccgctccg tcaccgtccg gctgcctggc ctgcacaaca gccttgtgaa   1620
actgaagcat ggggcaggag ttgccatgga tggccaggac gtccagctcc ccctcctgaa   1680
aggtgacctc cgcatccagc atacagtgac ggcctccgtg cgcctcagct acggggagga   1740
cctgcagatg gactgggatg gccgcgggag gctgctggtg aagctgtccc ccgtctatgc   1800
cgggaagacc tgcggcctgt gtgggaatta caatggcaac cagggcgacg acttccttac   1860
cccctctggg ctggcggagc cccgggtgga ggacttcggg aacgcctgga agctgcacgg   1920
ggactgccag gacctgcaga agcagcacag cgatccctgc gccctcaacc cgcgcatgac   1980
caggttctcc gaggaggcgt gcgcggtcct gacgtccccc acattcgagg cctgccatcg   2040
tgccgtcagc ccgctgccct acctgcggaa ctgccgctac gacgtgtgct cctgctcgga   2100
cggccgcgag tgcctgtgcg gcgccctggc cagctatgcc gcggcctgcg cggggagagg   2160
cgtgcgcgtc gcgtggcgcg agccaggccg ctgtgagctg aactgccgcga aaggccaggt   2220
gtacctgcag tgcgggaccc cctgcaacct gacctgccgc tctctctctt acccggatga   2280
ggaatgcaat gaggcctgcc tggagggctg cttctgcccc ccagggctct acatggatga   2340
gagggggggac tgcgtgccca aggcccagtg cccctgttac tatgacggtg agatcttcca   2400
gccagaagac atcttctcag accatcacac catgtgctac tgtgaggatg gcttcatgca   2460
ctgtaccatg agtggagtcc ccggaagctt gctgcctgac gctgtcctca gcagtccct   2520
gtctcatcgc agcaaaagga gcctatcctg tcggcccccc atggtcaagc tggtgtgtcc   2580
cgctgacaac ctgcgggctg aagggctcga gtgtaccaaa acgtgccaga actatgacct   2640
ggagtgcatg agcatgggct gtgtctctgg ctgcctctgc cccccgggca tggtccggca   2700
tgagaacaga tgtgtggccc tggaaaggtg tccctgcttc catcagggca aggagtatgc   2760
ccctggagaa acagtgaaga ttggctgcaa cacttgtgtc tgtcgggacc ggaagtggaa   2820
ctgcacagac catgtgtgtg atgccacgtg ctccacgatc ggcatggccc actacctcac   2880
cttcgacggg ctcaaatacc tgttccccgg ggagtgccag tacgttctgg tgcaggatta   2940
ctgcggcagt aaccctggga cctttcggat cctagtgggg aataagggat gcagccaccc   3000
ctcagtgaaa tgcaagaaac gggtcaccat cctggtggag ggaggagaga ttgagctgtt   3060
tgacggggag gtgaatgtga agaggcccat gaaggatgag actcactttg aggtggtgga   3120
gtctggccgg tacatcattc tgctgctggg caaagccctc tccgtggtct gggaccgcca   3180
cctgagcatc tccgtggtcc tgaagcagac ataccaggag aaagtgtgtg gcctgtgtgg   3240
gaattttgat ggcatccaga caatgacct caccagcagc aacctccaag tggaggaaga   3300
ccctgtggac tttgggaact cctggaaagt gagctcgcag tgtgctgaca ccagaaaagt   3360
gcctctggac tcatcccctg ccacctgcca taacaacatc atgaagcaga cgatggtgga   3420
ttcctcctgt agaatcctta ccagtgacgt cttccaggac tgcaacaagc tggtggaccc   3480
cgagccatat ctggatgtct gcatttacga cacctgctcc tgtgagtcca ttggggactg   3540
cgcctgcttc tgcgacacca ttgctgccta tgcccacgtg tgtgcccagc atggcaaggt   3600
ggtgacctgg aggacggcca cattgtgccc ccagagctgc gaggagagga atctccggga   3660
gaacgggtat gagtgtgagt ggcgctataa cagctgtgca cctgcctgtc aagtcacgtg   3720
tcagcaccct gagccactgg cctgccctgt gcagtgtgtg gagggctgcc atgcccactg   3780
ccctccaggg aaaatcctgg atgagctttt gcagacctgc gttgaccctg aagactgtcc   3840
agtgtgtgag gtggctggcc ggcgttttgc ctcaggaaag aaagtcacct tgaatcccag   3900
```

-continued

```
tgaccctgag cactgccaga tttgccactg tgatgttgtc aacctcacct gtgaagcctg    3960
ccaggagccg ggaggcctgg tggtgcctcc cacagatgcc ccggtgagcc ccaccactct    4020
gtatgtggag gacatctcgg aaccgccgtt gcacgatttc tactgcagca ggctactgga    4080
cctggtcttc ctgctggatg gctcctccag gctgtccgag gctgagtttg aagtgctgaa    4140
ggcctttgtg gtggacatga tggagcggct gcgcatctcc cagaagtggg tccgcgtggc    4200
cgtggtggag taccacgacg gctcccacgc ctacatcggg ctcaaggacc ggaagcgacc    4260
gtcagagctg cggcgcattg ccagccaggt gaagtatgcg ggcagccagg tggcctccac    4320
cagcgaggtc ttgaaataca cactgttcca aatcttcagc aagatcgacc ccctgaagc    4380 ctcccgcatc accctgctcc tgatggccag ccaggagccc aacggatgt cccggaactt    4440 tgtccgctac gtccagggcc tgaagaagaa gaaggtcatt gtgatcccgg tgggcattgg    4500
gccccatgcc aacctcaagc agatccgcct catcgagaag caggcccctg agaacaaggc    4560
cttcgtgctg agcagtgtgg atgagctgga gcagcaaagg gacgagatcg ttagctacct    4620
ctgtgacctt gcccctgaag cccctcctcc tactctgccc ccgacatgg cacaagtcac    4680 tgtgggcccg gggctcttgg gggtttcgac cctggggccc aagaggaact ccatggttct    4740
ggatgtggcg ttcgtcctgg aaggatcgga caaaattggt gaagccgact tcaacaggag    4800
caaggagttc atggaggagg tgattcagcg gatggatgtg ggccaggaca gcatccacgt    4860
cacggtgctg cagtactcct acatggtgac tgtggagtac cccttcagcg aggcacagtc    4920
caaaggggac atcctgcagc gggtgcgaga gatccgctac cagggcggca acaggaccaa    4980
cactgggctg gccctgcggt acctctctga ccacagcttc ttggtcagcc agggtgaccg    5040
ggagcaggcg cccaacctgg tctacatggt caccggaaat cctgcctctg atgagatcaa    5100
gaggctgcct ggagacatcc aggtggtgcc cattggagtg ggcccaatg ccaacgtgca    5160 ggagctggag aggattggct ggcccaatgc ccctatcctc atccaggact ttgagacgct    5220
cccccgagag gctcctgacc tggtgctgca gaggtgctgc tccggagagg ggctgcagat    5280
ccccaccctc tcccctgcac ctgactgcag ccagcccctg acgtgatcc ttctcctgga    5340 tggctcctcc agtttcccag cttcttattt tgatgaaatg aagagtttcg ccaaggcttt    5400
catttcaaaa gccaatatag ggcctcgtct cactcaggtg tcagtgctgc agtatggaag    5460
catcaccacc attgacgtgc catggaacgt ggtcccggag aaagcccatt tgctgagcct    5520
tgtggacgtc atgcagcggg agggaggccc cagccaaatc ggggatgcct tgggctttgc    5580
tgtgcgatac ttgacttcag aaatgcatgg tgccaggccg ggagcctcaa aggcggtggt    5640
catcctggtc acggacgtct ctgtggattc agtggatgca gcagctgatg ccgccaggtc    5700
caacagagtg acagtgttcc ctattggaat tggagatcgc tacgatgcag cccagctacg    5760
gatcttggca ggcccagcag gcgactccaa cgtggtgaag ctccagcgaa tcgaagacct    5820
ccctaccatg gtcaccttgg gcaattcctt cctccacaaa ctgtgctctg atttgttag    5880 gatttgcatg gatgaggatg ggaatgagaa gaggcccggg gacgtctgga ccttgccaga    5940
ccagtgccac accgtgactt gccagccaga tggccagacc ttgctgaaga gtcatcgggt    6000
caactgtgac cgggggctga ggccttcgtg ccctaacagc cagtcccctg ttaaagtgga    6060
agagacctgt ggctgccgct ggacctgccc ctgcgtgtgc acaggcagct ccactcggca    6120
catcgtgacc tttgatgggc agaatttcaa gctgactggc agctgttctt atgtcctatt    6180
tcaaaacaag gagcaggacc tggaggtgat tctccataat ggtgcctgca gccctggagc    6240
```

-continued

```
aaggcagggc tgcatgaaat ccatcgaggt gaagcacagt gccctctccg tcgagctgca    6300
cagtgacatg gaggtgacgg tgaatgggag actggtctct gttccttacg tgggtgggaa    6360
catggaagtc aacgtttatg gtgccatcat gcatgaggtc agattcaatc accttggtca    6420
catcttcaca ttcactccac aaaacaatga gttccaactg cagctcagcc caagactttt    6480
tgcttcaaag acgtatggtc tgtgtgggat ctgtgatgag aacggagcca atgacttcat    6540
gctgagggat ggcacagtca ccacagactg gaaaacactt gttcaggaat ggactgtgca    6600
gcggccaggg cagacgtgcc agcccatcct ggaggagcag tgtcttgtcc ccgacagctc    6660
ccactgccag gtcctcctct taccactgtt tgctgaatgc acaaggtcc tggctccagc     6720
cacattctat gccatctgcc agcaggacag ttgccaccag gagcaagtgt gtgaggtgat    6780
cgcctcttat gccccacctct gtcggaccaa cggggtctgc gttgactgga ggacacctga   6840
tttctgtgct atgtcatgcc caccatctct ggtctacaac cactgtgagc atggctgtcc    6900
ccggcactgt gatggcaacg tgagctcctg tggggaccat ccctccgaag gctgtttctg    6960
ccctccagat aaagtcatgt tggaaggcag ctgtgtccct gaagaggcct gcactcagtg    7020
cattggtgag gatggagtcc agcaccagtt cctggaagcc tgggtcccgg accaccagcc    7080
ctgtcagatc tgcacatgcc tcagcgggcg aaggtcaac tgcacaacgc agccctgccc     7140
cacggccaaa gctcccacgt gtggcctgtg tgaagtagcc cgcctccgcc agaatgcaga    7200
ccagtgctgc cccgagtatg agtgtgtgtg tgacccagtg agctgtgacc tgcccccagt    7260
gcctcactgt gaacgtggcc tccagcccac actgaccaac cctggcgagt gcagacccaa    7320
cttcacctgc gcctgcagga aggaggagtg caaaagagtg tccccaccct cctgcccccc    7380
gcaccgtttg cccaccccttc ggaagaccca gtgctgtgat gagtatgagt gtgcctgcaa   7440
ctgtgtcaac tccacagtga gctgtcccct tgggtacttg gcctcaactg ccaccaatga    7500
ctgtggctgt accacaacca cctgccttcc cgacaaggtg tgtgtccacc gaagcaccat    7560
ctaccctgtg ggccagttct gggaggaggg ctgcgatgtg tgcacctgca ccgacatgga    7620
ggatgccgtg atgggcctcc gcgtggccca gtgctcccag aagccctgtg aggacagctg    7680
tcggtcgggc ttcacttacg ttctgcatga aggcgagtgc tgtggaaggt gcctgccatc    7740
tgcctgtgag gtggtgactg gctcaccgcg ggggactcc cagtcttcct ggaagagtgt     7800
cggctcccag tgggcctccc cggagaaccc ctgcctcatc aatgagtgtg tccgagtgaa    7860
ggaggaggtc tttatacaac aaaggaacgt ctcctgcccc cagctggagg tccctgtctg    7920
cccctcgggc tttcagctga gctgtaagac ctcagcgtgc tgcccaagct gtcgctgtga    7980
gcgcatggag gcctgcatgc tcaatggcac tgtcattggg cccgggaaga ctgtgatgat    8040
cgatgtgtgc acgacctgcc gctgcatggt gcaggtgggg gtcatctctg gattcaagct    8100
ggagtgcagg aagaccacct gcaacccctg cccctgggt tacaaggaag aaaataacac     8160
aggtgaatgt tgtgggagat gtttgcctac ggcttgcacc attcagctaa ggaggggaca   8220
gatcatgaca ctgaagcgtg atgagacgct ccaggatggc tgtgatactc acttctgcaa    8280
ggtcaatgag agaggagagt acttctggga gaagagggtc acaggctgcc caccctttga    8340
tgaacacaag tgtctggctg agggaggtaa aattatgaaa attccaggca cctgctgtga    8400
cacatgtgag gagcctgagt gcaacgacat cactgccagg ctgcagtatg tcaaggtggg    8460
aagctgtaag tctgaagtag aggtggatat ccactactgc caggggcaaat gtgccagcaa    8520
agccatgtac tccattgaca tcaacgatgt gcaggaccag tgctcctgct gctctccgac    8580
acggacggag cccatgcagg tggccctgca ctgcaccaat ggctctgttg tgtaccatga    8640
```

```
                                                                           -continued ggttctcaat gccatggagt gcaaatgctc ccccaggaag tgcagcaagt gaggctgctg        8700
cagctgcatg ggtgcctgct gctgcctgcc ttggcctgat ggccaggcca gagtgctgcc        8760
agtcctctgc atgttctgct cttgtgccct tctgagccca caataaaggc tgagctctta        8820
tcttgcaaaa ggc                                                           8833
```

<210> SEQ ID NO 2
<211> LENGTH: 2783
<212> TYPE: PRT
<213> ORGANISM: Artificial Sequence
<220> FEATURE:
<223> OTHER INFORMATION: VWF amino acid sequences

<400> SEQUENCE: 2

```
Met Ile Pro Ala Arg Phe Ala Gly Val Leu Leu Ile Leu Pro Gly
1               5                   10                  15

Thr Leu Cys Ala Glu Gly Thr Arg Gly Arg Ser Ser Thr Ala Arg Cys
                20                  25                  30

Ser Leu Phe Gly Ser Asp Phe Val Asn Thr Phe Asp Gly Ser Met Tyr
                35                  40                  45

Ser Phe Ala Gly Tyr Cys Ser Tyr Leu Leu Ala Gly Gly Cys Gln Lys
50                  55                      60

Arg Ser Phe Ser Ile Ile Gly Asp Phe Gln Asn Gly Lys Arg Val Ser
65                  70                  75                  80

Leu Ser Val Tyr Leu Gly Glu Phe Phe Asp Ile His Leu Phe Val Asn
                85                  90                  95

Gly Thr Val Thr Gln Gly Asp Gln Arg Val Ser Met Pro Tyr Ala Ser
                100                 105                 110

Lys Leu Glu Thr Glu Ala Gly Tyr Tyr Lys Leu Ser Gly Glu Ala Tyr
                115                 120                 125

Gly Phe Val Ala Arg Ile Asp Gly Ser Gly Asn Phe Gln Val Leu Leu
130                 135                 140

Ser Asp Arg Tyr Phe Asn Lys Thr Cys Gly Leu Cys Gly Asn Phe Asn
145                 150                 155                 160

Ile Phe Ala Glu Asp Asp Phe Met Thr Gln Glu Gly Thr Leu Thr Ser
                165                 170                 175

Asp Pro Tyr Asp Phe Ala Asn Ser Trp Ala Leu Ser Ser Gly Glu Gln
                180                 185                 190

Trp Cys Glu Arg Pro Ser Ser Cys Asn Ile Ser Ser Gly Glu Met
                195                 200                 205

Gln Lys Gly Leu Trp Glu Gln Cys Gln Leu Leu Lys Ser Thr Ser Val
                210                 215                 220

Phe Ala Arg Cys His Pro Leu Val Asp Pro Glu Pro Phe Cys Glu Lys
225                 230                 235                 240

Thr Leu Cys Glu Cys Ala Gly Gly Leu Glu Cys Ala Cys Pro Ala Leu
                245                 250                 255

Leu Glu Tyr Ala Arg Thr Cys Ala Gln Glu Gly Met Val Leu Tyr Gly
                260                 265                 270

Trp Thr Asp His Ser Ala Cys Ser Pro Val Cys Pro Ala Gly Met Glu
                275                 280                 285

Tyr Arg Gln Cys Val Ser Pro Cys Ala Arg Thr Cys Gln Ser Leu His
                290                 295                 300

Ile Asn Glu Met Cys Gln Glu Arg Cys Val Asp Gly Cys Ser Cys Pro
305                 310                 315                 320
```

-continued

```
Glu Gly Gln Leu Leu Asp Glu Gly Leu Cys Val Glu Ser Thr Glu Cys
                325                 330                 335

Pro Cys Val His Ser Gly Lys Arg Tyr Pro Pro Gly Thr Ser Leu Ser
            340                 345                 350

Arg Asp Cys Asn Thr Cys Ile Cys Arg Asn Ser Gln Trp Ile Cys Ser
        355                 360                 365

Asn Glu Glu Cys Pro Gly Glu Cys Leu Val Thr Gly Gln Ser His Phe
    370                 375                 380

Lys Ser Phe Asp Asn Arg Tyr Phe Thr Phe Ser Gly Ile Cys Gln Tyr
385                 390                 395                 400

Leu Leu Ala Arg Asp Cys Gln Asp His Ser Phe Ser Ile Val Ile Glu
                405                 410                 415

Thr Val Gln Cys Ala Asp Asp Arg Asp Ala Val Cys Thr Arg Ser Val
            420                 425                 430

Thr Val Arg Leu Pro Gly Leu His Asn Ser Leu Val Lys Leu Lys His
        435                 440                 445

Gly Ala Gly Val Ala Met Asp Gly Gln Asp Val Gln Leu Pro Leu Leu
    450                 455                 460

Lys Gly Asp Leu Arg Ile Gln His Thr Val Thr Ala Ser Val Arg Leu
465                 470                 475                 480

Ser Tyr Gly Glu Asp Leu Gln Met Asp Trp Asp Gly Arg Gly Arg Leu
                485                 490                 495

Leu Val Lys Leu Ser Pro Val Tyr Ala Gly Lys Thr Cys Gly Leu Cys
            500                 505                 510

Gly Asn Tyr Asn Gly Asn Gln Gly Asp Asp Phe Leu Thr Pro Ser Gly
        515                 520                 525

Leu Ala Glu Pro Arg Val Glu Asp Phe Gly Asn Ala Trp Lys Leu His
    530                 535                 540

Gly Asp Cys Gln Asp Leu Gln Lys Gln His Ser Asp Pro Cys Ala Leu
545                 550                 555                 560

Asn Pro Arg Met Thr Arg Phe Ser Glu Glu Ala Cys Ala Val Leu Thr
                565                 570                 575

Ser Pro Thr Phe Glu Ala Cys His Arg Ala Val Ser Pro Leu Pro Tyr
            580                 585                 590

Leu Arg Asn Cys Arg Tyr Asp Val Cys Ser Cys Ser Asp Gly Arg Glu
        595                 600                 605

Cys Leu Cys Gly Ser Tyr Ala Ala Ala Cys Ala Gly Arg Gly Val Arg
    610                 615                 620

Val Ala Trp Arg Glu Pro Gly Arg Cys Glu Leu Asn Cys Pro Lys Gly
625                 630                 635                 640

Gln Val Tyr Leu Gln Cys Gly Thr Pro Cys Asn Leu Thr Cys Arg Ser
                645                 650                 655

Leu Ser Tyr Pro Asp Glu Glu Cys Asn Glu Ala Cys Leu Glu Gly Cys
            660                 665                 670

Phe Cys Pro Pro Met Asp Glu Arg Gly Asp Cys Val Pro Lys Ala Gln
        675                 680                 685

Cys Pro Cys Tyr Tyr Asp Gly Glu Ile Phe Gln Pro Glu Asp Ile Phe
    690                 695                 700

Ser Asp His His Thr Met Cys Tyr Cys Glu Asp Gly Phe Met His Cys
705                 710                 715                 720

Thr Met Ser Gly Val Pro Gly Ser Leu Leu Pro Asp Ala Val Leu Ser
                725                 730                 735

Ser Pro Leu Ser His Arg Ser Lys Arg Ser Leu Ser Cys Arg Pro Pro
```

-continued

```
                740                745                750
Met Val Lys Leu Val Cys Pro Ala Asp Asn Leu Arg Ala Glu Gly Leu
            755                760                765
Glu Cys Thr Lys Thr Cys Gln Asn Tyr Asp Leu Glu Cys Met Ser Met
            770                775                780
Gly Cys Val Ser Gly Cys Leu Cys Pro Pro Gly Met Val Arg His Glu
785                790                795                800
Asn Arg Cys Glu Arg Cys Pro Cys Phe His Gln Gly Lys Glu Tyr Ala
                805                810                815
Pro Gly Glu Thr Val Lys Ile Gly Cys Asn Thr Cys Val Cys Arg Asp
                820                825                830
Arg Lys Trp Asn Cys Thr Asp His Val Cys Asp Ala Thr Cys Ser Thr
                835                840                845
Ile Gly Met Ala His Tyr Leu Thr Phe Asp Gly Leu Lys Tyr Leu Phe
                850                855                860
Pro Gly Glu Cys Gln Tyr Val Leu Val Gln Asp Tyr Cys Gly Ser Asn
865                870                875                880
Pro Gly Thr Phe Arg Ile Leu Val Gly Asn Lys Gly Cys Ser His Pro
                885                890                895
Ser Val Lys Cys Lys Lys Arg Val Thr Ile Leu Val Glu Gly Gly Glu
                900                905                910
Ile Glu Leu Phe Asp Gly Glu Val Asn Val Lys Arg Pro Met Lys Asp
                915                920                925
Glu Thr His Phe Glu Val Val Glu Ser Gly Arg Tyr Ile Ile Leu Leu
                930                935                940
Leu Gly Lys Ala Leu Ser Val Val Trp Asp Arg His Leu Ser Ile Ser
945                950                955                960
Val Val Leu Lys Gln Thr Tyr Gln Glu Lys Val Cys Gly Leu Cys Gly
                965                970                975
Asn Phe Asp Gly Ile Gln Asn Asn Asp Leu Thr Ser Ser Asn Leu Gln
                980                985                990
Val Glu Glu Asp Pro Val Asp Phe  Gly Asn Ser Trp Lys  Val Ser Ser
                995               1000               1005
Gln Cys  Ala Asp Thr Arg Lys  Val Pro Leu Asp Ser   Ser Pro Ala
    1010               1015               1020
Thr Cys  His Asn Asn Ile Met  Lys Gln Thr Met Val   Asp Ser Ser
    1025               1030               1035
Cys Arg  Ile Leu Thr Ser Asp  Val Phe Gln Asp Cys   Asn Lys Leu
    1040               1045               1050
Val Asp  Pro Glu Pro Tyr Leu  Asp Val Cys Ile Tyr   Asp Thr Cys
    1055               1060               1065
Ser Cys  Glu Ser Ile Gly Asp  Cys Ala Cys Phe Cys   Asp Thr Ile
    1070               1075               1080
Ala Ala  Tyr Ala His Val Cys  Ala Gln His Gly Lys   Val Val Thr
    1085               1090               1095
Trp Arg  Thr Ala Thr Leu Cys  Pro Gln Ser Cys Glu   Glu Arg Asn
    1100               1105               1110
Leu Arg  Glu Asn Gly Tyr Glu  Cys Glu Trp Arg Tyr   Asn Ser Cys
    1115               1120               1125
Ala Pro  Ala Cys Gln Val Thr  Cys Gln His Pro Glu   Pro Leu Ala
    1130               1135               1140
Cys Pro  Val Gln Cys Val Glu  Gly Cys His Ala His   Cys Pro Pro
    1145               1150               1155
```

```
Gly Lys Ile Leu Asp Glu Leu Leu Gln Thr Cys Val Asp Pro Glu
    1160              1165               1170
Asp Cys Pro Val Cys Glu Val Ala Gly Arg Arg Phe Ala Ser Gly
    1175              1180               1185
Lys Lys Val Thr Leu Asn Pro Ser Asp Pro Glu His Cys Gln Ile
    1190              1195               1200
Cys His Cys Asp Val Val Asn Leu Thr Cys Glu Ala Cys Gln Glu
    1205              1210               1215
Pro Gly Gly Leu Val Val Pro Pro Thr Asp Ala Pro Val Ser Pro
    1220              1225               1230
Thr Thr Leu Tyr Val Glu Asp Ile Ser Glu Pro Pro Leu His Asp
    1235              1240               1245
Phe Tyr Cys Ser Arg Leu Leu Asp Leu Val Phe Leu Leu Asp Gly
    1250              1255               1260
Ser Ser Arg Leu Ser Glu Ala Glu Phe Glu Val Leu Lys Ala Phe
    1265              1270               1275
Val Val Asp Met Met Glu Arg Leu Arg Ile Ser Gln Lys Trp Val
    1280              1285               1290
Arg Val Ala Val Val Glu Tyr His Asp Gly Ser His Ala Tyr Ile
    1295              1300               1305
Gly Leu Lys Asp Arg Lys Arg Pro Ser Glu Leu Arg Arg Ile Ala
    1310              1315               1320
Ser Gln Val Lys Tyr Ala Gly Ser Gln Val Ala Ser Thr Ser Glu
    1325              1330               1335
Val Leu Lys Tyr Thr Leu Phe Gln Ile Phe Ser Lys Ile Asp Arg
    1340              1345               1350
Pro Glu Ala Ser Arg Ile Thr Leu Leu Leu Met Ala Ser Gln Glu
    1355              1360               1365
Pro Gln Arg Met Ser Arg Asn Phe Val Arg Tyr Val Gln Gly Leu
    1370              1375               1380
Lys Lys Lys Lys Val Ile Val Ile Pro Val Gly Ile Gly Pro His
    1385              1390               1395
Ala Asn Leu Lys Gln Ile Arg Leu Ile Glu Lys Gln Ala Pro Glu
    1400              1405               1410
Asn Lys Ala Phe Val Leu Ser Ser Val Asp Glu Leu Glu Gln Gln
    1415              1420               1425
Arg Asp Glu Ile Val Ser Tyr Leu Cys Asp Leu Ala Pro Glu Ala
    1430              1435               1440
Pro Pro Pro Thr Leu Pro Pro Asp Met Ala Gln Val Thr Val Gly
    1445              1450               1455
Pro Gly Leu Leu Gly Val Ser Thr Leu Gly Pro Lys Arg Asn Ser
    1460              1465               1470
Met Val Leu Asp Val Ala Phe Val Leu Glu Gly Ser Asp Lys Ile
    1475              1480               1485
Gly Glu Ala Asp Phe Asn Arg Ser Lys Glu Phe Met Glu Glu Val
    1490              1495               1500
Ile Gln Arg Met Asp Val Gly Gln Asp Ser Ile His Val Thr Val
    1505              1510               1515
Leu Gln Tyr Ser Tyr Met Val Thr Val Glu Tyr Pro Phe Ser Glu
    1520              1525               1530
Ala Gln Ser Lys Gly Asp Ile Leu Gln Arg Val Arg Glu Ile Arg
    1535              1540               1545
```

```
Tyr Gln Gly Gly Asn Arg Thr Asn Thr Gly Leu Ala Leu Arg Tyr
1550                1555                1560

Leu Ser Asp His Ser Phe Leu Val Ser Gln Gly Asp Arg Glu Gln
1565                1570                1575

Ala Pro Asn Leu Val Tyr Met Val Thr Gly Asn Pro Ala Ser Asp
1580                1585                1590

Glu Ile Lys Arg Leu Pro Gly Asp Ile Gln Val Pro Ile Gly
1595                1600                1605

Val Gly Pro Asn Ala Asn Val Gln Glu Leu Glu Arg Ile Gly Trp
1610                1615                1620

Pro Asn Ala Pro Ile Leu Ile Gln Asp Phe Glu Thr Leu Pro Arg
1625                1630                1635

Glu Ala Pro Asp Leu Val Leu Gln Arg Cys Cys Ser Gly Glu Gly
1640                1645                1650

Leu Gln Ile Pro Thr Leu Ser Pro Ala Pro Asp Cys Ser Gln Pro
1655                1660                1665

Leu Asp Val Ile Leu Leu Leu Asp Gly Ser Ser Ser Phe Pro Ala
1670                1675                1680

Ser Tyr Phe Asp Glu Met Lys Ser Phe Ala Lys Ala Phe Ile Ser
1685                1690                1695

Lys Ala Asn Ile Gly Pro Arg Leu Thr Gln Val Ser Val Leu Gln
1700                1705                1710

Tyr Gly Ser Ile Thr Thr Ile Asp Val Pro Trp Asn Val Val Pro
1715                1720                1725

Glu Lys Ala His Leu Leu Ser Leu Val Asp Val Met Gln Arg Glu
1730                1735                1740

Gly Gly Pro Ser Gln Ile Gly Asp Ala Leu Gly Phe Ala Val Arg
1745                1750                1755

Tyr Leu Thr Ser Glu Met His Gly Ala Arg Pro Gly Ala Ser Lys
1760                1765                1770

Ala Val Val Ile Leu Val Thr Asp Val Ser Val Asp Ser Val Asp
1775                1780                1785

Ala Ala Ala Asp Ala Ala Arg Ser Asn Arg Val Thr Val Phe Pro
1790                1795                1800

Ile Gly Ile Gly Asp Arg Tyr Asp Ala Ala Gln Leu Arg Ile Leu
1805                1810                1815

Ala Gly Pro Ala Gly Asp Ser Asn Val Val Lys Leu Gln Arg Ile
1820                1825                1830

Glu Asp Leu Pro Thr Met Val Thr Leu Gly Asn Ser Phe Leu His
1835                1840                1845

Lys Leu Cys Ser Gly Phe Val Arg Ile Cys Met Asp Glu Asp Gly
1850                1855                1860

Asn Glu Lys Arg Pro Gly Asp Val Trp Thr Leu Pro Asp Gln Cys
1865                1870                1875

His Thr Val Thr Cys Gln Pro Asp Gly Gln Thr Leu Leu Lys Ser
1880                1885                1890

His Arg Val Asn Cys Asp Arg Gly Leu Arg Pro Ser Cys Pro Asn
1895                1900                1905

Ser Gln Ser Pro Val Lys Val Glu Glu Thr Cys Gly Cys Arg Trp
1910                1915                1920

Thr Cys Pro Cys Val Cys Thr Gly Ser Ser Thr Arg His Ile Val
1925                1930                1935

Thr Phe Asp Gly Gln Asn Phe Lys Leu Thr Gly Ser Cys Ser Tyr
```

```
                1940                1945                1950

Val Leu Phe Gln Asn Lys Glu Gln Asp Leu Glu Val Ile Leu His
            1955                1960                1965

Asn Gly Ala Cys Ser Pro Gly Ala Arg Gln Gly Cys Met Lys Ser
            1970                1975                1980

Ile Glu Val Lys His Ser Ala Leu Ser Val Glu Leu His Ser Asp
            1985                1990                1995

Met Glu Val Thr Val Asn Gly Arg Leu Val Ser Val Pro Tyr Val
            2000                2005                2010

Gly Gly Asn Met Glu Val Asn Val Tyr Gly Ala Ile Met His Glu
            2015                2020                2025

Val Arg Phe Asn His Leu Gly His Ile Phe Thr Phe Thr Pro Gln
            2030                2035                2040

Asn Asn Glu Phe Gln Leu Gln Leu Ser Pro Lys Thr Phe Ala Ser
            2045                2050                2055

Lys Thr Tyr Gly Leu Cys Gly Ile Cys Asp Glu Asn Gly Ala Asn
            2060                2065                2070

Asp Phe Met Leu Arg Asp Gly Thr Val Thr Asp Trp Lys Thr
            2075                2080                2085

Leu Val Gln Glu Trp Thr Val Gln Arg Pro Gly Gln Thr Cys Gln
            2090                2095                2100

Pro Glu Gln Cys Leu Val Pro Asp Ser Ser His Cys Gln Val Leu
            2105                2110                2115

Leu Leu Pro Leu Phe Ala Glu Cys His Lys Val Leu Ala Pro Ala
            2120                2125                2130

Thr Phe Tyr Ala Ile Cys Gln Gln Asp Ser Cys His Gln Glu Gln
            2135                2140                2145

Val Cys Glu Val Ile Ala Ser Tyr Ala His Leu Cys Arg Thr Asn
            2150                2155                2160

Gly Val Cys Val Asp Trp Arg Thr Pro Asp Phe Cys Ala Met Ser
            2165                2170                2175

Cys Pro Pro Ser Leu Val Tyr Asn His Cys Glu His Gly Cys Pro
            2180                2185                2190

Arg His Cys Asp Gly Asn Val Ser Ser Cys Gly Asp His Pro Ser
            2195                2200                2205

Glu Gly Cys Phe Cys Pro Pro Asp Lys Val Met Leu Glu Gly Ser
            2210                2215                2220

Cys Val Pro Glu Glu Ala Cys Thr Gln Cys Ile Gly Glu Asp Gly
            2225                2230                2235

Val Gln His Gln Phe Leu Glu Ala Trp Val Pro Asp His Gln Pro
            2240                2245                2250

Cys Gln Ile Cys Thr Cys Leu Ser Gly Arg Lys Val Asn Cys Thr
            2255                2260                2265

Thr Gln Pro Cys Pro Thr Ala Lys Ala Pro Thr Cys Gly Leu Cys
            2270                2275                2280

Glu Val Ala Arg Leu Arg Gln Asn Ala Asp Gln Cys Cys Pro Glu
            2285                2290                2295

Tyr Glu Cys Val Cys Asp Pro Val Ser Cys Asp Leu Pro Pro Val
            2300                2305                2310

Pro His Cys Glu Arg Gly Leu Gln Pro Thr Leu Thr Asn Pro Gly
            2315                2320                2325

Glu Cys Arg Pro Asn Phe Thr Cys Ala Cys Arg Lys Glu Glu Cys
            2330                2335                2340
```

```
Lys Arg Val Ser Pro Ser Cys Pro His Arg Leu Pro Thr
2345                2350                2355

Leu Arg Lys Thr Gln Cys Cys Asp Glu Tyr Glu Cys Ala Cys Asn
2360                2365                2370

Cys Val Asn Ser Thr Val Ser Cys Pro Leu Gly Tyr Leu Ala Ser
2375                2380                2385

Thr Ala Thr Asn Asp Cys Gly Cys Thr Thr Thr Cys Leu Pro
2390                2395                2400

Asp Lys Val Cys Val His Arg Ser Thr Ile Tyr Pro Val Gly Gln
2405                2410                2415

Phe Trp Glu Glu Gly Cys Asp Val Cys Thr Cys Thr Asp Met Glu
2420                2425                2430

Asp Ala Val Met Gly Leu Arg Val Ala Gln Cys Ser Gln Lys Pro
2435                2440                2445

Cys Glu Asp Ser Cys Arg Ser Gly Phe Thr Tyr Val Leu His Glu
2450                2455                2460

Gly Glu Cys Cys Gly Arg Cys Leu Pro Ser Ala Cys Glu Val Val
2465                2470                2475

Thr Gly Ser Pro Arg Gly Asp Ser Gln Ser Ser Trp Lys Ser Val
2480                2485                2490

Gly Ser Gln Trp Glu Asn Pro Cys Leu Ile Asn Glu Cys Val Arg
2495                2500                2505

Val Lys Glu Glu Val Phe Ile Gln Gln Arg Asn Val Ser Cys Pro
2510                2515                2520

Gln Leu Glu Val Pro Val Cys Pro Ser Gly Phe Gln Leu Ser Cys
2525                2530                2535

Lys Thr Ser Ala Cys Cys Pro Ser Cys Arg Cys Glu Arg Met Glu
2540                2545                2550

Ala Cys Met Leu Asn Gly Thr Val Ile Gly Pro Gly Lys Thr Val
2555                2560                2565

Met Ile Asp Val Cys Thr Thr Cys Arg Cys Met Val Gln Val Gly
2570                2575                2580

Val Ile Ser Gly Phe Lys Leu Glu Cys Arg Lys Thr Thr Cys Asn
2585                2590                2595

Pro Cys Pro Leu Gly Tyr Lys Glu Glu Asn Asn Thr Gly Glu Cys
2600                2605                2610

Cys Gly Arg Cys Leu Pro Thr Ala Cys Thr Ile Gln Leu Arg Gly
2615                2620                2625

Gly Gln Ile Met Thr Leu Lys Arg Asp Glu Thr Leu Gln Asp Gly
2630                2635                2640

Cys Asp Thr His Phe Cys Lys Val Asn Glu Arg Gly Glu Tyr Phe
2645                2650                2655

Trp Glu Lys Arg Val Thr Gly Cys Pro Pro Phe Asp Glu His Lys
2660                2665                2670

Cys Leu Ala Glu Gly Gly Lys Ile Met Lys Ile Pro Gly Thr Cys
2675                2680                2685

Cys Asp Thr Cys Glu Glu Pro Glu Cys Asn Asp Ile Thr Ala Arg
2690                2695                2700

Leu Gln Tyr Val Lys Val Gly Ser Cys Lys Ser Glu Val Glu Val
2705                2710                2715

Asp Ile His Tyr Cys Gln Gly Lys Cys Ala Ser Lys Ala Met Tyr
2720                2725                2730
```

-continued

```
Ser Ile Asp Ile Asn Asp Val Gln Asp Gln Cys Ser Cys Cys Ser
    2735                2740                2745

Pro Thr Arg Thr Glu Pro Met Gln His Cys Thr Asn Gly Ser Val
2750                2755                2760

Val Tyr His Glu Val Leu Asn Ala Met Glu Cys Lys Cys Ser Pro
2765                2770                2775

Arg Lys Cys Ser Lys
    2780

<210> SEQ ID NO 3
<211> LENGTH: 2050
<212> TYPE: PRT
<213> ORGANISM: Artificial Sequence
<220> FEATURE:
<223> OTHER INFORMATION: VWF amino acid sequences

<400> SEQUENCE: 3

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300
```

```
Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
            325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
            355                 360                 365

Glu Arg Asn Leu Arg Glu Asn Gly Tyr Glu Cys Glu Trp Arg Tyr Asn
        370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
            405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
            435                 440                 445

Val Thr Leu Asn Pro Ser Asp Pro Glu His Cys Gln Ile Cys His Cys
450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
            485                 490                 495

Glu Asp Ile Ser Glu Pro Pro Leu His Asp Phe Tyr Cys Ser Arg Leu
            500                 505                 510

Leu Asp Leu Val Phe Leu Leu Asp Gly Ser Ser Arg Leu Ser Glu Ala
        515                 520                 525

Glu Phe Glu Val Leu Lys Ala Phe Val Val Asp Met Met Glu Arg Leu
530                 535                 540

Arg Ile Ser Gln Lys Trp Val Arg Val Ala Val Val Glu Tyr His Asp
545                 550                 555                 560

Gly Ser His Ala Tyr Ile Gly Leu Lys Asp Arg Lys Arg Pro Ser Glu
            565                 570                 575

Leu Arg Arg Ile Ala Ser Gln Val Lys Tyr Ala Gly Ser Gln Val Ala
            580                 585                 590

Ser Thr Ser Glu Val Leu Lys Tyr Thr Leu Phe Gln Ile Phe Ser Lys
        595                 600                 605

Ile Asp Arg Pro Glu Ala Ser Arg Ile Thr Leu Leu Leu Met Ala Ser
610                 615                 620

Gln Glu Pro Gln Arg Met Ser Arg Asn Phe Val Arg Tyr Val Gln Gly
625                 630                 635                 640

Leu Lys Lys Lys Lys Val Ile Val Ile Pro Val Gly Ile Gly Pro His
            645                 650                 655

Ala Asn Leu Lys Gln Ile Arg Leu Ile Glu Lys Gln Ala Pro Glu Asn
            660                 665                 670

Lys Ala Phe Val Leu Ser Ser Val Asp Glu Leu Glu Gln Gln Arg Asp
        675                 680                 685

Glu Ile Val Ser Tyr Leu Cys Asp Leu Ala Pro Glu Ala Pro Pro Pro
        690                 695                 700

Thr Leu Pro Pro Asp Met Ala Gln Val Thr Val Gly Pro Gly Leu Leu
705                 710                 715                 720

Gly Val Ser Thr Leu Gly Pro Lys Arg Asn Ser Met Val Leu Asp Val
```

-continued

```
                725                 730                 735
Ala Phe Val Leu Glu Gly Ser Asp Lys Ile Gly Glu Ala Asp Phe Asn
            740                 745                 750

Arg Ser Lys Glu Phe Met Glu Val Ile Gln Arg Met Asp Val Gly
            755                 760                 765

Gln Asp Ser Ile His Val Thr Val Leu Gln Tyr Ser Tyr Met Val Thr
    770                 775                 780

Val Glu Tyr Pro Phe Ser Glu Ala Gln Ser Lys Gly Asp Ile Leu Gln
785                 790                 795                 800

Arg Val Arg Glu Ile Arg Tyr Gln Gly Gly Asn Arg Thr Asn Thr Gly
                805                 810                 815

Leu Ala Leu Arg Tyr Leu Ser Asp His Ser Phe Leu Val Ser Gln Gly
                820                 825                 830

Asp Arg Glu Gln Ala Pro Asn Leu Val Tyr Met Val Thr Gly Asn Pro
                835                 840                 845

Ala Ser Asp Glu Ile Lys Arg Leu Pro Gly Asp Ile Gln Val Val Pro
        850                 855                 860

Ile Gly Val Gly Pro Asn Ala Asn Val Gln Glu Leu Glu Arg Ile Gly
865                 870                 875                 880

Trp Pro Asn Ala Pro Ile Leu Ile Gln Asp Phe Glu Thr Leu Pro Arg
                885                 890                 895

Glu Ala Pro Asp Leu Val Leu Gln Arg Cys Cys Ser Gly Glu Gly Leu
            900                 905                 910

Gln Ile Pro Thr Leu Ser Pro Ala Pro Asp Cys Ser Gln Pro Leu Asp
            915                 920                 925

Val Ile Leu Leu Leu Asp Gly Ser Ser Ser Phe Pro Ala Ser Tyr Phe
930                 935                 940

Asp Glu Met Lys Ser Phe Ala Lys Ala Phe Ile Ser Lys Ala Asn Ile
945                 950                 955                 960

Gly Pro Arg Leu Thr Gln Val Ser Val Leu Gln Tyr Gly Ser Ile Thr
                965                 970                 975

Thr Ile Asp Val Pro Trp Asn Val Val Pro Glu Lys Ala His Leu Leu
            980                 985                 990

Ser Leu Val Asp Val Met Gln Arg Glu Gly Gly Pro Ser Gln Ile Gly
        995                 1000                1005

Asp Ala Leu Gly Phe Ala Val Arg Tyr Leu Thr Ser Glu Met His
    1010                1015                1020

Gly Ala Arg Pro Gly Ala Ser Lys Ala Val Val Ile Leu Val Thr
    1025                1030                1035

Asp Val Ser Val Asp Ser Val Asp Ala Ala Ala Asp Ala Ala Arg
    1040                1045                1050

Ser Asn Arg Val Thr Val Phe Pro Ile Gly Ile Gly Asp Arg Tyr
    1055                1060                1065

Asp Ala Ala Gln Leu Arg Ile Leu Ala Gly Pro Ala Gly Asp Ser
    1070                1075                1080

Asn Val Val Lys Leu Gln Arg Ile Glu Asp Leu Pro Thr Met Val
    1085                1090                1095

Thr Leu Gly Asn Ser Phe Leu His Lys Leu Cys Ser Gly Phe Val
    1100                1105                1110

Arg Ile Cys Met Asp Glu Asp Gly Asn Glu Lys Arg Pro Gly Asp
    1115                1120                1125

Val Trp Thr Leu Pro Asp Gln Cys His Thr Val Thr Cys Gln Pro
    1130                1135                1140
```

-continued

Asp Gly Gln Thr Leu Leu Lys Ser His Arg Val Asn Cys Asp Arg
1145                    1150                    1155

Gly Leu Arg Pro Ser Cys Pro Asn Ser Gln Ser Pro Val Lys Val
1160                    1165                    1170

Glu Glu Thr Cys Gly Cys Arg Trp Thr Cys Pro Cys Val Cys Thr
1175                    1180                    1185

Gly Ser Ser Thr Arg His Ile Val Thr Phe Asp Gly Gln Asn Phe
1190                    1195                    1200

Lys Leu Thr Gly Ser Cys Ser Tyr Val Leu Phe Gln Asn Lys Glu
1205                    1210                    1215

Gln Asp Leu Glu Val Ile Leu His Asn Gly Ala Cys Ser Pro Gly
1220                    1225                    1230

Ala Arg Gln Gly Cys Met Lys Ser Ile Glu Val Lys His Ser Ala
1235                    1240                    1245

Leu Ser Val Glu Leu His Ser Asp Met Glu Val Thr Val Asn Gly
1250                    1255                    1260

Arg Leu Val Ser Val Pro Tyr Val Gly Gly Asn Met Glu Val Asn
1265                    1270                    1275

Val Tyr Gly Ala Ile Met His Glu Val Arg Phe Asn His Leu Gly
1280                    1285                    1290

His Ile Phe Thr Phe Thr Pro Gln Asn Asn Glu Phe Gln Leu Gln
1295                    1300                    1305

Leu Ser Pro Lys Thr Phe Ala Ser Lys Thr Tyr Gly Leu Cys Gly
1310                    1315                    1320

Ile Cys Asp Glu Asn Gly Ala Asn Asp Phe Met Leu Arg Asp Gly
1325                    1330                    1335

Thr Val Thr Thr Asp Trp Lys Thr Leu Val Gln Glu Trp Thr Val
1340                    1345                    1350

Gln Arg Pro Gly Gln Thr Cys Gln Pro Ile Leu Glu Glu Gln Cys
1355                    1360                    1365

Leu Val Pro Asp Ser Ser His Cys Gln Val Leu Leu Leu Pro Leu
1370                    1375                    1380

Phe Ala Glu Cys His Lys Val Leu Ala Pro Ala Thr Phe Tyr Ala
1385                    1390                    1395

Ile Cys Gln Gln Asp Ser Cys His Gln Glu Gln Val Cys Glu Val
1400                    1405                    1410

Ile Ala Ser Tyr Ala His Leu Cys Arg Thr Asn Gly Val Cys Val
1415                    1420                    1425

Asp Trp Arg Thr Pro Asp Phe Cys Ala Met Ser Cys Pro Pro Ser
1430                    1435                    1440

Leu Val Tyr Asn His Cys Glu His Gly Cys Pro Arg His Cys Asp
1445                    1450                    1455

Gly Asn Val Ser Ser Cys Gly Asp His Pro Ser Glu Gly Cys Phe
1460                    1465                    1470

Cys Pro Pro Asp Lys Val Met Leu Glu Gly Ser Cys Val Pro Glu
1475                    1480                    1485

Glu Ala Cys Thr Gln Cys Ile Gly Glu Asp Gly Val Gln His Gln
1490                    1495                    1500

Phe Leu Glu Ala Trp Val Pro Asp His Gln Pro Cys Gln Ile Cys
1505                    1510                    1515

Thr Cys Leu Ser Gly Arg Lys Val Asn Cys Thr Thr Gln Pro Cys
1520                    1525                    1530

```
Pro Thr Ala Lys Ala Pro Thr Cys Gly Leu Cys Glu Val Ala Arg
1535                1540                1545

Leu Arg Gln Asn Ala Asp Gln Cys Cys Pro Glu Tyr Glu Cys Val
    1550                1555                1560

Cys Asp Pro Val Ser Cys Asp Leu Pro Pro Val Pro His Cys Glu
1565                1570                1575

Arg Gly Leu Gln Pro Thr Leu Thr Asn Pro Gly Glu Cys Arg Pro
    1580                1585                1590

Asn Phe Thr Cys Ala Cys Arg Lys Glu Cys Lys Arg Val Ser
1595                1600                1605

Pro Pro Ser Cys Pro Pro His Arg Leu Pro Thr Leu Arg Lys Thr
    1610                1615                1620

Gln Cys Cys Asp Glu Tyr Glu Cys Ala Cys Asn Cys Val Asn Ser
1625                1630                1635

Thr Val Ser Cys Pro Leu Gly Tyr Leu Ala Ser Thr Ala Thr Asn
    1640                1645                1650

Asp Cys Gly Cys Thr Thr Thr Cys Leu Pro Asp Lys Val Cys
1655                1660                1665

Val His Arg Ser Thr Ile Tyr Pro Val Gly Gln Phe Trp Glu Glu
    1670                1675                1680

Gly Cys Asp Val Cys Thr Cys Thr Asp Met Glu Asp Ala Val Met
1685                1690                1695

Gly Leu Arg Val Ala Gln Cys Ser Gln Lys Pro Cys Glu Asp Ser
    1700                1705                1710

Cys Arg Ser Gly Phe Thr Tyr Val Leu His Glu Gly Glu Cys Cys
1715                1720                1725

Gly Arg Cys Leu Pro Ser Ala Cys Glu Val Val Thr Gly Ser Pro
    1730                1735                1740

Arg Gly Asp Ser Gln Ser Ser Trp Lys Ser Val Gly Ser Gln Trp
1745                1750                1755

Ala Ser Pro Glu Asn Pro Cys Leu Ile Asn Glu Cys Val Arg Val
    1760                1765                1770

Lys Glu Glu Val Phe Ile Gln Gln Arg Asn Val Ser Cys Pro Gln
1775                1780                1785

Leu Glu Val Pro Val Cys Pro Ser Gly Phe Gln Leu Ser Cys Lys
    1790                1795                1800

Thr Ser Ala Cys Cys Pro Ser Cys Arg Cys Glu Arg Met Glu Ala
1805                1810                1815

Cys Met Leu Asn Gly Thr Val Ile Gly Pro Gly Lys Thr Val Met
    1820                1825                1830

Ile Asp Val Cys Thr Thr Cys Arg Cys Met Val Gln Val Gly Val
1835                1840                1845

Ile Ser Gly Phe Lys Leu Glu Cys Arg Lys Thr Thr Cys Asn Pro
    1850                1855                1860

Cys Pro Leu Gly Tyr Lys Glu Glu Asn Asn Thr Gly Glu Cys Cys
1865                1870                1875

Gly Arg Cys Leu Pro Thr Ala Cys Thr Ile Gln Leu Arg Gly Gly
    1880                1885                1890

Gln Ile Met Thr Leu Lys Arg Asp Glu Thr Leu Gln Asp Gly Cys
1895                1900                1905

Asp Thr His Phe Cys Lys Val Asn Glu Arg Gly Glu Tyr Phe Trp
    1910                1915                1920

Glu Lys Arg Val Thr Gly Cys Pro Pro Phe Asp Glu His Lys Cys
```

```
                        1925                1930                1935

Leu Ala Glu Gly Gly Lys Ile Met Lys Ile Pro Gly Thr Cys Cys
            1940                1945                1950

Asp Thr Cys Glu Glu Pro Glu Cys Asn Asp Ile Thr Ala Arg Leu
            1955                1960                1965

Gln Tyr Val Lys Val Gly Ser Cys Lys Ser Glu Val Glu Val Asp
            1970                1975                1980

Ile His Tyr Cys Gln Gly Lys Cys Ala Ser Lys Ala Met Tyr Ser
            1985                1990                1995

Ile Asp Ile Asn Asp Val Gln Asp Gln Cys Ser Cys Cys Ser Pro
            2000                2005                2010

Thr Arg Thr Glu Pro Met Gln Val Ala Leu His Cys Thr Asn Gly
            2015                2020                2025

Ser Val Val Tyr His Glu Val Leu Asn Ala Met Glu Cys Lys Cys
            2030                2035                2040

Ser Pro Arg Lys Cys Ser Lys
            2045                2050

<210> SEQ ID NO 4
<211> LENGTH: 3012
<212> TYPE: PRT
<213> ORGANISM: Artificial Sequence
<220> FEATURE:
<223> OTHER INFORMATION: VWF - FVIII fusion proteins

<400> SEQUENCE: 4

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
```

-continued

```
           225                 230                 235                 240
       Asn Asn Asp Leu Thr Ser Ser Asn Leu Gln Val Glu Glu Asp Pro Val
                       245                 250                 255
       Asp Phe Gly Asn Ser Trp Lys Val Ser Ser Gln Cys Ala Asp Thr Arg
                       260                 265                 270
       Lys Val Pro Leu Asp Ser Ser Pro Ala Thr Cys His Asn Asn Ile Met
                       275                 280                 285
       Lys Gln Thr Met Val Asp Ser Ser Cys Arg Ile Leu Thr Ser Asp Val
                       290                 295                 300
       Phe Gln Asp Cys Asn Lys Leu Val Asp Pro Glu Pro Tyr Leu Asp Val
       305                 310                 315                 320
       Cys Ile Tyr Asp Thr Cys Ser Cys Glu Ser Ile Gly Asp Cys Ala Cys
                       325                 330                 335
       Phe Cys Asp Thr Ile Ala Ala Tyr Ala His Val Cys Ala Gln His Gly
                       340                 345                 350
       Lys Val Val Thr Trp Arg Thr Ala Thr Leu Cys Pro Gln Ser Cys Glu
                       355                 360                 365
       Glu Arg Asn Leu Arg Glu Asn Gly Tyr Glu Cys Glu Trp Arg Tyr Asn
       370                 375                 380
       Ser Cys Ala Pro Ala Cys Gln Val Thr Cys Gln His Pro Glu Pro Leu
       385                 390                 395                 400
       Ala Cys Pro Val Gln Cys Val Glu Gly Cys His Ala His Cys Pro Pro
                       405                 410                 415
       Gly Lys Ile Leu Asp Glu Leu Leu Gln Thr Cys Val Asp Pro Glu Asp
                       420                 425                 430
       Cys Pro Val Cys Glu Val Ala Gly Arg Arg Phe Ala Ser Gly Lys Lys
                       435                 440                 445
       Val Thr Leu Asn Pro Ser Asp Pro Glu His Cys Gln Ile Cys His Cys
                       450                 455                 460
       Asp Val Val Asn Leu Thr Cys Glu Ala Cys Gln Glu Pro Gly Gly Leu
       465                 470                 475                 480
       Val Val Pro Pro Thr Asp Ala Pro Val Ser Pro Thr Thr Leu Tyr Val
                       485                 490                 495
       Glu Asp Ile Ser Glu Pro Pro Leu His Asp Phe Tyr Cys Ser Arg Leu
                       500                 505                 510
       Leu Asp Leu Val Phe Leu Leu Asp Gly Ser Ser Arg Leu Ser Glu Ala
                       515                 520                 525
       Glu Phe Glu Val Leu Lys Ala Phe Val Val Asp Met Met Glu Arg Leu
                       530                 535                 540
       Arg Ile Ser Gln Lys Trp Val Arg Val Ala Val Val Glu Tyr His Asp
       545                 550                 555                 560
       Gly Ser His Ala Tyr Ile Gly Leu Lys Asp Arg Lys Arg Tyr Tyr Leu
                       565                 570                 575
       Gly Ala Val Glu Leu Ser Trp Asp Tyr Met Gln Ser Asp Leu Gly Glu
                       580                 585                 590
       Leu Pro Val Asp Ala Arg Phe Pro Pro Arg Val Pro Lys Ser Phe Pro
                       595                 600                 605
       Phe Asn Thr Ser Val Val Tyr Lys Lys Thr Leu Phe Val Glu Phe Thr
                       610                 615                 620
       Asp His Leu Phe Asn Ile Ala Lys Pro Arg Pro Pro Trp Met Gly Leu
       625                 630                 635                 640
       Leu Gly Pro Thr Ile Gln Ala Glu Val Tyr Asp Thr Val Val Ile Thr
                       645                 650                 655
```

```
Leu Lys Asn Met Ala Ser His Pro Val Ser Leu His Ala Val Gly Val
            660                 665                 670

Ser Tyr Trp Lys Ala Ser Glu Gly Ala Glu Tyr Asp Asp Gln Thr Ser
            675                 680                 685

Gln Arg Glu Lys Glu Asp Asp Lys Val Phe Pro Gly Gly Ser His Thr
        690                 695                 700

Tyr Val Trp Gln Val Leu Lys Glu Asn Gly Pro Met Ala Ser Asp Pro
705                 710                 715                 720

Leu Cys Leu Thr Tyr Ser Tyr Leu Ser His Val Asp Leu Val Lys Asp
                725                 730                 735

Leu Asn Ser Gly Leu Ile Gly Ala Leu Leu Val Cys Arg Glu Gly Ser
            740                 745                 750

Leu Ala Lys Glu Lys Thr Gln Thr His Lys Phe Ile Leu Leu Phe Ala
            755                 760                 765

Val Phe Asp Glu Gly Lys Ser Trp His Ser Glu Thr Lys Asn Ser Leu
770                 775                 780

Met Gln Asp Arg Asp Ala Ala Ser Ala Arg Ala Trp Pro Lys Met His
785                 790                 795                 800

Thr Val Asn Gly Tyr Val Asn Arg Ser Leu Pro Gly Leu Ile Gly Cys
            805                 810                 815

His Arg Lys Ser Val Tyr Trp His Val Ile Gly Met Gly Thr Thr Pro
            820                 825                 830

Glu Val His Ser Ile Phe Leu Glu Gly His Thr Phe Leu Val Arg Asn
            835                 840                 845

His Arg Gln Ala Ser Leu Glu Ile Ser Pro Ile Thr Phe Leu Thr Ala
            850                 855                 860

Gln Thr Leu Leu Met Asp Leu Gly Gln Phe Leu Leu Phe Cys His Ile
865                 870                 875                 880

Ser Ser His Gln His Asp Gly Met Glu Ala Tyr Val Lys Val Asp Ser
                885                 890                 895

Cys Pro Glu Glu Pro Gln Leu Arg Met Lys Asn Asn Glu Glu Ala Glu
            900                 905                 910

Asp Tyr Asp Asp Asp Leu Thr Asp Ser Glu Met Asp Val Val Arg Phe
        915                 920                 925

Asp Asp Asp Asn Ser Pro Ser Phe Ile Gln Ile Arg Ser Val Ala Lys
    930                 935                 940

Lys His Pro Lys Thr Trp Val His Tyr Ile Ala Ala Glu Glu Glu Asp
945                 950                 955                 960

Trp Asp Tyr Ala Pro Leu Val Leu Ala Pro Asp Asp Arg Ser Tyr Lys
                965                 970                 975

Ser Gln Tyr Leu Asn Asn Gly Pro Gln Arg Ile Gly Arg Lys Tyr Lys
            980                 985                 990

Lys Val Arg Phe Met Ala Tyr Thr Asp Glu Thr Phe Lys Thr Arg Glu
            995                 1000                1005

Ala Ile Gln His Glu Ser Gly Ile Leu Gly Pro Leu Leu Tyr Gly
        1010                1015                1020

Glu Val Gly Asp Thr Leu Leu Ile Ile Phe Lys Asn Gln Ala Ser
    1025                1030                1035

Arg Pro Tyr Asn Ile Tyr Pro His Gly Ile Thr Asp Val Arg Pro
        1040                1045                1050

Leu Tyr Ser Arg Arg Leu Pro Lys Gly Val Lys His Leu Lys Asp
    1055                1060                1065
```

```
Phe Pro Ile Leu Pro Gly Glu Ile Phe Lys Tyr Lys Trp Thr Val
1070                1075                1080

Thr Val Glu Asp Gly Pro Thr Lys Ser Asp Pro Arg Cys Leu Thr
1085                1090                1095

Arg Tyr Tyr Ser Ser Phe Val Asn Met Glu Arg Asp Leu Ala Ser
1100                1105                1110

Gly Leu Ile Gly Pro Leu Leu Ile Cys Tyr Lys Glu Ser Val Asp
1115                1120                1125

Gln Arg Gly Asn Gln Ile Met Ser Asp Lys Arg Asn Val Ile Leu
1130                1135                1140

Phe Ser Val Phe Asp Glu Asn Arg Ser Trp Tyr Leu Thr Glu Asn
1145                1150                1155

Ile Gln Arg Phe Leu Pro Asn Pro Ala Gly Val Gln Leu Glu Asp
1160                1165                1170

Pro Glu Phe Gln Ala Ser Asn Ile Met His Ser Ile Asn Gly Tyr
1175                1180                1185

Val Phe Asp Ser Leu Gln Leu Ser Val Cys Leu His Glu Val Ala
1190                1195                1200

Tyr Trp Tyr Ile Leu Ser Ile Gly Ala Gln Thr Asp Phe Leu Ser
1205                1210                1215

Val Phe Phe Ser Gly Tyr Thr Phe Lys His Lys Met Val Tyr Glu
1220                1225                1230

Asp Thr Leu Thr Leu Phe Pro Phe Ser Gly Glu Thr Val Phe Met
1235                1240                1245

Ser Met Glu Asn Pro Gly Leu Trp Ile Leu Gly Cys His Asn Ser
1250                1255                1260

Asp Phe Arg Asn Arg Gly Met Thr Ala Leu Leu Lys Val Ser Ser
1265                1270                1275

Cys Asp Lys Asn Thr Gly Asp Tyr Tyr Glu Asp Ser Tyr Glu Asp
1280                1285                1290

Ile Ser Ala Tyr Leu Leu Val Trp Phe Val Trp Phe Val Trp Phe
1295                1300                1305

Ser Lys Asn Asn Ala Ile Glu Pro Arg Ser Arg His Cys Asp Gly
1310                1315                1320

Asn Val Ser Ser Cys Gly Asp His Pro Ser Glu Gly Cys Phe Cys
1325                1330                1335

Pro Pro Asp Lys Val Met Leu Glu Gly Ser Cys Val Pro Val Trp
1340                1345                1350

Phe Val Trp Phe Val Trp Phe Val Trp Phe Val Trp Phe Glu Glu
1355                1360                1365

Ala Cys Thr Gln Cys Ile Gly Glu Asp Gly Val Gln His Gln Phe
1370                1375                1380

Leu Glu Ala Trp Val Pro Asp His Gln Pro Cys Gln Ile Cys Thr
1385                1390                1395

Cys Leu Ser Gly Arg Lys Val Asn Cys Thr Thr Gln Pro Cys Pro
1400                1405                1410

Thr Ala Lys Val Trp Phe Val Trp Phe Val Trp Phe Val Trp Phe
1415                1420                1425

Val Trp Phe Ala Pro Thr Cys Gly Leu Cys Glu Val Ala Arg Leu
1430                1435                1440

Arg Gln Asn Ala Asp Gln Cys Cys Pro Glu Tyr Glu Cys Val Cys
1445                1450                1455

Asp Pro Val Ser Cys Asp Leu Pro Pro Val Pro His Cys Glu Arg
```

-continued

```
            1460                1465                1470
Gly Leu Gln Pro Thr Leu Thr Asn Val Trp Phe Val Trp Phe Val
    1475                1480                1485
Trp Phe Val Trp Phe Val Trp Phe Pro Gly Glu Cys Arg Pro Asn
    1490                1495                1500
Phe Thr Cys Ala Cys Arg Lys Glu Glu Cys Lys Arg Val Ser Pro
    1505                1510                1515
Pro Ser Cys Pro Pro His Arg Leu Pro Thr Leu Arg Lys Thr Gln
    1520                1525                1530
Cys Cys Asp Glu Tyr Glu Cys Ala Cys Asn Cys Asn Val Trp
    1535                1540                1545
Phe Val Trp Phe Val Trp Phe Val Trp Phe Val Trp Phe Ser Thr
    1550                1555                1560
Val Ser Cys Pro Leu Gly Tyr Leu Ala Ser Thr Ala Thr Asn Asp
    1565                1570                1575
Cys Gly Cys Thr Thr Thr Cys Leu Pro Asp Lys Val Cys Val
    1580                1585                1590
His Arg Ser Thr Ile Tyr Pro Val Gly Gln Phe Trp Glu Glu Gly
    1595                1600                1605
Cys Asp Val Val Trp Phe Val Trp Phe Val Trp Phe Val Trp Phe
    1610                1615                1620
Val Trp Phe Cys Thr Cys Thr Asp Met Glu Asp Ala Val Met Gly
    1625                1630                1635
Leu Arg Val Ala Gln Cys Ser Gln Lys Pro Cys Glu Asp Ser Cys
    1640                1645                1650
Arg Ser Gly Phe Thr Tyr Val Leu His Glu Gly Glu Cys Cys Gly
    1655                1660                1665
Arg Cys Leu Pro Ser Ala Cys Glu Val Trp Phe Val Trp Phe Val
    1670                1675                1680
Trp Phe Val Trp Phe Val Trp Phe Val Val Thr Gly Ser Pro Arg
    1685                1690                1695
Gly Asp Ser Gln Ser Ser Trp Lys Ser Val Gly Ser Gln Trp Ala
    1700                1705                1710
Ser Pro Glu Asn Pro Cys Leu Ile Asn Glu Cys Val Arg Val Lys
    1715                1720                1725
Glu Glu Val Phe Ile Gln Gln Arg Asn Val Ser Cys Pro Val Trp
    1730                1735                1740
Phe Val Trp Phe Val Trp Phe Val Trp Phe Val Trp Phe Gln Leu
    1745                1750                1755
Glu Val Pro Val Cys Pro Ser Gly Phe Gln Leu Ser Cys Lys Thr
    1760                1765                1770
Ser Ala Cys Cys Pro Ser Cys Arg Cys Glu Arg Met Glu Ala Cys
    1775                1780                1785
Met Leu Asn Gly Thr Val Ile Gly Pro Gly Lys Ala Leu Lys Gln
    1790                1795                1800
Phe Arg Leu Pro Leu Glu Glu Thr Glu Leu Glu Lys Arg Ile Ile
    1805                1810                1815
Val Asp Asp Thr Ser Thr Gln Trp Ser Lys Asn Met Lys His Leu
    1820                1825                1830
Thr Pro Ser Thr Leu Thr Gln Ile Asp Tyr Asn Glu Lys Glu Lys
    1835                1840                1845
Gly Ala Ile Thr Gln Ser Pro Leu Ser Asp Cys Leu Thr Arg Ser
    1850                1855                1860
```

His Ser Ile Pro Gln Ala Asn Arg Ser Pro Leu Pro Ile Ala Lys
    1865                1870                1875

Val Ser Ser Phe Pro Ser Ile Arg Pro Ile Tyr Leu Thr Arg Val
    1880                1885                1890

Leu Phe Gln Asp Asn Ser Ser His Leu Pro Ala Ala Ser Tyr Arg
    1895                1900                1905

Lys Lys Asp Ser Gly Val Gln Glu Ser Ser His Phe Leu Gln Gly
    1910                1915                1920

Ala Lys Lys Asn Asn Leu Ser Leu Ala Ile Leu Thr Leu Glu Met
    1925                1930                1935

Thr Gly Asp Gln Arg Glu Val Gly Ser Leu Gly Thr Ser Ala Thr
    1940                1945                1950

Asn Ser Val Thr Tyr Lys Lys Val Glu Asn Thr Val Leu Pro Lys
    1955                1960                1965

Pro Asp Leu Pro Lys Thr Ser Gly Lys Val Glu Leu Leu Pro Lys
    1970                1975                1980

Val His Ile Tyr Gln Lys Asp Leu Phe Pro Thr Glu Thr Ser Asn
    1985                1990                1995

Gly Ser Pro Gly His Leu Asp Leu Val Glu Gly Ser Leu Leu Gln
    2000                2005                2010

Gly Thr Glu Gly Ala Ile Lys Trp Asn Glu Ala Asn Arg Pro Gly
    2015                2020                2025

Lys Val Pro Phe Leu Arg Val Ala Thr Glu Ser Ser Ala Lys Thr
    2030                2035                2040

Pro Ser Lys Leu Leu Asp Pro Leu Ala Trp Asp Asn His Tyr Gly
    2045                2050                2055

Thr Gln Ile Pro Lys Glu Glu Trp Lys Ser Gln Glu Lys Ser Pro
    2060                2065                2070

Glu Lys Thr Ala Phe Lys Lys Lys Asp Thr Ile Leu Ser Leu Asn
    2075                2080                2085

Ala Cys Glu Ser Asn His Ala Ile Ala Ala Ile Asn Glu Gly Gln
    2090                2095                2100

Asn Lys Pro Glu Ile Glu Val Thr Trp Ala Lys Gln Gly Arg Thr
    2105                2110                2115

Glu Arg Leu Cys Ser Gln Asn Pro Pro Val Leu Lys Arg His Gln
    2120                2125                2130

Arg Glu Ile Thr Arg Thr Thr Leu Gln Ser Asp Gln Glu Glu Ile
    2135                2140                2145

Asp Tyr Asp Asp Thr Ile Ser Val Glu Met Lys Lys Glu Asp Phe
    2150                2155                2160

Asp Ile Tyr Asp Glu Asp Glu Asn Gln Ser Pro Arg Ser Phe Gln
    2165                2170                2175

Lys Lys Thr Arg His Tyr Phe Ile Ala Ala Val Glu Arg Leu Trp
    2180                2185                2190

Asp Tyr Gly Met Ser Ser Ser Pro His Val Leu Arg Asn Arg Ala
    2195                2200                2205

Gln Ser Gly Ser Val Pro Gln Phe Lys Lys Val Val Phe Gln Glu
    2210                2215                2220

Phe Thr Asp Gly Ser Phe Thr Gln Pro Leu Tyr Arg Gly Glu Leu
    2225                2230                2235

Asn Glu His Leu Gly Leu Leu Gly Pro Tyr Ile Arg Ala Glu Val
    2240                2245                2250

```
Glu Asp Asn Ile Met Val Thr Phe Arg Asn Gln Ala Ser Arg Pro
2255                2260                2265

Tyr Ser Phe Tyr Ser Ser Leu Ile Ser Tyr Glu Glu Asp Gln Arg
2270                2275                2280

Gln Gly Ala Glu Pro Arg Lys Asn Phe Val Lys Pro Asn Glu Thr
2285                2290                2295

Lys Thr Tyr Phe Trp Lys Val Gln His His Met Ala Pro Thr Lys
2300                2305                2310

Asp Glu Phe Asp Cys Lys Ala Trp Ala Tyr Phe Ser Asp Val Asp
2315                2320                2325

Leu Glu Lys Asp Val His Ser Gly Leu Ile Gly Pro Leu Leu Val
2330                2335                2340

Cys His Thr Asn Thr Leu Asn Pro Ala His Gly Arg Gln Val Thr
2345                2350                2355

Val Gln Glu Phe Ala Leu Phe Phe Thr Ile Phe Asp Glu Thr Lys
2360                2365                2370

Ser Trp Tyr Phe Thr Glu Asn Met Glu Arg Asn Cys Arg Ala Pro
2375                2380                2385

Cys Asn Ile Gln Met Glu Asp Pro Thr Phe Lys Glu Asn Tyr Arg
2390                2395                2400

Phe His Ala Ile Asn Gly Tyr Ile Met Asp Thr Leu Pro Gly Leu
2405                2410                2415

Val Met Ala Gln Asp Gln Arg Ile Arg Trp Tyr Leu Leu Ser Met
2420                2425                2430

Gly Ser Asn Glu Asn Ile His Ser Ile His Phe Ser Gly His Val
2435                2440                2445

Phe Thr Val Arg Lys Lys Glu Glu Tyr Lys Met Ala Leu Tyr Asn
2450                2455                2460

Leu Tyr Pro Gly Val Phe Glu Thr Val Glu Met Leu Pro Ser Lys
2465                2470                2475

Ala Gly Ile Trp Arg Val Glu Cys Leu Ile Gly Glu His Leu His
2480                2485                2490

Ala Gly Met Ser Thr Leu Phe Leu Val Tyr Ser Asn Lys Cys Gln
2495                2500                2505

Thr Pro Leu Gly Met Ala Ser Gly His Ile Arg Asp Phe Gln Ile
2510                2515                2520

Thr Ala Ser Gly Gln Tyr Gly Gln Trp Ala Pro Lys Leu Ala Arg
2525                2530                2535

Leu His Tyr Ser Gly Ser Ile Asn Ala Trp Ser Thr Lys Glu Pro
2540                2545                2550

Phe Ser Trp Ile Lys Val Asp Leu Leu Ala Pro Met Ile Ile His
2555                2560                2565

Gly Ile Lys Thr Gln Gly Ala Arg Gln Lys Phe Ser Ser Leu Tyr
2570                2575                2580

Ile Ser Gln Phe Ile Ile Met Tyr Ser Leu Asp Gly Lys Lys Trp
2585                2590                2595

Gln Thr Tyr Arg Gly Asn Ser Thr Gly Thr Leu Met Val Phe Phe
2600                2605                2610

Gly Asn Val Asp Ser Ser Gly Ile Lys His Asn Ile Phe Asn Pro
2615                2620                2625

Pro Ile Ile Ala Arg Tyr Ile Arg Leu His Pro Thr His Tyr Ser
2630                2635                2640

Ile Arg Ser Thr Leu Arg Met Glu Leu Met Gly Cys Asp Leu Asn
```

|  |  | 2645 |  |  |  | 2650 |  |  |  | 2655 |  |
|---|---|---|---|---|---|---|---|---|---|---|---|

Ser Cys Ser Met Pro Leu Gly Met Glu Ser Lys Ala Ile Ser Asp
2660 2665 2670

Ala Gln Ile Thr Ala Ser Ser Tyr Phe Thr Asn Met Phe Ala Thr
2675 2680 2685

Trp Ser Pro Ser Lys Ala Arg Leu His Leu Gln Gly Arg Ser Asn
2690 2695 2700

Ala Trp Arg Pro Gln Val Asn Asn Pro Lys Glu Trp Leu Gln Val
2705 2710 2715

Asp Phe Gln Lys Thr Met Lys Val Thr Gly Val Thr Thr Gln Gly
2720 2725 2730

Val Lys Ser Leu Leu Thr Ser Met Tyr Val Lys Glu Phe Leu Ile
2735 2740 2745

Ser Ser Ser Gln Asp Gly His Gln Trp Thr Leu Phe Phe Gln Asn
2750 2755 2760

Gly Lys Val Lys Val Phe Gln Gly Asn Gln Asp Ser Phe Thr Pro
2765 2770 2775

Val Val Asn Ser Leu Asp Pro Pro Leu Leu Thr Arg Tyr Leu Arg
2780 2785 2790

Ile His Pro Gln Ser Trp Val His Gln Ile Ala Leu Arg Met Glu
2795 2800 2805

Val Leu Gly Cys Glu Ala Gln Asp Leu Tyr Arg Lys Thr Thr Cys
2810 2815 2820

Asn Pro Cys Pro Leu Gly Tyr Lys Glu Glu Asn Thr Gly Glu
2825 2830 2835

Cys Cys Gly Arg Cys Leu Pro Thr Ala Cys Thr Ile Gln Leu Arg
2840 2845 2850

Gly Gly Gln Ile Met Thr Leu Lys Arg Asp Glu Thr Leu Gln Asp
2855 2860 2865

Gly Cys Asp Thr His Phe Cys Lys Val Asn Glu Arg Gly Glu Tyr
2870 2875 2880

Phe Trp Glu Lys Arg Val Thr Gly Cys Pro Pro Phe Asp Glu His
2885 2890 2895

Lys Cys Leu Ala Glu Gly Gly Lys Ile Met Lys Ile Pro Gly Thr
2900 2905 2910

Cys Cys Asp Thr Cys Glu Glu Pro Glu Cys Asn Asp Ile Thr Ala
2915 2920 2925

Arg Leu Gln Tyr Val Lys Val Gly Ser Cys Lys Ser Glu Val Glu
2930 2935 2940

Val Asp Ile His Tyr Cys Gln Gly Lys Cys Ala Ser Lys Ala Met
2945 2950 2955

Tyr Ser Ile Asp Ile Asn Asp Val Gln Asp Gln Cys Ser Cys Cys
2960 2965 2970

Ser Pro Thr Arg Thr Glu Pro Met Gln Val Ala Leu His Cys Thr
2975 2980 2985

Asn Gly Ser Val Val Tyr His Glu Val Leu Asn Ala Met Glu Cys
2990 2995 3000

Lys Cys Ser Pro Arg Lys Cys Ser Lys
3005 3010

<210> SEQ ID NO 5
<211> LENGTH: 2154
<212> TYPE: PRT
<213> ORGANISM: Artificial Sequence
<220> FEATURE:
<223> OTHER INFORMATION: VWF-FVIII fusion proteins

<400> SEQUENCE: 5

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr His Lys Phe Ile Leu Leu Phe Ala Val Phe Asp Glu Gly Lys
    210                 215                 220

Ser Trp His Ser Glu Thr Lys Asn Ser Leu Met Gln Asp Arg Asp Ala
225                 230                 235                 240

Ala Ser Ala Arg Ala Trp Pro Lys Met His Thr Val Asn Gly Tyr Val
                245                 250                 255

Asn Arg Ser Leu Pro Gly Leu Ile Gly Cys His Arg Lys Ser Val Tyr
            260                 265                 270

Trp His Val Ile Gly Met Gly Thr Thr Pro Glu Val His Ser Ile Phe
        275                 280                 285

Leu Glu Gly His Thr Phe Leu Val Arg Asn His Arg Gln Ala Ser Leu
    290                 295                 300

Glu Ile Ser Pro Ile Thr Phe Leu Thr Ala Gln Thr Leu Leu Met Asp
305                 310                 315                 320

Leu Gly Gln Phe Leu Leu Phe Cys His Ile Ser Ser His Gln His Asp
                325                 330                 335

Gly Met Glu Ala Tyr Val Lys Val Asp Ser Cys Pro Glu Glu Pro Gln
            340                 345                 350

Leu Arg Met Lys Asn Asn Glu Glu Ala Glu Asp Tyr Asp Asp Asp Leu
        355                 360                 365

Thr Asp Ser Glu Met Asp Val Val Arg Phe Asp Asp Asp Asn Ser Pro
    370                 375                 380

Ser Phe Ile Gln Ile Arg Ser Val Ala Lys Lys His Pro Lys Thr Trp
385                 390                 395                 400
```

```
Val His Tyr Ile Ala Ala Glu Glu Asp Trp Asp Tyr Ala Pro Leu
                405                 410                 415

Val Leu Ala Pro Asp Asp Arg Ser Tyr Lys Ser Gln Tyr Leu Asn Asn
            420                 425                 430

Gly Pro Gln Arg Ile Gly Arg Lys Tyr Lys Lys Val Arg Phe Met Ala
            435                 440                 445

Tyr Thr Asp Glu Thr Phe Lys Thr Arg Glu Ala Ile Gln His Glu Ser
        450                 455                 460

Gly Ile Leu Gly Pro Leu Leu Tyr Gly Glu Val Gly Asp Thr Leu Leu
465                 470                 475                 480

Ile Ile Phe Lys Asn Gln Ala Ser Arg Pro Tyr Asn Ile Tyr Pro His
                485                 490                 495

Gly Ile Thr Asp Val Arg Pro Leu Tyr Ser Arg Arg Leu Pro Lys Gly
            500                 505                 510

Val Lys His Leu Lys Asp Phe Pro Ile Leu Pro Gly Glu Ile Phe Lys
            515                 520                 525

Tyr Lys Trp Thr Val Thr Val Glu Asp Gly Pro Thr Lys Ser Asp Pro
        530                 535                 540

Arg Cys Leu Thr Arg Tyr Tyr Ser Ser Phe Val Asn Met Glu Arg Asp
545                 550                 555                 560

Leu Ala Ser Gly Leu Ile Gly Pro Leu Leu Ile Cys Tyr Lys Glu Ser
                565                 570                 575

Val Asp Gln Arg Gly Asn Gln Ile Met Ser Asp Lys Arg Asn Val Ile
            580                 585                 590

Leu Phe Ser Val Phe Asp Glu Asn Arg Ser Trp Tyr Leu Thr Glu Asn
            595                 600                 605

Ile Gln Arg Phe Leu Pro Asn Pro Ala Gly Val Gln Leu Glu Asp Pro
        610                 615                 620

Glu Phe Gln Ala Ser Asn Ile Met His Ser Ile Asn Gly Tyr Val Phe
625                 630                 635                 640

Asp Ser Leu Gln Leu Ser Val Cys Leu His Glu Val Ala Tyr Trp Tyr
                645                 650                 655

Ile Leu Ser Ile Gly Ala Gln Thr Asp Phe Leu Ser Val Phe Phe Ser
            660                 665                 670

Gly Tyr Thr Phe Lys His Lys Met Val Tyr Glu Asp Thr Leu Thr Leu
            675                 680                 685

Phe Pro Phe Ser Gly Glu Thr Val Phe Met Ser Met Glu Asn Pro Gly
        690                 695                 700

Leu Trp Ile Leu Gly Cys His Asn Ser Asp Phe Arg Asn Arg Gly Met
705                 710                 715                 720

Thr Ala Leu Leu Lys Val Ser Ser Cys Asp Lys Asn Thr Gly Asp Tyr
                725                 730                 735

Tyr Glu Asp Ser Tyr Glu Asp Ile Ser Ala Tyr Leu Leu Ser Lys Asn
            740                 745                 750

Asn Ala Ile Glu Pro Arg Ser Arg His Cys Asp Gly Asn Val Ser Ser
            755                 760                 765

Cys Gly Asp His Pro Ser Glu Gly Cys Phe Cys Pro Pro Asp Lys Val
        770                 775                 780

Met Leu Glu Gly Ser Cys Val Pro Glu Glu Ala Cys Thr Gln Cys Ile
785                 790                 795                 800

Gly Glu Asp Gly Val Gln His Gln Phe Leu Glu Ala Trp Val Pro Asp
                805                 810                 815
```

His Gln Pro Cys Gln Ile Cys Thr Cys Leu Ser Gly Arg Lys Val Asn
                    820                 825                 830

Cys Thr Thr Gln Pro Cys Pro Thr Ala Lys Ala Pro Thr Cys Gly Leu
            835                 840                 845

Cys Glu Val Ala Arg Leu Arg Gln Asn Ala Asp Gln Cys Cys Pro Glu
        850                 855                 860

Tyr Glu Cys Val Cys Asp Pro Val Ser Cys Asp Leu Pro Pro Val Pro
865                 870                 875                 880

His Cys Glu Arg Gly Leu Gln Pro Thr Leu Thr Asn Pro Gly Glu Cys
                885                 890                 895

Arg Pro Asn Phe Thr Cys Ala Cys Arg Lys Glu Glu Cys Lys Arg Val
            900                 905                 910

Ser Pro Pro Ser Cys Pro Pro His Arg Leu Pro Thr Leu Arg Lys Thr
        915                 920                 925

Gln Cys Cys Asp Glu Tyr Glu Cys Ala Cys Asn Cys Val Asn Ser Thr
    930                 935                 940

Val Ser Cys Pro Leu Gly Tyr Leu Ala Ser Thr Ala Thr Asn Asp Cys
945                 950                 955                 960

Gly Cys Thr Thr Thr Thr Cys Leu Pro Asp Lys Val Cys Val His Arg
                965                 970                 975

Ser Thr Ile Tyr Pro Val Gly Gln Phe Trp Glu Glu Gly Cys Asp Val
            980                 985                 990

Cys Thr Cys Thr Asp Met Glu Asp Ala Val Met Gly Leu Arg Val Ala
        995                 1000                1005

Gln Cys Ser Gln Lys Pro Cys Glu Asp Ser Cys Arg Ser Gly Phe
    1010                1015                1020

Thr Tyr Val Leu His Glu Gly Glu Cys Cys Gly Arg Cys Leu Pro
    1025                1030                1035

Ser Ala Cys Glu Val Val Thr Gly Ser Pro Arg Gly Asp Ser Gln
    1040                1045                1050

Ser Ser Trp Lys Ser Val Gly Ser Gln Trp Ala Ser Pro Glu Asn
    1055                1060                1065

Pro Cys Leu Ile Asn Glu Cys Val Arg Val Lys Glu Glu Val Phe
    1070                1075                1080

Ile Gln Gln Arg Asn Val Ser Cys Pro Gln Leu Glu Val Pro Val
    1085                1090                1095

Cys Pro Ser Gly Phe Gln Leu Ser Cys Lys Thr Ser Ala Cys Cys
    1100                1105                1110

Pro Ser Cys Arg Cys Glu Arg Met Glu Ala Cys Met Leu Asn Gly
    1115                1120                1125

Thr Val Ile Gly Pro Gly Lys Ala Leu Lys Gln Phe Arg Leu Pro
    1130                1135                1140

Leu Glu Glu Thr Glu Leu Glu Lys Arg Ile Ile Val Asp Asp Thr
    1145                1150                1155

Ser Thr Gln Trp Ser Lys Asn Met Lys His Leu Thr Pro Ser Thr
    1160                1165                1170

Leu Thr Gln Ile Asp Tyr Asn Glu Lys Glu Lys Gly Ala Ile Thr
    1175                1180                1185

Gln Ser Pro Leu Ser Asp Cys Leu Thr Arg Ser His Ser Ile Pro
    1190                1195                1200

Gln Ala Asn Arg Ser Pro Leu Pro Ile Ala Lys Val Ser Ser Phe
    1205                1210                1215

Pro Ser Ile Arg Pro Ile Tyr Leu Thr Arg Val Leu Phe Gln Asp

-continued

```
                1220                1225                1230
Asn Ser Ser His Leu Pro Ala Ala Ser Tyr Arg Lys Lys Asp Ser
    1235                1240                1245
Gly Val Gln Glu Ser Ser His Phe Leu Gln Gly Ala Lys Lys Asn
    1250                1255                1260
Asn Leu Ser Leu Ala Ile Leu Thr Leu Glu Met Thr Gly Asp Gln
    1265                1270                1275
Arg Glu Val Gly Ser Leu Gly Thr Ser Ala Thr Asn Ser Val Thr
    1280                1285                1290
Tyr Lys Lys Val Glu Asn Thr Val Leu Pro Lys Pro Asp Leu Pro
    1295                1300                1305
Lys Thr Ser Gly Lys Val Glu Leu Leu Pro Lys Val His Ile Tyr
    1310                1315                1320
Gln Lys Asp Leu Phe Pro Thr Glu Thr Ser Asn Gly Ser Pro Gly
    1325                1330                1335
His Leu Asp Leu Val Glu Gly Ser Leu Leu Gln Gly Thr Glu Gly
    1340                1345                1350
Ala Ile Lys Trp Asn Glu Ala Asn Arg Pro Gly Lys Val Pro Phe
    1355                1360                1365
Leu Arg Val Ala Thr Glu Ser Ser Ala Lys Thr Pro Ser Lys Leu
    1370                1375                1380
Leu Asp Pro Leu Ala Trp Asp Asn His Tyr Gly Thr Gln Ile Pro
    1385                1390                1395
Lys Glu Glu Trp Lys Ser Gln Glu Lys Ser Pro Glu Lys Thr Ala
    1400                1405                1410
Phe Lys Lys Lys Asp Thr Ile Leu Ser Leu Asn Ala Cys Glu Ser
    1415                1420                1425
Asn His Ala Ile Ala Ala Ile Asn Glu Gly Gln Asn Lys Pro Glu
    1430                1435                1440
Ile Glu Val Thr Trp Ala Lys Gln Gly Arg Thr Glu Arg Leu Cys
    1445                1450                1455
Ser Gln Asn Pro Pro Val Leu Lys Arg His Gln Arg Glu Ile Thr
    1460                1465                1470
Arg Thr Thr Leu Gln Ser Asp Gln Glu Glu Ile Asp Tyr Asp Asp
    1475                1480                1485
Thr Ile Ser Val Glu Met Lys Lys Glu Asp Phe Asp Ile Tyr Asp
    1490                1495                1500
Glu Asp Glu Asn Gln Ser Pro Arg Ser Phe Gln Lys Lys Thr Arg
    1505                1510                1515
His Tyr Phe Ile Ala Ala Val Glu Arg Leu Trp Asp Tyr Gly Met
    1520                1525                1530
Ser Ser Ser Pro His Val Leu Arg Asn Arg Ala Gln Ser Gly Ser
    1535                1540                1545
Val Pro Gln Phe Lys Lys Val Val Phe Gln Glu Phe Thr Asp Gly
    1550                1555                1560
Ser Phe Thr Gln Pro Leu Tyr Arg Gly Glu Leu Asn Glu His Leu
    1565                1570                1575
Gly Leu Leu Gly Pro Tyr Ile Arg Ala Glu Val Glu Asp Asn Ile
    1580                1585                1590
Met Val Thr Phe Arg Asn Gln Ala Ser Arg Pro Tyr Ser Phe Tyr
    1595                1600                1605
Ser Ser Leu Ile Ser Tyr Glu Glu Asp Gln Arg Gln Gly Ala Glu
    1610                1615                1620
```

-continued

```
Pro Arg Lys Asn Phe Val Lys Pro Asn Glu Thr Lys Thr Tyr Phe
    1625            1630                1635

Trp Lys Val Gln His His Met Ala Pro Thr Lys Asp Glu Phe Asp
    1640            1645                1650

Cys Lys Ala Trp Ala Tyr Phe Ser Asp Val Asp Leu Glu Lys Asp
    1655            1660                1665

Val His Ser Gly Leu Ile Gly Pro Leu Leu Val Cys His Thr Asn
    1670            1675                1680

Thr Leu Asn Pro Ala His Gly Arg Gln Val Thr Val Gln Glu Phe
    1685            1690                1695

Ala Leu Phe Phe Thr Ile Phe Asp Glu Thr Lys Ser Trp Tyr Phe
    1700            1705                1710

Thr Glu Asn Met Glu Arg Asn Cys Arg Ala Pro Cys Asn Ile Gln
    1715            1720                1725

Met Glu Asp Pro Thr Phe Lys Glu Asn Tyr Arg Phe His Ala Ile
    1730            1735                1740

Asn Gly Tyr Ile Met Asp Thr Leu Pro Gly Leu Val Met Ala Gln
    1745            1750                1755

Asp Gln Arg Ile Arg Trp Tyr Leu Leu Ser Met Gly Ser Asn Glu
    1760            1765                1770

Asn Ile His Ser Ile His Phe Ser Gly His Val Phe Thr Val Arg
    1775            1780                1785

Lys Lys Glu Glu Tyr Lys Met Ala Leu Tyr Asn Leu Tyr Pro Gly
    1790            1795                1800

Val Phe Glu Thr Val Glu Met Leu Pro Ser Lys Ala Gly Ile Trp
    1805            1810                1815

Arg Val Glu Cys Leu Ile Gly Glu His Leu His Ala Gly Met Ser
    1820            1825                1830

Thr Leu Phe Leu Val Tyr Ser Asn Lys Cys Gln Thr Pro Leu Gly
    1835            1840                1845

Met Ala Ser Gly His Ile Arg Asp Phe Gln Ile Thr Ala Ser Gly
    1850            1855                1860

Gln Tyr Gly Gln Trp Ala Pro Lys Leu Ala Arg Leu His Tyr Ser
    1865            1870                1875

Gly Ser Ile Asn Ala Trp Ser Thr Lys Glu Pro Phe Ser Trp Ile
    1880            1885                1890

Lys Val Asp Leu Leu Ala Pro Met Ile Ile His Gly Ile Lys Thr
    1895            1900                1905

Gln Gly Ala Arg Gln Lys Phe Ser Ser Leu Tyr Ile Ser Gln Phe
    1910            1915                1920

Ile Ile Met Tyr Ser Leu Asp Gly Lys Lys Trp Gln Thr Tyr Arg
    1925            1930                1935

Gly Asn Ser Thr Gly Thr Leu Met Val Phe Phe Gly Asn Val Asp
    1940            1945                1950

Ser Ser Gly Ile Lys His Asn Ile Phe Asn Pro Pro Ile Ile Ala
    1955            1960                1965

Arg Tyr Ile Arg Leu His Pro Thr His Tyr Ser Ile Arg Ser Thr
    1970            1975                1980

Leu Arg Met Glu Leu Met Gly Cys Asp Leu Asn Ser Cys Ser Met
    1985            1990                1995

Pro Leu Gly Met Glu Ser Lys Ala Ile Ser Asp Ala Gln Ile Thr
    2000            2005                2010
```

```
Ala Ser Ser Tyr Phe Thr Asn Met Phe Ala Thr Trp Ser Pro Ser
    2015            2020                2025

Lys Ala Arg Leu His Leu Gln Gly Arg Ser Asn Ala Trp Arg Pro
    2030            2035                2040

Gln Val Asn Asn Pro Lys Glu Trp Leu Gln Val Asp Phe Gln Lys
    2045            2050                2055

Thr Met Lys Val Thr Gly Val Thr Thr Gln Gly Val Lys Ser Leu
    2060            2065                2070

Leu Thr Ser Met Tyr Val Lys Glu Phe Leu Ile Ser Ser Ser Gln
    2075            2080                2085

Asp Gly His Gln Trp Thr Leu Phe Phe Gln Asn Gly Lys Val Lys
    2090            2095                2100

Val Phe Gln Gly Asn Gln Asp Ser Phe Thr Pro Val Val Asn Ser
    2105            2110                2115

Leu Asp Pro Pro Leu Leu Thr Arg Tyr Leu Arg Ile His Pro Gln
    2120            2125                2130

Ser Trp Val His Gln Ile Ala Leu Arg Met Glu Val Leu Gly Cys
    2135            2140                2145

Glu Ala Gln Asp Leu Tyr
    2150
```

SEPARATION OF VWF AND VWF PROPEPTIDE BY CHROMATOGRAPHIC METHODS

CROSS REFERENCE TO RELATED APPLICATIONS

This application claims priority to U.S. Provisional No. 62/646,109, filed on Mar. 21, 2018, which is hereby incorporated by reference in its entirety.

FIELD OF THE INVENTION

The present invention relates to methods for separating mature von Willebrand Factor VWF) from von Willebrand Factor pro-peptide (VWF-PP).

BACKGROUND OF THE INVENTION

In the course of protein maturation within a cell, the protein to be matured undergoes posttranslational modifications. These modifications include among others acetylation, methylation, glycosylation and proteolytic cleavage. These modifications are in many cases necessary for the protein function and activity and they may also influence the efficiency of proteins, in particular of enzymes.

Pro-proteins or protein precursors are inactive proteins that are turned into an active form by one or more of these post-translational modifications, in particular, by the cleavage of a pro-peptide from the pro-protein.

The active form of these proteins may be useful therapeutic and/or diagnostic proteins. However, the active proteins are usually available at very low amounts in living organisms. As such, the active proteins are produced recombinantly from their pro-proteins which are preferably activated in vitro by contacting them with recombinant activation enzymes (e.g., proteases).

von Willebrand Factor (VWF) is a glycoprotein circulating in plasma as a series of multimers ranging in size from about 500 to 20,000 kD. The full length of cDNA of VWF has been cloned; the propolypeptide corresponds to amino acid residues 23 to 764 of the full length prepro-VWF (Eikenboom et al (1995) Haemophilia, 1, 77-90). Multimeric forms of VWF are composed of 250 kD polypeptide subunits linked together by disulfide bonds. VWF mediates the initial platelet adhesion to the sub-endothelium of the damaged vessel wall, with the larger multimers exhibiting enhanced hemostatic activity. Multimerized VWF binds to the platelet surface glycoprotein Gp1bα, through an interaction in the A1 domain of VWF, facilitating platelet adhesion. Other sites on VWF mediate binding to the blood vessel wall. Thus, VWF forms a bridge between the platelet and the vessel wall that is essential to platelet adhesion and primary hemostasis under conditions of high shear stress. Normally, endothelial cells secrete large polymeric forms of VWF and those forms of VWF that have a lower molecular weight arise from proteolytic cleavage. The multimers of exceptionally large molecular masses are stored in the Weibel-Pallade bodies of the endothelial cells and liberated upon stimulation by agonists such as thrombin and histamine.

Industrially, VWF, in particular recombinant VWF (rVWF), is synthesized and expressed together with rFVIII in a genetically engineered cell lines, such as an engineered CHO cell line. The function of the co-expressed rVWF is to stabilize rFVIII in the cell culture process. rVWF is synthesized in the cell as pre-propeptide VWF (prepro-VWF), containing a large pro-peptide (VWF-PP) attached to the N-terminus of the mature VWF (matVWF) subunit. Upon maturation in the endoplasmatic reticulum and Golgi apparatus, the VWF-PP is cleaved off by the action of the cellular protease furin and is secreted as a homopolymer of identical subunits, consisting of dimers of the expressed protein. In some cases, furin cleavage produces a heterodimeric complex comprising a mature VWF non-covalently associated with a VWF pro-peptide.

VWF-PP can be separated from mature VWF by in vitro treatment with furin or furin-like proteases (Schlokat U. et al. (1996) Biotechnol. Appl. Biochem. 24:257-267; Preininger A. et al. (1999) Cytotechnology 30:1-15). Furin belongs to the family of the pro-protein convertases and is dependent on $Ca^{2+}$. This enzyme specifically cleaves the C-terminal peptide bond of arginine within a specific sequence, containing arginine at positions −1 and −4. This sequence can be found in numerous human proteins, showing that furin plays a major role in the maturation of a number of human pro-peptide-proteins. Furin used in the method of the present invention is preferably of recombinant origin. Recombinantly produced proteases are advantageously employed because they can be produced in high quantities. In some embodiments, furin is obtained from crude cell culture supernatant of a cell line secreting said protease or cell extract.

Current conventional methods produce mature VWF by either incubating the pre-propeptide VWF with proteases in a liquid phase whereby the maturation itself (e.g., the cleavage of the pro-peptide from the pro-protein) occurs in an unbound state in free solution, or as described for example in WO2000/049047, by immobilizing the protease on a solid carrier, which is contacted and incubated with a preparation comprising VWF-PP (see, e.g., WO2000/049047). VWF is synthesized by endothelial cells and megakaryocytes as pre-propeptide VWF ("prepro-VWF") that consists to a large extent of repeated domains. Upon cleavage of the signal peptide, prepro-VWF dimerizes through disulfide linkages at the carboxy-terminus region in the endoplasmic reticulum. Additional disulfide linkages are formed near the amino-terminus of the subunits to form multimers in the Golgi. The assembly to multimers is followed by the proteolytic cleavage of the VWF propeptide by the pro-peptide processing protease furin. After cleavage, the VWF pro-peptide remains non-covalently associated with the VWF multimer to form a mature VWF/VWF-PP complex. Upon stimulation, the complex is secreted into the blood and the VWF pro-peptide dissociates from the VWF multimers. Therapeutically effective mature VWF multimers can be produced by recombinantly expressing pro-VWF in mammalian cell lines and processing the pro-VWF protein to mature VWF through a series of in vitro cleavage and purification steps. However, there remains a need in the art for producing high purity, therapeutically effective mature VWF multimer preparations (mat-rVWF) and the present invention meets this need by providing methods for obtaining high purity, mat-rVWF preparations, where the method comprises, for example, after furin maturation, the addition of a chelating agent and/or increasing the pH to a pH of at least 7 during the purification process to facilitate separation of the VWF-propeptide from mat-rVWF.

BRIEF SUMMARY OF THE INVENTION

The present invention provides a method for obtaining a composition comprising a high purity, propeptide depleted mature recombinant rVWF (mat-rVWF), said method comprising the steps of:

a) providing a solution comprising mat-rVWF/rVWF-PP complex, mat-rVWF, and rVWF propeptide (rVWF-PP);
b) inducing dissociation of said mat-rVWF/rVWF-PP complex in said solution in a) into mat-rVWF and rVWF-PP, wherein said dissociation occurs by disruption of the non-covalently associated mat-rVWF and rVWF-PP, wherein said dissociation is induced by:
   i. addition of at least one chelating agent, or
   ii. increasing the pH to a pH of at least 7; and
c) collecting said mat-rVWF to obtain a high purity, mat-rVWF composition, wherein said high purity, mat-rVWF composition comprises at least 95% mature rVWF and less than 5% rVWF-PP.

In some embodiments, the high purity, mat-rVWF composition comprises at least 96% mat-rVWF and less than 4% rVWF-PP, at least 97% mat-rVWF and less than 3% rVWF-PP, at least 98% mat-rVWF and less than 2% rVWF-PP, at least 99% mat-rVWF and less than 1% rVWF-PP, or at least 99.5% mat-rVWF and less than 0.5% rVWF-PP, or 99.9% mat-rVWF and less than 0.1% rVWF-PP.

In some embodiments, the solution is selected from the group consisting of a cell culture medium, an antibody column flow-through solution, and a buffered solution.

In some embodiments, the solution has been treated with furin prior to step a).

In some embodiments, the solution is an antibody column flow-through solution.

In some embodiments, the at least one chelating agent is a divalent cation chelating agent. In some embodiments, the divalent cation chelating agent is selected from the group consisting of EDTA, EGTA, CDTA, and citrate.

In some embodiments, the pH is increased to at least 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. In some embodiments, the pH is increased to at least about 7.2 to about 7.8. In some embodiments, the pH is increased to at least about 7.6. In some embodiments, the pH is increased by the addition of basic amino acids, Tris, NaOH, Tricine, or ethanolamine.

In some embodiments, the collecting in step b) of the method described herein comprises one or more protein separation methods. In some embodiments, the one or more protein separation methods is selected from the group consisting of ion exchange chromatography (IEC), size exclusion chromatography (SEC), physical size separation by membrane technology, and affinity chromatography. In some embodiments, the protein separation method is size exclusion chromatography (SEC). In some embodiments, the one or more protein separation method is ion exchange chromatography (IEC). In some embodiments, the ion exchange chromatography (IEC) is cation exchange chromatography. In some embodiments, the ion exchange chromatography (IEC) is a combination of anion exchange chromatography and cation exchange chromatography.

In some embodiments, the one or more protein separation methods comprise a buffer system, wherein said buffer system comprises one or more buffers. In some embodiments, the said one or more buffers includes wash buffers, wherein said one or more wash buffers include one, two, three, four, and/or five wash buffers, wherein when said one or more buffers includes five wash buffers, the first, second, third, and/or fifth wash buffers have a higher pH than the fourth wash buffer, and when said one or more buffers includes four wash buffers, the first, second, and/or fourth wash buffers have a higher pH than the third wash buffer. In some embodiments, the method further comprises a viral inactivation treatment step after the first wash buffer, and optionally the pH of the viral inactivation treatment step has a higher pH than said third and/or fourth wash buffer. In some embodiments, the one or more buffers comprise said one or more chelating agents. In some embodiments, the one or more buffers exhibit a pH of at least 7.

In some embodiments, the or more protein separation methods comprise a buffer system, wherein said buffer system comprises one or more loading buffers. In some embodiments, the one or more loading buffers comprise said one or more chelating agents. In some embodiments, the one or more loading buffers exhibit a pH of at least 7.

In some embodiments, the one or more protein separation methods comprise a buffer system, wherein said buffer system comprises one or more load, wash, and/or elution buffers. In some embodiments, the one or more load, wash, and/or elution buffers comprise said one or more chelating agents. In some embodiments, the one or more load, wash, and/or elution buffers exhibit a pH of at least 7. In some embodiments, the one or more load, wash, and/or elution buffers comprise said one or more chelating agents and exhibit a pH of at least 7.

In some embodiments, the buffering system is selected from the group consisting of glycine HEPES (4-(2-hydroxyethyl)-1-piperazineethanesulfonic acid), TrisHCl (Tris(hydroxymethyl)-aminomethane), histidine, imidazole, acetate citrate, MES, and 2-(N-morpholino)ethanesulfonic acid.

In some embodiments, the buffer further comprises one or more monovalent cations. In some embodiments, the one or more monovalent cations are selected from the group consisting of Na+, K+, Li+, and Cs+. In some embodiments, the monovalent cation is Na+.

In some embodiments, the buffer further comprises one or more monovalent, divalent and/or trivalent anions. In some embodiments, the one or more monovalent, divalent and/or trivalent anions are selected from the group consisting of $Cl^-$, $acetate^-$, $SO_4^{2-}$, $Br^-$, and $citrate^{3-}$.

In some embodiments, the buffer system comprises at least one buffer exhibiting a conductivity of ≥0.5 mS/cm at 25° C. In some embodiments, the buffer system comprises at least one buffer exhibiting a conductivity of 15.0±0.2 mS/cm at 25° C.

In some embodiments, the buffer further comprises one or more nonionic detergents. In some embodiments, the nonionic detergent is selected from the group consisting of Triton X100, Tween 80, and Tween 20.

In some embodiments, the buffer further comprises one or more additional substances selected from the group consisting of non-reducing sugars, sugar alcohols, and polyols.

In some embodiments, the high purity mat-rVWF composition comprises a host cell (HC) impurity level of ≤2.0%. In some embodiments, the high purity, mat-rVWF composition comprises a host cell (HC) impurity level of ≤0.6%.

In some embodiments, the solution comprising mat-rVWF/rVWF-PP complex, mat-rVWF, and rVWF-PP is derived from a capture step for rVWF.

In some embodiments, the solution comprising mat-rVWF/rVWF-PP complex, mat-rVWF, and rVWF-PP is derived from a method comprising a FVIII immunoaffinity step and anion exchange chromatography step.

The present invention als provides a method for obtaining a composition comprising a high purity, propeptide depleted mature recombinant rVWF (high purity mat-rVWF), said method comprising the steps of:
a) loading a solution comprising pro-rVWF, mat-rVWF/rVWF-PP complex, mat-rVWF, and/or rVWF propeptide (rVWF-PP) onto an anion exchange column, wherein said pro-rVWF, mat-rVWF/rVWF-PP complex, and mat-rVWF are bound to said anion exchange column;
b) washing said anion exchange column in a) containing said bound pro-rVWF, mat-rVWF/rVWF-PP complex, and mat-rVWF with one or more wash buffers;
c) treating said column in b) comprising the bound pro-rVWF, mat-rVWF/rVWF-PP complex, and mat-rVWF with furin, wherein said furin cleaves said pro-rVWF into mat-rVWF and rVWF-PP;
d) eluting said bound pro-rVWF, mat-rVWF/rVWF-PP complex, and mat-rVWF from the column in c) with an elution buffer, wherein said elution buffer induces dissociation of said rVWF-PP from mat-rVWF non-covalently associated with said rVWF-PP, and wherein said dissociation is induced by:
  i. addition of at least one chelating agent into said elution buffer, or
  ii. increasing the pH of said elution buffer to a pH of at least 7; and
e) collecting said mat-rVWF separately from said rVWF-PP to obtain a high purity mat-rVWF composition, wherein said high purity mat-rVWF composition comprises at least 95% mature rVWF and less than 5% rVWF-PP.

In some embodiments, a) and b) occur simultaneously in a single step.

In some embodiments, the said one or more buffers includes wash buffers, wherein said one or more wash buffers include one, two, three, four, and/or five wash buffers, wherein when said one or more buffers includes five wash buffers, the first, second, third, and/or fifth wash buffers have a higher pH than the fourth wash buffer, and when said one or more buffers includes four wash buffers, the first, second, and/or fourth wash buffers have a higher pH than the third wash buffer. In some embodiments, the method further comprises a viral inactivation treatment step after the first wash buffer, and optionally the pH of the viral inactivation treatment step has a higher pH than said third and/or fourth wash buffer.

In some embodiments, the solution in a) comprises the flow through from a monoclonal antibody column, wherein said monoclonal antibody is a FVIII monoclonal antibody.

In some embodiments, the solution in a) is selected from the group consisting of a cell culture medium, an antibody column flow-through solution, and a buffered solution.

In some embodiments, the at least one chelating agent is a divalent cation chelating agent. In some embodiments, the divalent cation chelating agent is selected from the group consisting of EDTA, EGTA, CDTA, and citrate.

In some embodiments, the pH is increased to at least 7.1, 7.2, 7.3, 7.4, 7.5, 7.6, 7.7, 7.8, 7.9, or 8.0. In some embodiments, the pH is increased to at least about 7.2 to about 7.8. In some embodiments, the pH is increased to at least about 7.6. In some embodiments, the pH is increased by the addition of basic amino acids. In some embodiments, the one or more wash buffers in b) comprise said one or more chelating agents. In some embodiments, the one or more wash buffers in b) exhibit a pH of at least 7. In some embodiments, the one or more wash buffers in b) comprise said one or more chelating agents and exhibit a pH of at least 7.

In some embodiments, the method further comprises a step of viral inactivation, wherein said viral inactivation occurs before, after, or concurrently with the washing step and/or the elution step, but before the collecting step. In some embodiments, the viral inactivation treatment inactivates lipid enveloped viruses. In some embodiments, the viral inactivation treatment is a solvent and detergent (S/D) treatment.

In some embodiments, the one or more buffers comprise a buffer selected from the group consisting of glycine HEPES (4-(2-hydroxyethyl)-1-piperazineethanesulfonic acid), TrisHCl (Tris(hydroxymethyl)-aminomethane), histidine, imidazole, acetate citrate, MES, and 2-(N-morpholino) ethanesulfonic acid.

In some embodiments, the one or more buffers further comprise one or more monovalent cations. In some embodiments, the one or more monovalent cations are selected from the group consisting of Na+, K+, Li+, and Cs+. In some embodiments, the monovalent cation is Na+.

In some embodiments, the one or more buffers further comprise one or more monovalent, divalent, and/or trivalent anions. In some embodiments, the one or more monovalent, divalent and/or trivalent anions are selected from the group consisting of Cl⁻, acetate⁻, $SO_4^{2-}$, Br⁻, and citrate³⁻.

In some embodiments, the one or more buffers comprise at least one buffer exhibiting a conductivity of ≥0.5 mS/cm at 25° C. In some embodiments, the one or more buffers comprise at least one buffer exhibiting a conductivity of 15.0±0.2 mS/cm at 25° C.

In some embodiments, the one or more buffers further comprise one or more nonionic detergents. In some embodiments, the nonionic detergent is selected from the group consisting of Triton X100, Tween 80, and Tween 20.

In some embodiments, the said one or more buffers further comprise one or more additional substances selected from the group consisting of non-reducing sugars, sugar alcohols, and polyols.

In some embodiments, the high purity mat-rVWF composition comprises a host cell (HC) impurity level of ≤2.0%. In some embodiments, the high purity mat-rVWF composition comprises a host cell (HC) impurity level of ≤0.6%.

In some embodiments, the high purity mat-rVWF composition is used for the production of a pharmaceutical composition.

The present invention further provides a pharmaceutical composition comprising high purity mat-rVWF generated by the method according to any of the preceding claims and a pharmaceutically acceptable buffer. In some embodiments, the pharmaceutical composition comprises 50 mM Glycine, 10 mM Taurine, 5% (w/w) Sucrose, 5% (w/w) D-Mannitol, 0.1% Polysorbate 80, 2 mM $CaCl_2$, 150 mM NaCl, wherein said composition has a pH of about pH 7.4.

Other objects, advantages and embodiments of the invention will be apparent from the detailed description following.

BRIEF DESCRIPTION OF THE DRAWINGS

FIG. 2 provides a table of the purification results.

FIG. 6 provides a table of the reagents used and a table of the results for Example 2.

FIG. 9 shows a western blot illustrating the separation of rVWF and rVWF propeptide by the method of Example 2 and Example 3.

FIG. 11 provides a table of the results for Example 4.

FIG. 12 shows a silver stained protein gel and a western blot illustrating the separation of mat-rVWF and rVWF propeptide (rVWF-PP) by the method of Example 4.

FIG. 14 provides a table of the results for Example 5.

FIG. 16 provides a table of the results for Example 6.

FIG. 18 provides a table of the results for Example 7.

FIG. 20 provides a table of the results for Example 8.

FIG. 21 shows a silver stained protein gel illustrating the separation of mat-rVWF and rVWF propeptide (rVWF-PP) by the method of Example 8.

FIG. 22 shows a western blot illustrating the separation of rVWF and rVWF propeptide by the method of Example 8. The 1% agarose gel shows the multimeric pattern of the products.

FIG. 25 provides a table of the results for Example 9.

FIG. 26 provides a table of the products for Example 9.

FIG. 28 shows a western blot illustrating the separation of rVWF and rVWF propeptide by the method of Example 9. The 1% agarose gel shows the multimeric pattern of the products.

FIG. 30 shows the purity of the product containing fractions obtained for enhanced cation exchange chromatography (CEX) as used for Examples 1, 2, 3, 6, 8, and 9.

FIG. 31 shows the depletion factor of product related impurities for Examples 1, 2, 3, 6, 8, and 9.

FIG. 32 shows the purity of the product containing fractions obtained for enhanced size exclusion chromatography (SEC) as used for Examples 4 and 5.

FIG. 33 shows the depletion factor of product related impurities for Examples 4 and 5.

FIG. 34 shows the buffer formulations and materials used in the TMAE separation method.

FIG. 35 shows the loading conditions for the furin-processed mature VWF/VWF-propeptide complex.

FIG. 36 shows the details of the buffers, conditions, parameters, and flow rates of the chromatography method.

FIG. 40 provides a table highlighting some of the advantages of the cation exchange chromatography method described herein.

FIG. 42 provides a table highlighting some of the advantages of the optimized SEC buffer (SQC buffer). The SQC buffer includes at least one chelating agent and was shown to reduce the amount of VWF-PP in the purified mature VWF fraction.

FIG. 43A shows the currently used process. FIG. 43B shows the process described herein which includes an improved CAT (UNO_S) step.

FIG. 44 provides a table of the chromatography hardware of step CAT in the first generation (Gen 1) process and the second generation (Gen 2) process.

FIG. 45 depicts a table of wash and elution conditions of the Gen 2 process.

FIG. 46 shows a comparison table of the $1^{st}$ and $2^{nd}$ generation rVWF small scale polishing steps on UNO_Sphere S (step CAT).

FIG. 47 depicts a table of the cleaning and sanitization procedure for the UNO_Sphere S column.

FIG. 48 depicts a table of the composition of buffers for the CAT polishing step.

FIG. 49A shows the entire chromatogram, including the CIP procedure. FIG. 49B depicts the 36% buffer B wash and the gradient elution phase. The UV absorption is shown in blue (280 nm) and magenta (254 nm).

FIG. 52 shows rVWF:Ag data of the different runs of the study.

FIG. 53 shows rVWF Risto Co activity data of the different runs of the study.

FIG. 54 shows pro-peptide concentration (pro-peptide (µg/mg rVWF:Ag)) data of the different runs of the study.

FIG. 55 shows pro-peptide concentration (pro-peptide (µg PP/1000 U Risto)) data of the different runs of the study.

FIG. 56 shows analytical key results in the eluate pools of the different runs of the study.

FIG. 57 shows the targeted CAT-E criteria for a successful method development.

FIG. 58 provides exemplary embodiments of the anion exchange, cation exchange, and size exclusion chromatography methods for us in separation of mat-rVWF and rVWF-PP.

FIG. 59 shows the various VWF forms: pro-VWF (also referred to as pro-rVWF), matVWF/VWF-PP complex (also referred to as mat-rVWF/VWF-PP complex), matVWF (also referred to as mat-rVWF), and VWF-PP (also referred to as rVWF-PP).

FIG. 60A-60S shows VWF nucleic acid and amino acid sequences.

FIG. 61 shows the DF3338/042 western blot and raw data for analysis.

FIG. 62 shows the DF3362/023 western blot and raw data for analysis.

FIG. 63 shows the comparison of the data from FIG. 61 and FIG. 62.

FIG. 64A-64C shows the amino acid sequence for an exemplary VWF FVIII fusion protein wherein an active FVIII is embedded in an VWF motif (VWF 764 to 1336-FVIII heavy chain 24 to 760-VWF 2218 to 2593-FVIII light chain 1333 to 2351-VWF 2620 to 2813).

FIG. 65A-65C shows the amino acid sequence for an exemplary VWF-FVIII fusion protein wherein the n-glycosylation rich domain replaces the FVIII-B-domain (FVIII heavy chain 19 to 760-vWF 2218 to 2593-FVIII light chain 1333 to 2351).

FIG. 66 depicts a table of buffers and compositions used in the variant vWF purification process described in Example 14.

FIG. 68 shows analytical key results of the run.

Figure 1:
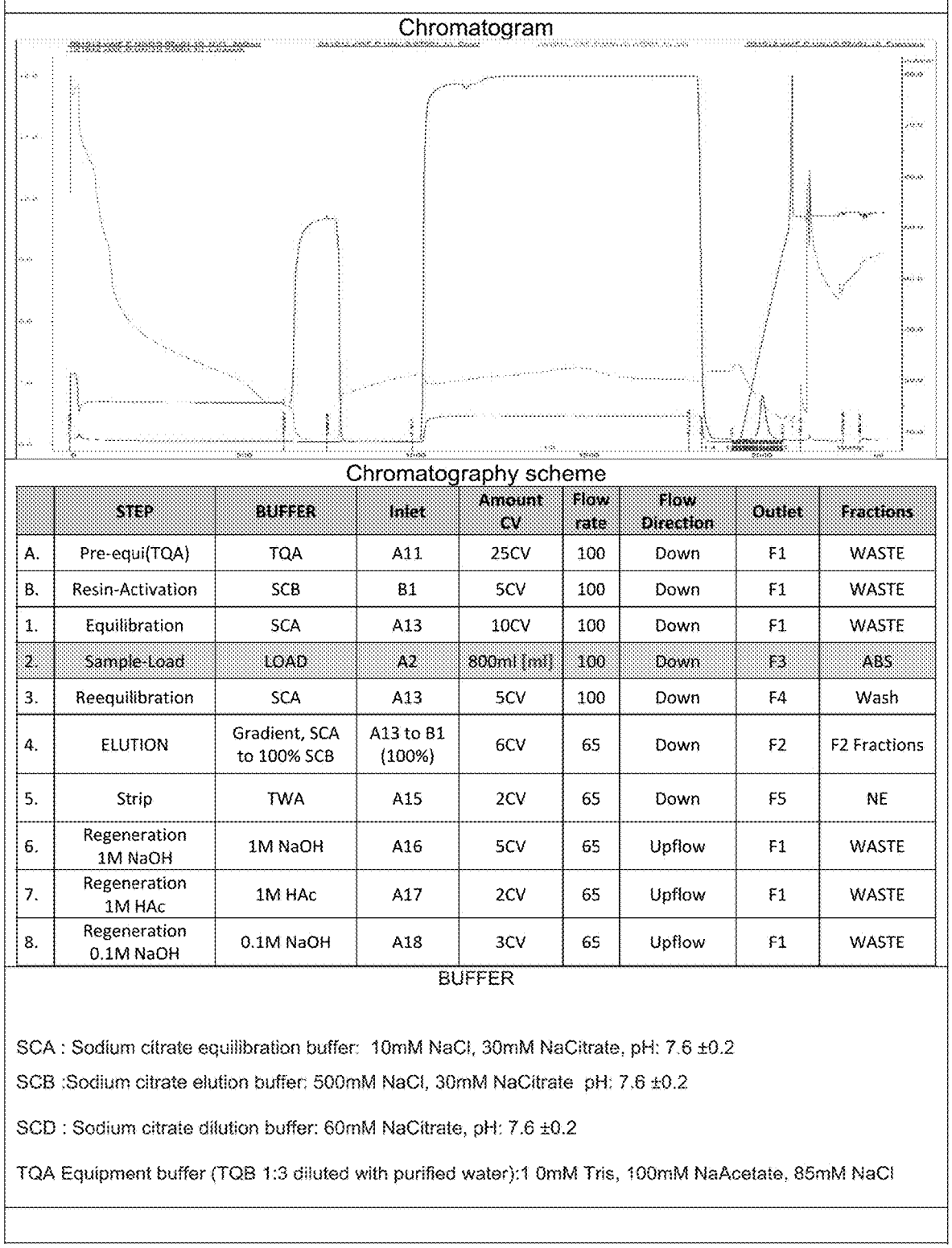
FIG. 1 shows purification of maturated rVWF on a cation exchanger as represented in Example 1.

The term "VWF complex" or "mat-VWF/VWF-PP complex" refers to a non-covalently linked heterodimeric structure comprising a mature VWF subunit and VWF propeptide. The VWF complex can be generated as a product of furin cleavage between the propeptide portion and mature VWF portion of the pre-propeptide VWF. When "r" is included prior to the VWF designation, this refers to the recombinant version. In some embodiments, the methods described herein apply to recombinant VWF (rVWF).

The term "mature VWF" or "mat-VWF," refers to a mature VWF subunit of about 2050 amino acid residues. A mature VWF subunit can be part of a pre-propeptide VWF or a VWF complex. Mature VWF can be referred to as "free VWF" upon separation (isolation) from a VWF propeptide. When "r" is included prior to the VWF designation, this refers to the recombinant version. In some embodiments, the methods described herein apply to recombinant VWF (rVWF).

The term "VWF propeptide" or "VWF-PP," refers to a VWF propeptide of about 741 amino acid residues. A VWF propeptide can be part of a pre-propeptide VWF or a VWF complex. For instance, in a VWF complex a VWF propeptide is non-covalently associated with a mature VWF subunit. A VWF propeptide can be referred to as "free VWF propeptide" upon separation (isolation) from a mature VWF. When "r" is included prior to the VWF designation, this refers to the recombinant version. In some embodiments, the methods described herein apply to recombinant VWF (rVWF).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. VWF is the predominant species present in a preparation is substantially purified. The term "purified" in some embodiments denotes that a nucleic acid or protein gives rise to essentially one band in an electrophoretic gel. In other embodiments, it means that the nucleic acid or protein is at least 50% pure, more preferably at least 60%, 65%, 70%, 75%, 80%, 85%, 90%, 95%, 96%, 97%, 98%, 99% or more pure. "Purify" or "purification" in other embodiments means removing at least one contaminant from the composition to be purified. In this sense, purification does not require that the purified compound be homogenous, e.g., 100% pure.

As used herein, the term "about" denotes an approximate range of plus or minus 10% from a specified value. For instance, the language "about 20%" encompasses a range of 18-22%.

III. Detailed Description of Embodiments

The present invention relates to a method for obtaining a highly pure composition comprising free mature recombinant von Willebrand Factor (rVWF) comprising the steps: dissociating mature rVWF from rVWF pro-peptide using a solution (e.g., dissociation solution) comprising at least one chelating agent or having a pH of at least 7; separating the free mature rVWF from the rVWF pro-peptide; and collecting the free mature rVWF composition comprising at least 95% free mature rVWF and less than 5% rVWF pro-peptide.

The method of the present invention is particularly suited for the in vitro separation of mature VWF from its VWF propeptide. In some embodiments, the separation is induced by adding one or more chelating agents to a solution comprising mature VWF and VWF-PP, increasing the pH of the solution to at least 7.0, or a combination thereof. In some embodiments, the pH is increased to a range from pH 7.0 to pH 9.0.

The separation method may include using one or more protein separation methods, such as, but not limited to, chromatographic methods for isolating mature VWF from VWF-PP. The method can produce a high purity, free mature rVWF composition. In some embodiments, the free mature rVWF composition comprises at least 95% free mature rVWF and less than 5% free rVWF-PP and/or matVWF/VWF-PP complex. In some cases, the free mature rVWF composition comprises at least 96% free mature rVWF and less than 4% free rVWF-PP and/or matVWF/VWF-PP complex, at least 97% free mature rVWF and less than 3% free rVWF-PP and/or matVWF/VWF-PP complex, at least 98% free mature rVWF and less than 2% free rVWF-PP and/or matVWF/VWF-PP complex, at least 99% free mature rVWF and less than 1% free rVWF-PP and/or matVWF/VWF-PP complex, at least 99.5% free mature rVWF and less than 0.5% free rVWF-PP and/or matVWF/VWF-PP complex.

a. Anion Exchange Chromatography Purification

In one aspect of the present method, mature rVWF (mat-rVWF) is separated from rVWF-PP using anion exchange (AEX) chromatography. In some cases, remaining host cell derived impurities such as CHO host cell proteins, process related impurities such as recombinant furin and low molecular weight viral inactivation reagents, media compounds such as soy peptone, and other product related impurities are removed from the mature VWF In another aspect of the present method, mature rVWF is separated from rVWF-PP such as residual rVWF-PP or free rVWF-PP using anion exchange chromatography. For separation, the starting composition, loading solution, or loading composition can comprise a low pH and at least one chelating agent. The loading composition can be applied to an anion exchanger operated in flow through mode. In some embodiments, the loading solution comprises pro-rVWF, mat-rVWF/rVWF-PP complex, mat-rVWF, and/or rVWF propeptide (rVWF-PP). In some embodiments, the anion exchanger is operated in binding mode and mature VWF and VWF-PP are separated using a gradient elution buffer comprising at least one chelating agent. In other embodiments, the gradient elution buffer has a neutral to high pH, such as a pH ranging from pH 6.0 to pH 9.0. In another embodiment, the gradient elution buffer comprises one or more chelating agents and has a pH of 7.0 or higher, e.g., pH 7.0 to pH 9.0. For instance, the gradient elution buffer can include EDTA and have a pH of 8.5.

In some embodiments, the present invention provides a method for obtaining a composition comprising a high purity, propeptide depleted mature recombinant rVWF (high purity mat-rVWF), said method comprising the steps of: (a) loading a solution comprising pro-rVWF, mat-rVWF/rVWF-PP complex, mat-rVWF, and/or rVWF propeptide (rVWF-PP) onto an anion exchange column, wherein said pro-rVWF, mat-rVWF/rVWF-PP complex, and mat-rVWF are bound to said anion exchange column; (b) washing said anion exchange column in a) containing said bound pro-rVWF, mat-rVWF/rVWF-PP complex, and mat-rVWF with one or more wash buffers; (c) treating said column in b) comprising the bound pro-rVWF, mat-rVWF/rVWF-PP complex, and mat-rVWF with furin, wherein said furin cleaves said pro-rVWF into mat-rVWF and rVWF-PP; (d) eluting said bound pro-rVWF, mat-rVWF/rVWF-PP complex, and mat-rVWF from the column in c) with an elution buffer, wherein said elution buffer induces dissociation of said rVWF-PP from mat-rVWF non-covalently associated with said rVWF-PP, and wherein said dissociation is induced by: (i) addition of at least one chelating agent into said elution buffer, or (ii) increasing the pH of said elution buffer to a pH of at least 7; and (e) collecting said mat-rVWF separately from said rVWF-PP to obtain a high purity mat-rVWF composition, wherein said high purity mat-rVWF composition comprises at least 95% mature rVWF and less than 5% rVWF-PP.

In some embodiments, a) and b) occur simultaneously in a single step. In some embodiments, the solution in a) comprises the flow through from a immunoaffinity purification method. In some embodiments, the solution in a) comprises the flow through from a monoclonal antibody column, wherein said monoclonal antibody is a FVIII monoclonal antibody. In some embodiments, the solution in a) is selected from the group consisting of a cell culture medium, an antibody column flow-through solution, and a buffered solution.

In some embodiments of step (b) washing said anion exchange column in a) containing said bound pro-rVWF, mat-rVWF/rVWF-PP complex, and mat-rVWF employs washing with one or more wash buffers, wherein one or more wash buffers includes one, two, three, four, and/or five wash buffers. In some embodiments, the second wash buffer comprises components for viral inactivation. In some embodiments, when four or five wash buffers are employed, the second wash buffer comprises components for viral inactivation. In some embodiments, when four or five wash buffers are employed, the second or third wash buffer comprises components for viral inactivation treatment. In some embodiments, the viral inactivation treatment is a solvent and detergent (S/D) treatment. In some embodiments, when five wash buffers are employed the first, second, third, and/or fifth wash buffers have a higher pH than the fourth wash buffer. In some embodiments, when five wash buffers are employed the first, second, third, and fifth wash buffers have a pH of about pH 7 to pH 8, and the fourth wash buffer has a pH of about pH 5 to 6. In some embodiments, when five wash buffers are employed the first, second, third, and/or fifth wash buffers have a pH of around pH 7.4 to pH 7.5, and the fourth wash buffer has a pH of about pH 5.5. In some embodiments, the viral inactivation treatment step occurs with a buffer that has a pH higher than the fourth wash buffer. In some embodiments, when four wash buffers are employed, a viral inactivation treatment step is employed after the first wash buffer. In some embodiments, when four wash buffers are employed, the first, second, and fourth wash buffers have a higher pH than the third wash buffer. In some embodiments, the viral inactivation treatment step occurs with a buffer that has a pH higher than the third wash buffer. In some embodiments, the viral inactivation step occurs with a buffer that has the same pH as the first, second, and/or fourth wash buffers. In some embodiments, when four wash buffers are employed the first, second, and fourth wash buffers have a pH of about pH 7 to about pH 8, and the third wash buffer has a pH of about pH 5 to about pH 6. In some embodiments, when four wash buffers are employed the first, second, and fourth wash buffers have a pH of about pH 7.4 to pH 7.5, and the third wash buffer has a pH of about pH 5.5.

Anion exchange chromatography can be performed as recognized by those skilled in the art. In some embodiments, the anion exchanger includes, but is not limited to, a STREAMLINE Q XL™, POROS 50 PI™, Q SEPHAROSE™, Emphase™ AEX Hybrid Purifier, Nuvia Q, POROS 50 HQ, Capto Q, Capto Q impress, Unosphere Q, Q Ceramic HYPERD® F, TOYOPEARL® Q, TOYOPEARL® Super Q, mixed mode AEX resins (e.g., Capto Adhere, Capto Q adhere impress, or MEP Hypercell), as well as any DEAE, TMAE, tertiary or quaternary amine, or PEI-based resins. In some embodiments, the anion exchanger is a membrane anion exchanger. In some embodiments, the membrane anion exchanger includes, but is not limited to, a Sartobind Q®, Sartobind STIC® PA, Mustang Q®, or ChromaSorb®. In some embodiments, the anion exchanger is a Fractogel TMAE column (Merck-Millipore) or an equivalent thereof.

In some embodiments, the loading concentration of pro-VWF is from about 90 IU/ml to about 270 IU/ml resin, e.g., about 90 IU/ml-about 270 IU/ml, about 100 IU/ml-about 270 IU/ml, about 110 IU/ml-about 270 IU/ml, about 120 IU/ml-about 270 IU/ml, about 130 IU/ml-about 270 IU/ml, about 130 IU/ml-about 270 IU/ml, about 140 IU/ml-about 270 IU/ml, about 150 IU/ml-about 270 IU/ml, about 90 IU/ml-about 250 IU/ml, about 100 IU/ml-about 250 IU/ml, about 110 IU/ml-about 250 IU/ml, about 120 IU/ml-about 250 IU/ml, about 130 IU/ml-about 250 IU/ml, about 130 IU/ml-about 250 IU/ml, about 140 IU/ml-about 250 IU/ml, about 150 IU/ml-about 250 IU/ml, about 90 IU/ml-about 200 IU/ml, about 100 IU/ml-about 200 IU/ml, about 110 IU/ml-about 200 IU/ml, about 120 IU/ml-about 200 IU/ml, about 130 IU/ml-about 200 IU/ml, about 130 IU/ml-about 200 IU/ml, about 140 IU/ml-about 200 IU/ml, about 150 IU/ml-about 200 IU/ml, about 90 IU/ml-about 100 IU/ml, about 100 IU/ml-about 150 IU/ml, about 150 IU/ml-about 200 IU/ml, about 200 IU/ml-about 250 IU/ml, or about 250 IU/ml-about 270 IU/ml resin.

In some embodiments, the anion exchange method comprises a buffer system. In some embodiments, the buffer system comprised one or more elution buffers. In some embodiments, the buffer system comprises one or more wash buffers. In some embodiments, the buffer system comprises at least one elution buffer and at least one wash buffer. In some embodiments, the buffer system comprises at least two elution buffers and at least two wash buffers.

In some embodiments, the loading concentration is from about 90 IU/ml to about 270 IU/ml resin, e.g., about 90 IU/ml-about 270 IU/ml, about 100 IU/ml-about 270 IU/ml, about 110 IU/ml-about 270 IU/ml, about 120 IU/ml-about 270 IU/ml, about 130 IU/ml-about 270 IU/ml, about 130 IU/ml-about 270 IU/ml, about 140 IU/ml-about 270 IU/ml, about 150 IU/ml-about 270 IU/ml, about 90 IU/ml-about 250 IU/ml, about 100 IU/ml-about 250 IU/ml, about 110 IU/ml-about 250 IU/ml, about 120 IU/ml-about 250 IU/ml, about 130 IU/ml-about 250 IU/ml, about 130 IU/ml-about 250 IU/ml, about 140 IU/ml-about 250 IU/ml, about 150 IU/ml-about 250 IU/ml, about 90 IU/ml-about 200 IU/ml, about 100 IU/ml-about 200 IU/ml, about 110 IU/ml-about 200 IU/ml, about 120 IU/ml-about 200 IU/ml, about 130 IU/ml-about 200 IU/ml, about 130 IU/ml-about 200 IU/ml, about 140 IU/ml-about 200 IU/ml, about 150 IU/ml-about 200 IU/ml, about 90 IU/ml-about 100 IU/ml, about 100 IU/ml-about 150 IU/ml, about 150 IU/ml-about 200 IU/ml, about 200 IU/ml-about 250 IU/ml, or about 250 IU/ml-about 270 IU/ml resin.

In some embodiments, the pH of the starting composition, loading solution, or loading composition comprises pro-rVWF, mat-rVWF/rVWF-PP complex, mat-rVWF, and/or rVWF propeptide (rVWF-PP) is from pH 6.0 to pH 9.0, e.g., pH 6.0-pH 9.0, pH 6.3-pH 9.0, pH 6.5-pH 9.0, pH 7.0-pH 9.0, pH 7.5-pH 9.0, pH 7.7.0-pH 9.0, pH 8.0-pH 9.0, pH 6.0-pH 8.5, pH 6.5-pH 8.5, pH 7.0-pH 8.5, pH 7.5-pH 8.5, pH 6.0-pH 8.0, pH 6.5-pH 8.0, pH 7.0-pH 8.0, pH 7.5-pH 8.0, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6, pH 8.7, pH 8.8, pH 8.9, or pH 9.0.

In some embodiments, the conductivity of the starting composition, loading solution, or loading composition comprises pro-rVWF, mat-rVWF/rVWF-PP complex, mat-rVWF, and/or rVWF propeptide (rVWF-PP) is from about 5 mS/cm to about 40 mS/cm, e.g., about 5 mS/cm-about 40 mS/cm, about 10 mS/cm-about 40 mS/cm, about 15 mS/cm-about 40 mS/cm, about 20 mS/cm-about 40 mS/cm, about 25 mS/cm-about 40 mS/cm, about 30 mS/cm-about 40 mS/cm, about 10 mS/cm-about 40 mS/cm, about 10 mS/cm-about 30 mS/cm, about 5 mS/cm-about 15 mS/cm, about 15 mS/cm-about 30 mS/cm, or about 20 mS/cm-about 40 mS/cm.

In some embodiments, the starting composition, loading solution, or loading composition comprises pro-rVWF, mat-rVWF/rVWF-PP complex, mat-rVWF, and/or rVWF propeptide (rVWF-PP) is diluted with a buffer comprising sodium citrate, such as, but not limited to, 10 mM-80 mM sodium citrate, 15 mM-80 mM sodium citrate, 10 mM-80 mM sodium citrate, 15 mM-60 mM sodium citrate, 20 mM-60 mM sodium citrate, 10 mM sodium citrate, 20 mM sodium citrate, 30 mM sodium citrate, 40 mM sodium citrate, 50 mM sodium citrate, 55 mM sodium citrate, 60 mM sodium citrate, 65 mM sodium citrate, 70 mM sodium citrate, 75 mM sodium citrate, 80 mM sodium citrate, or the like.

In some embodiments, the first wash buffer comprises at least one chelating agent, and optionally has a pH ranging from pH 6.0 to pH 9.0. In some embodiments, the first wash buffer has a pH ranging from pH 6.0 to pH 9.0, and optionally comprises at least one chelating agent. In some embodiments, the first wash buffer has a pH ranging from pH 6.0 to pH 6.9. In some embodiments, the second wash buffer has a pH ranging from pH 7.0 to pH 9.0. In some embodiments, the first wash buffer can comprise at least one chelating agent and has a pH ranging from pH 6.0 to pH 6.9. In some embodiments, the wash elution buffer has a pH of less than 7. In one embodiments, the second wash buffer has a pH of greater than 7. In some embodiments, when two wash buffers are employed, the first wash buffer has a pH of less than 7 and the second wash buffer has a pH of greater than 7.

In some embodiments, the one or more wash buffers comprise a NaCl concentration of 120 mM to 200 mM, 130 mM to 200 mM, 140 mM to 200 mM, 150 mM to 200 mM, 120 mM to 190 mM, 130 mM to 190 mM, 140 mM to 190 mM, 150 mM to 190 mM, 120 mM to 180 mM, 130 mM to 180 mM, 140 mM to 180 mM, 150 mM to 180 mM, 120 mM, 125 mM, 130 mM, 135 mM, 140 mM, 145 mM, 150 mM, 155 mM, 160 mM, 165 mM, 170 mM, 175 mM, 180 mM, 185 mM, 190 mM, 195 mM, or 200 mM.

In some embodiments, the starting composition, loading solution, or loading composition comprising mature VWF and VWF-PP is contacted with a buffer comprising at least one chelating agent, and optionally the buffer has a pH of ranging from pH 6.0 to pH 9.0. In some embodiments, the starting composition, loading solution, or loading composition is contacted with a buffer having a pH ranging from pH 6.0 to pH 9.0, and optionally the buffer comprises at least one chelating agent. In some embodiments, the buffer has a pH ranging from pH 7.0 to pH 9.0. In some embodiments the buffer is a wash buffer. In some embodiments, the buffer is an elution buffer. In some embodiments the buffer is a wash buffer with a pH of 6.0 to 6.9. In some embodiments, the buffer is an elution buffer with a pH of 7.0 to 9.0. In some embodiments, the starting composition, loading solution, or loading composition comprising mature VWF and VWF-PP is contacted first with a wash buffer having a pH from 6.0 to 6.9 and a second with at least one elution buffer having a pH from 7.0 to 9.0.

In some embodiments, mature VWF is eluted in the anion exchange chromatography step using one elution buffer. In some embodiments, mature VWF is eluted in the anion exchange chromatography step using a gradient elution method comprising more than one elution buffer. For example, the elution can be performed using two elution buffers, such as, for example, a first elution buffer and a second elution buffer. In some embodiments, the first elution buffer comprises at least one chelating agent, and optionally has a pH ranging from pH 6.0 to pH 9.0. In some embodiments, the first elution buffer has a pH ranging from pH 6.0 to pH 9.0, and optionally comprises at least one chelating agent. In some embodiments, the first elution buffer has a pH ranging from pH 6.0 to pH 6.9. In some embodiments, the second elution buffer has a pH ranging from pH 7.0 to pH 9.0. In some embodiments, the first elution buffer can comprise at least one chelating agent and has a pH ranging from pH 6.0 to pH 6.9. In some embodiments, the first elution buffer has a pH of less than 7. In one embodiments, the second elution buffer has a pH of greater than 7. In some embodiments, when two elution buffers are employed, the first elution buffer has a pH of less than 7 and the second elution buffer has a pH of greater than 7.

In some embodiments, the pH of the wash buffer for the anion exchange chromatography step is from pH 6.0 to pH 9.0, e.g., pH 6.0-pH 9.0, pH 6.3-pH 9.0, pH 6.5-pH 9.0, pH 7.0-pH 9.0, pH 7.5-pH 9.0, pH 7.7.0-pH 9.0, pH 8.0-pH 9.0, pH 6.0-pH 8.5, pH 6.5-pH 8.5, pH 7.0-pH 8.5, pH 7.5-pH 8.5, pH 6.0-pH 8.0, pH 6.5-pH 8.0, pH 7.0-pH 8.0, pH 7.5-pH 8.0, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6, pH 8.7, pH 8.8, pH 8.9, pH 9.0. In some embodiments, this includes when there are two elution buffers, for example a first and second elution buffer.

In some embodiments, the pH of the elution buffer for the anion exchange chromatography step is from pH 6.0 to pH 9.0, e.g., pH 6.0-pH 9.0, pH 6.3-pH 9.0, pH 6.5-pH 9.0, pH 7.0-pH 9.0, pH 7.5-pH 9.0, pH 7.7.0-pH 9.0, pH 8.0-pH 9.0, pH 6.0-pH 8.5, pH 6.5-pH 8.5, pH 7.0-pH 8.5, pH 7.5-pH 8.5, pH 6.0-pH 8.0, pH 6.5-pH 8.0, pH 7.0-pH 8.0, pH 7.5-pH 8.0, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6, pH 8.7, pH 8.8, pH 8.9, pH 9.0. In some embodiments, this includes when there are two elution buffers, for example a first and second elution buffer.

In some embodiments, the pH of the elution buffer is increased as compared to the starting solution in step a), is increased as compared to a first elution buffer when two elution buffers are employed, and/or is increased as compared to a wash buffer when a wash buffer is employed. In some embodiments, when a wash buffer and an elution buffer is employed, the wash buffer has a pH of less than 7 and the elution buffer has a pH of greater than 7. In some embodiments, when two elution buffers are employed, one elution buffer has a pH of less than 7 and the other elution buffer has a pH of greater than 7. In some embodiments, when a wash buffer and two elution buffers are employed, the wash buffer has a pH of less than 7 and both the elution buffers have a pH of greater than 7. In some embodiments, when a wash buffer and two elution buffers are employed, the wash buffer and the first elution buffer have a pH of less than 7 and the second elution buffer has a pH of greater than 7. In some embodiments, when two wash buffers and two elution buffers are employed, the wash buffers and the first elution buffer have a pH of less than 7 and the second elution buffer has a pH of greater than 7. In some embodiments, when two wash buffers and two elution buffers are employed, both wash buffers have a pH of less than 7 and both the elution buffers have a pH of greater than 7. In some embodiments, when two wash buffers and two elution buffers are employed, the first wash buffer has a pH of less than 7 and the second wash buffer and both elution buffers have a pH of greater than 7.

In some embodiments, the pH of the one or more wash and/or elution buffers is increased to at least 7.1, 7.2, 7.3, 7.4, 7.5, 7.6, 7.7, 7.8, 7.9, or 8.0, as compared to the loading solution comprising pro-rVWF, mat-rVWF/rVWF-PP complex, mat-rVWF, and/or rVWF propeptide (rVWF-PP), as recited in step (a) of the method. In some embodiments, the pH of the buffer is increased to at least 7.1, 7.2, 7.3, 7.4, 7.5, 7.6, 7.7, 7.8, 7.9, or 8.0 in order to induce dissociation of the mat-rVWF/rVWF-PP complex in the solution in step (a) of the method into mat-rVWF and rVWF-PP, wherein said dissociation occurs by disruption of the non-covalently associated mat-rVWF and rVWF-PP. In some embodiments, the pH of the loading solution is increased to at least about 7.2 to about 7.8. In some embodiments, the pH of the loading solution is increased to at least about 7.6. In some embodiments, the pH of the loading solution is increased by the addition of basic amino acids. In some embodiments, the pH of at the loading solution is increased to at least 7. In some embodiments, the pH of the one or more wash buffers is increased to at least about 7.2 to about 7.8. In some embodiments, the pH of the one or more wash buffers is increased to at least about 7.6. In some embodiments, the pH of the one or more wash buffers is increased by the addition of basic amino acids. In some embodiments, the one or more wash buffers exhibit a pH of at least 7. In some embodiments, the pH of the one or more elution buffers is increased to at least about 7.2 to about 7.8. In some embodiments, the pH of the one or more elution buffers is increased to at least about 7.6. In some embodiments, the pH of the one or more elution buffers is increased by the addition of basic amino acids. In some embodiments, the one or more elution buffers exhibit a pH of at least 7.

In some embodiments, the one or more buffers (including wash and/or elution buffers) comprise one or more chelating agents. In some embodiments, the elution buffer includes at least one chelating agent. The chelating agent can be a divalent cation chelating agent. In some embodiments, the at least one chelating agent is a divalent cation chelating agent. In some embodiments, the divalent cation chelating agent is selected from the group consisting of EDTA, EGTA, CDTA, and citrate. In some embodiments, the divalent cation chelating agent is selected from the group consisting of NTA, DTPA, EDDS, EDTA, EGTA, CDTA, and citrate. In some embodiments, the chelating agent is NTA. In some embodiments, the chelating agent is DTPA. In some embodiments, the chelating agent is EDDS. In some embodiments, the chelating agent is EDTA. In some embodiments, the chelating agent is EGTA In some embodiments, the chelating agent is CDTA. In some embodiments, the chelating agent is citrate. In some embodiments, the one or more wash buffers in b) comprise said one or more chelating agents and exhibit a pH of at least 7.

In some embodiments, the one or more buffers (including wash and/or elution buffers) comprise sodium citrate in a range including but not limited to, 10 mM-80 mM sodium citrate, 15 mM-80 mM sodium citrate, 10 mM-80 mM sodium citrate, 15 mM-60 mM sodium citrate, 20 mM-60 mM sodium citrate, 10 mM sodium citrate, 20 mM sodium citrate, 30 mM sodium citrate, 40 mM sodium citrate, 50 mM sodium citrate, 55 mM sodium citrate, 60 mM sodium citrate, 65 mM sodium citrate, 70 mM sodium citrate, 75 mM sodium citrate, 80 mM sodium citrate, or the like.

In some embodiments, a first elution buffer further comprises sodium citrate, in a range including but not limited to, 10 mM-60 mM sodium citrate, 15 mM-60 mM sodium citrate, 10 mM-50 mM sodium citrate, 15 mM-50 mM sodium citrate, 20 mM-60 mM sodium citrate, 10 mM sodium citrate, 20 mM sodium citrate, 30 mM sodium citrate, 40 mM sodium citrate, 50 mM sodium citrate, 60 mM sodium citrate, or the like.

In some embodiments, a second elution buffer further comprises sodium citrate, such as, but not limited to, 10 mM-60 mM sodium citrate, 15 mM-60 mM sodium citrate, 10 mM-50 mM sodium citrate, 15 mM-50 mM sodium citrate, 20 mM-60 mM sodium citrate, 10 mM sodium citrate, 20 mM sodium citrate, 30 mM sodium citrate, 40 mM sodium citrate, 50 mM sodium citrate, 60 mM sodium citrate, or the like.

In some embodiments, the elution buffer A and/or elution buffer B of the anion exchange chromatography step comprises about 0.5 mM to about 20 mM EDTA, e.g., about 0.5 mM-about 20 mM, about 1 mM-about 20 mM, about 1.5 mM-about 20 mM, about 2 mM-about 20 mM, about 3 mM-about 20 mM, about 5 mM-about 20 mM, about 0.5 mM-about 15 mM, about 1 mM-about 10 mM, about 1 mM-about 5 mM, about 5 mM, about 0.5 mM, about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, or the like.

In some embodiments, the citrate can be found in the eluent after the rVWF-propeptide has been removed using an anion exchange method. In some embodiments, the citrate can be found in the eluent after the rVWF-propeptide has been removed using a stepwise anion exchange elution method. In some embodiments, the citrate can be found in the eluent after the rVWF-propeptide has been removed using a gradient anion exchange elution method. In some embodiments, the anion exchange counter-ion is citrate$^{3-}$.

Any of the buffers (buffer systems) described herein can be selected from the group consisting of glycine, HEPES (4-(2-hydroxyethyl)-1-piperazineethanesulfonic acid), TrisHCl (Tris(hydroxymethyl)-aminomethane), histidine, imidazole, acetate citrate, citrate, acetate, MES, phosphate, TrisHCl, Bis-Tris, Histidine, Imidazol, ArgininHCl, LysinHCl, and 2-(N-morpholino)ethanesulfonic acid, as single buffers or as a combination of two or more buffers. In some embodiments, the buffer comprises glycine. In some embodiments, the buffer comprises HEPES (4-(2-hydroxyethyl)-1-piperazineethanesulfonic acid). In some embodiments, the buffer comprises TrisHCl (Tris(hydroxymethyl)-aminomethane). In some embodiments, the buffer comprises histidine. In some embodiments, the buffer comprises imidazole. In some embodiments, the buffer comprises acetate citrate. In some embodiments, the buffer comprises citrate. In some embodiments, the buffer comprises acetate. In some embodiments, the buffer comprises MES. In some embodiments, the buffer comprises phosphate. In some embodiments, the buffer comprises TrisHCl. In some embodiments, the buffer comprises Bis-Tris. In some embodiments, the buffer comprises Histidine. In some embodiments, the buffer comprises Imidazole. In some embodiments, the buffer comprises Arginine HCl. In some embodiments, the buffer comprises LysinHCl. In some embodiments, the buffer comprises 2-(N-morpholino)ethanesulfonic acid. In some embodiments, the buffer comprises one, two, three, or four of the buffers listed herein.

In some embodiments, the one or more buffers are selected from the group consisting of glycine HEPES (4-(2-hydroxyethyl)-1-piperazineethanesulfonic acid), TrisHCl (Tris(hydroxymethyl)-aminomethane), histidine, imidazole, acetate citrate, MES, and 2-(N-morpholino)ethanesulfonic acid.

In some embodiments, the one or more buffers comprise at least one buffer exhibiting a conductivity of ≥0.5 mS/cm at 25° C. In some embodiments, the one or more buffers comprise at least one buffer exhibiting a conductivity of 20.0±0.2 mS/cm at 25° C. In some embodiments, the one or more buffers comprise at least one buffer exhibiting a conductivity of 17.0±0.2 mS/cm at 25° C. In some embodiments, the one or more buffers comprise at least one buffer exhibiting a conductivity of 15.0±0.2 mS/cm at 25° C. In some embodiments, the one or more buffers comprise at least one buffer exhibiting a conductivity of 12.0±0.2 mS/cm at 25° C. In some embodiments, the one or more buffers comprise at least one buffer exhibiting a conductivity of 10.0±0.2 mS/cm at 25° C. In some embodiments, the one or more buffers comprise at least one buffer exhibiting a conductivity of 5.0±0.2 mS/cm at 25° C. In some embodiments, the one or more buffers comprise at least one buffer exhibiting a conductivity of 2.0±0.2 mS/cm at 25° C.

In some embodiments, the flow rate of one or more wash steps of the present method is about 10 cm/h to about 200 cm/h, e.g., about 10 cm/h, about 15 cm/h, about 20 cm/h, about 25 cm/h, about 30 cm/h, about 35 cm/h, about 40 cm/h, about 45 cm/h, about 50 cm/h, about 55 cm/h, about 60 cm/h, about 65 cm/h, about 70 cm/h, about 75 cm/h, about 80 cm/h, about 85 cm/h, about 90 cm/h, about 95 cm/h, about 100 cm/h, about 105 cm/h, about 110 cm/h, about 115 cm/h, about 120 cm/h, about 125 cm/h, about 130 cm/h, about 135 cm/h, about 140 cm/h, about 145 cm/h, about 150 cm/h, about 155 cm/h, about 160 cm/h, about 165 cm/h, about 170 cm/h, about 175 cm/h, about 180 cm/h, about 185 cm/h, about 190 cm/h, about 195 cm/h, or about 200 cm/h. Depending on the resin, in some embodiments the flow rate can be up to 600 cm/h.

In some embodiments, the flow rate of one or more elution steps of the present method is about 10 cm/h to about 200 cm/h, e.g., about 10 cm/h, about 15 cm/h, about 20 cm/h, about 25 cm/h, about 30 cm/h, about 35 cm/h, about 40 cm/h, about 45 cm/h, about 50 cm/h, about 55 cm/h, about 60 cm/h, about 65 cm/h, about 70 cm/h, about 75 cm/h, about 80 cm/h, about 85 cm/h, about 90 cm/h, about 95 cm/h, about 100 cm/h, about 105 cm/h, about 110 cm/h, about 115 cm/h, about 120 cm/h, about 125 cm/h, about 130 cm/h, about 135 cm/h, about 140 cm/h, about 145 cm/h, about 150 cm/h, about 155 cm/h, about 160 cm/h, about 165 cm/h, about 170 cm/h, about 175 cm/h, about 180 cm/h, about 185 cm/h, about 190 cm/h, about 195 cm/h, or about 200 cm/h. Depending on the resin, in some embodiments the flow rate can be up to 600 cm/h.

In some embodiments, the one or more buffers further comprise one or more nonionic detergents. In some embodiments, the nonionic detergent is selected from the group consisting of Triton X-100, Tween 80, and Tween 20. In some embodiments, the nonionic detergent is Triton X-100. In some embodiments, the nonionic detergent is Tween 80. In some embodiments, the nonionic detergent is Tween 20.

In some embodiments, the said one or more buffers further comprise one or more additional substances selected from the group consisting of non-reducing sugars, sugar alcohols, and polyols. In some embodiments, the one or more buffers further comprises one or more non-reducing sugars. In some embodiments, the non-reducing sugar includes but is not limited to sucrose, trehalose, mannitol, sorbitol, galactitol, and/or xylitol. In some embodiments, the one or more buffers further comprises one or more sugar alcohols. In some embodiments, the one or more buffers further comprises one or more polyols. In some embodiments, the sugar alcohol or polyol includes but is not limited to mannitol, xylitol, erythritol, threitol, sorbitol, and/or glycerol. In some embodiments, the buffers further comprise ethylene glycol, propylene glycol, glycerol, 1,2,3-Propanetriol), meso-erythritol, and/or erythritol (meso-1,2,3,4-Butantetrol).

In some embodiments, the buffer can include one or more monovalent cations. In some embodiments, the one or more monovalent cations are selected from the group consisting of $Na^+$, $K^+$, $Li^+$, $Cs^+$, and $NH_4^+$. For instance, the monovalent cation can be $Na^+$. In other embodiments, the buffer includes one or more monovalent, divalent and/or trivalent anions. The one or more monovalent, divalent and/or trivalent anions can be selected from the group consisting of $Cl^-$, acetate$^-$, $SO_4^{2-}$, $Br^-$, citrate$^{3-}$, $PO_4^{3-}$, and $BO_3^{3-}$. In some embodiments, the buffer comprises one or more additional substances selected from the group consisting of non-reducing sugars, and sugar alcohols. In some embodiments, the one or more buffers further comprise one or more monovalent cations. In some embodiments, the one or more monovalent cations are selected from the group consisting $Na^+$, $K^+$, $Li^-$, and $Cs^+$. In some embodiments, the monovalent cation is Na+. In some embodiments, the one or more buffers further comprise one or more monovalent, divalent, and/or trivalent anions. In some embodiments, the one or more monovalent, divalent and/or trivalent anions are selected from the group consisting of $Cl^-$, acetate$^-$, $SO_4^{2-}$, $Br^-$, and citrate$^{3-}$.

The pH of any of the buffers can be adjusted (increased) by adding an amino acid, Tris, NaOH, ethanolamine, and the like.

In some embodiments, the anion exchange method buffer chelator combination comprises citrate, malate (malic acid), and tartrate (tartaric acid).

b. Cation Exchange Chromatography Purification

In one aspect of the present method, mature VWF (matVWF) is separated from VWF-PP using cation exchange (CEX) chromatography. In some cases, remaining host cell derived impurities such as CHO host cell proteins, process related impurities such as recombinant furin and low molecular weight viral inactivation reagents, media compounds such as soy peptone, and other product related impurities are removed from the mature VWF.

In another aspect of the present method, mature VWF is separated from VWF-PP such as residual VWF-PP or free VWF-PP using cation exchange chromatography. For separation, the starting composition, loading solution, or loading composition can comprise a low pH and at least one chelating agent. In some embodiments, the starting composition, loading solution, or loading composition comprises pro-rVWF, mat-rVWF/rVWF-PP complex, mat-rVWF, and/or rVWF propeptide (rVWF-PP). In some embodiments, the cation exchanger is operated in binding mode and mature VWF and VWF-PP are separated using a gradient elution buffer comprising at least one chelating agent. In other embodiments, the gradient elution buffer has a neutral to high pH, such as a pH ranging from pH 6.0 to pH 9.0. In another embodiment, the gradient elution buffer comprises one or more chelating agents and has a pH of 7.0 or higher, e.g., pH 7.0 to pH 9.0. For instance, the gradient elution buffer can include EDTA and have a pH of 8.5.

In some embodiments, the present invention provides a method for obtaining a composition comprising a high purity, propeptide depleted mature recombinant rVWF (high purity mat-rVWF), said method comprising the steps of: (a) loading a solution comprising pro-rVWF, mat-rVWF/rVWF-PP complex, mat-rVWF, and/or rVWF propeptide (rVWF-PP) onto a cation exchange column, wherein said pro-rVWF, mat-rVWF/rVWF-PP complex, and mat-rVWF are bound to said cation exchange column; (b) washing said cation exchange column in a) containing said bound pro-rVWF, mat-rVWF/rVWF-PP complex, and mat-rVWF with one or more wash buffers; (c) treating said column in b) comprising the bound pro-rVWF, mat-rVWF/rVWF-PP complex, and mat-rVWF with furin, wherein said furin cleaves said pro-rVWF into mat-rVWF and rVWF-PP; (d) eluting said bound pro-rVWF, mat-rVWF/rVWF-PP complex, and mat-rVWF from the column in c) with an elution buffer, wherein said elution buffer induces dissociation of said rVWF-PP from mat-rVWF non-covalently associated with said rVWF-PP, and wherein said dissociation is induced by: (i) addition of at least one chelating agent into said elution buffer, or (ii) increasing the pH of said elution buffer to a pH of at least 7; and (e) collecting said mat-rVWF separately from said rVWF-PP to obtain a high purity mat-rVWF composition, wherein said high purity mat-rVWF composition comprises at least 95% mature rVWF and less than 5% rVWF-PP.

In some embodiments, a) and b) occur simultaneously in a single step. In some embodiments, the solution in a) comprises the flow through from a immunoaffinity purification method. In some embodiments, the solution in a) comprises the flow through from a monoclonal antibody column, wherein said monoclonal antibody is a FVIII monoclonal antibody. In some embodiments, the solution in a) is selected from the group consisting of a cell culture medium, an antibody column flow-through solution, and a buffered solution.

The cation exchanger can be operated in binding mode to separate the mature VWF and VWF-PP. Cation exchange chromatography can be performed as recognized by those skilled in the art. In some embodiments, the cation exchanger includes, but is not limited to, POROS® S (Applied Biosystems), Convective Interaction Media (CIM®; BIA Separation), Toyopearl Gigacap S (Tosoh Bioscience, Montgomeryville, Pa.), Toyopearl Gigacap CM (Tosoh), Toyopearl SP (Tosoha), Toyopearl CM (Tosoh), MacroPrep S (Bio-rad, Hercules, Calif.), UNOsphereS (Bio-rad, Hercules, Calif.), MacroprepCM ((Bio-rad, Hercules, Calif.), Fractogel EMD SO3 (Merck), Fractogel EMD COO (Merck), Fractogel EMD SE Hicap (Merck), Cellufine Sulfate (JNC), CM and SP Trisacryl (Pall), CM and S HyperD (Pall), S and CM Sepharose CL (GE Healthcare), S and CM Sepharose FF (GE Healthcare), S and CM CAPTO™ (GE Healthcare), MonoS (GE Healthcare), Source S (GE Healthcare), Nuvia S (Merck), or Cellufine phosphate (JNC). In some embodiments, the cation exchanger is a membrane cation exchanger. In some embodiments, the membrane cation exchanger includes, but is not limited to, Mustang S (Pall) or Sartobind® S. In some embodiments, the cation exchanger is a UNO_Sphere S column (Bio-Rad) or an equivalent thereof.

In some embodiments of step (b) washing said cation exchange column in a) containing said bound pro-rVWF, mat-rVWF/rVWF-PP complex, and mat-rVWF employs washing with one or more wash buffers, wherein one or more wash buffers includes one, two, three, four, and/or five wash buffers. In some embodiments, the second wash buffer comprises components for viral inactivation. In some embodiments, when four or five wash buffers are employed, the second wash buffer comprises components for viral inactivation. In some embodiments, when four or five wash buffers are employed, the second or third wash buffer comprises components for viral inactivation treatment. In some embodiments, the viral inactivation treatment is a solvent and detergent (S/D) treatment. In some embodiments, when five wash buffers are employed the first, second, third, and/or fifth wash buffers have a higher pH than the fourth wash buffer. In some embodiments, when five wash buffers are employed the first, second, third, and fifth wash buffers have a pH of about pH 7 to pH 8, and the fourth wash buffer has a pH of about pH 5 to 6. In some embodiments, when five wash buffers are employed the first, second, third, and/or fifth wash buffers have a pH of around pH 7.4 to pH 7.5, and the fourth wash buffer has a pH of about pH 5.5. In some embodiments, the viral inactivation treatment step occurs with a buffer that has a pH higher than the fourth wash buffer. In some embodiments, when four wash buffers are employed, a viral inactivation treatment step is employed after the first wash buffer. In some embodiments, when four wash buffers are employed, the first, second, and fourth wash buffers have a higher pH than the third wash buffer. In some embodiments, the viral inactivation treatment step occurs with a buffer that has a pH higher than the third wash buffer. In some embodiments, the viral inactivation step occurs with a buffer that has the same pH as the first, second, and/or fourth wash buffers. In some embodiments, when four wash buffers are employed the first, second, and fourth wash buffers have a pH of about pH 7 to about pH 8, and the third wash buffer has a pH of about pH 5 to about pH 6. In some embodiments, when four wash buffers are employed the first, second, and fourth wash buffers have a pH of about pH 7.4 to pH 7.5, and the third wash buffer has a pH of about pH 5.5.

In some embodiments, the loading concentration of pro-VWF is from about 90 IU/ml to about 270 IU/ml resin, e.g., about 90 IU/ml-about 270 IU/ml, about 100 IU/ml-about 270 IU/ml, about 110 IU/ml-about 270 IU/ml, about 120 IU/ml-about 270 IU/ml, about 130 IU/ml-about 270 IU/ml, about 130 IU/ml-about 270 IU/ml, about 140 IU/ml-about 270 IU/ml, about 150 IU/ml-about 270 IU/ml, about 90 IU/ml-about 250 IU/ml, about 100 IU/ml-about 250 IU/ml, about 110 IU/ml-about 250 IU/ml, about 120 IU/ml-about 250 IU/ml, about 130 IU/ml-about 250 IU/ml, about 130 IU/ml-about 250 IU/ml, about 140 IU/ml-about 250 IU/ml, about 150 IU/ml-about 250 IU/ml, about 90 IU/ml-about 200 IU/ml, about 100 IU/ml-about 200 IU/ml, about 110 IU/ml-about 200 IU/ml, about 120 IU/ml-about 200 IU/ml, about 130 IU/ml-about 200 IU/ml, about 130 IU/ml-about 200 IU/ml, about 140 IU/ml-about 200 IU/ml, about 150 IU/ml-about 200 IU/ml, about 90 IU/ml-about 100 IU/ml, about 100 IU/ml-about 150 IU/ml, about 150 IU/ml-about 200 IU/ml, about 200 IU/ml-about 250 IU/ml, or about 250 IU/ml-about 270 IU/ml resin.

In some embodiments, the cation exchange method comprises a buffer system. In some embodiments, the buffer system comprised one or more elution buffers. In some embodiments, the buffer system comprises one or more wash buffers. In some embodiments, the buffer system comprises at least one elution buffer and at least one wash buffer. In some embodiments, the buffer system comprises at least two elution buffers and at least two wash buffers.

In some embodiments, the first wash buffer comprises at least one chelating agent, and optionally has a pH ranging from pH 6.0 to pH 9.0. In some embodiments, the first wash buffer has a pH ranging from pH 6.0 to pH 9.0, and optionally comprises at least one chelating agent. In some embodiments, the first wash buffer has a pH ranging from pH 6.0 to pH 6.9. In some embodiments, the second wash buffer has a pH ranging from pH 7.0 to pH 9.0. In some embodiments, the first wash buffer can comprise at least one chelating agent and has a pH ranging from pH 6.0 to pH 6.9. In some embodiments, the wash elution buffer has a pH of less than 7. In one embodiments, the second wash buffer has a pH of greater than 7. In some embodiments, when two wash buffers are employed, the first wash buffer has a pH of less than 7 and the second wash buffer has a pH of greater than 7.

In some embodiments, the one or more wash buffers comprise a NaCl concentration of 120 mM to 200 mM, 130 mM to 200 mM, 140 mM to 200 mM, 150 mM to 200 mM, 120 mM to 190 mM, 130 mM to 190 mM, 140 mM to 190 mM, 150 mM to 190 mM, 120 mM to 180 mM, 130 mM to 180 mM, 140 mM to 180 mM, 150 mM to 180 mM, 120 mM, 125 mM, 130 mM, 135 mM, 140 mM, 145 mM, 150 mM, 155 mM, 160 mM, 165 mM, 170 mM, 175 mM, 180 mM, 185 mM, 190 mM, 195 mM, or 200 mM.

In some embodiments, the starting composition, loading solution, or loading composition comprising mature VWF and VWF-PP is contacted with a buffer comprising at least one chelating agent, and optionally the buffer has a pH of ranging from pH 6.0 to pH 9.0. In some embodiments, the starting composition, loading solution, or loading composition is contacted with a buffer having a pH ranging from pH 6.0 to pH 9.0, and optionally the buffer comprises at least one chelating agent. In some embodiments, the buffer has a pH ranging from pH 7.0 to pH 9.0. In some embodiments the buffer is a wash buffer. In some embodiments, the buffer is an elution buffer. In some embodiments the buffer is a wash buffer with a pH of 6.0 to 6.9. In some embodiments, the buffer is an elution buffer with a pH of 7.0 to 9.0. In some embodiments, the starting composition, loading solution, or loading composition comprising mature VWF and VWF-PP is contacted first with a wash buffer having a pH from 6.0 to 6.9 and a second with at least one elution buffer having a pH from 7.0 to 9.0.

In some embodiments, mature VWF is eluted in the anion exchange chromatography step using one elution buffer. In some embodiments, mature VWF is eluted in the anion exchange chromatography step using a gradient elution method comprising more than one elution buffer. For example, the elution can be performed using two elution buffers, such as, for example, a first elution buffer and a second elution buffer. In some embodiments, the first elution buffer comprises at least one chelating agent, and optionally has a pH ranging from pH 6.0 to pH 9.0. In some embodiments, the first elution buffer has a pH ranging from pH 6.0 to pH 9.0, and optionally comprises at least one chelating agent. In some embodiments, the first elution buffer has a pH ranging from pH 6.0 to pH 6.9. In some embodiments, the second elution buffer has a pH ranging from pH 7.0 to pH 9.0. In some embodiments, the first elution buffer can comprise at least one chelating agent and has a pH ranging from pH 6.0 to pH 6.9. In some embodiments, the first elution buffer has a pH of less than 7. In one embodiments, the second elution buffer has a pH of greater than 7. In some embodiments, when two elution buffers are employed, the first elution buffer has a pH of less than 7 and the second elution buffer has a pH of greater than 7.

In some embodiments, the pH of the wash buffer for the cation exchange chromatography step is from pH 6.0 to pH 9.0, e.g., pH 6.0-pH 9.0, pH 6.3-pH 9.0, pH 6.5-pH 9.0, pH 7.0-pH 9.0, pH 7.5-pH 9.0, pH 7.7.0-pH 9.0, pH 8.0-pH 9.0, pH 6.0-pH 8.5, pH 6.5-pH 8.5, pH 7.0-pH 8.5, pH 7.5-pH 8.5, pH 6.0-pH 8.0, pH 6.5-pH 8.0, pH 7.0-pH 8.0, pH 7.5-pH 8.0, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6, pH 8.7, pH 8.8, pH 8.9, pH 9.0. In some embodiments, this includes when there are two elution buffers, for example a first and second elution buffer.

In some embodiments, the pH of the elution buffer for the cation exchange chromatography step is from pH 6.0 to pH 9.0, e.g., pH 6.0-pH 9.0, pH 6.3-pH 9.0, pH 6.5-pH 9.0, pH 7.0-pH 9.0, pH 7.5-pH 9.0, pH 7.7.0-pH 9.0, pH 8.0-pH 9.0, pH 6.0-pH 8.5, pH 6.5-pH 8.5, pH 7.0-pH 8.5, pH 7.5-pH 8.5, pH 6.0-pH 8.0, pH 6.5-pH 8.0, pH 7.0-pH 8.0, pH 7.5-pH 8.0, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6, pH 8.7, pH 8.8, pH 8.9, pH 9.0. In some embodiments, this includes when there are two elution buffers, for example a first and second elution buffer.

In some embodiments, the pH of the elution buffer is increased as compared to the starting solution in step a), is increased as compared to a first elution buffer when two elution buffers are employed, and/or is increased as compared to a wash buffer when a wash buffer is employed. In some embodiments, when a wash buffer and an elution buffer is employed, the wash buffer has a pH of less than 7 and the elution buffer has a pH of greater than 7. In some embodiments, when two elution buffers are employed, one elution buffer has a pH of less than 7 and the other elution buffer has a pH of greater than 7. In some embodiments, when a wash buffer and two elution buffers are employed, the wash buffer has a pH of less than 7 and both the elution buffers have a pH of greater than 7. In some embodiments, when a wash buffer and two elution buffers are employed, the wash buffer and the first elution buffer have a pH of less than 7 and the second elution buffer has a pH of greater than 7. In some embodiments, when two wash buffers and two elution buffers are employed, the wash buffers and the first elution buffer have a pH of less than 7 and the second elution buffer has a pH of greater than 7. In some embodiments, when two wash buffers and two elution buffers are employed, both wash buffers have a pH of less than 7 and both the elution buffers have a pH of greater than 7. In some embodiments, when two wash buffers and two elution buffers are employed, the first wash buffer has a pH of less than 7 and the second wash buffer and both elution buffers have a pH of greater than 7.

In some embodiments, the pH of the one or more wash and/or elution buffers is increased to at least 7.1, 7.2, 7.3, 7.4, 7.5, 7.6, 7.7, 7.8, 7.9, or 8.0, as compared to the loading solution comprising pro-rVWF, mat-rVWF/rVWF-PP complex, mat-rVWF, and/or rVWF propeptide (rVWF-PP), as recited in step (a) of the method. In some embodiments, the pH of the buffer is increased to at least 7.1, 7.2, 7.3, 7.4, 7.5, 7.6, 7.7, 7.8, 7.9, or 8.0 in order to induce dissociation of the mat-rVWF/rVWF-PP complex in the solution in step (a) of the method into mat-rVWF and rVWF-PP, wherein said dissociation occurs by disruption of the non-covalently associated mat-rVWF and rVWF-PP. In some embodiments, the pH of the loading solution is increased to at least about 7.2 to about 7.8. In some embodiments, the pH of the loading solution is increased to at least about 7.6. In some embodiments, the pH of the loading solution is increased by the addition of basic amino acids. In some embodiments, the pH of at the loading solution is increased to at least 7. In some embodiments, the pH of the one or more wash buffers is increased to at least about 7.2 to about 7.8. In some embodiments, the pH of the one or more wash buffers is increased to at least about 7.6. In some embodiments, the pH of the one or more wash buffers is increased by the addition of basic amino acids. In some embodiments, the one or more wash buffers exhibit a pH of at least 7. In some embodiments, the pH of the one or more elution buffers is increased to at least about 7.2 to about 7.8. In some embodiments, the pH of the one or more elution buffers is increased to at least about 7.6. In some embodiments, the pH of the one or more elution buffers is increased by the addition of basic amino acids. In some embodiments, the one or more elution buffers exhibit a pH of at least 7.

In some embodiments, the pH of the loading solution comprising pro-rVWF, mat-rVWF/rVWF-PP complex, mat-rVWF, and/or rVWF propeptide (rVWF-PP) is from pH 6.0 to pH 9.0, e.g., pH 6.0-pH 9.0, pH 6.3-pH 9.0, pH 6.5-pH 9.0, pH 7.0-pH 9.0, pH 7.5-pH 9.0, pH 7.7.0-pH 9.0, pH 8.0-pH 9.0, pH 6.0-pH 8.5, pH 6.5-pH 8.5, pH 7.0-pH 8.5, pH 7.5-pH 8.5, pH 6.0-pH 8.0, pH 6.5-pH 8.0, pH 7.0-pH 8.0, pH 7.5-pH 8.0, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6, pH 8.7, pH 8.8, pH 8.9, or pH 9.0.

In some embodiments, the conductivity of the starting composition, loading solution, or loading composition comprising pro-rVWF, mat-rVWF/rVWF-PP complex, mat-rVWF, and/or rVWF propeptide (rVWF-PP) is from about 5 mS/cm to about 40 mS/cm, e.g., about 5 mS/cm-about 40 mS/cm, about 10 mS/cm-about 40 mS/cm, about 15 mS/cm-about 40 mS/cm, about 20 mS/cm-about 40 mS/cm, about 25 mS/cm-about 40 mS/cm, about 30 mS/cm-about 40 mS/cm, about 10 mS/cm-about 40 mS/cm, about 10 mS/cm-about 30 mS/cm, about 5 mS/cm-about 15 mS/cm, about 15 mS/cm-about 30 mS/cm, or about 20 mS/cm-about 40 mS/cm.

In some embodiments, the loading solution comprising pro-rVWF, mat-rVWF/rVWF-PP complex, mat-rVWF, and/or rVWF propeptide (rVWF-PP) is diluted with a buffer comprising sodium citrate, such as, but not limited to, 10 mM-80 mM sodium citrate, 15 mM-80 mM sodium citrate, 10 mM-80 mM sodium citrate, 15 mM-60 mM sodium citrate, 20 mM-60 mM sodium citrate, 10 mM sodium citrate, 20 mM sodium citrate, 30 mM sodium citrate, 40 mM sodium citrate, 50 mM sodium citrate, 55 mM sodium citrate, 60 mM sodium citrate, 65 mM sodium citrate, 70 mM sodium citrate, 75 mM sodium citrate, 80 mM sodium citrate, or the like.

In some embodiments, the pH of the wash buffer for the cation exchange chromatography step is from pH 6.0 to pH 9.0, e.g., pH 6.0-pH 9.0, pH 6.3-pH 9.0, pH 6.5-pH 9.0, pH 7.0-pH 9.0, pH 7.5-pH 9.0, pH 7.7.0-pH 9.0, pH 8.0-pH 9.0, pH 6.0-pH 8.5, pH 6.5-pH 8.5, pH 7.0-pH 8.5, pH 7.5-pH 8.5, pH 6.0-pH 8.0, pH 6.5-pH 8.0, pH 7.0-pH 8.0, pH 7.5-pH 8.0, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6, pH 8.7, pH 8.8, pH 8.9, or pH 9.0.

In some embodiments, the pH of the elution buffer for the cation exchange chromatography step is from pH 6.0 to pH 9.0, e.g., pH 6.0-pH 9.0, pH 6.3-pH 9.0, pH 6.5-pH 9.0, pH 7.0-pH 9.0, pH 7.5-pH 9.0, pH 7.7.0-pH 9.0, pH 8.0-pH 9.0, pH 6.0-pH 8.5, pH 6.5-pH 8.5, pH 7.0-pH 8.5, pH 7.5-pH 8.5, pH 6.0-pH 8.0, pH 6.5-pH 8.0, pH 7.0-pH 8.0, pH 7.5-pH 8.0, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6, pH 8.7, pH 8.8, pH 8.9, or pH 9.0.

In some embodiments, the pH of the elution buffer is increased as compared to the starting solution in step a), is increased as compared to a first elution buffer when two elution buffers are employed, and/or is increased as compared to a wash buffer when a wash buffer is employed. In some embodiments, when a wash buffer and an elution buffer is employed, the wash buffer has a pH of less than 7 and the elution buffer has a pH of greater than 7. In some embodiments, when two elution buffers are employed, one elution buffer has a pH of less than 7 and the other elution buffer has a pH of greater than 7. In some embodiments, when a wash buffer and two elution buffers are employed, the wash buffer has a pH of less than 7 and both the elution buffers have a pH of greater than 7. In some embodiments, when a wash buffer and two elution buffers are employed, the wash buffer and the first elution buffer have a pH of less than 7 and the second elution buffer has a pH of greater than 7. In some embodiments, when two wash buffers and two elution buffers are employed, the wash buffers and the first elution buffer have a pH of less than 7 and the second elution buffer has a pH of greater than 7. In some embodiments, when two wash buffers and two elution buffers are employed, both wash buffers have a pH of less than 7 and both the elution buffers have a pH of greater than 7. In some embodiments, when two wash buffers and two elution buffers are employed, the first wash buffer has a pH of less than 7 and the second wash buffer and both elution buffers have a pH of greater than 7.

In some embodiments, the pH of the one or more wash and/or elution buffers is increased to at least 7.1, 7.2, 7.3, 7.4, 7.5, 7.6, 7.7, 7.8, 7.9, or 8.0, as compared to the loading solution comprising pro-rVWF, mat-rVWF/rVWF-PP complex, mat-rVWF, and/or rVWF propeptide (rVWF-PP), as recited in step (a) of the method. In some embodiments, the pH of the buffer is increased to at least 7.1, 7.2, 7.3, 7.4, 7.5, 7.6, 7.7, 7.8, 7.9, or 8.0 in order to induce dissociation of the mat-rVWF/rVWF-PP complex in the solution in step (a) of the method into mat-rVWF and rVWF-PP, wherein said dissociation occurs by disruption of the non-covalently associated mat-rVWF and rVWF-PP. In some embodiments, the pH of the loading solution is increased to at least about 7.2 to about 7.8. In some embodiments, the pH of the loading solution is increased to at least about 7.6. In some embodiments, the pH of the loading solution is increased by the addition of basic amino acids. In some embodiments, the pH of at the loading solution is increased to at least 7. In some embodiments, the pH of the one or more wash buffers is increased to at least about 7.2 to about 7.8. In some embodiments, the pH of the one or more wash buffers is increased to at least about 7.6. In some embodiments, the pH of the one or more wash buffers is increased by the addition of basic amino acids. In some embodiments, the one or more wash buffers exhibit a pH of at least 7. In some embodiments, the pH of the one or more elution buffers is increased to at least about 7.2 to about 7.8. In some embodiments, the pH of the one or more elution buffers is increased to at least about 7.6. In some embodiments, the pH of the one or more elution buffers is increased by the addition of basic amino acids. In some embodiments, the one or more elution buffers exhibit a pH of at least 7.

In some embodiments, the one or more buffers (including wash and/or elution buffers) comprise one or more chelating agents. In some embodiments, the elution buffer includes at least one chelating agent. The chelating agent can be a divalent cation chelating agent. In some embodiments, the at least one chelating agent is a divalent cation chelating agent. In some embodiments, the divalent cation chelating agent is selected from the group consisting of EDTA, EGTA, CDTA, and citrate. In some embodiments, the divalent cation chelating agent is selected from the group consisting of NTA, DTPA, EDDS, EDTA, EGTA, CDTA, and citrate. In some embodiments, the divalent cation chelating agent is selected from the group consisting of citrate, EDTA, DTPA, NTA, and EDDS. In some embodiments, the chelating agent is NTA. In some embodiments, the chelating agent is DTPA. In some embodiments, the chelating agent is EDDS. In some embodiments, the chelating agent is EDTA. In some embodiments, the chelating agent is EGTA. In some embodiments, the chelating agent is CDTA. In some embodiments, the chelating agent is citrate. In some embodiments, the one or more wash buffers in b) comprise said one or more chelating agents and exhibit a pH of at least 7.

Any of the buffers (buffer systems) described herein can be selected from the group consisting of glycine, HEPES (4-(2-hydroxyethyl)-1-piperazineethanesulfonic acid), TrisHCl (Tris(hydroxymethyl)-aminomethane), histidine, imidazole, acetate citrate, citrate, acetate, MES, phosphate, TrisHCl, Bis-Tris, Histidine, Imidazol, ArgininHCl, LysinHCl, and 2-(N-morpholino)ethanesulfonic acid, as single buffers or as a combination of two or more buffers. In some embodiments, the one or more buffers are selected from the group consisting of glycine HEPES (4-(2-hydroxyethyl)-1-piperazineethanesulfonic acid), TrisHCl (Tris(hydroxymethyl)-aminomethane), histidine, imidazole, acetate citrate, MES, and 2-(N-morpholino)ethanesulfonic acid. In some embodiments, the buffer comprises citrate, acetate, MES, HEPES, Phosphate, TrisHCl, and/or Bis-Tris. In some embodiments, the buffer comprises glycine. In some embodiments, the buffer comprises HEPES (4-(2-hydroxyethyl)-1-piperazineethanesulfonic acid). In some embodiments, the buffer comprises TrisHCl (Tris(hydroxymethyl)-aminomethane). In some embodiments, the buffer comprises histidine. In some embodiments, the buffer comprises imidazole. In some embodiments, the buffer comprises acetate citrate. In some embodiments, the buffer comprises citrate. In some embodiments, the buffer comprises acetate. In some embodiments, the buffer comprises MES. In some embodiments, the buffer comprises HEPES. In some embodiments, the buffer comprises phosphate. In some embodiments, the buffer comprises Tris-HCl. In some embodiments, the buffer comprises Bis-Tris. In some embodiments, the buffer comprises Histidine. In some embodiments, the buffer comprises Imidazole. In some embodiments, the buffer comprises Arginine HCl. In some embodiments, the buffer comprises Lysine HCl. In some embodiments, the buffer comprises 2-(N-morpholino)ethanesulfonic acid. In some embodiments, the buffer comprises one, two, three, or four of the buffers listed herein.

In some embodiments, the one or more buffers (including wash and/or elution buffers) comprise sodium citrate in a range including but not limited to, 10 mM-80 mM sodium citrate, 15 mM-80 mM sodium citrate, 10 mM-80 mM sodium citrate, 15 mM-60 mM sodium citrate, 20 mM-60 mM sodium citrate, 10 mM sodium citrate, 20 mM sodium citrate, 30 mM sodium citrate, 40 mM sodium citrate, 50 mM sodium citrate, 55 mM sodium citrate, 60 mM sodium citrate, 65 mM sodium citrate, 70 mM sodium citrate, 75 mM sodium citrate, 80 mM sodium citrate, or the like.

In some embodiments, a first elution buffer further comprises sodium citrate, in a range including but not limited to, 10 mM-60 mM sodium citrate, 15 mM-60 mM sodium citrate, 10 mM-50 mM sodium citrate, 15 mM-50 mM sodium citrate, 20 mM-60 mM sodium citrate, 10 mM sodium citrate, 20 mM sodium citrate, 30 mM sodium citrate, 40 mM sodium citrate, 50 mM sodium citrate, 60 mM sodium citrate, or the like.

In some embodiments, a second elution buffer further comprises sodium citrate, such as, but not limited to, 10 mM-60 mM sodium citrate, 15 mM-60 mM sodium citrate, 10 mM-50 mM sodium citrate, 15 mM-50 mM sodium citrate, 20 mM-60 mM sodium citrate, 10 mM sodium citrate, 20 mM sodium citrate, 30 mM sodium citrate, 40 mM sodium citrate, 50 mM sodium citrate, 60 mM sodium citrate, or the like.

In some embodiments, the one or more buffers (including wash and/or elution buffers) of the cation exchange chromatography step comprise EDTA, so long as the desired rVWF species remains bound to the cation exchange resin. In some embodiments, the one or more buffers (including wash and/or elution buffers) of the cation exchange chromatography step comprises about 0.5 mM to about 20 mM EDTA, e.g., about 0.5 mM-about 20 mM, about 1 mM-about 20 mM, about 1.5 mM-about 20 mM, about 2 mM-about 20 mM, about 3 mM-about 20 mM, about 5 mM-about 20 mM, about 0.5 mM-about 15 mM, about 1 mM-about 10 mM, about 1 mM-about 5 mM, about 5 mM, about 0.5 mM, about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, or the like, so long as the desired rVWF species remains bound to the cation exchange resin. In some embodiments, the buffers comprising EDTA are employed as part of a stepwise cation exchange elution. In some embodiments, the buffers comprising EDTA are employed as part of a gradient cation exchange elution. In some embodiments, when EDTA is employed as part of the buffers used in a stepwise cation exchange elution the counter-ion in Na+. In some embodiments, when EDTA is employed as part of the buffers used in a gradient cation exchange elution the counter-ion in Na+.

In some embodiments, the citrate can be found in the eluent after the rVWF-propeptide has been removed using a cation exchange method. In some embodiments, the citrate can be found in the eluent after the rVWF-propeptide has been removed using a stepwise cation exchange elution method. In some embodiments, the citrate can be found in the eluent after the rVWF-propeptide has been removed using a gradient cation exchange elution method. In some embodiments, the cation exchange counter-ion is Na⁺.

In some embodiments, the conductivity of the buffers (including wash and/or elution buffers), ranges from 5 mS/cm to 40 mS/cm, e.g., 5 mS/cm-40 mS/cm, 10 mS/cm-40 mS/cm, 15 mS/cm-40 mS/cm, 20 mS/cm-40 mS/cm, 5 mS/cm-15 mS/cm, 10 mS/cm-25 mS/cm, 15 mS/cm-30 mS/cm, 20 mS/cm-30 mS/cm, or 30 mS/cm-40 mS/cm.

In some embodiments, the conductivity of at least one wash buffer is from about 5 mS/cm to about 40 mS/cm, e.g., about 5 mS/cm-about 40 mS/cm, about 10 mS/cm-about 40 mS/cm, about 15 mS/cm-about 40 mS/cm, about 20 mS/cm-about 40 mS/cm, about 25 mS/cm-about 40 mS/cm, about 30 mS/cm-about 40 mS/cm, about 10 mS/cm-about 40 mS/cm, about 10 mS/cm-about 30 mS/cm, about 5 mS/cm-about 13 mS/cm, about 5 mS/cm-about 15 mS/cm, about 15 mS/cm-about 30 mS/cm, about 18 mS/cm-about 40 mS/cm, or about 20 mS/cm-about 40 mS/cm. In other embodiments, the conductivity of two or more wash buffers is from about 5 mS/cm to about 40 mS/cm, e.g., about 5 mS/cm-about 40 mS/cm, about 10 mS/cm-about 40 mS/cm, about 15 mS/cm-about 40 mS/cm, about 20 mS/cm-about 40 mS/cm, about 25 mS/cm-about 40 mS/cm, about 30 mS/cm-about 40 mS/cm, about 10 mS/cm-about 40 mS/cm, about 10 mS/cm-about 30 mS/cm, about 5 mS/cm-about 13 mS/cm, about 5 mS/cm-about 15 mS/cm, about 15 mS/cm-about 30 mS/cm, about 18 mS/cm-about 40 mS/cm, or about 20 mS/cm-about 40 mS/cm.

In some embodiments, the conductivity of at least one elution buffer is from about 5 mS/cm to about 40 mS/cm, e.g., about 5 mS/cm-about 40 mS/cm, about 10 mS/cm-about 40 mS/cm, about 15 mS/cm-about 40 mS/cm, about 20 mS/cm-about 40 mS/cm, about 25 mS/cm-about 40 mS/cm, about 30 mS/cm-about 40 mS/cm, about 10 mS/cm-about 40 mS/cm, about 10 mS/cm-about 30 mS/cm, about 5 mS/cm-about 13 mS/cm, about 5 mS/cm-about 15 mS/cm, about 15 mS/cm-about 30 mS/cm, about 18 mS/cm-about 40 mS/cm, or about 20 mS/cm-about 40 mS/cm. In other embodiments, the conductivity of two or more wash buffers is from about 5 mS/cm to about 40 mS/cm, e.g., about 5 mS/cm-about 40 mS/cm, about 10 mS/cm-about 40 mS/cm, about 15 mS/cm-about 40 mS/cm, about 20 mS/cm-about 40 mS/cm, about 25 mS/cm-about 40 mS/cm, about 30 mS/cm-about 40 mS/cm, about 10 mS/cm-about 40 mS/cm, about 10 mS/cm-about 30 mS/cm, about 5 mS/cm-about 13 mS/cm, about 5 mS/cm-about 15 mS/cm, about 15 mS/cm-about 30 mS/cm, about 18 mS/cm-about 40 mS/cm, or about 20 mS/cm-about 40 mS/cm.

In some embodiments, the pH of the wash buffer is from pH 6.0 to pH 9.0, e.g., pH 6.0-pH 9.0, pH 6.3-pH 9.0, pH 6.5-pH 9.0, pH 7.0-pH 9.0, pH 7.5-pH 9.0, pH 7.7.0-pH 9.0, pH 8.0-pH 9.0, pH 6.0-pH 8.5, pH 6.5-pH 8.5, pH 7.0-pH 8.5, pH 7.5-pH 8.5, pH 6.0-pH 8.0, pH 6.5-pH 8.0, pH 7.0-pH 8.0, pH 7.5-pH 8.0, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6, pH 8.7, pH 8.8, pH 8.9, pH 9.0.

In one aspect, the method described herein includes a gradient elution step. The gradient elution step can remove product impurities and process-related impurities to optimize yield of mature VWF. In some cases, the gradient elution step separates a higher percentage of VWF propeptide from mature VWF compared to a prior art method.

In some embodiments, the conductivity of the one or more elution buffers is from about 5 mS/cm to about 40 mS/cm, e.g., about 5 mS/cm-about 40 mS/cm, about 10 mS/cm-about 40 mS/cm, about 15 mS/cm-about 40 mS/cm, about 20 mS/cm-about 40 mS/cm, about 25 mS/cm-about 40 mS/cm, about 30 mS/cm-about 40 mS/cm, about 10 mS/cm-about 40 mS/cm, about 10 mS/cm-about 30 mS/cm, about 5 mS/cm-about 13 mS/cm, about 5 mS/cm-about 15 mS/cm, about 15 mS/cm-about 30 mS/cm, about 18 mS/cm-about 40 mS/cm, or about 20 mS/cm-about 40 mS/cm. In other embodiments, the conductivity of two or more wash buffers is from about 5 mS/cm to about 40 mS/cm, e.g., about 5 mS/cm-about 40 mS/cm, about 10 mS/cm-about 40 mS/cm, about 15 mS/cm-about 40 mS/cm, about 20 mS/cm-about 40 mS/cm, about 25 mS/cm-about 40 mS/cm, about 30 mS/cm-about 40 mS/cm, about 10 mS/cm-about 40 mS/cm, about 10 mS/cm-about 30 mS/cm, about 5 mS/cm-about 13 mS/cm, about 5 mS/cm-about 15 mS/cm, about 15 mS/cm-about 30 mS/cm, about 18 mS/cm-about 40 mS/cm, or about 20 mS/cm-about 40 mS/cm.

In some embodiments, the flow rate of one or more wash steps of the present method is about 10 cm/h to about 200 cm/h, e.g., about 10 cm/h, about 15 cm/h, about 20 cm/h, about 25 cm/h, about 30 cm/h, about 35 cm/h, about 40 cm/h, about 45 cm/h, about 50 cm/h, about 55 cm/h, about 60 cm/h, about 65 cm/h, about 70 cm/h, about 75 cm/h, about 80 cm/h, about 85 cm/h, about 90 cm/h, about 95 cm/h, about 100 cm/h, about 105 cm/h, about 110 cm/h, about 115 cm/h, about 120 cm/h, about 125 cm/h, about 130 cm/h, about 135 cm/h, about 140 cm/h, about 145 cm/h, about 150 cm/h, about 155 cm/h, about 160 cm/h, about 165 cm/h, about 170 cm/h, about 175 cm/h, about 180 cm/h, about 185 cm/h, about 190 cm/h, about 195 cm/h, or about 200 cm/h. Depending on the resin, in some embodiments the flow rate can be up to 600 cm/h.

In some embodiments, the flow rate of one or more elution steps of the present method is about 10 cm/h to about 200 cm/h, e.g., about 10 cm/h, about 15 cm/h, about 20 cm/h, about 25 cm/h, about 30 cm/h, about 35 cm/h, about 40 cm/h, about 45 cm/h, about 50 cm/h, about 55 cm/h, about 60 cm/h, about 65 cm/h, about 70 cm/h, about 75 cm/h, about 80 cm/h, about 85 cm/h, about 90 cm/h, about 95 cm/h, about 100 cm/h, about 105 cm/h, about 110 cm/h, about 115 cm/h, about 120 cm/h, about 125 cm/h, about 130 cm/h, about 135 cm/h, about 140 cm/h, about 145 cm/h, about 150 cm/h, about 155 cm/h, about 160 cm/h, about 165 cm/h, about 170 cm/h, about 175 cm/h, about 180 cm/h, about 185 cm/h, about 190 cm/h, about 195 cm/h, or about 200 cm/h. Depending on the resin, in some embodiments the flow rate can be up to 600 cm/h.

In some embodiments, the one or more buffers further comprise one or more nonionic detergents. In some embodiments, the nonionic detergent is selected from the group consisting of Triton X-100, Tween 80, and Tween 20. In some embodiments, the nonionic detergent is Triton X-100. In some embodiments, the nonionic detergent is Tween 80. In some embodiments, the nonionic detergent is Tween 20.

In some embodiments, the said one or more buffers further comprise one or more additional substances selected from the group consisting of non-reducing sugars, sugar alcohols, and polyols. In some embodiments, the one or more buffers further comprises one or more non-reducing sugars. In some embodiments, the non-reducing sugar includes but is not limited to sucrose, trehalose, mannitol, sorbitol, galactitol, and/or xylitol. In some embodiments, the one or more buffers further comprises one or more sugar alcohols. In some embodiments, the one or more buffers further comprises one or more polyols. In some embodiments, the sugar alcohol or polyol includes but is not limited to mannitol, xylitol, erythritol, threitol, sorbitol, and/or glycerol. In some embodiments, the buffers further comprise sorbitol, mannitol, xylitol, sucrose, trehalose, ethylene glycol, propylene glycol, glycerol, 1,2,3-Propanetriol, meso-erythritol, and/or erythritol (meso-1,2,3,4-Butantetriol).

The pH of any of the buffers can be adjusted (increased) by adding an amino acid, Tris, NaOH, ethanolamine, and the like.

Any of the buffers (buffer systems) described herein can be selected from the group consisting of Citrate, Acetate, MES, HEPES, Phosphate, TrisHCl, Bis-Tris, as single buffers or as a combination of two or more buffers. In some embodiments, the buffer comprises glycine. In some embodiments, the buffer comprises Citrate. In some embodiments, the buffer comprises Acetate. In some embodiments, the buffer comprises MES. In some embodiments, the buffer comprises HEPES. In some embodiments, the buffer comprises phosphate. In some embodiments, the buffer comprises TrisHCl. In some embodiments, the buffer comprises Bis-Tris. In some embodiments, the buffer comprises one, two, three, or four of the buffers listed herein.

In some embodiments, the cation exchange method buffer chelator combination comprises citrate, malate (malic acid), and tartrate (tartaric acid).

c. Size Exclusion Chromatography Purification

In one aspect of the present invention, mature VWF and VWF-PP are separated by way of size exclusion chromatography (SEC). In some cases, remaining host cell derived impurities such as CHO host cell proteins, process related impurities such as recombinant furin and low molecular weight viral inactivation reagents, media compounds such as soy peptone, and other product related impurities are removed from the mature VWF.

In another aspect of the present method, mature VWF is separated from VWF-PP such as residual VWF-PP or free VWF-PP using size exclusion chromatography. For separation, the starting or loading composition can comprise a low pH and at least one chelating agent. In other embodiments, the gradient elution buffer has a neutral to high pH, such as a pH ranging from pH 6.0 to pH 9.0. In another embodiment, the gradient elution buffer comprises one or more chelating agents and has a pH of 7.0 or higher, e.g., pH 7.0 to pH 9.0. For instance, the gradient elution buffer can include EDTA and have a pH of 8.5.

In some embodiments, the present invention provides a method for obtaining a composition comprising a high purity, propeptide depleted mature recombinant rVWF (high purity mat-rVWF), said method comprising the steps of: (a) loading a solution comprising pro-rVWF, mat-rVWF/rVWF-PP complex, mat-rVWF, and/or rVWF propeptide (rVWF-PP) onto an size exclusion column, wherein said pro-rVWF, mat-rVWF/rVWF-PP complex, and mat-rVWF are bound to said size exclusion column; (b) washing said size exclusion column in a) containing said bound pro-rVWF, mat-rVWF/rVWF-PP complex, and mat-rVWF with one or more wash buffers; (c) treating said column in b) comprising the bound pro-rVWF, mat-rVWF/rVWF-PP complex, and mat-rVWF with furin, wherein said furin cleaves said pro-rVWF into mat-rVWF and rVWF-PP; (d) eluting said bound pro-rVWF, mat-rVWF/rVWF-PP complex, and mat-rVWF from the column in c) with an elution buffer, wherein said elution buffer induces dissociation of said rVWF-PP from mat-rVWF non-covalently associated with said rVWF-PP, and wherein said dissociation is induced by: (i) addition of at least one chelating agent into said elution buffer, or (ii) increasing the pH of said elution buffer to a pH of at least 7; and (e) collecting said mat-rVWF separately from said rVWF-PP to obtain a high purity mat-rVWF composition, wherein said high purity mat-rVWF composition comprises at least 95% mature rVWF and less than 5% rVWF-PP.

In some embodiments, a) and b) occur simultaneously in a single step. In some embodiments, the solution in a) comprises the flow through from a immunoaffinity purification method. In some embodiments, the solution in a) comprises the flow through from a monoclonal antibody column, wherein said monoclonal antibody is a FVIII monoclonal antibody. In some embodiments, the solution in a) is selected from the group consisting of a cell culture medium, an antibody column flow-through solution, and a buffered solution.

In some embodiments, the separation buffer has a neutral to high pH. In other embodiments, the buffer comprises at least one chelating agent. In some embodiments, the buffer comprises at least one chelating agent and has a neutral to high pH. For example, the separation buffer can contain a chelating agent and have a pH of 6.0 or higher, or in some cases, a pH of 7.0 or higher.

In some embodiments, the loading concentration of pro-VWF is from about 90 IU/ml to about 270 IU/ml resin, e.g., about 90 IU/ml-about 270 IU/ml, about 100 IU/ml-about 270 IU/ml, about 110 IU/ml-about 270 IU/ml, about 120 IU/ml-about 270 IU/ml, about 130 IU/ml-about 270 IU/ml, about 130 IU/ml-about 270 IU/ml, about 140 IU/ml-about 270 IU/ml, about 150 IU/ml-about 270 IU/ml, about 90 IU/ml-about 250 IU/ml, about 100 IU/ml-about 250 IU/ml, about 110 IU/ml-about 250 IU/ml, about 120 IU/ml-about 250 IU/ml, about 130 IU/ml-about 250 IU/ml, about 130 IU/ml-about 250 IU/ml, about 140 IU/ml-about 250 IU/ml, about 150 IU/ml-about 250 IU/ml, about 90 IU/ml-about 200 IU/ml, about 100 IU/ml-about 200 IU/ml, about 110 IU/ml-about 200 IU/ml, about 120 IU/ml-about 200 IU/ml, about 130 IU/ml-about 200 IU/ml, about 130 IU/ml-about 200 IU/ml, about 140 IU/ml-about 200 IU/ml, about 150 IU/ml-about 200 IU/ml, about 90 IU/ml-about 100 IU/ml, about 100 IU/ml-about 150 IU/ml, about 150 IU/ml-about 200 IU/ml, about 200 IU/ml-about 250 IU/ml, or about 250 IU/ml-about 270 IU/ml resin.

In some embodiments, the pH of the starting composition, loading solution, or loading composition comprises pro-rVWF, mat-rVWF/rVWF-PP complex, mat-rVWF, and/or rVWF propeptide (rVWF-PP) is from pH 6.0 to pH 9.0, e.g., pH 6.0-pH 9.0, pH 6.3-pH 9.0, pH 6.5-pH 9.0, pH 7.0-pH 9.0, pH 7.5-pH 9.0, pH 7.7.0-pH 9.0, pH 8.0-pH 9.0, pH 6.0-pH 8.5, pH 6.5-pH 8.5, pH 7.0-pH 8.5, pH 7.5-pH 8.5, pH 6.0-pH 8.0, pH 6.5-pH 8.0, pH 7.0-pH 8.0, pH 7.5-pH 8.0, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6, pH 8.7, pH 8.8, pH 8.9, or pH 9.0.

In some embodiments, the size exclusion method comprises a buffer system. In some embodiments, the buffer system comprises one or more separation buffers. In some embodiments, the buffer system comprises at least one separation buffer. In some embodiments, the buffer system comprises at least two separation buffers. In some embodiments the buffer system comprises at least a first separation buffer and at least a second separation buffer.

In some embodiments, the first separation buffer comprises at least one chelating agent, and optionally has a pH ranging from pH 6.0 to pH 9.0. In some embodiments, the separation wash buffer has a pH ranging from pH 6.0 to pH 9.0, and optionally comprises at least one chelating agent. In some embodiments, the first separation buffer has a pH ranging from pH 6.0 to pH 6.9. In some embodiments, the second separation buffer has a pH ranging from pH 7.0 to pH 9.0. In some embodiments, the first separation buffer can comprise at least one chelating agent and has a pH ranging from pH 6.0 to pH 6.9. In some embodiments, the first separation buffer has a pH of less than 7. In some embodiments, the second separation buffer has a pH of greater than 7. In some embodiments, when two separation buffers are employed, the first separation buffer has a pH of less than 7 and the second separation buffer has a pH of greater than 7.

In some embodiments, the starting solution comprising mature rVWF and rVWF-PP is contacted with a separation buffer comprising at least one chelating agent, and optionally the buffer has a pH of ranging from pH 6.0 to pH 9.0. In some embodiments, the starting solution is contacted with a buffer having a pH ranging from pH 6.0 to pH 9.0, and optionally the buffer comprises at least one chelating agent. In some embodiments, the buffer has a pH ranging from pH 7.0 to pH 9.0. In some embodiments the buffer is a first separation buffer with a pH of 6.0 to 6.9. In some embodiments, the buffer is a second separation buffer with a pH of 7.0 to 9.0. In some embodiments, the starting solution comprising mature rVWF and rVWF-PP is contacted first with a first buffer having a pH from 6.0 to 6.9 and a second separation buffer having a pH from 7.0 to 9.0.

In some embodiments, the pH of the one or more separation buffers is from pH 6.0 to pH 9.0, e.g., pH 6.0-pH 9.0, pH 6.3-pH 9.0, pH 6.5-pH 9.0, pH 7.0-pH 9.0, pH 7.5-pH 9.0, pH 7.7.0-pH 9.0, pH 8.0-pH 9.0, pH 6.0-pH 8.5, pH 6.5-pH 8.5, pH 7.0-pH 8.5, pH 7.5-pH 8.5, pH 6.0-pH 8.0, pH 6.5-pH 8.0, pH 7.0-pH 8.0, pH 7.5-pH 8.0, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6, pH 8.7, pH 8.8, pH 8.9, or pH 9.0.

In some embodiments, the pH of the elution buffer is increased as compared to the starting solution in step a), is increased as compared to a first separation buffer when two separation buffers are employed, and/or is increased as compared to a first separation buffer when a second separation buffer is employed. In some embodiments, when a first separation buffer and as second separation buffer are employed, the first separation buffer has a pH of less than 7 and the second separation buffer has a pH of greater than 7.

In some embodiments, the pH of the one or more separation buffers is increased to at least 7.1, 7.2, 7.3, 7.4, 7.5, 7.6, 7.7, 7.8, 7.9, or 8.0, as compared to the loading solution comprising pro-rVWF, mat-rVWF/rVWF-PP complex, mat-rVWF, and/or rVWF propeptide (rVWF-PP), as recited in step (a) of the method. In some embodiments, the pH of the buffer is increased to at least 7.1, 7.2, 7.3, 7.4, 7.5, 7.6, 7.7, 7.8, 7.9, or 8.0 in order to induce dissociation of the mat-rVWF/rVWF-PP complex in the solution in step (a) of the method into mat-rVWF and rVWF-PP, wherein said dissociation occurs by disruption of the non-covalently associated mat-rVWF and rVWF-PP. In some embodiments, the pH of the loading solution is increased to at least about 7.2 to about 7.8. In some embodiments, the pH of the loading solution is increased to at least about 7.6. In some embodiments, the pH of the loading solution is increased by the addition of basic amino acids. In some embodiments, the pH of at the loading solution is increased to at least 7. In some embodiments, the pH of the one or more wash buffers is increased to at least about 7.2 to about 7.8. In some embodiments, the pH of the one or more wash buffers is increased to at least about 7.6. In some embodiments, the pH of the one or more separation buffers is increased by the addition of basic amino acids. In some embodiments, the one or more separation buffers exhibit a pH of at least 7.

In some embodiments, the one or more separation buffers comprise one or more chelating agents. In some embodiments, the elution buffer includes at least one chelating agent. The chelating agent can be a divalent cation chelating agent. In some embodiments, the at least one chelating agent is a divalent cation chelating agent. In some embodiments, the divalent cation chelating agent is selected from the group consisting of EDTA, EGTA, CDTA, and citrate. In some embodiments, the divalent cation chelating agent is selected from the group consisting of NTA, DTPA, EDDS, EDTA, EGTA, CDTA, and citrate. In some embodiments, the chelating agent is NTA. In some embodiments, the chelating agent is DTPA. In some embodiments, the chelating agent is EDDS. In some embodiments, the chelating agent is EDTA. In some embodiments, the chelating agent is EGTA. In some embodiments, the chelating agent is CDTA. In some embodiments, the chelating agent is citrate. In some embodiments, the one or more wash buffers in b) comprise said one or more chelating agents and exhibit a pH of at least 7.

In some embodiments, the one or more separation buffers include at least one chelating agent. The chelating agent can be a divalent cation chelating agent. In some embodiments, the divalent cation chelating agent is selected from the group consisting of nitrilo-2,2',2"-triacetic acid (NTA), Diethylenetriaminepentaacetic acid; Diethylenetriamine-N,N,N',N', N"-pentaacetic acid (DTPA), Ethylenediamine-N,N'-disuccinic acid (EDDS), Ethylenediaminetetraacetic acid (EDTA), EGTA, CDTA, and citrate. In some embodiments, the divalent cation chelating agent is selected from the group consisting of NTA, DTPA, EDDS, EDTA, and citrate. In some embodiments, the chelating agent is NTA. In some embodiments, the chelating agent is DTPA. In some embodiments, the chelating agent is EDDS. In some embodiments, the chelating agent is EDTA. In some embodiments, the chelating agent is EGTA. In some embodiments, the chelating agent is CDTA. In some embodiments, the chelating agent is citrate.

In some embodiments, the elution buffer A and/or elution buffer B of the anion exchange chromatography step comprises about 0.5 mM to about 20 mM EDTA, e.g., about 0.5 mM-about 20 mM, about 1 mM-about 20 mM, about 1.5 mM-about 20 mM, about 2 mM-about 20 mM, about 3 mM-about 20 mM, about 5 mM-about 20 mM, about 0.5 mM-about 15 mM, about 1 mM-about 10 mM, about 1 mM-about 5 mM, about 5 mM, about 0.5 mM, about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, or the like.

In some embodiments, the one or more separation buffers comprise sodium citrate in a range including but not limited to, 10 mM-500 mM sodium citrate, 15 mM-400 mM sodium citrate, 10 mM-400 mM sodium citrate, 15 mM-350 mM sodium citrate, 20 mM-350 mM sodium citrate, 10 mM sodium citrate, 20 mM sodium citrate, 30 mM sodium citrate, 40 mM sodium citrate, 50 mM sodium citrate, 55 mM sodium citrate, 60 mM sodium citrate, 65 mM sodium citrate, 70 mM sodium citrate, 75 mM sodium citrate, 80 mM sodium citrate, 90 mM sodium citrate, 100 mM sodium citrate, 110 mM sodium citrate, 120 mM sodium citrate, 130 mM sodium citrate, 140 mM sodium citrate, 150 mM sodium citrate, 160 mM sodium citrate, 170 mM sodium citrate, 180 mM sodium citrate, 190 mM sodium citrate, 200 mM sodium citrate, 210 mM sodium citrate, 220 mM sodium citrate, 230 mM sodium citrate, 240 mM sodium citrate, 250 mM sodium citrate, 260 mM sodium citrate, 270 mM sodium citrate, 280 mM sodium citrate, 290 mM sodium citrate, 300 mM sodium citrate, 310 mM sodium citrate, 320 mM sodium citrate, 330 mM sodium citrate, 340 mM sodium citrate, 350 mM sodium citrate, 360 mM sodium citrate, 370 mM sodium citrate, 380 mM sodium citrate, 390 mM sodium citrate, 400 mM sodium citrate, 410 mM sodium citrate, 420 mM sodium citrate, 430 mM sodium citrate, 440 mM sodium citrate, 450 mM sodium citrate, 460 mM sodium citrate, 470 mM sodium citrate, 480 mM sodium citrate, 490 mM sodium citrate, 500 mM sodium citrate, 510 mM sodium citrate, 520 mM sodium citrate, 530 mM sodium citrate, 540 mM sodium citrate, 550 mM sodium citrate, 560 mM sodium citrate, 570 mM sodium citrate, 580 mM sodium citrate, 590 mM sodium citrate, or 600 mM sodium citrate, or the like.

In some embodiments, the one or more separation buffers further comprises sodium citrate, in a range including but not limited to, 10 mM-500 mM sodium citrate, 15 mM-400 mM sodium citrate, 10 mM-400 mM sodium citrate, 15 mM-350 mM sodium citrate, 20 mM-350 mM sodium citrate, 10 mM sodium citrate, 20 mM sodium citrate, 30 mM sodium citrate, 40 mM sodium citrate, 50 mM sodium citrate, 55 mM sodium citrate, 60 mM sodium citrate, 65 mM sodium citrate, 70 mM sodium citrate, 75 mM sodium citrate, 80 mM sodium citrate, 90 mM sodium citrate, 100 mM sodium citrate, 110 mM sodium citrate, 120 mM sodium citrate, 130 mM sodium citrate, 140 mM sodium citrate, 150 mM sodium citrate, 160 mM sodium citrate, 170 mM sodium citrate, 180 mM sodium citrate, 190 mM sodium citrate, 200 mM sodium citrate, 210 mM sodium citrate, 220 mM sodium citrate, 230 mM sodium citrate, 240 mM sodium citrate, 250 mM sodium citrate, 260 mM sodium citrate, 270 mM sodium citrate, 280 mM sodium citrate, 290 mM sodium citrate, 300 mM sodium citrate, 310 mM sodium citrate, 320 mM sodium citrate, 330 mM sodium citrate, 340 mM sodium citrate, 350 mM sodium citrate, 360 mM sodium citrate, 370 mM sodium citrate, 380 mM sodium citrate, 390 mM sodium citrate, 400 mM sodium citrate, 410 mM sodium citrate, 420 mM sodium citrate, 430 mM sodium citrate, 440 mM sodium citrate, 450 mM sodium citrate, 460 mM sodium citrate, 470 mM sodium citrate, 480 mM sodium citrate, 490 mM sodium citrate, 500 mM sodium citrate, 510 mM sodium citrate, 520 mM sodium citrate, 530 mM sodium citrate, 540 mM sodium citrate, 550 mM sodium citrate, 560 mM sodium citrate, 570 mM sodium citrate, 580 mM sodium citrate, 590 mM sodium citrate, or 600 mM sodium citrate, or the like.

In some embodiments, the one or more separation buffers further comprises sodium citrate, such as, but not limited to, 10 mM-500 mM sodium citrate, 15 mM-400 mM sodium citrate, 10 mM-400 mM sodium citrate, 15 mM-350 mM sodium citrate, 20 mM-350 mM sodium citrate, 10 mM sodium citrate, 20 mM sodium citrate, 30 mM sodium citrate, 40 mM sodium citrate, 50 mM sodium citrate, 55 mM sodium citrate, 60 mM sodium citrate, 65 mM sodium citrate, 70 mM sodium citrate, 75 mM sodium citrate, 80 mM sodium citrate, 90 mM sodium citrate, 100 mM sodium citrate, 110 mM sodium citrate, 120 mM sodium citrate, 130 mM sodium citrate, 140 mM sodium citrate, 150 mM sodium citrate, 160 mM sodium citrate, 170 mM sodium citrate, 180 mM sodium citrate, 190 mM sodium citrate, 200 mM sodium citrate, 210 mM sodium citrate, 220 mM sodium citrate, 230 mM sodium citrate, 240 mM sodium citrate, 250 mM sodium citrate, 260 mM sodium citrate, 270 mM sodium citrate, 280 mM sodium citrate, 290 mM sodium citrate, 300 mM sodium citrate, 310 mM sodium citrate, 320 mM sodium citrate, 330 mM sodium citrate, 340 mM sodium citrate, 350 mM sodium citrate, 360 mM sodium citrate, 370 mM sodium citrate, 380 mM sodium citrate, 390 mM sodium citrate, 400 mM sodium citrate, 410 mM sodium citrate, 420 mM sodium citrate, 430 mM sodium citrate, 440 mM sodium citrate, 450 mM sodium citrate, 460 mM sodium citrate, 470 mM sodium citrate, 480 mM sodium citrate, 490 mM sodium citrate, 500 mM sodium citrate, 510 mM sodium citrate, 520 mM sodium citrate, 530 mM sodium citrate, 540 mM sodium citrate, 550 mM sodium citrate, 560 mM sodium citrate, 570 mM sodium citrate, 580 mM sodium citrate, 590 mM sodium citrate, or 600 mM sodium citrate, or the like.

In some embodiments, the conductivity of the separation buffer is from about 5 mS/cm to about 40 mS/cm, e.g., about 5 mS/cm-about 40 mS/cm, about 10 mS/cm-about 40 mS/cm, about 15 mS/cm-about 40 mS/cm, about 20 mS/cm-about 40 mS/cm, about 25 mS/cm-about 40 mS/cm, about 30 mS/cm-about 40 mS/cm, about 10 mS/cm-about 40 mS/cm, about 10 mS/cm-about 30 mS/cm, about 5 mS/cm-about 13 mS/cm, about 5 mS/cm-about 15 mS/cm, about 15 mS/cm-about 30 mS/cm, about 18 mS/cm-about 40 mS/cm, or about 20 mS/cm-about 40 mS/cm.

Any of the buffers (buffer systems) described herein can be selected from the group consisting of Citrate, Acetate, MES, HEPES, phosphate, TrisHCl, Bis-Tris, Histidine, Imidazole, Arginine HCl, Lysine HCl, Glycine, Glycylglycine, borate, MOPS, bicine, tricine, TAPS, TAPSO, and PIPES, as single buffers or as a combination of two or more buffers. In some embodiments, the buffer comprises glycine. In some embodiments, the buffer comprises Citrate, Acetate, MES, HEPES, Phosphate, TrisHCl, Bis-Tris, Histidine, Imidazol, ArgininHCl, LysinHCl, Glycine, Glycylglycine, borate, MOPS, bicine, tricine, TAPS, TAPSO, and/or PIPES. In some embodiments, the buffer comprises Citrate. In some embodiments, the buffer comprises Acetate. In some embodiments, the buffer comprises MES. In some embodiments, the buffer comprises HEPES. In some embodiments, the buffer comprises phosphate. In some embodiments, the buffer comprises Tris-HCl. In some embodiments, the buffer comprises Bis-Tris.

In some embodiments, the buffer comprises Histidine. In some embodiments, the buffer comprises Imidazole. In some embodiments, the buffer comprises Arginine HCl. In some embodiments, the buffer comprises Lysine HCl. In some embodiments, the buffer comprises Glycine. In some embodiments, the buffer comprises Glycylglycine. In some embodiments, the buffer comprises borate. In some embodiments, the buffer comprises MOPS. In some embodiments, the buffer comprises bicine. In some embodiments, the buffer comprises tricine. In some embodiments, the buffer comprises TAPS. In some embodiments, the buffer comprises TAPSO. In some embodiments, the buffer comprises and PIPES. In some embodiments, the buffer comprises one, two, three, or four of the buffers listed herein.

In some embodiments, the one or more separation buffers further comprise one or more nonionic detergents. In some embodiments, the nonionic detergent is selected from the group consisting of Triton X-100, Tween 80, and Tween 20. In some embodiments, the nonionic detergent is Triton X-100. In some embodiments, the nonionic detergent is Tween 80. In some embodiments, the nonionic detergent is Tween 20.

In some embodiments, the flow rate use during the one or more separation buffer steps of the present method is about 10 cm/h to about 200 cm/h, e.g., about 10 cm/h, about 15 cm/h, about 20 cm/h, about 25 cm/h, about 30 cm/h, about 35 cm/h, about 40 cm/h, about 45 cm/h, about 50 cm/h, about 55 cm/h, about 60 cm/h, about 65 cm/h, about 70 cm/h, about 75 cm/h, about 80 cm/h, about 85 cm/h, about 90 cm/h, about 95 cm/h, about 100 cm/h, about 105 cm/h, about 110 cm/h, about 115 cm/h, about 120 cm/h, about 125 cm/h, about 130 cm/h, about 135 cm/h, about 140 cm/h, about 145 cm/h, about 150 cm/h, about 155 cm/h, about 160 cm/h, about 165 cm/h, about 170 cm/h, about 175 cm/h, about 180 cm/h, about 185 cm/h, about 190 cm/h, about 195 cm/h, or about 200 cm/h. Depending on the resin, in some embodiments the flow rate can be up to 600 cm/h.

In some embodiments, the flow rate use during the one or more separation buffer steps of the present method is about 10 cm/h to about 200 cm/h, e.g., about 10 cm/h, about 15 cm/h, about 20 cm/h, about 25 cm/h, about 30 cm/h, about 35 cm/h, about 40 cm/h, about 45 cm/h, about 50 cm/h, about 55 cm/h, about 60 cm/h, about 65 cm/h, about 70 cm/h, about 75 cm/h, about 80 cm/h, about 85 cm/h, about 90 cm/h, about 95 cm/h, about 100 cm/h, about 105 cm/h, about 110 cm/h, about 115 cm/h, about 120 cm/h, about 125 cm/h, about 130 cm/h, about 135 cm/h, about 140 cm/h, about 145 cm/h, about 150 cm/h, about 155 cm/h, about 160 cm/h, about 165 cm/h, about 170 cm/h, about 175 cm/h, about 180 cm/h, about 185 cm/h, about 190 cm/h, about 195 cm/h, or about 200 cm/h. Depending on the resin, in some embodiments the flow rate can be up to 600 cm/h.

In some embodiments, the said one or more buffers further comprise one or more additional substances selected from the group consisting of non-reducing sugars, sugar alcohols, and polyols. In some embodiments, the one or more buffers further comprises one or more non-reducing sugars. In some embodiments, the non-reducing sugar includes but is not limited to sucrose, trehalose, mannitol, sorbitol, galactitol, and/or xylitol. In some embodiments, the one or more buffers further comprises one or more sugar alcohols. In some embodiments, the one or more buffers further comprises one or more polyols. In some embodiments, the sugar alcohol or polyol includes but is not limited to mannitol, xylitol, erythritol, threitol, sorbitol, and/or glycerol. In some embodiments, the buffers further comprise sorbitol, mannitol, xylitol, sucrose, trehalose, ethylene glycol, propylene glycol, glycerol, 1,2,3-Propanetriol, meso-erythritol, and/or erythritol (meso-1,2,3,4-Butantetrol).

In some embodiments, the size exclusion chromatography method buffer chelator combination comprises citrate, malate (malic acid), and tartrate (tartaric acid).

D. Immunoaffinity Purification

In some embodiments, the solution comprising pro-rVWF, mat-rVWF/rVWF-PP complex, mat-rVWF, and/or rVWF propeptide (rVWF-PP) is obtained from an immunoaffinity purification method, including for example, a monoclonal antibody column. In some embodiments, the monoclonal antibody column comprises a FVIII monoclonal antibody. In some embodiments, the monoclonal antibody column comprises a VWF monoclonal antibody. Such columns and methods are known in the art and have been described. See, for example, Zimmerman et al. (U.S. Pat. No. 4,361,509; incorporated by reference herein for all purposes) which describes a method of purifying factor VIII, wherein factor VIII/VWF complex is bound to a monoclonal anti-VWF antibody, and factor VIII is dissociated from the complex by means of $CaCl_2$) ions. The immunoaffinity carrier to which vWF is still adsorbed is regenerated by means of a chaotropic agent, in particular NaSCN, a vWF/NaSCN solution being incurred as a by-product and being discarded.

Other methods include those described in U.S. Pat. No. 6,579,723, also incorporated by reference herein in its entirety, which describes a method for recovering highly purified vWF or factor VIII/vWF-complex, using an immunoaffinity chromatography procedure. Such method employs recovery of VWF from an immunoaffinity, adsorbent by using an eluting agent containing a zwitterionic species. The presence of the zwitterionic species allows for the use of mild conditions throughout the preparation, facilitating retention of molecular integrity, activity, and incorporation of the recovered proteins into pharmaceutical preparations without the need for additional stabilizers or preservatives.

Any such methods can be employed with the current purification method in order to obtain the solution comprising pro-rVWF, mat-rVWF/rVWF-PP complex, mat-rVWF, and/or rVWF propeptide (rVWF-PP). IN some embodiments, the immunoaffinity purification optionally occurs prior to step (a) in any of the described purification procedures described herein, including those based on cation exchanged, anion exchange, and/or size exclusion chromatography procedures.

E. Free Mature VWF

In some embodiments, the host cell (HC) impurity level of the composition provided herein is equal to or less than 2.0 ppm, e.g., 2.0 ppm, 1.9 ppm, 1.8 ppm, 1.7 ppm, 1.6 ppm, 1.5 ppm, 1.4 ppm, 0.3 ppm, 1.2 ppm, 1.1 ppm, 1.0 ppm, 0.9 ppm, 0.8 ppm, 0.7 ppm, 0.6 ppm, 0.5 ppm, 0.4 ppm, 0.3 ppm, 0.2 ppm, 0.1 ppm, 0.09 ppm, 0.08 ppm, 0.07 ppm, 0.06 ppm, 0.05 ppm, 0.04 ppm, 0.03 ppm, 0.02 ppm, 0.01 ppm or less. In other embodiments, the host cell impurity level of the composition provided herein is equal to or less than 0.6 ppm, e.g., 0.6 ppm, 0.5 ppm, 0.4 ppm, 0.3 ppm, 0.2 ppm, 0.1 ppm, 0.09 ppm, 0.08 ppm, 0.07 ppm, 0.06 ppm, 0.05 ppm, 0.04 ppm, 0.03 ppm, 0.02 ppm, 0.01 ppm, or less.

In some embodiments, the host cell (HC) impurity level of the composition provided herein is equal to or less than 5.0% (e.g., ≤5.0%). In some embodiments, the host cell (HC) impurity level of the composition provided herein is equal to or less than 4.0% (e.g., ≤4.0%). In some embodiments, the host cell (HC) impurity level of the composition provided herein is equal to or less than 3.0% (e.g., ≤3.0%). In some embodiments, the host cell (HC) impurity level of the composition provided herein is equal to or less than 2.0% (e.g., ≤1.0%). In some embodiments, the host cell (HC) impurity level of the composition provided herein is equal to or less than 2.0% (e.g., ≤1.0%). In some embodiments, the a host cell (HC) impurity level is equal to or less than 0.9% (e.g., ≤0.9%). In some embodiments, the host cell (HC) impurity level is equal to or less than 0.8% (e.g., ≤0.8%). In some embodiments, the host cell (HC) impurity level is equal to or less than 0.7% (e.g., ≤0.7%). In some embodiments, the host cell (HC) impurity level is equal to or less than 0.6% (e.g., ≤0.6%). In some embodiments, the host cell (HC) impurity level is equal to or less than 0.5% (e.g., ≤0.5%). In some embodiments, the host cell (HC) impurity level is equal to or less than 0.4% (e.g., ≤0.4%). In some embodiments, the host cell (HC) impurity level is equal to or less than 0.3% (e.g., ≤0.3%). In some embodiments, the host cell (HC) impurity level is equal to or less than 0.2% (e.g., ≤0.2%). In some embodiments, the host cell (HC) impurity level is equal to or less than 0.1% (e.g., ≤0.1%).

In some embodiments, the rVWF-PP impurity is less than 15%, less than 10%, less than 5%, less than 4%, less than 3%, less than 2%, less than 1%, less than 0.5%, less than 0.4%, less than 0.3%, less than 0.2%, less than 0.1%, or less than 0.05%. In some embodiments, the rVWF-PP impurity is less than 15%. In some embodiments, the rVWF-PP impurity is less than 10%. In some embodiments, the rVWF-PP impurity is less than 5%. In some embodiments, the rVWF-PP impurity is less than 4%. In some embodiments, the rVWF-PP impurity is less than 3%. In some embodiments, the rVWF-PP impurity is less than 2%. In some embodiments, the rVWF-PP impurity is less than 1%. In some embodiments, the rVWF-PP impurity is less than 0.5%. In some embodiments, the rVWF-PP impurity is less than 0.4%. In some embodiments, the rVWF-PP impurity is less than 0.3%. In some embodiments, the rVWF-PP impurity is less than 0.2%. In some embodiments, the rVWF-PP impurity is less than 0.1%. In some embodiments, the rVWF-PP impurity is less than 0.05%.

TABLE 1

Exemplary VWF-PP removal capacity

| Step | Load, VWF-PP impurity % (w/w) | Eluate, VWF-PP impurity % (w/w) |
|---|---|---|
| AEX | ~30%* | ~12% |
| CEX | ~30% | ~<0.1% |
| SEC | ~12% | ~<0.1% |

*either pre-maturated before load or maturated to completion by in-vitro maturation on column (as currently done in the process and part of a claim of a different patent)

F. Recombinant VFW Production

The free mature recombinant von Willebrand Factor (rVWF) of the present invention can be produced recombinantly. One skilled in the art recognizes useful methods for expressing a recombinant protein in a host cell. In some instances, the method includes expressing a nucleic acid sequence encoding rVWF in a host cell such as a CHO cell and culturing the resulting host cell under certain conditions to produce rVWF, prepro-VWF, pro-VWF, and the like.

In certain embodiments, the nucleic acid sequence comprising a sequence coding for VWF can be an expression vector. The vector can be delivered by a virus or can be a plasmid. The nucleic acid sequence coding for the protein can be a specific gene or a biologically functional part thereof. In one embodiment, the protein is at least a biologically active part of VWF. The nucleic acid sequence can further comprise other sequences suitable for a controlled expression of a protein such as promoter sequences, enhancers, TATA boxes, transcription initiation sites, polylinkers, restriction sites, poly-A-sequences, protein processing sequences, selection markers, and the like which are generally known to a person of ordinary skill in the art.

A wide variety of vectors can be used for the expression of the VWF and can be selected from eukaryotic expression vectors. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

In some aspects, the rVWF used in the methods of the present invention is produced by expression in a mammalian cell culture using methods known in the art. In particular embodiments, the mammalian culture comprises CHO cells. In further embodiments, the rVWF is co-expressed with recombinant Factor VIII (rFVIII) in the same culture. In such embodiments, the rVWF and the rFVIII are purified together (co-purified) or separately using methods known in the art. In other embodiments, the rVWF is expressed in a culture that does not contain rFVIII.

In some embodiments, rVWF is expressed and isolated from a suitable eukaryotic host system. Examples of eukaryotic cells include, without limitation, mammalian cells, such as CHO, COS, HEK 293, BHK, SK-Hep, and HepG2; insect cells, e.g., SF9 cells, SF21 cells, S2 cells, and High Five cells; and yeast cells, e.g., Saccharomyces or Schizosaccharomyces cells. In one embodiment, the VWF can be expressed in yeast cells, insect cells, avian cells, mammalian cells, and the like. For example, in a human cell line, a hamster cell line, or a murine cell line. In one particular embodiment, the cell line is a CHO, BHK, or HEK cell line. Typically, mammalian cells, e.g., CHO cell from a continuous cell line, can be used to express the VWF of the present invention. In certain instances, VWF protein is expressed and isolated from a CHO cell expression system.

VWF can be produced in a cell culture system or according to any cell culture method recognized by those in the art. In some embodiments, the cell cultures can be performed in large bioreactors under conditions suitable for providing high volume-specific culture surface areas to achieve high cell densities and protein expression. One means for providing such growth conditions is to use microcarriers for cell-culture in stirred tank bioreactors. The concept of cell-growth on microcarriers was first described by van Wezel (van Wezel, A. L., Nature, 1967, 216:64-5) and allows for cell attachment on the surface of small solid particles suspended in the growth medium. These methods provide for high surface-to-volume ratios and thus allow for efficient nutrient utilization. Furthermore, for expression of secreted proteins in eukaryotic cell lines, the increased surface-to-volume ratio allows for higher levels of secretion and thus higher protein yields in the supernatant of the culture. Finally, these methods allow for the easy scale-up of eukaryotic expression cultures.

The cells expressing VWF can be bound to a spherical or a porous microcarrier during cell culture growth. The microcarrier can be a microcarrier selected from the group of microcarriers based on dextran, collagen, plastic, gelatine and cellulose and others as described in Butler (1988. In: Spier & Griffiths, Animal Cell Biotechnology 3:283-303). It is also possible to grow the cells to a biomass on spherical microcarriers and subculture the cells when they have reached final fermenter biomass and prior to production of the expressed protein on a porous microcarrier or vice versa. Suitable spherical microcarriers can include smooth surface microcarriers, such as Cytodex™ 1, Cytodex™ 2, and Cytodex™ 3 (GE Healthcare) and macroporous microcarriers such as Cytopore™ 1, Cytopore™ 2, Cytoline™ 1, and Cytoline™ 2 (GE Healthcare).

In a further embodiment, the VWF propeptide is cleaved from the non-mature VWF in vitro through exposure of the pro-VWF to furin. In some embodiments, the furin used for propeptide cleavage is recombinant furin.

In certain embodiments, rVWF is expressed in cells cultured in cell culture media that produces high molecular weight rVWF. The terms "cell culture solution," "cell culture medium or media," and "cell culture supernatant" refer to aspects of cell culture processes generally well known in the art. In the context of the present invention, a cell culture solution can include cell culture media and cell culture supernatant. The cell culture media are externally added to the cell culture solution, optionally together with supplements, to provide nutrients and other components for culturing the cells expressing VWF. The cell culture supernatant refers to a cell culture solution comprising the nutrients and other components from the cell culture medium as well as products released, metabolized, and/or excreted from the cells during culture. In further embodiments, the media can be animal protein-free and chemically defined. Methods of preparing animal protein-free and chemically defined culture media are known in the art, for example in US 2006/0094104, US 2007/0212770, and US 2008/0009040, which are both incorporated herein for all purposes and in particular for all teachings related to cell culture media. "Protein free" and related terms refers to protein that is from a source exogenous to or other than the cells in the culture, which naturally shed proteins during growth. In another embodiment, the culture medium is polypeptide free. In another embodiment, the culture medium is serum free. In another embodiment the culture medium is animal protein free. In another embodiment the culture medium is animal component free. In another embodiment, the culture medium contains protein, e.g., animal protein from serum such as fetal calf serum. In another embodiment, the culture has recombinant proteins exogenously added. In another embodiment, the proteins are from a certified pathogen free animal. The term "chemically defined" as used herein shall mean, that the medium does not comprise any undefined supplements, such as, for example, extracts of animal components, organs, glands, plants, or yeast. Accordingly, each component of a chemically defined medium is accurately defined. In a preferred embodiment, the media are animal-component free and protein free.

In certain embodiments, the culture of cells expressing VWF can be maintained for at least about 7 days, or at least about 14 days, 21 days, 28 days, or at least about 5 weeks, 6 weeks, 7 weeks, or at least about 2 months, or 3, 4, 5, 6, 7, 8, 9, 10, 11, 12, 13, 14, 15, 16, 17, 18 months or longer. The cell density at which a cell-culture is maintained at for production of a recombinant VWF protein will depend upon the culture-conditions and medium used for protein expression. One of skill in the art will readily be able to determine the optimal cell density for a cell-culture producing an VWF. In one embodiment, the culture is maintained at a cell density of between about $0.5 \times 10^6$ and $4 \times 10^7$ cells/ml for an extended period of time. In other embodiments, the cell density is maintained at a concentration of between about $1.0 \times 10^6$ and about $1.0 \times 10^7$ cells/ml for an extended period of time. In other embodiments, the cell density is maintained at a concentration of between about $1.0 \times 10^6$ and about $4.0 \times 10^6$ cells/ml for an extended period of time. In other embodiments, the cell density is maintained at a concentration of between about $1.0 \times 10^6$ and about $4.0 \times 10^6$ cells/ml for an extended period of time. In yet other embodiments, the cell density may be maintained at a concentration between about $2.0 \times 10^6$ and about $4.0 \times 10^6$, or between about $1.0 \times 10^6$ and about $2.5 \times 10^6$, or between about $1.5 \times 10^6$ and about $3.5 \times 10^6$, or any other similar range, for an extended period of time. After an appropriate time in cell culture, the rVWF can be isolated from the expression system using methods known in the art.

In a specific embodiment, the cell density of the continuous cell culture for production of rVWF is maintained at a concentration of no more than $2.5 \times 10^6$ cells/mL for an extended period. In other specific embodiments, the cell density is maintained at no more than $2.0 \times 10^6$ cells/mL, $1.5 \times 10^6$ cells/mL, $1.0 \times 10^6$ cells/mL, $0.5 \times 10^6$ cells/mL, or less. In one embodiment, the cell density is maintained at between $1.5 \times 10^6$ cells/mL and $2.5 \times 10^6$ cells/mL.

In one embodiment of the cell cultures described above, the cell culture solution comprises a medium supplement comprising copper. Such cell culture solutions are described, for example, in U.S. Pat. Nos. 8,852,888 and 9,409,971, which is hereby incorporated by reference in its entirety for all purposes and in particular for all teachings related to cell culture methods and compositions for producing recombinant VWF.

The polynucleotide and amino acid sequences of prepro-VWF are set out in SEQ ID NO: 1 and SEQ ID NO:2, respectively, and are available at GenBank Accession Nos. NM_000552 (*Homo sapiens* von Willebrand factor (VWF) mRNA) and NP_000543, respectively. The amino acid sequence corresponding to the mature VWF protein is set out in SEQ ID NO: 3 (corresponding to amino acids 764-2813 of the full length prepro-VWF amino acid sequence). In some embodiments, the VWF exhibits at least 80%, at least 85%, at least 90%, at least 95%, at least 96%, at least 97%, at least 98%, at least 99%, or at least 100% identity to the sequence of SEQ ID NO:3. In some embodiments, the mat-rVWF of the invention exhibits at least 80%, at least 85%, at least 90%, at least 95%, at least 96%, at least 97%, at least 98%, at least 99%, or at least 100% identity to the sequence of SEQ ID NO:3. See, for example, U.S. Pat. No. 8,597,910, U.S. Patent Publication No. 2016/0129090, as well as FIG. 60.

One form of useful rVWF has at least the property of in vivo-stabilizing, e.g. binding, of at least one Factor VIII (FVIII) molecule and having optionally a glycosylation pattern which is pharmacologically acceptable. Specific examples thereof include VWF without the A2 domain thus resistant to proteolysis (Lankhof et al., Thromb. Haemost. 77: 1008-1013, 1997), and a VWF fragment from Val 449 to Asn 730 including the glycoprotein 1b-binding domain and binding sites for collagen and heparin (Pietu et al., Biochem. Biophys. Res. Commun. 164: 1339-1347, 1989). The determination of the ability of a VWF to stabilize at least one FVIII molecule is, in one aspect, carried out in VWF-deficient mammals according to methods known in the state in the art.

The rVWF of the present invention can be produced by any method known in the art. One specific example is disclosed in WO86/06096 published on Oct. 23, 1986 and U.S. patent application Ser. No. 07/559,509, filed on Jul. 23, 1990, which is incorporated herein by reference with respect to the methods of producing recombinant VWF. Thus, methods are known in the art for (i) the production of recombinant DNA by genetic engineering, e.g. via reverse transcription of RNA and/or amplification of DNA, (ii) introducing recombinant DNA into prokaryotic or eukaryotic cells by transfection, e.g. via electroporation or microinjection, (iii) cultivating the transformed cells, e.g. in a continuous or batchwise manner, (iv) expressing VWF, e.g. constitutively or upon induction, and (v) isolating the VWF, e.g. from the culture medium or by harvesting the transformed cells, in order to (vi) obtain purified rVWF, e.g. via anion exchange chromatography or affinity chromatography. A recombinant VWF is, in one aspect, made in transformed host cells using recombinant DNA techniques well known in the art. For instance, sequences coding for the polypeptide could be excised from DNA using suitable restriction enzymes. Alternatively, the DNA molecule is, in another aspect, synthesized using chemical synthesis techniques, such as the phosphoramidate method. Also, in still another aspect, a combination of these techniques is used.

The invention also provides vectors encoding polypeptides of the invention in an appropriate host. The vector comprises the polynucleotide that encodes the polypeptide operatively linked to appropriate expression control sequences. Methods of effecting this operative linking, either before or after the polynucleotide is inserted into the vector, are well known. Expression control sequences include promoters, activators, enhancers, operators, ribosomal binding sites, start signals, stop signals, cap signals, polyadenylation signals, and other signals involved with the control of transcription or translation. The resulting vector having the polynucleotide therein is used to transform an appropriate host. This transformation may be performed using methods well known in the art.

Any of a large number of available and well-known host cells are used in the practice of this invention. The selection of a particular host is dependent upon a number of factors recognized by the art, including, for example, compatibility with the chosen expression vector, toxicity of the peptides encoded by the DNA molecule, rate of transformation, ease of recovery of the peptides, expression characteristics, biosafety and costs. A balance of these factors must be struck with the understanding that not all host cells are equally effective for the expression of a particular DNA sequence. Within these general guidelines, useful microbial host cells include, without limitation, bacteria, yeast and other fungi, insects, plants, mammalian (including human) cells in culture, or other hosts known in the art.

Transformed host cells are cultured under conventional fermentation conditions so that the desired compounds are expressed. Such fermentation conditions are well known in the art. Finally, the polypeptides are purified from culture media or the host cells themselves by methods well known in the art.

Depending on the host cell utilized to express a compound of the invention, carbohydrate (oligosaccharide) groups are optionally attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids not counting proline. The structures of N-linked and O-linked oligosaccharides and the sugar residues found in each type are different. One type of sugar that is commonly found on both N-linked and O-linked oligosaccharides is N-acetylneuraminic acid (referred to as sialic acid). Sialic acid is usually the terminal residue of both N-linked and O-linked oligosaccharides and, by virtue of its negative charge, in one aspect, confers acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). In other aspects, such sites are glycosylated by synthetic or semi-synthetic procedures known in the art.

In some embodiments, sialysation (also referred to as sialylation), can be performed on the column as part of the purification procedures described herein (including the anion exchange, cation exchange, size exclusion, and/or immunoaffinity methods). In some embodiments, the sialylation results in increased stability of the rVWF as compared to rVWF that has not undergone sialylation. In some embodiments, the sialylation results in increased stability of the rVWF in blood circulation (for example, after administration to a subject) as compared to rVWF that has not undergone sialylation. In some embodiments, the increased stability of salivated rVWF results in an increase of 10%, 20%, 30%, 40%, 50%, 60%, 70%, 80%, 90%, or more as compared rVWF that has not undergone sialylation. In some embodiments, the sialylation results in increased half-life for the rVWF as compared to rVWF that has not undergone sialylation. In some embodiments, the sialylation results in increased half-life for the rVWF in blood circulation (for example, after administration to a subject) as compared to rVWF that has not undergone sialylation. In some embodiments, the increased half-life of sialylated rVWF results in an increase of 10%, 20%, 30%, 40%, 50%, 60%, 70%, 80%, 90%, or more as compared rVWF that has not undergone sialylation. In some embodiments, the increased half-life of sialylated rVWF results in rVWF that is stable for 1 hour, 2 hours, 3 hours, 4 hours, 6 hours, 12 hours, 24 hours or more in blood circulation (for example, after administration to a subject) as compared to rVWF that has not undergone sialylation. In some embodiments, sialylation increases the number of 2,3 sialylation and/or 2,6 sialylation. In some embodiments, sialylation is increased by the addition of 2,3 sialyltransferase and/or 2,6 sialyltransferase and CMP-NANA (Cytidine-5'-monophospho-N-acetylneuraminic acid sodium salt) as an additional buffer step. In some embodiments, sialylation is increased by the addition of 2,3 sialyltransferase and CMP-NANA (Cytidine-5'-monophospho-N-acetylneuraminic acid sodium salt) as an additional buffer step. In some embodiments, 2,3 sialylation is increased by the addition of 2,3 sialyltransferase and CMP-NANA (Cytidine-5'-monophospho-N-acetylneuraminic acid sodium salt) as an additional buffer step. In some embodiments, in order to increase sialylation, the bound protein (for example, bound rVWF) is treated with sialidase (e.g., neuraminidase) to remove the 2,3 sialylation and then a wash step is applied to remove the sialidase and introduce 2,6 sialylation. In some embodiments, the 2,6 sialylation in introduced by the addition of 2,6 sialyltransferase and CMP-NANA In some embodiments, 2,6 sialylation is increased by the addition of 2,6 sialyltransferase and CMP-NANA (Cytidine-5'-monophospho-N-acetylneuraminic acid sodium salt) as an additional buffer step. In some embodiments, 2,3 sialylation and/or 2,6 sialylation are increased by the addition of 2,3 sialyltransferase and/or 2,6 sialyltransferase and CMP-NANA (Cytidine-5'-monophospho-N-acetylneuraminic acid sodium salt) as an additional buffer step. In some embodiments, CMP-NANA is chemically or enzymatic modified to transfer modified sialic acid to potential free position. In some embodiments, sialylation is performed by loading rVWF onto the resin, washing with one or more buffers as described herein to deplete unwanted impurities, apply one or more buffers containing sialyltransferase and CMP-NANA at conditions that allow additional sialylation, and washing with one or more buffers to deplete excess of the sialylation reagents, and eluting with one or more buffers the enhanced rVWF (e.g., the rVWF with increased sialylation). In some embodiments, the sialylation process is performed as part of a cation exchange method, an anion exchange method, a size exclusion method, or an immunoaffinity purification method, as described herein.

Alternatively, the compounds are made by synthetic methods using, for example, solid phase synthesis techniques. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527'. Solid phase synthesis is the preferred technique of making individual peptides since it is the most cost-effective method of making small peptides Fragments, variants and analogs of VWF can be produced according to methods that are well-known in the art. Fragments of a polypeptide can be prepared using, without limitation, enzymatic cleavage (e.g., trypsin, chymotrypsin) and also using recombinant means to generate a polypeptide fragments having a specific amino acid sequence. Polypeptide fragments may be generated comprising a region of the protein having a particular activity, such as a multimerization domain or any other identifiable VWF domain known in the art.

Methods of making polypeptide analogs are also well-known. Amino acid sequence analogs of a polypeptide can be substitutional, insertional, addition or deletion analogs. Deletion analogs, including fragments of a polypeptide, lack one or more residues of the native protein which are not essential for function or immunogenic activity. Insertional analogs involve the addition of, e.g., amino acid(s) at a non-terminal point in the polypeptide. This analog may include, for example and without limitation, insertion of an immunoreactive epitope or simply a single residue. Addition analogs, including fragments of a polypeptide, include the addition of one or more amino acids at either or both termini of a protein and include, for example, fusion proteins. Combinations of the aforementioned analogs are also contemplated.

Substitutional analogs typically exchange one amino acid of the wild-type for another at one or more sites within the protein, and may be designed to modulate one or more properties of the polypeptide without the complete loss of other functions or properties. In one aspect, substitutions are conservative substitutions. "Conservative amino acid substitution" is substitution of an amino acid with an amino acid having a side chain or a similar chemical character. Similar amino acids for making conservative substitutions include those having an acidic side chain (glutamic acid, aspartic acid); a basic side chain (arginine, lysine, histidine); a polar amide side chain (glutamine, asparagine); a hydrophobic, aliphatic side chain (leucine, isoleucine, valine, alanine, glycine); an aromatic side chain (phenylalanine, tryptophan, tyrosine); a small side chain (glycine, alanine, serine, threonine, methionine); or an aliphatic hydroxyl side chain (serine, threonine).

In one aspect, analogs are substantially homologous or substantially identical to the recombinant VWF from which they are derived. Analogs include those which retain at least some of the biological activity of the wild-type polypeptide, e.g. blood clotting activity.

Polypeptide variants contemplated include, without limitation, polypeptides chemically modified by such techniques as ubiquitination, glycosylation, including polysialation (or polysialylation), conjugation to therapeutic or diagnostic agents, labeling, covalent polymer attachment such as pegylation (derivatization with polyethylene glycol), introduction of non-hydrolyzable bonds, and insertion or substitution by chemical synthesis of amino acids such as ornithine, which do not normally occur in human proteins. Variants retain the same or essentially the same binding properties of non-modified molecules of the invention. Such chemical modification may include direct or indirect (e.g., via a linker) attachment of an agent to the VWF polypeptide. In the case of indirect attachment, it is contemplated that the linker may be hydrolyzable or non-hydrolyzable.

Preparing pegylated polypeptide analogs will in one aspect comprise the steps of (a) reacting the polypeptide with polyethylene glycol (such as a reactive ester or aldehyde derivative of PEG) under conditions whereby the binding construct polypeptide becomes attached to one or more PEG groups, and (b) obtaining the reaction product(s). In general, the optimal reaction conditions for the acylation reactions are determined based on known parameters and the desired result. For example, the larger the ratio of PEG:protein, the greater the percentage of poly-pegylated product. In some embodiments, the binding construct has a single PEG moiety at the N-terminus. Polyethylene glycol (PEG) may be attached to the blood clotting factor to, for example, provide a longer half-life in vivo. The PEG group may be of any convenient molecular weight and is linear or branched. The average molecular weight of the PEG ranges from about 2 kiloDalton ("kD") to about 100 kDa, from about 5 kDa to about 50 kDa, or from about 5 kDa to about 10 kDa. In certain aspects, the PEG groups are attached to the blood clotting factor via acylation or reductive alkylation through a natural or engineered reactive group on the PEG moiety (e.g., an aldehyde, amino, thiol, or ester group) to a reactive group on the blood clotting factor (e.g., an aldehyde, amino, or ester group) or by any other technique known in the art.

Methods for preparing polysialylated polypeptide are described in United States Patent Publication 20060160948, Fernandes et Gregoriadis; Biochim. Biophys. Acta 1341: 26-34, 1997, and Saenko et al., Haemophilia 12:42-51, 2006. Briefly, a solution of colominic acid (CA) containing 0.1 M $NaIO_4$ is stirred in the dark at room temperature to oxidize the CA. The activated CA solution is dialyzed against, e.g., 0.05 M sodium phosphate buffer, pH 7.2 in the dark and this solution was added to a rVWF solution and incubated for 18 h at room temperature in the dark under gentle shaking. Free reagents are optionally be separated from the rVWF-polysialic acid conjugate by, for example, ultrafiltration/diafiltration. Conjugation of rVWF with polysialic acid is achieved using glutaraldehyde as cross-linking reagent (Migneault et al., Biotechniques 37: 790-796, 2004).

It is further contemplated in another aspect that a polypeptide of the invention is a fusion protein with a second agent which is a polypeptide. In one embodiment, the second agent which is a polypeptide, without limitation, is an enzyme, a growth factor, an antibody, a cytokine, a chemokine, a cell-surface receptor, the extracellular domain of a cell surface receptor, a cell adhesion molecule, or fragment or active domain of a protein described above. In a related embodiment, the second agent is a blood clotting factor such as Factor VIII, Factor VII, and/or Factor IX. In some embodiments, the second agent is a fusion protein. The fusion protein contemplated is made by chemical or recombinant techniques well-known in the art. In some embodiments, the fusion protein is a rVWF-FVIII fusion protein. In some embodiments, the fusion protein is a rVWF-FVIII fusion protein, wherein an active FVIII is embedded in an VWF motif. In some embodiments, the fusion protein is a rVWF-FVIII fusion protein, wherein an active FVIII is embedded in an VWF motif such that the VWF is full length. In some embodiments, the fusion protein is a rVWF-FVIII fusion protein, wherein an active FVIII is embedded in an VWF motif, wherein parts of the VWF sequence are deleted and replaced by a FVIII-sequence. In some embodiments of the rVWF-FVIII fusion protein, the FVIII is a B-domain deleted FVIII. In some embodiments of the rVWF-FVIII fusion protein, the N-glycosylation rich domain replaces the FVIII-B-domain. In some embodiments of the rVWF-FVIII fusion protein, the vWF-N glycosylation rich domain is fused to the full length FVIII and/or truncated forms thereof.

In some embodiments of the rVWF-FVIII fusion protein, the fusion protein comprises:
- a VWF peptide comprising positions 764 to 1336 of the VWF peptide,
- a FVIII peptide comprising positions 24 to 760 of the FVIII heavy chain peptide,
- a VWF peptide comprising positions 2218 to 2593 of the VWF peptide,
- a FVIII peptide comprising positions 1333 to 2351 of the FVIII light chain peptide, and
- a VWF peptide comprising positions 2620 to 2813 of the VWF peptide.

In this embodiment of the rVWF-FVIII fusion protein, the position of amino acids is counted from the first position—including Pro and/or signal peptide. In this embodiment of the rVWF-FVIII fusion protein, position 764 in VWF corresponds to position 1 of the mature rVWF (mat-rVWF) and position 20 in FVIII corresponds to position 1 of the mature FVIII peptide. In some embodiments of the rVWF-FVIII fusion protein, the fusion protein sequence is provided in FIG. 64.

In some embodiments of the rVWF-FVIII fusion protein, the fusion protein comprises:
- a FVIII peptide comprising positions FVIII heavy chain 19 to 760 of the FVIII heavy chain peptide,
- a VWF peptide comprising positions 2218 to 2593 of the VWF peptide, and
- a FVIII peptide comprising positions 1333 to 2351 of the FVIII light chain peptide.

In this embodiment of the rVWF-FVIII fusion protein, the position of amino acids is counted from the first position—including Pro and/or signal peptide. In this embodiment of the rVWF-FVIII fusion protein, position 764 in VWF corresponds to position 1 of the mature rVWF (mat-rVWF) and position 20 in FVIII corresponds to position 1 of the mature FVIII peptide. In some embodiments of the rVWF-FVIII fusion protein, the fusion protein sequence is provided in FIG. 65.

It is also contemplated in another aspect that prepro-VWF and pro-VWF polypeptides will provide a therapeutic benefit in the formulations of the present invention. For example, U.S. Pat. No. 7,005,502 describes a pharmaceutical preparation comprising substantial amounts of pro-VWF that induces thrombin generation in vitro. In addition to recombinant, biologically active fragments, variants, or other analogs of the naturally-occurring mature VWF, the present invention contemplates the use of recombinant biologically active fragments, variants, or analogs of the pre-pro-VWF (set out in SEQ ID NO:2) or pro-VWF polypeptides (amino acid residues 23 to 764 of SEQ ID NO: 2) in the formulations described herein.

Polynucleotides encoding fragments, variants and analogs may be readily generated by a worker of skill to encode biologically active fragments, variants, or analogs of the naturally-occurring molecule that possess the same or similar biological activity to the naturally-occurring molecule. In various aspects, these polynucleotides are prepared using PCR techniques, digestion/ligation of DNA encoding molecule, and the like. Thus, one of skill in the art will be able to generate single base changes in the DNA strand to result in an altered codon and a missense mutation, using any method known in the art, including, but not limited to site-specific mutagenesis. As used herein, the phrase "moderately stringent hybridization conditions" means, for example, hybridization at 42° C. in 50% formamide and washing at 60° C. in 0.1×SSC, 0.1% SDS. It is understood by those of skill in the art that variation in these conditions occurs based on the length and GC nucleotide base content of the sequences to be hybridized. Formulas standard in the art are appropriate for determining exact hybridization conditions. See Sambrook et al., 9.47-9.51 in Molecular Cloning, Cold Spring Harbor Laboratory Press, Cold Spring Harbor, N.Y. (1989).

G. Viral Inactivation

In some embodiments, the method described herein further comprises a step of viral inactivation. The viral inactivation step can occur before, after, or concurrently with the washing step and/or the elution step, but before the collecting step. The viral inactivation treatment can inactivate lipid enveloped viruses. In some embodiments, the viral inactivation treatment is a solvent and detergent (S/D) treatment. In some embodiments, the viral inactivation treatment includes the use of ethylene glycol, propylenglyol in section alcohols and/or one or more organic solvent(s).

As used herein, the term "inactivating virus" or "virus inactivation" refers to a process where a virus can no longer infect cells, replicate, and propagate, and per se virus removal. As such, the term "virus inactivation" refers generally to the process of making a fluid disclosed herein completely free of infective viral contaminants. Any degree of viral inactivation using the methods disclosed herein is desirable. However, it is desirable to achieve the degree of viral inactivation necessary to meet strict safety guidelines for pharmaceuticals. These guidelines are set forth by the WHO and well known to those of skill in the art.

The methods disclosed herein, may further comprise a step of removing a virus from the mixture after incubation. As used herein, the term "removing a virus" or "virus removal" refers to a process that depletes a virus from a mixture disclosed herein, such that the virus particles are effectively extracted from the mixture. The virus can be a viable virus or an inactivated virus. Removal is typically accomplished by size exclusion chromatography or positive adsorption chromatography where the protein of interest binds to a chromatographic resin, including for example, an anion exchange resin or cation exchange resin as described herein. After removal, the amount of a virus remaining is an amount that has substantially no long term or permanent detrimental effect when administered to a subject in need thereof, including for example, a human being.

In one embodiment, a mixture after removal of virus is essentially free of the virus. As used herein, the term "essentially free of a virus" means that only trace amounts of a virus can be detected or confirmed by the instrument or process being used to detect or confirm the presence or activity of the virus and that such trace amount of the virus is insufficient to be deleterious to the health of the human being. In an aspect of this embodiment, a mixture after removal of virus is entirely free of the virus. As used herein, the term "entirely free of a virus" means that the presence of virus cannot be detected or confirmed within the detection range of the instrument or process being used to detect or confirm the presence or activity of the virus. A protein contained within a mixture that is essentially free or entirely free of a virus can be used to make a pharmaceutical composition that is safe to administer to a human being because the virus is insufficient to be deleterious to the health of the human being.

In other aspects of this embodiment, a mixture after removal of virus comprises less than 10 PFU/mL of a virus, such as, e.g., less than 1 PFU/mL of a virus, less than $1 \times 10^{-1}$ PFU/mL of a virus, $1 \times 10^{-2}$ PFU/mL of a virus, or $1 \times 10^{-3}$ PFU/mL of a virus.

In yet other aspects of this embodiment, a mixture after removal of virus comprises less than an ID50 for a virus, such as, e.g., at least 10-fold less than the ID50 for a virus, at least 100-fold less than the ID50 for a virus, at least 200-fold less than the ID50 for a virus, at least 300-fold less than the ID50 for a virus, at least 400-fold less than the ID50 for a virus, at least 500-fold less than the ID50 for a virus, at least 600-fold less than the ID50 for a virus, at least 700-fold less than the ID50 for a virus, at least 800-fold less than the ID50 for a virus, at least 900-fold less than the ID50 for a virus, or at least 1000-fold less than the ID50 for a virus.

The viral inactivation may be carried out in conjunction with protein purification or not. In some embodiments, the method comprises immobilizing the protein on a support; and treating the immobilized protein with a detergent-solvent mixture comprising a non-ionic detergent and an organic solvent. In some embodiments, the support is a chromatographic resin. In certain embodiments, the detergent-solvent mixture comprises 1% Triton X-100, 0.3% Tri-N-butyl phosphate, and 0.3% Polysorbate 80 (Tween 80). The solvent-detergent mixture treatment can continue for a prolonged time, e.g., for 30 minutes to 1 hour, while the protein remains immobilized on the chromatographic resin, e.g., on a cation exchange resin; and/or solvent-detergent treatment may occur at 2° C. to 10° C. This approach to virus inactivation surprisingly can reduce the formation of protein aggregates during treatment with a detergent-solvent mixture by a significant amount, e.g., by more than 50%, as compared to treatment with a solvent-detergent mixture while the protein is not immobilized in solution.

In some embodiments, the method of inactivating a lipid-coat containing virus comprises the steps of: i) providing a fluid comprising a protein having an activity; ii) mixing an organic solvent and a surfactant with the fluid, thereby creating a mixture; and iii) incubating the mixture for no more than about 120 minutes; wherein both steps (ii) and (iii) are performed at a temperature of no higher than about 20° C.; wherein the mixture after incubation is essentially free of a viable lipid-coat containing virus; and wherein the protein after incubation has an activity of at least 25% of the activity provided in step (i).

In other embodiments, a protein essentially free of a lipid-coat containing virus can be obtained from a method comprising the steps of: i) providing a fluid comprising a protein having an activity; ii) mixing an organic solvent and a surfactant with the fluid, thereby creating a mixture; and iii) incubating the mixture for no more than about 120 minutes; wherein both steps (ii) and (iii) are performed at a temperature of no higher than about 20° C.; wherein the mixture after incubation is essentially free of a viable lipid-coat containing virus; and wherein the protein after incubation has an activity of at least 25% of the activity provided in step (a).

In another embodiment, the method of inactivating a lipid-coat containing virus comprises the steps of: i) providing a fluid comprising a blood coagulation protein having an activity (e.g., VWF); ii) mixing an organic solvent and a surfactant with the fluid, thereby creating a mixture; and iii) incubating the mixture for no more than about 120 minutes; wherein both steps (ii) and (iii) are performed at a temperature of no higher than about 20° C.; wherein the mixture after incubation is essentially free of a viable lipid-coat containing virus; and wherein the Factor VIII after incubation has an activity of at least 25% of the activity provided in step (i).

In some instances, the organic solvent is an ether, an alcohol, a dialkylphosphate or a trialkylphosphate. In certain embodiments, the ether is selected from dimethyl ether, diethyl ether, ethyl propyl ether, methyl-butyl ether, methyl isopropyl ether, and/or methyl isobutyl ether.

In some embodiments, the alcohol is selected from methanol, ethanol, propanol, isopropanol, n-butanol, isobutanol, n-pentanol, and/or isopentanol. In some embodiments, the dialkylphosphate is selected from di-(n-butyl)phosphate, di-(t-butyl)phosphate, di-(n-hexyl)phosphate, di-(2-ethylhexyl)phosphate, di-(n-decyl)phosphate, and/or ethyl di(n-butyl) phosphate. In some embodiments, the trialkylphosphate is selected from tri-(n-butyl)phosphate, tri-(t-butyl) phosphate, tri-(n-hexyl)phosphate, tri-(2-ethylhexyl) phosphate, and/or tri-(n-decyl)phosphate.

In some instances, the final concentration of the organic solvent is from about 0.1% (v/v) to about 5.0% (v/v), about 0.1% (v/v) to about 1.0% (v/v), about 0.2% (v/v) to about 0.5% (v/v), or about 0.2% (v/v) to about 0.4% (v/v), about 0.3% (v/v).

In some instances, the surfactant is selected from an ionic surfactant, a zwitterionic (amphoteric) surfactant, and/or a non-ionic surfactant. The ionic surfactant can be an anion surfactant or cationic surfactant.

In certain embodiments, the anionic surfactant is selected from an alkyl sulfate, an alkyl ether sulfate, a docusate, a sulfonate fluorosurfactant, an alkyl benzene sulfonate, an alkyl aryl ether phosphate, an alkyl ether phosphate, an; alkyl carboxylate, a sodium lauroyl sarcosinate, and/or a carboxylate fluorosurfactant. In some embodiments, the alkyl sulfate is selected from ammonium lauryl sulfate or sodium lauryl sulfate (SDS). In other embodiments, the alkyl ether sulfate is sodium laureth sulfate and/or sodium myreth sulfate. In some embodiments, the docusate is dioctyl sodium sulfosuccinate.

In some embodiments, the sulfonate fluorosurfactant is selected from perfluorooctanesulfonate (PFOS) and/or perfluorobutanesulfonate. In some embodiments, the alkyl carboxylate is selected from a fatty acid salt and/or sodium stearate. In some embodiments, the carboxylate fluorosurfactant is perfluorononanoate and peril uoroocta noate. In some embodiments, the cationic surfactant is selected from an alkyltrimethylammonium salt, cetylpyridinium chloride (CPC), polyethoxylated tallow amine (POEA), benzalkonium chloride (BAC), benzethonium chloride (BZT), 5-bromo-5-nitro-1,3-dioxane, dimethyldioctadecylammonium chloride, dioctadecyldimethylammonium bromide (DODAB), a pH-dependent primary amine, a pH-dependent secondary amine, and/or a pH-dependent tertiary amine. In some embodiments, the alkyltrimethylammonium salt is selected from cetyl trimethylammonium bromide (CTAB) and/or cetyl trimethylammonium chloride (CTAC). In some embodiments, the primary amine becomes positively charged at pH<10 or the secondary amine becomes charged at pH<4.

In some embodiments, the cationic surfactant is octenidine dihydrochloride.

In some embodiments, the zwitterionic surfactant is selected from 3-[(3-cholamidopropyl) dimethylammonio]-1-propanesulfonate (CHAPS), a sultaine, a betaine, and/or a lecithin. In some embodiments, the sultaine is cocamidopropyl hydroxysultaine. In some embodiments, the betaine is cocamidopropyl betaine.

In some embodiments, the non-ionic surfactant is selected from a polyoxyethylene glycol sorbitan alkyl ester, a poloxamer, an alkyl phenol polyglycol ether, a polyethylene glycol alkyl aryl ether, a polyoxyethylene glycol alkyl ether, 2-dodecoxyethanol (LUBROL®-PX), a polyoxyethylene glycol octylphenol ether, a polyoxyethylene glycol alkylphenol ether, a phenoxypolyethoxylethanol, a glucoside alkyl ether, a maltoside alkyl ether, a thioglucoside alkyl ether, a digitonin, a glycerol alkyl ester, an alkyl aryl polyether sulfate, an alcohol sulfonate, a sorbitan alkyl ester, a cocamide ethanolamine, sucrose monolaurate, dodecyl dimethylamine oxide, and/or sodium cholate. In some embodiments, the polyoxyethylene glycol sorbitan alkyl ester is selected from polysorbate 20 sorbitan monooleate (TWEEN® 20), polysorbate 40 sorbitan monooleate (TWEEN® 40), polysorbate 60 sorbitan monooleate (TWEEN® 60), polysorbate 61 sorbitan monooleate (TWEEN® 61), polysorbate 65 sorbitan monooleate (TWEEN® 65), polysorbate 80 sorbitan monooleate (TWEEN® 80), and/or polysorbate 81 sorbitan monooleate (TWEEN® 81).

In some embodiments, the poloxamer is selected from Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), and/or Poloxamer 407 (PLURONIC® F127).

In some embodiments, the polyoxyethylene glycol alkyl ether is selected from octaethylene glycol monododecyl ether, pentaethylene glycol monododecyl ether, BRIJ® 30, and/or BRIJ® 35.

In some cases, the polyoxyethylene glycol octylphenol ether is selected from polyoxyethylene (4-5) p-t-octyl phenol (TRITON® X-45), and/or polyoxyethylene octyl phenyl ether (TRITON® X-100). In some embodiments, the polyoxyethylene glycol alkylphenol ether is nonoxynol-9.

In some embodiments, the phenoxypolyethoxylethanol is selected from nonyl phenoxypolyethoxylethanol and/or octyl phenoxypolyethoxylethanol.

In some embodiments, the glucoside alkyl ether is octyl glucopyranoside. In some embodiments, the maltoside alkyl ether is dodecyl maltopyranoside. In some embodiments, the thioglucoside alkyl ether is heptyl thioglucopyranoside. In some embodiments, the glycerol alkyl ester is glyceryl laurate. In some embodiments, the cocamide ethanolamine is selected from cocamide monoethanolamine and/or cocamide diethanolamine.

In some embodiments, the final concentration of the surfactant is from about 0.1% (v/v) to about 10.0% (v/v), or about 0.5% (v/v) to about 5.0% (v/v). In some cases, the surfactant is a plurality of surfactants.

Useful methods for viral inactivation are described, for example, in U.S. Pat. Nos. 6,190,609 and 9,315,560, and U.S. Appl. Publication No. 2017/0327559, the disclosures of which are herein incorporated by reference in their entireties.

Viral inactivation can be performed as recognized by those skilled in the art. For instance, the solvent tri(n-butyl) phosphate (TNBP) and detergents such as, but not limited to, polysorbate 80 and triton X-100 are effective for inactivating lipid enveloped viruses. Viral inactivation can be performed at room temperatures such as 14° C. to about 25° C. for about 1 hour or more. In some cases, the incubation time is not longer than two hours.

In some embodiments, the viral inactivation treatment is stopped by adding a buffer comprising a sodium citrate buffer to the virus inactivated material. In some instances, the sodium citrate buffer comprises from about 40 mM to about 100 mM sodium citrate buffer, e.g., about 40 mM, about 50 mM, about 60 mM, about 70 mM, about 80 mM, about 90 mM, or about 100 mM sodium citrate buffer.

H. VFW Maturation

Furin is part of a protein family referred to as SPC (subtilisin-like proprotein convertases), PC (proprotein convertases) or in some cases PACE (paired basic amino acid cleaving enzyme). Members of the furin protein family include but are not limited to Furin, Kex2, PC2, PC1/PC3, PACE4, PC4, PC5 and/or PC7. As part of the present invention, methods provides methods for maturation of pro-VWF (pro-rVWF) into a mat-VWF/VWF-PP (mat-rVWF/rVWF-PP) complex by treatment with furin. Any of these furin family members can be employed in the methods of VWF maturation.

In some embodiments, the pro-VWF is furin matured on an anion exchange column or resin, on a cation exchange column or resin, or as part of a size separation chromatography method. In some embodiments, the pro-VWF is furin matured on an anion exchange column or resin and/or as part of an anion exchange chromatography procedure. In some embodiments, the pro-VWF is furin matured on a cation exchange column or resin and/or as part of a cation exchange chromatography procedure. In some embodiments, the pro-VWF is furin matured as part of a size exclusion chromatography procedure. Such methods have been described, for example, in U.S. Pat. No. 8,058,411, incorporated by reference herein in its entirety for all purposes.

In order to facilitate the maturation process and to provide pro-VWF immobilized on the resin at an elevated concentration, in some embodiments of the invention, the chromatographic resin is packed in a chromatographic column. Since the concentration of pro-VWF in the course of its in vitro maturation influences the maturation efficiency, it is advantageous to pack the chromatographic resin in a column. Furthermore, the use of chromatographic columns allows the efficient control of the parameters of maturation in a more reproducible manner and makes it simpler to perform the maturation of VWF in vitro. In some embodiments, the furin concentration is about 1, about 2, about 3, or about 4 units of recombinant active furin per IU of VWF:Ag (10 µg of pro-rVWF). In some embodiments, the furin concentration is about 2-3 units of recombinant active furin per IU of VWF:Ag (10 µg of pro-rVWF). In some embodiments, the furin concentration is about 1-2 units of recombinant active furin per IU of VWF:Ag (10 µg of pro-rVWF). In some embodiments, the furin concentration is about 2 units of recombinant active furin per IU of VWF:Ag (10 µg of pro-rVWF).

In some embodiments, when the pro-VWF is immobilized on an anion exchange resin and incubated with a solution exhibiting pro-VWF convertase activity, the conductivity measured at 25° C. is below 25 mS/cm. In some embodiments, when the pro-VWF is immobilized on an anion exchange resin and incubated with a solution exhibiting pro-VWF convertase activity, the conductivity measured at 25° C. is below 20 mS/cm. In some embodiments, when the pro-VWF is immobilized on an anion exchange resin and incubated with a solution exhibiting pro-VWF convertase activity, the conductivity measured at 25° C. is below 16 mS/cm. In some embodiments, when the pro-VWF is immobilized on an anion exchange resin and incubated with a solution exhibiting pro-VWF convertase activity, the conductivity measured at 25° C. is between 16 mS/cm and 25 mS/cm. In some embodiments, when the pro-VWF is immobilized on an anion exchange resin and incubated with a solution exhibiting pro-VWF convertase activity, the conductivity measured at 25° C. is between 20 mS/cm and 25 mS/cm. Pro-rVWF as well as mat-rVWF can be efficiently immobilized on anion exchange resins at these conductivity levels. Consequently, the buffers applied in the course of the present method have to be adapted correspondingly to maintain the conductivity levels. In some embodiments, the conductivity is such that the furin and/or PACE enzyme is in active form and full or partially in the mobile phase.

In some embodiments, mat-rVWF is eluted from an anion exchange resin at a conductivity when measured at 250° C. of at least 40 mS/cm. In some embodiments, mat-rVWF is eluted from an anion exchange resin at a conductivity when measured at 250° C. of at least 60 mS/cm. In some embodiments, mat-rVWF is eluted from an anion exchange resin at a conductivity when measured at 250° C. of at least 80 mS/cm. In some embodiments, mat-rVWF is eluted from an anion exchange resin at a conductivity when measured at 250° C. of between 40 mS/cm and 80 mS/cm. In some embodiments, mat-rVWF is eluted from an anion exchange resin at a conductivity when measured at 250° C. of between 60 mS/cm and 80 mS/cm. In some embodiments, the desired rVWF species starts to elute at a conductivity of between about 12 to 16 mS/cm/25° C. with an anion exchange resin (for example with TMAE). In some embodiments the main amount (bulk) of the rVWF desired species was eluted between about 55 to 60 mS/cm/25° C. with an anion exchange resin. In some embodiments, the desired rVWF species starts to elute at a conductivity of between about 18 to 24 mS/cm/25° C. with a cation exchange resin. In some embodiments the main amount (bulk) of the rVWF desired species was eluted between about 36 to 42 mS/cm/25° C. with a cation exchange resin. In some embodiments, the desired rVWF is mature rVWF (e.g., mat-rVWF). IN some embodiments, the main amount (bulk) includes at least about 30%, 40%, 50%, 60%, 70%, 80%, 90% or more of the total amount of the desired species that elutes.

In some embodiments, further washing steps before the mat-rVWF is eluted from the anion exchange resin are employed. In some embodiments, further washing steps before the mat-rVWF is eluted from the cation exchange resin are employed.

For their proteolytic activity many proteases need co-factors like bivalent metal ions. Furin and furin protein family members require calcium ions for activity. Therefore, if furin is used to mature pro-rVWF in vitro calcium salts are employed. In some embodiments, the calcium salt is a soluble calcium salt. In some embodiments, the calcium salt is calcium chloride ($CaCl_2$)). In some embodiments, the calcium salt is calcium acetate. In some embodiments, other bivalent metal ions are employed, including for example, but not limited to, $Be^{2+}$, $Ba^{2+}$, $Mg^{2+}$, $Mn^{2+}$, $Sr^{2+}$, $Zn^{2+}$, $Co^{2+}$, $Ni^{2+}$, $Cd^{2+}$, and/or $Cu^{2+}$. In some embodiments, a combination of two or more bivalent cations are employed. In some embodiments, $Ca^{2+}$ and $Mg^{2+}$ are employed in combination. In some embodiments, the calcium salt is a soluble magnesium salt. In some embodiments, the magnesium salt is magnesium chloride ($MgCl_2$). In some embodiments, the furin protein family formulation for use in the maturation comprises a soluble calcium salt at a concentration of 0.01 to 10 mM. In some embodiments, the furin protein family formulation for use in the maturation comprises a soluble magnesium salt at a concentration of 0.01 to 10 mM. In some embodiments, the furin protein family formulation for use in the maturation comprises $CaCl_2$ at a concentration of 0.01 to 10 mM. In some embodiments, the furin protein family formulation for use in the maturation comprises $MgCl_2$ at a concentration of 0.01 to 10 mM. In some embodiments, the furin protein family formulation for use in the maturation comprises $CaCl_2$ at a concentration of 0.1 to 5 mM. In some embodiments, the furin protein family formulation for use in the maturation comprises $MgCl_2$ at a concentration of 0.1 to 5 mM. In some embodiments, the furin protein family formulation for use in the maturation comprises $CaCl_2$ at a concentration of 0.2 to 2 mM. In some embodiments, the furin protein family formulation for use in the maturation comprises $MgCl_2$ at a concentration of 0.2 to 2 mM. In some embodiments, the furin protein family formulation for use in the maturation comprises furin. In some embodiments, the furin concentration is about 1, about 2, about 3, or about 4 units of recombinant active furin per IU of VWF:Ag (10 g of pro-rVWF). In some embodiments, the furin concentration is about 2-3 units of recombinant active furin per IU of VWF:Ag (10 g of pro-rVWF). In some embodiments, the furin concentration is about 1-2 units of recombinant active furin per IU of VWF:Ag (10 g of pro-rVWF). In some embodiments, the furin concentration is about 2 units of recombinant active furin per IU of VWF:Ag (10 g of pro-rVWF).

The incubation time of furin with the immobilized pro-rVWF may vary depending on the system used. Also factors like temperature, buffers etc. influence the efficiency of the maturation process. Generally, the maturation process is terminated in less than 48 hours. In some embodiments, the maturation process can occur in less than 1 minute. In some embodiments, the maturation process can occur in less than 40 hours, 36 hours, 30 hours, 24 hours, 20 hours, 16 hours, 10 hours, 5 hours, 2 hours, 1 hour or less. In some embodiments, the incubation for pro-rVWF maturation is performed for less than 1 minute to 48 hours. In some embodiments, the incubation for pro-rVWF maturation is performed for 10 minutes to 42 hours. In some embodiments, the incubation for pro-rVWF maturation is performed for 20 minutes to 36 hours. In some embodiments, the incubation for pro-rVWF maturation is performed for 30 minutes to 24 hours. In some embodiments, due to the high specificity of furin, "overactivation" of VWF (further proteolytic degradation) does not occur even after prolonged incubation time.

In some embodiments, the maturation process depends also on the temperature chosen in the course of the incubation. The optimal enzymatic activity of furin varies with the temperature.

In some embodiments, the incubation for pro-rVWF maturation is performed at a temperature of 2° C. to 40° C. In some embodiments, the incubation for pro-rVWF maturation is performed at a temperature of 4° C. to 370° C. In some embodiments, the incubation for pro-rVWF maturation is performed at low temperatures such as 2° C. In some embodiments, the maximum temperatures employed are lower than 50° C., in order to avoid and/or prevent protein degradation. In some embodiments, the maximum temperatures employed are lower than 45° C., in order to avoid and/or prevent protein degradation.

In some embodiments, the pro-VWF (or pro-rVWF) is converted into mat-VWF (or mat-rVWF) by treatment with furin or a furin family member, as described above. In some embodiments, furin treatment results in at least 95%, at least 96%, at least 97%, at least 98%, at least 99%, at least 99.5% conversion of the pro-rVWF into mat-rVWF and rVWF-PP. In some embodiments after size separation in the presence of the addition of at least one chelating agent and/or increasing the pH to a pH of at least 7, there is less than 5% rVWF-PP, less than 4% rVWF-PP, less than 3% rVWF-PP, less than 2% rVWF-PP, less than 1% rVWF-PP, less than 0.5% rVWF-PP, less than 0.4% rVWF-PP, less than 0.1% rVWF, or less than 0.05% rVWF-PP in the eluate.

TABLE 2

Exemplary pro-VWF removal (based on furin treatment)

| Step | Load, VWF-PP impurity % (w/w) | Eluate, VWF-PP impurity % (w/w) |
|---|---|---|
| AEX | ~70% | ~0.5% |
| CEX | ~0.5% | ~0.5% |
| SEC | ~0.5% | ~0.5% |

I. VFW Multimers

Assessment of the number and percentage of rVWF multimers can be conducted using methods known in the art, including without limitation methods using electrophoresis and size exclusion chromatography methods to separate VWF multimers by size, for example as discussed by Cumming et al., (J Clin Pathol., 1993 May; 46(5): 470-473, which is hereby incorporated by reference in its entirety for all purposes and in particular for all teachings related to assessment of VWF multimers). Such techniques may further include immunoblotting techniques (such as Western Blot), in which the gel is immunoblotted with a radiolabelled antibody against VWF followed by chemiluminescent detection (see, for example, Wen et al., J. Clin. Lab. Anal., 1993, 7: 317-323, which is hereby incorporated by reference in its entirety for all purposes and in particular for all teachings related to assessment of VWF multimers). Further assays for VWF include VWF:Antigen (VWF:Ag), VWF: Ristocetin Cofactor (VWF:RCof), and VWF:Collagen Binding Activity assay (VWF:CBA), which are often used for diagnosis and classification of Von Willebrand Disease (see, for example, Favaloro et al., Pathology, 1997, 29(4): 341-456; Sadler, J E, Annu Rev Biochem, 1998, 67:395-424; and Turecek et al., Semin Thromb Hemost, 2010, 36:510-521, which are hereby incorporated by reference in their entirety for all purposes and in particular for all teachings related to assays for VWF). In some embodiments, the mat-rVWF obtained using the present methods includes any multimer pattern present in the loading sample of the rVWF. In some embodiments, the mat-rVWF obtained using the present methods includes physiolocical occurring multimer patters as well as ultralarge VWF-multimer patterns.

J. VFW Assays

In primary hemostasis VWF serves as a bridge between platelets and specific components of the extracellular matrix, such as collagen. The biological activity of VWF in this process can be measured by different in vitro assays (Turecek et al., Semin Thromb Hemost, 2010, 36: 510-521).

The VWF:Ristocetin Cofactor (VWF:RCof) assay is based on the agglutination of fresh or formalin-fixed platelets induced by the antibiotic ristocetin in the presence of VWF. The degree of platelet agglutination depends on the VWF concentration and can be measured by the turbidimetric method, e.g., by use of an aggregometer (Weiss et al., J. Clin. Invest., 1973, 52: 2708-2716; Macfarlane et al., Thromb. Diath. Haemorrh., 1975, 34: 306-308). As provided herein, the specific ristocetin cofactor activity of the VWF (VWF:RCo) of the present invention is generally described in terms of mU/µg of VWF, as measured using in vitro assays.

In some embodiments, the mat-rVWF purified according to the methods of the present invention has a specific activity of at least about 20, 22.5, 25, 27.5, 30, 32.5, 35, 37.5, 40, 42.5, 45, 47.5, 50, 52.5, 55, 57.5, 60, 62.5, 65, 67.5, 70, 72.5, 75, 77.5, 80, 82.5, 85, 87.5, 90, 92.5, 95, 97.5, 100, 105, 110, 115, 120, 125, 130, 135, 140, 145, 150 or more mU/µg. In some embodiments, mat-rVWF used in the methods described herein has a specific activity of from 20 mU/µg to 150 mU/µg. In some embodiments, the mat-rVWF has a specific activity of from 30 mU/µg to 120 mU/µg. In some embodiments, the mat-rVWF has a specific activity from 40 mU/µg to 90 mU/µg. In some embodiments, the mat-rVWF has a specific activity selected from variations 1 to 133 found in Table 3, below.

TABLE 3

Exemplary embodiments for the specific activity of rVWF found in the compositions and used in the methods provided herein.

| (mU/µg) | |
|---|---|
| 20 | Var. 1 |
| 22.5 | Var. 2 |
| 25 | Var. 3 |
| 27.5 | Var. 4 |
| 30 | Var. 5 |
| 32.5 | Var. 6 |
| 35 | Var. 7 |
| 37.5 | Var. 8 |
| 40 | Var. 9 |
| 42.5 | Var. 10 |
| 45 | Var. 11 |
| 47.5 | Var. 12 |
| 50 | Var. 13 |
| 52.5 | Var. 14 |
| 55 | Var. 15 |
| 57.5 | Var. 16 |
| 60 | Var. 17 |
| 62.5 | Var. 18 |
| 65 | Var. 19 |
| 67.5 | Var. 20 |
| 70 | Var. 21 |
| 72.5 | Var. 22 |
| 75 | Var. 23 |
| 77.5 | Var. 24 |
| 80 | Var. 25 |
| 82.5 | Var. 26 |
| 85 | Var. 27 |
| 87.5 | Var. 28 |
| 90 | Var. 29 |
| 92.5 | Var. 30 |
| 95 | Var. 31 |
| 97.5 | Var. 32 |
| 100 | Var. 33 |
| 105 | Var. 34 |
| 110 | Var. 35 |
| 115 | Var. 36 |
| 120 | Var. 37 |
| 125 | Var. 38 |
| 130 | Var. 39 |

TABLE 3-continued

Exemplary embodiments for the specific activity of rVWF found in the compositions and used in the methods provided herein.

| (mU/µg) | |
|---|---|
| 135 | Var. 40 |
| 140 | Var. 41 |
| 145 | Var. 42 |
| 150 | Var. 43 |
| 20-150 | Var. 44 |
| 20-140 | Var. 45 |
| 20-130 | Var. 46 |
| 20-120 | Var. 47 |
| 20-110 | Var. 48 |
| 20-100 | Var. 49 |
| 20-90 | Var. 50 |
| 20-80 | Var. 51 |
| 20-70 | Var. 52 |
| 20-60 | Var. 53 |
| 20-50 | Var. 54 |
| 20-40 | Var. 55 |
| 30-150 | Var. 56 |
| 30-140 | Var. 57 |
| 30-130 | Var. 58 |
| 30-120 | Var. 59 |
| 30-110 | Var. 60 |
| 30-100 | Var. 61 |
| 30-90 | Var. 62 |
| 30-80 | Var. 63 |
| 30-70 | Var. 64 |
| 30-60 | Var. 65 |
| 30-50 | Var. 66 |
| 30-40 | Var. 67 |
| 40-150 | Var. 68 |
| 40-140 | Var. 69 |
| 40-130 | Var. 70 |
| 40-120 | Var. 71 |
| 40-110 | Var. 72 |
| 40-100 | Var. 73 |
| 40-90 | Var. 74 |
| 40-80 | Var. 75 |
| 40-70 | Var. 76 |
| 40-60 | Var. 77 |
| 40-50 | Var. 78 |
| 50-150 | Var. 79 |
| 50-140 | Var. 80 |
| 50-130 | Var. 81 |
| 50-120 | Var. 82 |
| 50-110 | Var. 83 |
| 50-100 | Var. 84 |
| 50-90 | Var. 85 |
| 50-80 | Var. 86 |
| 50-70 | Var. 87 |
| 50-60 | Var. 88 |
| 60-150 | Var. 89 |
| 60-140 | Var. 90 |
| 60-130 | Var. 91 |
| 60-120 | Var. 92 |
| 60-110 | Var. 93 |
| 60-100 | Var. 94 |
| 60-90 | Var. 95 |
| 60-80 | Var. 96 |
| 60-70 | Var. 97 |
| 70-150 | Var. 98 |
| 70-140 | Var. 99 |
| 70-130 | Var. 100 |
| 70-120 | Var. 101 |
| 70-110 | Var. 102 |
| 70-100 | Var. 103 |
| 70-90 | Var. 104 |
| 70-80 | Var. 105 |
| 80-150 | Var. 106 |
| 80-140 | Var. 107 |
| 80-130 | Var. 108 |
| 80-120 | Var. 109 |
| 80-110 | Var. 110 |
| 80-100 | Var. 111 |
| 80-90 | Var. 112 |
| 90-150 | Var. 113 |
| 90-140 | Var. 114 |
| 90-130 | Var. 115 |
| 90-120 | Var. 116 |
| 90-110 | Var. 117 |
| 90-100 | Var. 118 |
| 100-150 | Var. 119 |
| 100-140 | Var. 120 |
| 100-130 | Var. 121 |
| 100-120 | Var. 122 |
| 100-110 | Var. 123 |
| 110-150 | Var. 124 |
| 110-140 | Var. 125 |
| 110-130 | Var. 126 |
| 110-120 | Var. 127 |
| 120-150 | Var. 128 |
| 120-140 | Var. 129 |
| 120-130 | Var. 130 |
| 130-150 | Var. 131 |
| 130-140 | Var. 132 |
| 140-150 | Var. 133 |

Var. = Variation

The mat-rVWF of the present invention is highly multimeric comprising about 10 to about 40 subunits. In further embodiments, the multimeric rVWF produced using methods of the present invention comprise about 10-30, 12-28, 14-26, 16-24, 18-22, 20-21 subunits. In some embodiments, the rVWF is present in multimers varying in size from dimers to multimers of over 40 subunits (>10 million Daltons). The largest multimers provide multiple binding sites that can interact with both platelet receptors and subendothelial matrix sites of injury, and are the most hemostatically active form of VWF. In some embodiments, the mat-rVWF of the present invention comprises ultralarge multimers (ULMs). Generally, high and ultralarge multimers are considered to be hemostatically most effective (see, for example, Turecek, P., Hämostaseologie, (Vol. 37): Supplement 1, pages S15-S25 (2017)). In some embodiments, the mat-rVWF is between 500 kDa and 20,000 kDa. In some embodiments, any desired multimer pattern can be obtained using the methods described. In some embodiments, when anion exchange and/or cation exchanger methods are employed, the pH, conductivity, and/or counterion concentration of the buffers in the one or more wash step(s) or the gradient buffers can be manipulated to obtain the desired multimer pattern. In some embodiments, then size exclusion chromatography methods are employed, the collection criteria can be employed to obtain the desired multimer pattern. In some embodiments, the described multimer pattern comprises ultralarge multimers. In some embodiments, the ultralarge multimers are at least 10,000 kDa, at least 11,000 kDa, at least 12,000 kDa, at least 13,000 kDa, at least 14,000 kDa, at least 15,000 kDa, at least 16,000 kDa, at least 17,000 kDa, at least 18,000 kDa, at least 19,000 kDa, at least 20,000 kDa. In some embodiments, the ultralarge multimers are between about 10,000 kDa and 20,000 kDa. In some embodiments, the ultralarge multimers are between about 11,000 kDa and 20,000 kDa. In some embodiments, the ultralarge multimers are between about 12,000 kDa and 20,000 kDa. In some embodiments, the ultralarge multimers are between about 13,000 kDa and 20,000 kDa. In some embodiments, the ultralarge multimers are between about 14,000 kDa and 20,000 kDa. In some embodiments, the ultralarge multimers are between about 15,000 kDa and 20,000 kDa. In some embodiments, the ultralarge multimers are between about 16,000 kDa and 20,000 kDa. In some embodiments, the ultralarge multimers are between about 17,000 kDa and 20,000 kDa. In some embodiments, the ultralarge multimers are between about 18,000 kDa and 20,000 kDa. In some embodiments, the ultralarge multimers are between about 19,000 kDa and 20,000 kDa. In some embodiments, the mat-rVWF obtained using the present methods includes any multimer pattern present in the loading sample of the rVWF. In some embodiments, the mat-rVWF obtained using the present methods includes physiolocical occurring multimer patters as well as ultra large VWF-multimer patterns.

In some embodiments, the mat-rVWF composition prepared by the purification method described herein has a distribution of rVWF oligomers characterized in that 95% of the oligomers have between 6 subunits and 20 subunits. In some embodiments, the mat-rVWF composition has a distribution of rVWF oligomers characterized in that 95% of the oligomers have a range of subunits selected from variations 458 to 641 found in 4.

TABLE 4

Exemplary embodiments for the distribution of rVWF oligomers found in the compositions and used in the methods provided herein.

| Subunits | |
|---|---|
| 2-40 | Var. 458 |
| 2-38 | Var. 459 |
| 2-36 | Var. 460 |
| 2-34 | Var. 461 |
| 2-32 | Var. 462 |
| 2-30 | Var. 463 |
| 2-28 | Var. 464 |
| 2-26 | Var. 465 |
| 2-24 | Var. 466 |
| 2-22 | Var. 467 |
| 2-20 | Var. 468 |
| 2-18 | Var. 469 |
| 2-16 | Var. 470 |
| 2-14 | Var. 471 |
| 2-12 | Var. 472 |
| 2-10 | Var. 473 |
| 2-8 | Var. 474 |
| 4-40 | Var. 475 |
| 4-38 | Var. 476 |
| 4-36 | Var. 477 |
| 4-34 | Var. 478 |
| 4-32 | Var. 479 |
| 4-30 | Var. 480 |
| 4-28 | Var. 481 |
| 4-26 | Var. 482 |
| 4-24 | Var. 483 |
| 4-22 | Var. 484 |
| 4-20 | Var. 485 |
| 4-18 | Var. 486 |
| 4-16 | Var. 487 |
| 4-14 | Var. 488 |
| 4-12 | Var. 489 |
| 4-10 | Var. 490 |
| 4-8 | Var. 491 |
| 6-40 | Var. 492 |
| 6-38 | Var. 493 |
| 6-36 | Var. 494 |
| 6-34 | Var. 495 |
| 6-32 | Var. 496 |
| 6-30 | Var. 497 |
| 6-28 | Var. 498 |
| 6-26 | Var. 499 |
| 6-24 | Var. 500 |
| 6-22 | Var. 501 |
| 6-20 | Var. 502 |
| 6-18 | Var. 503 |
| 6-16 | Var. 504 |
| 6-14 | Var. 505 |
| 6-12 | Var. 506 |
| 6-10 | Var. 507 |
| 6-8 | Var. 508 |
| 8-40 | Var. 509 |
| 8-38 | Var. 510 |
| 8-36 | Var. 511 |
| 8-34 | Var. 512 |
| 8-32 | Var. 513 |
| 8-30 | Var. 514 |
| 8-28 | Var. 515 |
| 8-26 | Var. 516 |
| 8-24 | Var. 517 |
| 8-22 | Var. 518 |
| 8-20 | Var. 519 |
| 8-18 | Var. 520 |
| 8-16 | Var. 521 |
| 8-14 | Var. 522 |
| 8-12 | Var. 523 |
| 8-10 | Var. 524 |
| 10-40 | Var. 525 |
| 10-38 | Var. 526 |
| 10-36 | Var. 527 |
| 10-34 | Var. 528 |
| 10-32 | Var. 529 |
| 10-30 | Var. 530 |
| 10-28 | Var. 531 |
| 10-26 | Var. 532 |
| 10-24 | Var. 533 |
| 10-22 | Var. 534 |
| 10-20 | Var. 535 |
| 10-18 | Var. 536 |
| 10-16 | Var. 537 |
| 10-14 | Var. 538 |
| 10-12 | Var. 539 |
| 12-40 | Var. 540 |
| 12-38 | Var. 541 |
| 12-36 | Var. 542 |
| 12-34 | Var. 543 |
| 12-32 | Var. 544 |
| 12-30 | Var. 545 |
| 12-28 | Var. 546 |
| 12-26 | Var. 547 |
| 12-24 | Var. 548 |
| 12-22 | Var. 549 |
| 12-20 | Var. 550 |
| 12-18 | Var. 551 |
| 12-16 | Var. 552 |
| 12-14 | Var. 553 |
| 14-40 | Var. 554 |
| 14-38 | Var. 555 |
| 14-36 | Var. 556 |
| 14-34 | Var. 557 |
| 14-32 | Var. 558 |
| 14-30 | Var. 559 |
| 14-28 | Var. 560 |
| 14-26 | Var. 561 |
| 14-24 | Var. 562 |
| 14-22 | Var. 563 |
| 14-20 | Var. 564 |
| 14-18 | Var. 565 |
| 14-16 | Var. 566 |
| 16-40 | Var. 567 |
| 16-38 | Var. 568 |
| 16-36 | Var. 569 |
| 16-34 | Var. 570 |
| 16-32 | Var. 571 |
| 16-30 | Var. 572 |
| 16-28 | Var. 573 |
| 16-26 | Var. 574 |
| 16-24 | Var. 575 |
| 16-22 | Var. 576 |
| 16-20 | Var. 577 |
| 16-18 | Var. 578 |
| 18-40 | Var. 579 |
| 18-38 | Var. 580 |
| 18-36 | Var. 581 |
| 18-34 | Var. 582 |

TABLE 4-continued

Exemplary embodiments for the distribution of rVWF oligomers found in the compositions and used in the methods provided herein.

| Subunits | |
|---|---|
| 18-32 | Var. 583 |
| 18-30 | Var. 584 |
| 18-28 | Var. 585 |
| 18-26 | Var. 586 |
| 18-24 | Var. 587 |
| 18-22 | Var. 588 |
| 18-20 | Var. 589 |
| 20-40 | Var. 590 |
| 20-38 | Var. 591 |
| 20-36 | Var. 592 |
| 20-34 | Var. 593 |
| 20-32 | Var. 594 |
| 20-30 | Var. 595 |
| 20-28 | Var. 596 |
| 20-26 | Var. 597 |
| 20-24 | Var. 598 |
| 20-22 | Var. 599 |
| 22-40 | Var. 600 |
| 22-38 | Var. 601 |
| 22-36 | Var. 602 |
| 22-34 | Var. 603 |
| 22-32 | Var. 604 |
| 22-30 | Var. 605 |
| 22-28 | Var. 606 |
| 22-26 | Var. 607 |
| 22-24 | Var. 608 |
| 24-40 | Var. 609 |
| 24-38 | Var. 610 |
| 24-36 | Var. 611 |
| 24-34 | Var. 612 |
| 24-32 | Var. 613 |
| 24-30 | Var. 614 |
| 24-28 | Var. 615 |
| 24-26 | Var. 616 |
| 26-40 | Var. 617 |
| 26-38 | Var. 618 |
| 26-36 | Var. 619 |
| 26-34 | Var. 620 |
| 26-32 | Var. 621 |
| 26-30 | Var. 622 |
| 26-28 | Var. 623 |
| 28-40 | Var. 624 |
| 28-38 | Var. 625 |
| 28-36 | Var. 626 |
| 28-34 | Var. 627 |
| 28-32 | Var. 628 |
| 28-30 | Var. 629 |
| 30-40 | Var. 630 |
| 30-38 | Var. 631 |
| 30-36 | Var. 632 |
| 30-34 | Var. 633 |
| 30-32 | Var. 634 |
| 32-40 | Var. 635 |
| 32-38 | Var. 636 |
| 32-36 | Var. 637 |
| 32-34 | Var. 638 |
| 34-40 | Var. 639 |
| 36-38 | Var. 640 |
| 38-40 | Var. 641 |

Var. = Variation

In some embodiments, the mat-rVWF composition prepared by the methods provided herein can be characterized according to the percentage of mat-rVWF molecules that are present in a particular higher order mat-rVWF multimer or larger multimer. For example, in one embodiment, at least 20% of mat-rVWF molecules in a mat-rVWF composition used in the methods described herein are present in an oligomeric complex of at least 10 subunits. In another embodiment, at least 20% of mat-rVWF molecules in a mat-rVWF composition used in the methods described herein are present in an oligomeric complex of at least 12 subunits. In yet other embodiments, a mat-rVWF composition used in the methods provided herein has a minimal percentage (e.g., has at least X %) of mat-rVWF molecules present in a particular higher-order mat-rVWF multimer or larger multimer (e.g., a multimer of at least Y subunits) according to any one of variations 134 to 457 found in Table 5 to Table 7.

TABLE 5

Exemplary embodiments for the percentage of rVWF molecules that are present in a particular higher order rVWF multimer or larger multimer found in the compositions and used in the methods provided herein.

| | | Minimal Number of Subunits in rVWF Multimer | | | | | |
|---|---|---|---|---|---|---|---|
| | | 6 | 8 | 10 | 12 | 14 | 16 |
| Minimal Percentage of rVWF Molecules | 10% | Var. 134 | Var. 152 | Var. 170 | Var. 188 | Var. 206 | Var. 224 |
| | 15% | Var. 135 | Var. 153 | Var. 171 | Var. 189 | Var. 207 | Var. 225 |
| | 20% | Var. 136 | Var. 154 | Var. 172 | Var. 190 | Var. 208 | Var. 226 |
| | 25% | Var. 137 | Var. 155 | Var. 173 | Var. 191 | Var. 209 | Var. 227 |
| | 30% | Var. 138 | Var. 156 | Var. 174 | Var. 192 | Var. 210 | Var. 228 |
| | 35% | Var. 139 | Var. 157 | Var. 175 | Var. 193 | Var. 211 | Var. 229 |
| | 40% | Var. 140 | Var. 158 | Var. 176 | Var. 194 | Var. 212 | Var. 230 |
| | 45% | Var. 141 | Var. 159 | Var. 177 | Var. 195 | Var. 213 | Var. 231 |
| | 50% | Var. 142 | Var. 160 | Var. 178 | Var. 196 | Var. 214 | Var. 232 |
| | 55% | Var. 143 | Var. 161 | Var. 179 | Var. 197 | Var. 215 | Var. 233 |
| | 60% | Var. 144 | Var. 162 | Var. 180 | Var. 198 | Var. 216 | Var. 234 |
| | 65% | Var. 145 | Var. 163 | Var. 181 | Var. 199 | Var. 217 | Var. 235 |
| | 70% | Var. 146 | Var. 164 | Var. 182 | Var. 200 | Var. 218 | Var. 236 |
| | 75% | Var. 147 | Var. 165 | Var. 183 | Var. 201 | Var. 219 | Var. 237 |
| | 80% | Var. 148 | Var. 166 | Var. 184 | Var. 202 | Var. 220 | Var. 238 |
| | 85% | Var. 149 | Var. 167 | Var. 185 | Var. 203 | Var. 221 | Var. 239 |
| | 90% | Var. 150 | Var. 168 | Var. 186 | Var. 204 | Var. 222 | Var. 240 |
| | 95% | Var. 151 | Var. 169 | Var. 187 | Var. 205 | Var. 223 | Var. 241 |

Var. = Variation

TABLE 6

Exemplary embodiments for the percentage of rVWF molecules that are present in a particular higher order rVWF multimer or larger multimer found in the compositions and used in the methods provided herein.

| | | Minimal Number of Subunits in rVWF Multimer | | | | | |
|---|---|---|---|---|---|---|---|
| | | 18 | 20 | 22 | 24 | 26 | 28 |
| Minimal Percentage of rVWF Molecules | 10% | Var. 242 | Var. 260 | Var. 278 | Var. 296 | Var. 314 | Var. 332 |
| | 15% | Var. 243 | Var. 261 | Var. 279 | Var. 297 | Var. 315 | Var. 333 |
| | 20% | Var. 244 | Var. 262 | Var. 280 | Var. 298 | Var. 316 | Var. 334 |
| | 25% | Var. 245 | Var. 263 | Var. 281 | Var. 299 | Var. 317 | Var. 335 |
| | 30% | Var. 246 | Var. 264 | Var. 282 | Var. 300 | Var. 318 | Var. 336 |
| | 35% | Var. 247 | Var. 265 | Var. 283 | Var. 301 | Var. 319 | Var. 337 |
| | 40% | Var. 248 | Var. 266 | Var. 284 | Var. 302 | Var. 320 | Var. 338 |
| | 45% | Var. 249 | Var. 267 | Var. 285 | Var. 303 | Var. 321 | Var. 339 |
| | 50% | Var. 250 | Var. 268 | Var. 286 | Var. 304 | Var. 322 | Var. 340 |
| | 55% | Var. 251 | Var. 269 | Var. 287 | Var. 305 | Var. 323 | Var. 341 |
| | 60% | Var. 252 | Var. 270 | Var. 288 | Var. 306 | Var. 324 | Var. 342 |
| | 65% | Var. 253 | Var. 271 | Var. 289 | Var. 307 | Var. 325 | Var. 343 |
| | 70% | Var. 254 | Var. 272 | Var. 290 | Var. 308 | Var. 326 | Var. 344 |
| | 75% | Var. 255 | Var. 273 | Var. 291 | Var. 309 | Var. 327 | Var. 345 |
| | 80% | Var. 256 | Var. 274 | Var. 292 | Var. 310 | Var. 328 | Var. 346 |
| | 85% | Var. 257 | Var. 275 | Var. 293 | Var. 311 | Var. 329 | Var. 347 |
| | 90% | Var. 258 | Var. 276 | Var. 294 | Var. 312 | Var. 330 | Var. 348 |
| | 95% | Var. 259 | Var. 277 | Var. 295 | Var. 313 | Var. 331 | Var. 349 |

Var. = Variation

TABLE 7

Exemplary embodiments for the percentage of rVWF molecules that are present in a particular higher order rVWF multimer or larger multimer found in the compositions and used in the methods provided herein.

| | | Minimal Number of Subunits in rVWF Multimer | | | | | |
|---|---|---|---|---|---|---|---|
| | | 30 | 32 | 34 | 36 | 38 | 40 |
| Minimal Percentage of rVWF Molecules | 10% | Var. 350 | Var. 368 | Var. 386 | Var. 404 | Var. 422 | Var. 440 |
| | 15% | Var. 351 | Var. 369 | Var. 387 | Var. 405 | Var. 423 | Var. 441 |
| | 20% | Var. 352 | Var. 370 | Var. 388 | Var. 406 | Var. 424 | Var. 442 |
| | 25% | Var. 353 | Var. 371 | Var. 389 | Var. 407 | Var. 425 | Var. 443 |
| | 30% | Var. 354 | Var. 372 | Var. 390 | Var. 408 | Var. 426 | Var. 444 |
| | 35% | Var. 355 | Var. 373 | Var. 391 | Var. 409 | Var. 427 | Var. 445 |
| | 40% | Var. 356 | Var. 374 | Var. 392 | Var. 410 | Var. 428 | Var. 446 |
| | 45% | Var. 357 | Var. 375 | Var. 393 | Var. 411 | Var. 429 | Var. 447 |
| | 50% | Var. 358 | Var. 376 | Var. 394 | Var. 412 | Var. 430 | Var. 448 |
| | 55% | Var. 359 | Var. 377 | Var. 395 | Var. 413 | Var. 431 | Var. 449 |
| | 60% | Var. 360 | Var. 378 | Var. 396 | Var. 414 | Var. 432 | Var. 450 |
| | 65% | Var. 361 | Var. 379 | Var. 397 | Var. 415 | Var. 433 | Var. 451 |
| | 70% | Var. 362 | Var. 380 | Var. 398 | Var. 416 | Var. 434 | Var. 452 |
| | 75% | Var. 363 | Var. 381 | Var. 399 | Var. 417 | Var. 435 | Var. 453 |
| | 80% | Var. 364 | Var. 382 | Var. 400 | Var. 418 | Var. 436 | Var. 454 |
| | 85% | Var. 365 | Var. 383 | Var. 401 | Var. 419 | Var. 437 | Var. 455 |
| | 90% | Var. 366 | Var. 384 | Var. 402 | Var. 420 | Var. 438 | Var. 456 |
| | 95% | Var. 367 | Var. 385 | Var. 403 | Var. 421 | Var. 439 | Var. 457 |

Var. = Variation

In accordance with the above, the mat-rVWF comprises a significant percentage of high molecular weight (HMW) mat-rVWF multimers. In further embodiments, the HMW rVWF multimer composition comprises at least 10%-80% mat-rVWF decamers or higher order multimers. In further embodiments, the composition comprises about 10-95%, 20-90%, 30-85%, 40-80%, 50-75%, 60-70% decamers or higher order multimers. In further embodiments, the HMW mat-rVWF multimer composition comprises at least about 10%, 20%, 30%, 40%, 50%, 60%, 70%, 80%, 90% decamers or higher order multimers.

Assessment of the number and percentage of mat-rVWF multimers can be conducted using methods known in the art, including without limitation methods using electrophoresis and size exclusion chromatography methods to separate mat-rVWF multimers by size, for example as discussed by Cumming et al, (J Clin Pathol. 1993 May; 46(5): 470-473, which is hereby incorporated by reference in its entirety for all purposes and in particular for all teachings related to assessment of mat-rVWF multimers). Such techniques may further include immunoblotting techniques (such as Western Blot), in which the gel is immunoblotted with a radiolabelled antibody against VWF followed by chemiluminescent detection (see for example Wen et al., (1993), J. Clin. Lab. Anal., 7: 317-323, which is hereby incorporated by reference in its entirety for all purposes and in particular for all teachings related to assessment of mat-rVWF multimers). Further assays for VWF include VWF:Antigen (VWF:Ag), VWF:Ristocetin Cofactor (VWF:RCof), and VWF:Collagen Binding Activity assay (VWF:CBA), which are often used for diagnosis and classification of Von Willebrand Disease. (see for example Favaloro et al., Pathology, 1997, 29(4): 341-456, which is hereby incorporated by reference in its entirety for all purposes and in particular for all teachings related to assays for VWF).

In some embodiments, the ratio of rFVIII procoagulant activity (IU rFVIII:C) to rVWF Ristocetin cofactor activity (IU rVWF:RCo) for the mat-rVWF prepared according to the methods of the present invention is between 3:1 and 1:5. In further embodiments, the ratio is between 2:1 and 1:4. In still further embodiments, the ratio is between 5:2 and 1:4. In further embodiments, the ratio is between 3:2 and 1:3. In still further embodiments, the ratio is about 1:1, 1:2, 1:3, 1:4, 1:5, 2:1, 2:3, 2:4, 2:5, 3:1, 3:2, 3:4, or 3:5. In further embodiments, the ratio is between 1:1 and 1:2. In yet further embodiments, the ratio is 1.1:1, 1.2:1, 1.3:1, 1.4:1, 1.5:1, 1.6:1, 1.7:1, 1.8:1, 1.9:1, or 2:1. In certain embodiments, the ratio of rFVIII procoagulant activity (IU rFVIII:C) to rVWF Ristocetin cofactor activity (IU rVWF:RCo) in a composition useful for a method described herein is selected from variations 1988 to 2140 found in Table 8.

Table 8. Exemplary embodiments for the ratio of rFVIII procoagulant activity (IU rFVIII:C) to rVWF Ristocetin cofactor activity (IU rVWF:RCo) in compositions and used in methods provided herein.

TABLE 8

Exemplary embodiments for the ratio of rFVIII procoagulant activity (IU rFVIII:C) to rVWF Ristocetin cofactor activity (IU rVWF:RCo) in compositions and used in methods provided herein.

| (IU rFVIII:C) to (IU rVWF:RCo) | |
|---|---|
| 4:1 | Var. 1988 |
| 3:1 | Var. 1989 |
| 2:1 | Var. 1990 |
| 3:2 | Var. 1991 |
| 4:3 | Var. 1992 |
| 1:1 | Var. 1993 |
| 5:6 | Var. 1994 |
| 4:5 | Var. 1995 |
| 3:4 | Var. 1996 |
| 2:3 | Var. 1997 |
| 3:5 | Var. 1998 |
| 1:2 | Var. 1999 |
| 2:5 | Var. 2000 |
| 1:3 | Var. 2001 |
| 1:4 | Var. 2002 |
| 1:5 | Var. 2003 |
| 1:6 | Var. 2004 |
| 4:1-1:6 | Var. 2005 |
| 4:1-1:5 | Var. 2006 |
| 4:1-1:4 | Var. 2007 |
| 4:1-1:3 | Var. 2008 |
| 4:1-2:5 | Var. 2009 |
| 4:1-1:2 | Var. 2010 |
| 4:1-3:5 | Var. 2011 |
| 4:1-2:3 | Var. 2012 |
| 4:1-3:4 | Var. 2013 |
| 4:1-4:5 | Var. 2014 |
| 4:1-5:6 | Var. 2015 |
| 4:1-1:1 | Var. 2016 |
| 4:1-4:3 | Var. 2017 |
| 4:1-3:2 | Var. 2018 |
| 4:1-2:1 | Var. 2019 |
| 4:1-3:1 | Var. 2020 |
| 3:1-1:6 | Var. 2021 |
| 3:1-1:5 | Var. 2022 |
| 3:1-1:4 | Var. 2023 |
| 3:1-1:3 | Var. 2024 |
| 3:1-2:5 | Var. 2025 |
| 3:1-1:2 | Var. 2026 |
| 3:1-3:5 | Var. 2027 |
| 3:1-2:3 | Var. 2028 |

TABLE 8-continued

Exemplary embodiments for the ratio of rFVIII procoagulant activity (IU rFVIII:C) to rVWF Ristocetin cofactor activity (IU rVWF:RCo) in compositions and used in methods provided herein.

| (IU rFVIII:C) to (IU rVWF:RCo) | |
|---|---|
| 3:1-3:4 | Var. 2029 |
| 3:1-4:5 | Var. 2030 |
| 3:1-5:6 | Var. 2031 |
| 3:1-1:1 | Var. 2032 |
| 3:1-4:3 | Var. 2033 |
| 3:1-3:2 | Var. 2034 |
| 3:1-2:1 | Var. 2035 |
| 2:1-1:6 | Var. 2036 |
| 2:1-1:5 | Var. 2037 |
| 2:1-1:4 | Var. 2038 |
| 2:1-1:3 | Var. 2039 |
| 2:1-2:5 | Var. 2040 |
| 2:1-1:2 | Var. 2041 |
| 2:1-3:5 | Var. 2042 |
| 2:1-2:3 | Var. 2043 |
| 2:1-3:4 | Var. 2044 |
| 2:1-4:5 | Var. 2045 |
| 2:1-5:6 | Var. 2046 |
| 2:1-1:1 | Var. 2047 |
| 2:1-4:3 | Var. 2048 |
| 2:1-3:2 | Var. 2049 |
| 3:2-1:6 | Var. 2050 |
| 3:2-1:5 | Var. 2051 |
| 3:2-1:4 | Var. 2052 |
| 3:2-1:3 | Var. 2053 |
| 3:2-2:5 | Var. 2054 |
| 3:2-1:2 | Var. 2055 |
| 3:2-3:5 | Var. 2056 |
| 3:2-2:3 | Var. 2057 |
| 3:2-3:4 | Var. 2058 |
| 3:2-4:5 | Var. 2059 |
| 3:2-5:6 | Var. 2060 |
| 3:2-1:1 | Var. 2061 |
| 3:2-4:3 | Var. 2062 |
| 4:3-1:6 | Var. 2063 |
| 4:3-1:5 | Var. 2064 |
| 4:3-1:4 | Var. 2065 |
| 4:3-1:3 | Var. 2066 |
| 4:3-2:5 | Var. 2067 |
| 4:3-1:2 | Var. 2068 |
| 4:3-3:5 | Var. 2069 |
| 4:3-2:3 | Var. 2070 |
| 4:3-3:4 | Var. 2071 |
| 4:3-4:5 | Var. 2072 |
| 4:3-5:6 | Var. 2073 |
| 4:3-1:1 | Var. 2074 |
| 1:1-1:6 | Var. 2075 |
| 1:1-1:5 | Var. 2076 |
| 1:1-1:4 | Var. 2077 |
| 1:1-1:3 | Var. 2078 |
| 1:1-2:5 | Var. 2079 |
| 1:1-1:2 | Var. 2080 |
| 1:1-3:5 | Var. 2081 |
| 1:1-2:3 | Var. 2082 |
| 1:1-3:4 | Var. 2083 |
| 1:1-4:5 | Var. 2084 |
| 1:1-5:6 | Var. 2085 |
| 5:6-1:6 | Var. 2086 |
| 5:6-1:5 | Var. 2087 |
| 5:6-1:4 | Var. 2088 |
| 5:6-1:3 | Var. 2089 |
| 5:6-2:5 | Var. 2090 |
| 5:6-1:2 | Var. 2091 |
| 5:6-3:5 | Var. 2092 |
| 5:6-2:3 | Var. 2093 |
| 5:6-3:4 | Var. 2094 |
| 5:6-4:5 | Var. 2095 |
| 4:5-1:6 | Var. 2096 |
| 4:5-1:5 | Var. 2097 |
| 4:5-1:4 | Var. 2098 |
| 4:5-1:3 | Var. 2099 |
| 4:5-2:5 | Var. 2100 |
| 4:5-1:2 | Var. 2101 |
| 4:5-3:5 | Var. 2102 |

TABLE 8-continued

Exemplary embodiments for the ratio of rFVIII procoagulant activity (IU rFVIII:C) to rVWF Ristocetin cofactor activity (IU rVWF:RCo) in compositions and used in methods provided herein.

| (IU rFVIII:C) to (IU rVWF:RCo) | |
|---|---|
| 4:5-2:3 | Var. 2103 |
| 4:5-3:4 | Var. 2104 |
| 3:4-1:6 | Var. 2105 |
| 3:4-1:5 | Var. 2106 |
| 3:4-1:4 | Var. 2107 |
| 3:4-1:3 | Var. 2108 |
| 3:4-2:5 | Var. 2109 |
| 3:4-1:2 | Var. 2110 |
| 3:4-3:5 | Var. 2111 |
| 3:4-2:3 | Var. 2112 |
| 2:3-1:6 | Var. 2113 |
| 2:3-1:5 | Var. 2114 |
| 2:3-1:4 | Var. 2115 |
| 2:3-1:3 | Var. 2116 |
| 2:3-2:5 | Var. 2117 |
| 2:3-1:2 | Var. 2118 |
| 2:3-3:5 | Var. 2119 |
| 3:5-1:6 | Var. 2120 |
| 3:5-1:5 | Var. 2121 |
| 3:5-1:4 | Var. 2122 |
| 3:5-1:3 | Var. 2123 |
| 3:5-2:5 | Var. 2124 |
| 3:5-1:2 | Var. 2125 |
| 1:2-1:6 | Var. 2126 |
| 1:2-1:5 | Var. 2127 |
| 1:2-1:4 | Var. 2128 |
| 1:2-1:3 | Var. 2129 |
| 1:2-2:5 | Var. 2130 |
| 2:5-1:6 | Var. 2131 |
| 2:5-1:5 | Var. 2132 |
| 2:5-1:4 | Var. 2133 |
| 2:5-1:3 | Var. 2134 |
| 1:3-1:6 | Var. 2135 |
| 1:3-1:5 | Var. 2136 |
| 1:3-1:4 | Var. 2137 |
| 1:4-1:6 | Var. 2138 |
| 1:4-1:5 | Var. 2139 |
| 1:5-1:6 | Var. 2140 |

Var. = Variation

In further embodiments, higher order mat-rVWF multimers of the invention are stable for about 1 to about 90 hours post-administration. In still further embodiments, the higher order mat-rVWF multimers are stable for about 5-80, 10-70, 15-60, 20-50, 25-40, 30-35 hours post-administration. In yet further embodiments, the higher order mat-rVWF multimers are stable for at least 3, 6, 12, 18, 24, 36, 48, 72 hours post-administration. In certain embodiments the stability of the mat-rVWF multimers is assessed in vitro.

In one embodiment, higher order mat-rVWF multimers used in the compositions and methods provided herein have a half-life of at least 12 hour post administration. In another embodiment, the higher order mat-rVWF multimers have a half-life of at least 24 hour post administration. In yet other embodiments, the higher order mat-rVWF multimers have a half-life selected from variations 642 to 1045 found in Table 9.

TABLE 9

Exemplary embodiments for the half-life of higher order rVWF multimers found in the compositions prepared by the methods provided herein.

| Hours | |
|---|---|
| at least 1 | Var. 642 |
| at least 2 | Var. 643 |

TABLE 9-continued

Exemplary embodiments for the half-life of higher order rVWF multimers found in the compositions prepared by the methods provided herein.

| Hours | |
|---|---|
| at least 3 | Var. 644 |
| at least 4 | Var. 645 |
| at least 5 | Var. 646 |
| at least 6 | Var. 647 |
| at least 7 | Var. 648 |
| at least 8 | Var. 649 |
| at least 9 | Var. 650 |
| at least 10 | Var. 651 |
| at least 11 | Var. 652 |
| at least 12 | Var. 653 |
| at least 14 | Var. 654 |
| at least 16 | Var. 655 |
| at least 18 | Var. 656 |
| at least 20 | Var. 657 |
| at least 22 | Var. 658 |
| at least 24 | Var. 659 |
| at least 27 | Var. 660 |
| at least 30 | Var. 661 |
| at least 33 | Var. 662 |
| at least 36 | Var. 663 |
| at least 39 | Var. 664 |
| at least 42 | Var. 665 |
| at least 45 | Var. 666 |
| at least 48 | Var. 667 |
| at least 54 | Var. 668 |
| at least 60 | Var. 669 |
| at least 66 | Var. 670 |
| at least 72 | Var. 671 |
| at least 78 | Var. 672 |
| at least 84 | Var. 673 |
| at least 90 | Var. 674 |
| 2-90 | Var. 675 |
| 2-84 | Var. 676 |
| 2-78 | Var. 677 |
| 2-72 | Var. 678 |
| 2-66 | Var. 679 |
| 2-60 | Var. 680 |
| 2-54 | Var. 681 |
| 2-48 | Var. 682 |
| 2-45 | Var. 683 |
| 2-42 | Var. 684 |
| 2-39 | Var. 685 |
| 2-36 | Var. 686 |
| 2-33 | Var. 687 |
| 2-30 | Var. 688 |
| 2-27 | Var. 689 |
| 2-24 | Var. 690 |
| 2-22 | Var. 691 |
| 2-20 | Var. 692 |
| 2-18 | Var. 693 |
| 2-16 | Var. 694 |
| 2-14 | Var. 695 |
| 2-12 | Var. 696 |
| 2-10 | Var. 697 |
| 2-8 | Var. 698 |
| 2-6 | Var. 699 |
| 2-4 | Var. 700 |
| 3-90 | Var. 701 |
| 3-84 | Var. 702 |
| 3-78 | Var. 703 |
| 3-72 | Var. 704 |
| 3-66 | Var. 705 |
| 3-60 | Var. 706 |
| 3-54 | Var. 707 |
| 3-48 | Var. 708 |
| 3-45 | Var. 709 |
| 3-42 | Var. 710 |
| 3-39 | Var. 711 |
| 3-36 | Var. 712 |
| 3-33 | Var. 713 |
| 3-30 | Var. 714 |
| 3-27 | Var. 715 |
| 3-24 | Var. 716 |
| 3-22 | Var. 717 |

TABLE 9-continued

Exemplary embodiments for the half-life of higher order rVWF multimers found in the compositions prepared by the methods provided herein.

| Hours | |
|---|---|
| 3-20 | Var. 718 |
| 3-18 | Var. 719 |
| 3-16 | Var. 720 |
| 3-14 | Var. 721 |
| 3-12 | Var. 722 |
| 3-10 | Var. 723 |
| 3-8 | Var. 724 |
| 3-6 | Var. 725 |
| 3-4 | Var. 726 |
| 4-90 | Var. 727 |
| 4-84 | Var. 728 |
| 4-78 | Var. 729 |
| 4-72 | Var. 730 |
| 4-66 | Var. 731 |
| 4-60 | Var. 732 |
| 4-54 | Var. 733 |
| 4-48 | Var. 734 |
| 4-45 | Var. 735 |
| 4-42 | Var. 736 |
| 4-39 | Var. 737 |
| 4-36 | Var. 738 |
| 4-33 | Var. 739 |
| 4-30 | Var. 740 |
| 4-27 | Var. 741 |
| 4-24 | Var. 742 |
| 4-22 | Var. 743 |
| 4-20 | Var. 744 |
| 4-18 | Var. 745 |
| 4-16 | Var. 746 |
| 4-14 | Var. 747 |
| 4-12 | Var. 748 |
| 4-10 | Var. 749 |
| 4-8 | Var. 750 |
| 4-6 | Var. 751 |
| 6-90 | Var. 752 |
| 6-84 | Var. 753 |
| 6-78 | Var. 754 |
| 6-72 | Var. 755 |
| 6-66 | Var. 756 |
| 6-60 | Var. 757 |
| 6-54 | Var. 758 |
| 6-48 | Var. 759 |
| 6-45 | Var. 760 |
| 6-42 | Var. 761 |
| 6-39 | Var. 762 |
| 6-36 | Var. 763 |
| 6-33 | Var. 764 |
| 6-30 | Var. 765 |
| 6-27 | Var. 766 |
| 6-24 | Var. 767 |
| 6-22 | Var. 768 |
| 6-20 | Var. 769 |
| 6-18 | Var. 770 |
| 6-16 | Var. 771 |
| 6-14 | Var. 772 |
| 6-12 | Var. 773 |
| 6-10 | Var. 774 |
| 6-8 | Var. 775 |
| 8-90 | Var. 776 |
| 8-84 | Var. 777 |
| 8-78 | Var. 778 |
| 8-72 | Var. 779 |
| 8-66 | Var. 780 |
| 8-60 | Var. 781 |
| 8-54 | Var. 782 |
| 8-48 | Var. 783 |
| 8-45 | Var. 784 |
| 8-42 | Var. 785 |
| 8-39 | Var. 786 |
| 8-36 | Var. 787 |
| 8-33 | Var. 788 |
| 8-30 | Var. 789 |
| 8-27 | Var. 790 |
| 8-24 | Var. 791 |
| 8-22 | Var. 792 |
| 8-20 | Var. 793 |
| 8-18 | Var. 794 |
| 8-16 | Var. 795 |
| 8-14 | Var. 796 |
| 8-12 | Var. 797 |
| 8-10 | Var. 798 |
| 10-90 | Var. 799 |
| 10-84 | Var. 800 |
| 10-78 | Var. 801 |
| 10-72 | Var. 802 |
| 10-66 | Var. 803 |
| 10-60 | Var. 804 |
| 10-54 | Var. 805 |
| 10-48 | Var. 806 |
| 10-45 | Var. 807 |
| 10-42 | Var. 808 |
| 10-39 | Var. 809 |
| 10-36 | Var. 810 |
| 10-33 | Var. 811 |
| 10-30 | Var. 812 |
| 10-27 | Var. 813 |
| 10-24 | Var. 814 |
| 10-22 | Var. 815 |
| 10-20 | Var. 816 |
| 10-18 | Var. 817 |
| 10-16 | Var. 818 |
| 10-14 | Var. 819 |
| 10-12 | Var. 820 |
| 12-90 | Var. 821 |
| 12-84 | Var. 822 |
| 12-78 | Var. 823 |
| 12-72 | Var. 824 |
| 12-66 | Var. 825 |
| 12-60 | Var. 826 |
| 12-54 | Var. 827 |
| 12-48 | Var. 828 |
| 12-45 | Var. 829 |
| 12-42 | Var. 830 |
| 12-39 | Var. 831 |
| 12-36 | Var. 832 |
| 12-33 | Var. 833 |
| 12-30 | Var. 834 |
| 12-27 | Var. 835 |
| 12-24 | Var. 836 |
| 12-22 | Var. 837 |
| 12-20 | Var. 838 |
| 12-18 | Var. 839 |
| 12-16 | Var. 840 |
| 12-14 | Var. 841 |
| 14-90 | Var. 842 |
| 14-84 | Var. 843 |
| 14-78 | Var. 844 |
| 14-72 | Var. 845 |
| 14-66 | Var. 846 |
| 14-60 | Var. 847 |
| 14-54 | Var. 848 |
| 14-48 | Var. 849 |
| 14-45 | Var. 850 |
| 14-42 | Var. 851 |
| 14-39 | Var. 852 |
| 14-36 | Var. 853 |
| 14-33 | Var. 854 |
| 14-30 | Var. 855 |
| 14-27 | Var. 856 |
| 14-24 | Var. 857 |
| 14-22 | Var. 858 |
| 14-20 | Var. 859 |
| 14-18 | Var. 860 |
| 14-16 | Var. 861 |
| 16-90 | Var. 862 |
| 16-84 | Var. 863 |
| 16-78 | Var. 864 |
| 16-72 | Var. 865 |

TABLE 9-continued

Exemplary embodiments for the half-life of higher order rVWF multimers found in the compositions prepared by the methods provided herein.

| Hours | |
|---|---|
| 16-66 | Var. 866 |
| 16-60 | Var. 867 |
| 16-54 | Var. 868 |
| 16-48 | Var. 869 |
| 16-45 | Var. 870 |
| 16-42 | Var. 871 |
| 16-39 | Var. 872 |
| 16-36 | Var. 873 |
| 16-33 | Var. 874 |
| 16-30 | Var. 875 |
| 16-27 | Var. 876 |
| 16-24 | Var. 877 |
| 16-22 | Var. 878 |
| 16-20 | Var. 879 |
| 16-18 | Var. 880 |
| 18-90 | Var. 881 |
| 18-84 | Var. 882 |
| 18-78 | Var. 883 |
| 18-72 | Var. 884 |
| 18-66 | Var. 885 |
| 18-60 | Var. 886 |
| 18-54 | Var. 887 |
| 18-48 | Var. 888 |
| 18-45 | Var. 889 |
| 18-42 | Var. 890 |
| 18-39 | Var. 891 |
| 18-36 | Var. 892 |
| 18-33 | Var. 893 |
| 18-30 | Var. 894 |
| 18-27 | Var. 895 |
| 18-24 | Var. 896 |
| 18-22 | Var. 897 |
| 18-20 | Var. 898 |
| 20-90 | Var. 899 |
| 20-84 | Var. 900 |
| 20-78 | Var. 901 |
| 20-72 | Var. 902 |
| 20-66 | Var. 903 |
| 20-60 | Var. 904 |
| 20-54 | Var. 905 |
| 20-48 | Var. 906 |
| 20-45 | Var. 907 |
| 20-42 | Var. 908 |
| 20-39 | Var. 909 |
| 20-36 | Var. 910 |
| 20-33 | Var. 911 |
| 20-30 | Var. 912 |
| 20-27 | Var. 913 |
| 20-24 | Var. 914 |
| 20-22 | Var. 915 |
| 22-90 | Var. 916 |
| 22-84 | Var. 917 |
| 22-78 | Var. 918 |
| 22-72 | Var. 919 |
| 22-66 | Var. 920 |
| 22-60 | Var. 921 |
| 22-54 | Var. 922 |
| 22-48 | Var. 923 |
| 22-45 | Var. 924 |
| 22-42 | Var. 925 |
| 22-39 | Var. 926 |
| 22-36 | Var. 927 |
| 22-33 | Var. 928 |
| 22-30 | Var. 929 |
| 22-27 | Var. 930 |
| 22-24 | Var. 931 |
| 24-90 | Var. 932 |
| 24-84 | Var. 933 |
| 24-78 | Var. 934 |
| 24-72 | Var. 935 |
| 24-66 | Var. 936 |
| 24-60 | Var. 937 |
| 24-54 | Var. 938 |
| 24-48 | Var. 939 |
| 24-45 | Var. 940 |
| 24-42 | Var. 941 |
| 24-39 | Var. 942 |
| 24-36 | Var. 943 |
| 24-33 | Var. 944 |
| 24-30 | Var. 945 |
| 24-27 | Var. 946 |
| 27-90 | Var. 947 |
| 27-84 | Var. 948 |
| 27-78 | Var. 949 |
| 27-72 | Var. 950 |
| 27-66 | Var. 951 |
| 27-60 | Var. 952 |
| 27-54 | Var. 953 |
| 27-48 | Var. 954 |
| 30-90 | Var. 955 |
| 30-84 | Var. 956 |
| 30-78 | Var. 957 |
| 30-72 | Var. 958 |
| 30-66 | Var. 959 |
| 30-60 | Var. 960 |
| 30-54 | Var. 961 |
| 30-48 | Var. 962 |
| 30-45 | Var. 963 |
| 30-42 | Var. 964 |
| 30-39 | Var. 965 |
| 30-36 | Var. 966 |
| 30-33 | Var. 967 |
| 33-90 | Var. 968 |
| 33-84 | Var. 969 |
| 33-78 | Var. 970 |
| 33-72 | Var. 971 |
| 33-66 | Var. 972 |
| 33-60 | Var. 973 |
| 33-54 | Var. 974 |
| 33-48 | Var. 975 |
| 33-45 | Var. 976 |
| 33-42 | Var. 977 |
| 33-29 | Var. 978 |
| 33-36 | Var. 979 |
| 36-90 | Var. 980 |
| 36-84 | Var. 981 |
| 36-78 | Var. 982 |
| 36-72 | Var. 983 |
| 36-66 | Var. 984 |
| 36-60 | Var. 985 |
| 36-54 | Var. 986 |
| 36-48 | Var. 987 |
| 36-45 | Var. 988 |
| 36-42 | Var. 989 |
| 36-39 | Var. 990 |
| 39-90 | Var. 991 |
| 39-84 | Var. 992 |
| 39-78 | Var. 993 |
| 39-72 | Var. 994 |
| 39-66 | Var. 995 |
| 39-60 | Var. 996 |
| 39-54 | Var. 997 |
| 39-48 | Var. 998 |
| 39-45 | Var. 999 |
| 39-42 | Var. 1000 |
| 42-90 | Var. 1001 |
| 42-84 | Var. 1002 |
| 42-78 | Var. 1003 |
| 42-72 | Var. 1004 |
| 42-66 | Var. 1005 |
| 42-60 | Var. 1006 |
| 42-54 | Var. 1007 |
| 42-48 | Var. 1008 |
| 42-45 | Var. 1009 |
| 45-90 | Var. 1010 |
| 45-84 | Var. 1011 |
| 45-78 | Var. 1012 |
| 45-72 | Var. 1013 |

TABLE 9-continued

Exemplary embodiments for the half-life of higher order rVWF multimers found in the compositions prepared by the methods provided herein.

Hours

| | |
|---|---|
| 45-66 | Var. 1014 |
| 45-60 | Var. 1015 |
| 45-54 | Var. 1016 |
| 45-48 | Var. 1017 |
| 48-90 | Var. 1018 |
| 48-84 | Var. 1019 |
| 48-78 | Var. 1020 |
| 48-72 | Var. 1021 |
| 48-66 | Var. 1022 |
| 48-60 | Var. 1023 |
| 48-54 | Var. 1024 |
| 54-90 | Var. 1025 |
| 54-84 | Var. 1026 |
| 54-78 | Var. 1027 |
| 54-72 | Var. 1028 |
| 54-66 | Var. 1029 |
| 54-60 | Var. 1030 |
| 60-90 | Var. 1031 |
| 60-84 | Var. 1032 |
| 60-78 | Var. 1033 |
| 60-72 | Var. 1034 |
| 60-66 | Var. 1035 |
| 66-90 | Var. 1036 |
| 66-84 | Var. 1037 |
| 66-78 | Var. 1038 |
| 66-72 | Var. 1039 |
| 72-90 | Var. 1040 |
| 72-84 | Var. 1041 |
| 72-78 | Var. 1042 |
| 78-90 | Var. 1043 |
| 78-84 | Var. 1044 |
| 84-90 | Var. 1045 |

Var. = Variation

In some embodiments, the pro-VWF and/or purified mat-rVWF purified in accordance with the present invention is not modified with any conjugation, post-translation or covalent modifications. In particular embodiments, the pro-VWF and/or purified mat-rVWF of the present invention is not modified with a water soluble polymer, including without limitation, a polyethylene glycol (PEG), a polypropylene glycol, a polyoxyalkylene, a polysialic acid, hydroxyl ethyl starch, a poly-carbohydrate moiety, and the like.

In some embodiments, the pro-VWF and/or purified mat-rVWF purified in accordance with the present invention is modified through conjugation, post-translation modification, or covalent modification, including modifications of the N- or C-terminal residues as well as modifications of selected side chains, for example, at free sulfhydryl-groups, primary amines, and hydroxyl-groups. In one embodiment, a water soluble polymer is linked to the protein (directly or via a linker) by a lysine group or other primary amine. In some embodiments, the pro-VWF and/or purified mat-rVWF of the present invention may be modified by conjugation of a water soluble polymer, including without limitation, a polyethylene glycol (PEG), a polypropylene glycol, a polyoxyalkylene, a polysialic acid, hydroxyl ethyl starch, a poly-carbohydrate moiety, and the like.

Water soluble polymers that may be used to modify the pro-VWF and/or purified mat-rVWF include linear and branched structures. The conjugated polymers may be attached directly to the coagulation proteins of the invention, or alternatively may be attached through a linking moiety. Non-limiting examples of protein conjugation with water soluble polymers can be found in U.S. Pat. Nos. 4,640,835; 4,496,689; 4,301,144; 4,670,417; 4,791,192, and 4,179,337, as well as in Abuchowski and Davis "Enzymes as Drugs," Holcenberg and Roberts, Eds., pp. 367 383, John Wiley and Sons, New York (1981), and Hermanson G., Bioconjugate Techniques 2nd Ed., Academic Press, Inc. 2008.

Protein conjugation may be performed by a number of well-known techniques in the art, for example, see Hermanson G., Bioconjugate Techniques 2nd Ed., Academic Press, Inc. 2008. Examples include linkage through the peptide bond between a carboxyl group on one of either the coagulation protein or water-soluble polymer moiety and an amine group of the other, or an ester linkage between a carboxyl group of one and a hydroxyl group of the other. Another linkage by which a coagulation protein of the invention could be conjugated to a water-soluble polymer compound is via a Schiff base, between a free amino group on the polymer moiety being reacted with an aldehyde group formed at the non-reducing end of the polymer by periodate oxidation (Jennings and Lugowski, J. Immunol. 1981; 127: 1011-8; Femandes and Gregonradis, Biochim Biophys Acta. 1997; 1341; 26-34). The generated Schiff Base can be stabilized by specific reduction with $NaCNBH_3$ to form a secondary amine. An alternative approach is the generation of terminal free amino groups on the polymer by reductive amination with $NH_4Cl$ after prior oxidation. Bifunctional reagents can be used for linking two amino or two hydroxyl groups. For example, a polymer containing an amino group can be coupled to an amino group of the coagulation protein with reagents like BS3 (Bis(sulfosuccinimidyl) suberate/ Pierce, Rockford, Ill.). In addition, heterobifunctional cross linking reagents like Sulfo-EMCS (N-ε-Maleimidocaproyloxy) sulfosuccinimide ester/Pierce) can be used for instance to link amine and thiol groups. In other embodiments, an aldehyde reactive group, such as PEG alkoxide plus diethyl acetal of bromoacetaldehyde; PEG plus DMSO and acetic anhydride, and PEG chloride plus the phenoxide of 4-hydroxybenzaldehyde, succinimidyl active esters, activated dithiocarbonate PEG, 2,4,5-trichlorophenylcloroformate and P-nitrophenylcloroformate activated PEG, may be used in the conjugation of a coagulation protein.

Another method for measuring the biological activity of VWF is the collagen binding assay, which is based on ELISA technology (Brown and Bosak, Thromb. Res., 1986, 43:303-311; Favaloro, Thromb. Haemost., 2000, 83 127-135). A microtiter plate is coated with type I or III collagen. Then the VWF is bound to the collagen surface and subsequently detected with an enzyme-labeled polyclonal antibody. The last step is a substrate reaction, which can be photometrically monitored with an ELISA reader.

Immunological assays of von Willebrand factors (VWF: Ag) are immunoassays that measure the concentration of the VWF protein in plasma. They give no indication as to VWF function. A number of methods exist for measuring VWF:Ag and these include both enzyme-linked immunosorbent assay (ELISA) or automated latex immunoassays (LIA.) Many laboratories now use a fully automated latex immunoassay. Historically laboratories used a variety of techniques including Laurell electroimmunoassay 'Laurell Rockets' but these are rarely used in most labs today.

K. VFW Formulations/Administration

The present method also provides for preparation of formulations from the VWF obtained by the purification methods provided herein. In some embodiments, the high purity mat-rVWF composition is used for the production of a pharmaceutical composition. In some embodiments, the mat-rVWF can be formulated into a lyophilized formulation.

In some embodiments, the formulations comprising a VWF polypeptide of the invention are lyophilized after purification and prior to administration to a subject. Lyophilization is carried out using techniques common in the art and should be optimized for the composition being developed (Tang et al., Pharm Res. 21:191-200, (2004) and Chang et al., Pharm Res. 13:243-9 (1996)).

A lyophilization cycle is, in one aspect, composed of three steps: freezing, primary drying, and secondary drying (A. P. Mackenzie, Phil Trans R Soc London, Ser B, Biol 278:167 (1977)). In the freezing step, the solution is cooled to initiate ice formation. Furthermore, this step induces the crystallization of the bulking agent. The ice sublimes in the primary drying stage, which is conducted by reducing chamber pressure below the vapor pressure of the ice, using a vacuum and introducing heat to promote sublimation. Finally, adsorbed or bound water is removed at the secondary drying stage under reduced chamber pressure and at an elevated shelf temperature. The process produces a material known as a lyophilized cake. Thereafter the cake can be reconstituted with either sterile water or suitable diluent for injection.

The lyophilization cycle not only determines the final physical state of excipients but also affects other parameters such as reconstitution time, appearance, stability and final moisture content. The composition structure in the frozen state proceeds through several transitions (e.g., glass transitions, wettings, and crystallizations) that occur at specific temperatures and the structure may be used to understand and optimize the lyophilization process. The glass transition temperature (Tg and/or Tg') can provide information about the physical state of a solute and can be determined by differential scanning calorimetry (DSC). Tg and Tg' are an important parameter that must be taken into account when designing the lyophilization cycle. For example, Tg' is important for primary drying. Furthermore, in the dried state, the glass transition temperature provides information on the storage temperature of the final product.

i. Pharmaceutical Formulations and Excipients in General

Excipients are additives that either impart or enhance the stability and delivery of a drug product (e.g., protein). Regardless of the reason for their inclusion, excipients are an integral component of a formulation and therefore need to be safe and well tolerated by patients. For protein drugs, the choice of excipients is particularly important because they can affect both efficacy and immunogenicity of the drug. Hence, protein formulations need to be developed with appropriate selection of excipients that afford suitable stability, safety, and marketability.

A lyophilized formulation is, in one aspect, at least comprised of one or more of a buffer, a bulking agent, and a stabilizer. In this aspect, the utility of a surfactant is evaluated and selected in cases where aggregation during the lyophilization step or during reconstitution becomes an issue. An appropriate buffering agent is included to maintain the formulation within stable zones of pH during lyophilization. A comparison of the excipient components contemplated for liquid and lyophilized protein formulations is provided in Table 10.

TABLE 10

Excipient components of lyophilized protein formulations

| Excipient component | Function in Lyophilized formulation |
|---|---|
| Buffer | Maintain pH of formulation during lyophilization and upon reconstitution |
| Tonicity agent/stabilizer | Stabilizers include cryo and lyprotectants<br>Examples include Polyols, sugars and polymers<br>Cryoprotectants protect proteins from freezing stresses<br>Lyoprotectants stabilize proteins in the freeze-dried state |
| Bulking agent | Used to enhance produce elegance and to prevent blowout<br>Provides structural strength to the lyo cake<br>Examples include mannitol and glycine |
| Surfactant | Employed if aggregation during the lyophilization process is an issue<br>May serve to reduce reconstitution times<br>Examples include polysorbate 20 and 80 |
| Anti-oxidant | Usually not employed, molecular reactions in the lyo cake are greatly retarded |
| Metal ions/chelating agent | May be included if a specific metal ion is included only as a co-factor or where the metal is required for protease activity<br>Chelating agents are generally not needed in lyo formulations |
| Preservatives | For multi-dose formulations only<br>Provides protection against microbial growth in formulation<br>Is usually included in the reconstitution diluent (e.g. bWFI) |

The principal challenge in developing formulations for proteins is stabilizing the product against the stresses of manufacturing, shipping and storage. The role of formulation excipients is to provide stabilization against these stresses. Excipients are also be employed to reduce viscosity of high concentration protein formulations in order to enable their delivery and enhance patient convenience. In general, excipients can be classified on the basis of the mechanisms by which they stabilize proteins against various chemical and physical stresses. Some excipients are used to alleviate the effects of a specific stress or to regulate a particular susceptibility of a specific protein. Other excipients have more general effects on the physical and covalent stabilities of proteins. The excipients described herein are organized either by their chemical type or their functional role in formulations. Brief descriptions of the modes of stabilization are provided when discussing each excipient type.

Given the teachings and guidance provided herein, those skilled in the art will know what amount or range of excipient can be included in any particular formulation to achieve a biopharmaceutical formulation of the invention that promotes retention in stability of the biopharmaceutical (e.g., a protein). For example, the amount and type of a salt to be included in a biopharmaceutical formulation of the invention is selected based on the desired osmolality (e.g., isotonic, hypotonic or hypertonic) of the final solution as well as the amounts and osmolality of other components to be included in the formulation.

By way of example, inclusion of about 5% sorbitol can achieve isotonicity while about 9% of a sucrose excipient is needed to achieve isotonicity. Selection of the amount or range of concentrations of one or more excipients that can be included within a biopharmaceutical formulation of the invention has been exemplified above by reference to salts, polyols and sugars. However, those skilled in the art will understand that the considerations described herein and further exemplified by reference to specific excipients are equally applicable to all types and combinations of excipients including, for example, salts, amino acids, other tonicity agents, surfactants, stabilizers, bulking agents, cryoprotectants, lyoprotectants, anti-oxidants, metal ions, chelating agents and/or preservatives.

Further, where a particular excipient is reported in molar concentration, those skilled in the art will recognize that the equivalent percent (%) w/v (e.g., (grams of substance in a solution sample/mL of solution)×100%) of solution is also contemplated.

Of course, a person having ordinary skill in the art would recognize that the concentrations of the excipients described herein share an interdependency within a particular formulation. By way of example, the concentration of a bulking agent may be lowered where, e.g., there is a high protein concentration or where, e.g., there is a high stabilizing agent concentration. In addition, a person having ordinary skill in the art would recognize that, in order to maintain the isotonicity of a particular formulation in which there is no bulking agent, the concentration of a stabilizing agent would be adjusted accordingly (e.g., a "tonicifying" amount of stabilizer would be used). Common excipients are known in the art and can be found in Powell et al., Compendium of Excipients fir Parenteral Formulations (1998), PDA J. Pharm. Sci. Technology, 52:238-311.

ii. Pharmaceutical Buffers and Buffering Agents

The stability of a pharmacologically active protein formulation is usually observed to be maximal in a narrow pH range. This pH range of optimal stability needs to be identified early during pre-formulation studies. Several approaches, such as accelerated stability studies and calorimetric screening studies, are useful in this endeavor (Remmele R. L. Jr., et al., Biochemistry, 38(16): 5241-7 (1999)). Once a formulation is finalized, the protein must be manufactured and maintained throughout its shelf-life. Hence, buffering agents are almost always employed to control pH in the formulation.

The buffer capacity of the buffering species is maximal at a pH equal to the pKa and decreases as pH increases or decreases away from this value. Ninety percent of the buffering capacity exists within one pH unit of its pKa. Buffer capacity also increases proportionally with increasing buffer concentration.

Several factors need to be considered when choosing a buffer. First and foremost, the buffer species and its concentration need to be defined based on its pKa and the desired formulation pH. Equally important is to ensure that the buffer is compatible with the protein and other formulation excipients, and does not catalyze any degradation reactions. A third important aspect to be considered is the sensation of stinging and irritation the buffer may induce upon administration. For example, citrate is known to cause stinging upon injection (Laursen T, et al., Basic Clin Pharmacol Toxicol., 98(2): 218-21 (2006)). The potential for stinging and irritation is greater for drugs that are administered via the subcutaneous (SC) or intramuscular (IM) routes, where the drug solution remains at the site for a relatively longer period of time than when administered by the IV route where the formulation gets diluted rapidly into the blood upon administration. For formulations that are administered by direct IV infusion, the total amount of buffer (and any other formulation component) needs to be monitored. One has to be particularly careful about potassium ions administered in the form of the potassium phosphate buffer, which can induce cardiovascular effects in a patient (Hollander-Rodriguez J C, et al., Am. Fam. Physician., 73(2): 283-90 (2006)).

Buffers for lyophilized formulations need additional consideration. Some buffers like sodium phosphate can crystallize out of the protein amorphous phase during freezing resulting in shifts in pH. Other common buffers such as acetate and imidazole may sublime or evaporate during the lyophilization process, thereby shifting the pH of formulation during lyophilization or after reconstitution.

The buffer system present in the compositions is selected to be physiologically compatible and to maintain a desired pH of the pharmaceutical formulation. In one embodiment, the pH of the solution is between pH 2.0 and pH 12.0. For example, the pH of the solution may be 2.0, 2.3, 2.5, 2.7, 3.0, 3.3, 3.5, 3.7, 4.0, 4.3, 4.5, 4.7, 5.0, 5.3, 5.5, 5.7, 6.0, 6.3, 6.5, 6.7, 7.0, 7.3, 7.5, 7.7, 8.0, 8.3, 8.5, 8.7, 9.0, 9.3, 9.5, 9.7, 10.0, 10.3, 10.5, 10.7, 11.0, 11.3, 11.5, 11.7, or 12.0.

The pH buffering compound may be present in any amount suitable to maintain the pH of the formulation at a predetermined level. In one embodiment, the pH buffering concentration is between 0.1 mM and 500 mM (1 M). For example, it is contemplated that the pH buffering agent is at least 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 25, 30, 40, 50, 60, 70, 80, 90, 100, 200, or 500 mM.

Exemplary pH buffering agents used to buffer the formulation as set out herein include, but are not limited to organic acids, glycine, histidine, glutamate, succinate, phosphate, acetate, citrate, Tris, HEPES, and amino acids or mixtures of amino acids, including, but not limited to aspartate, histidine, and glycine. In one embodiment of the present invention, the buffering agent is citrate.

In some embodiments, the formulation comprises 50 mM Glycine, 10 mM Taurine, 5% (w/w) Sucrose, 5% (w/w) D-Mannitol, 0.1% Polysorbate 80, 2 mM $CaCl_2$, 150 mM NaCl, and a pH 7.4. In some embodiments, the formulation comprises a high purity mat-rVWF, 50 mM Glycine, 10 mM Taurine, 5% (w/w) Sucrose, 5% (w/w) D-Mannitol, 0.1% Polysorbate 80, 2 mM $CaCl_2$, 150 mM NaCl, and a pH 7.4. In some embodiments, the formulation comprises vWF and/or r-vWF/rFVIII and 50 mM Glycine, 10 mM Taurine, 5% (w/w) Sucrose, 5% (w/w) D-Mannitol, 0.1% Polysorbate 80, 2 mM $CaCl_2$, 150 mM NaCl, and a pH 7.4.

iii. Pharmaceutical Stabilizers and Bulking Agents

In one aspect of the present pharmaceutical formulations, a stabilizer (or a combination of stabilizers) is added to prevent or reduce storage-induced aggregation and chemical degradation. A hazy or turbid solution upon reconstitution indicates that the protein has precipitated or at least aggregated. The term "stabilizer" means an excipient capable of preventing aggregation or physical degradation, including chemical degradation (for example, autolysis, deamidation, oxidation, etc.) in an aqueous state. Stabilizers contemplated include, but are not limited to, sucrose, trehalose, mannose, maltose, lactose, glucose, raffinose, cellobiose, gentiobiose, isomaltose, arabinose, glucosamine, fructose, mannitol, sorbitol, glycine, arginine HCL, poly-hydroxy compounds, including polysaccharides such as dextran, starch, hydroxyethyl starch, cyclodextrins, N-methyl pyrollidene, cellulose and hyaluronic acid, sodium chloride, (Carpenter et al., Develop. Biol. Standard 74:225, (1991)). In the present formulations, the stabilizer is incorporated in a concentration of about 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 30, 40, 50, 60, 70, 80, 90, 100, 200, 500, 700, 900, or 1000 mM. In one embodiment of the present invention, mannitol and trehalose are used as stabilizing agents.

If desired, the formulations also include appropriate amounts of bulking and osmolality regulating agents. Bulking agents include, for example and without limitation, mannitol, glycine, sucrose, polymers such as dextran, polyvinylpyrolidone, carboxymethylcellulose, lactose, sorbitol, trehalose, or xylitol. In one embodiment, the bulking agent is mannitol. The bulking agent is incorporated in a concentration of about 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 30, 40, 50, 60, 70, 80, 90, 100, 200, 500, 700, 900, or 1000 mM.

iv. Pharmaceutical Surfactants

Proteins have a high propensity to interact with surfaces making them susceptible to adsorption and denaturation at air-liquid, vial-liquid, and liquid-liquid (silicone oil) interfaces. This degradation pathway has been observed to be inversely dependent on protein concentration and results in either the formation of soluble and insoluble protein aggregates or the loss of protein from solution via adsorption to surfaces. In addition to container surface adsorption, surface-induced degradation is exacerbated with physical agitation, as would be experienced during shipping and handling of the product.

Surfactants are commonly used in protein formulations to prevent surface-induced degradation. Surfactants are amphipathic molecules with the capability of out-competing proteins for interfacial positions. Hydrophobic portions of the surfactant molecules occupy interfacial positions (e.g., air/liquid), while hydrophilic portions of the molecules remain oriented towards the bulk solvent. At sufficient concentrations (typically around the detergent's critical micellar concentration), a surface layer of surfactant molecules serves to prevent protein molecules from adsorbing at the interface. Thereby, surface-induced degradation is minimized. Surfactants contemplated herein include, without limitation, fatty acid esters of sorbitan polyethoxylates, e.g., polysorbate 20 and polysorbate 80. The two differ only in the length of the aliphatic chain that imparts hydrophobic character to the molecules, C-12 and C-18, respectively. Accordingly, polysorbate-80 is more surface-active and has a lower critical micellar concentration than polysorbate-20.

Detergents can also affect the thermodynamic conformational stability of proteins. Here again, the effects of a given detergent excipient will be protein specific. For example, polysorbates have been shown to reduce the stability of some proteins and increase the stability of others. Detergent destabilization of proteins can be rationalized in terms of the hydrophobic tails of the detergent molecules that can engage in specific binding with partially or wholly unfolded protein states. These types of interactions could cause a shift in the conformational equilibrium towards the more expanded protein states (e.g. increasing the exposure of hydrophobic portions of the protein molecule in complement to binding polysorbate). Alternatively, if the protein native state exhibits some hydrophobic surfaces, detergent binding to the native state may stabilize that conformation.

Another aspect of polysorbates is that they are inherently susceptible to oxidative degradation. Often, as raw materials, they contain sufficient quantities of peroxides to cause oxidation of protein residue side-chains, especially methionine. The potential for oxidative damage arising from the addition of stabilizer emphasizes the point that the lowest effective concentrations of excipients should be used in formulations. For surfactants, the effective concentration for a given protein will depend on the mechanism of stabilization.

Surfactants are also added in appropriate amounts to prevent surface related aggregation phenomenon during freezing and drying (Chang, B, J. Pharm. Sci. 85:1325, (1996)). Thus, exemplary surfactants include, without limitation, anionic, cationic, nonionic, zwitterionic, and amphoteric surfactants including surfactants derived from naturally-occurring amino acids. Anionic surfactants include, but are not limited to, sodium lauryl sulfate, dioctyl sodium sulfo succinate and dioctyl sodium sulfonate, chenodeoxycholic acid, N-lauroylsarcosine sodium salt, lithium dodecyl sulfate, 1-octanesulfonic acid sodium salt, sodium cholate hydrate, sodium deoxycholate, and glycodeoxycholic acid sodium salt. Cationic surfactants include, but are not limited to, benzalkonium chloride or benzethonium chloride, cetylpyridinium chloride monohydrate, and hexadecyltrimethylammonium bromide. Zwitterionic surfactants include, but are not limited to, CHAPS, CHAPSO, SB3-10, and SB3-12. Non-ionic surfactants include, but are not limited to, digitonin, Triton X-100, Triton X-114, TWEEN-20, and TWEEN-80. Surfactants also include, but are not limited to lauromacrogol 400, polyoxyl 40 stearate, polyoxyethylene hydrogenated castor oil 10, 40, 50 and 60, glycerol monostearate, polysorbate 40, 60, 65 and 80, soy lecithin and other phospholipids such as dioleyl phosphatidyl choline (DOPC), dimyristoylphosphatidyl glycerol (DMPG), dimyristoylphosphatidyl choline (DMPC), and (dioleyl phosphatidyl glycerol) DOPG; sucrose fatty acid ester, methyl cellulose and carboxymethyl cellulose. Compositions comprising these surfactants, either individually or as a mixture in different ratios, are therefore further provided. In one embodiment of the present invention, the surfactant is TWEEN-80. In the present formulations, the surfactant is incorporated in a concentration of about 0.01 to about 0.5 g/L. In formulations provided, the surfactant concentration is 0.005, 0.01, 0.02, 0.03, 0.05, 0.06, 0.07, 0.08, 0.09, 0.1, 0.2, 0.3, 0.4, 0.5, 0.6, 0.7, 0.8, 0.9 or 1.0 g/L.

v. Pharmaceutical Salts

Salts are often added to increase the ionic strength of the formulation, which can be important for protein solubility, physical stability, and isotonicity. Salts can affect the physical stability of proteins in a variety of ways. Ions can stabilize the native state of proteins by binding to charged residues on the protein's surface. Alternatively, salts can stabilize the denatured state by binding to peptide groups along the protein backbone (—CONH—). Salts can also stabilize the protein native conformation by shielding repulsive electrostatic interactions between residues within a protein molecule. Salts in protein formulations can also shield attractive electrostatic interactions between protein molecules that can lead to protein aggregation and insolubility. In formulations provided, the salt concentration is between 0.1, 1, 10, 20, 30, 40, 50, 80, 100, 120, 150, 200, 300, and 500 mM.

vi. Other Common Excipient Components: Pharmaceutical Amino Acids

Amino acids have found versatile use in protein formulations as buffers, bulking agents, stabilizers and antioxidants. Thus, in one aspect histidine and glutamic acid are employed to buffer protein formulations in the pH range of 5.5-6.5 and 4.0-5.5 respectively. The imidazole group of histidine has a pKa=6.0 and the carboxyl group of glutamic acid side chain has a pKa of 4.3 which makes these amino acids suitable for buffering in their respective pH ranges. Glutamic acid is particularly useful in such cases. Histidine is commonly found in marketed protein formulations, and this amino acid provides an alternative to citrate, a buffer known to sting upon injection. Interestingly, histidine has also been reported to have a stabilizing effect, with respect to aggregation when used at high concentrations in both liquid and lyophilized presentations (Chen B, et al., Pharm Res., 20(12): 1952-60 (2003)). Histidine was also observed by others to reduce the viscosity of a high protein concentration formulation. However, in the same study, the authors observed increased aggregation and discoloration in histidine containing formulations during freeze-thaw studies of the antibody in stainless steel containers. Another note of caution with histidine is that it undergoes photo-oxidation in the presence of metal ions (Tomita M, et al., Biochemistry, 8(12): 5149-60 (1969)). The use of methionine as an antioxidant in formulations appears promising; it has been observed to be effective against a number of oxidative stresses (Lam X M, et al., J Pharm ScL, 86(11): 1250-5 (1997)).

In various aspects, formulations are provided which include one or more of the amino acids glycine, proline, serine, arginine and alanine have been shown to stabilize proteins by the mechanism of preferential exclusion. Glycine is also a commonly used bulking agent in lyophilized formulations. Arginine has been shown to be an effective agent in inhibiting aggregation and has been used in both liquid and lyophilized formulations.

In formulations provided, the amino acid concentration is between 0.1, 1, 10, 20, 30, 40, 50, 80, 100, 120, 150, 200, 300, and 500 mM. In one embodiment of the present invention, the amino acid is glycine.

vii. Other Common Excipient Components: Pharmaceutical Antioxidants

Oxidation of protein residues arises from a number of different sources. Beyond the addition of specific antioxidants, the prevention of oxidative protein damage involves the careful control of a number of factors throughout the manufacturing process and storage of the product such as atmospheric oxygen, temperature, light exposure, and chemical contamination. The invention therefore contemplates the use of the pharmaceutical antioxidants including, without limitation, reducing agents, oxygen/free-radical scavengers, or chelating agents. Antioxidants in therapeutic protein formulations are, in one aspect, water-soluble and remain active throughout the product shelf-life. Reducing agents and oxygen/free-radical scavengers work by ablating active oxygen species in solution. Chelating agents such as EDTA are effective by binding trace metal contaminants that promote free-radical formation. For example, EDTA was utilized in the liquid formulation of acidic fibroblast growth factor to inhibit the metal ion catalyzed oxidation of cysteine residues.

In addition to the effectiveness of various excipients to prevent protein oxidation, the potential for the antioxidants themselves to induce other covalent or physical changes to the protein is of concern. For example, reducing agents can cause disruption of intramolecular disulfide linkages, which can lead to disulfide shuffling. In the presence of transition metal ions, ascorbic acid and EDTA have been shown to promote methionine oxidation in a number of proteins and peptides (Akers M J, and Defelippis M R. Peptides and Proteins as Parenteral Solutions. In: Pharmaceutical Formulation Development of Peptides and Proteins. Sven Frokjaer, Lars Hovgaard, editors. Pharmaceutical Science. Taylor and Francis, U K (1999)); Fransson J. R., /. Pharm. Sci. 86(9): 4046-1050 (1997); Yin J, et al., Pharm Res., 21(12): 2377-83 (2004)). Sodium thiosulfate has been reported to reduce the levels of light and temperature induced methionine-oxidation in rhuMab HER2; however, the formation of a thiosulfate-protein adduct was also reported in this study (Lam X M, Yang J Y, et al., J Pharm Sci. 86(11): 1250-5 (1997)). Selection of an appropriate antioxidant is made according to the specific stresses and sensitivities of the protein. Antioxidants contemplated in certain aspects include, without limitation, reducing agents and oxygen/free-radical scavengers, EDTA, and sodium thiosulfate.

viii. Other Common Excipient Components: Pharmaceutical Metal Ions

In general, transition metal ions are undesired in protein formulations because they can catalyze physical and chemical degradation reactions in proteins. However, specific metal ions are included in formulations when they are co-factors to proteins and in suspension formulations of proteins where they form coordination complexes (e.g., zinc suspension of insulin). Recently, the use of magnesium ions (10-120 mM) has been proposed to inhibit the isomerization of aspartic acid to isoaspartic acid (WO 2004039337).

Two examples where metal ions confer stability or increased activity in proteins are human deoxyribonuclease (rhDNase, Pulmozyme®), and Factor VIII. In the case of rhDNase, $Ca^{+2}$ ions (up to 100 mM) increased the stability of the enzyme through a specific binding site (Chen B, et al., / Pharm Sci., 88(4): 477-82 (1999)). In fact, removal of calcium ions from the solution with EGTA caused an increase in deamidation and aggregation. However, this effect was observed only with $Ca^{+2}$ ions; other divalent cations $Mg^{+2}$, $Mn^{+2}$ and $Zn^{+2}$ were observed to destabilize rhDNase. Similar effects were observed in Factor VIII. $Ca^{+2}$ and $Sr^{+2}$ ions stabilized the protein while others like $Mg^{+2}$, $Mn^{+2}$ and $Zn^{+2}$, $Cu^{+2}$ and $Fe^{+2}$ destabilized the enzyme (Fatouros, A., et al., Int. J. Pharm., 155, 121-131 (1997). In a separate study with Factor VIII, a significant increase in aggregation rate was observed in the presence of $Al^{+3}$ ions (Derrick T S, et al., /. Pharm. Sci., 93(10): 2549-57 (2004)). The authors note that other excipients like buffer salts are often contaminated with $Al^{+3}$ ions and illustrate the need to use excipients of appropriate quality in formulated products.

ix. Other Common Excipient Components: Pharmaceutical Preservatives

Preservatives are necessary when developing multi-use parenteral formulations that involve more than one extraction from the same container. Their primary function is to inhibit microbial growth and ensure product sterility throughout the shelf-life or term of use of the drug product. Commonly used preservatives include, without limitation, benzyl alcohol, phenol and m-cresol. Although preservatives have a long history of use, the development of protein formulations that includes preservatives can be challenging. Preservatives almost always have a destabilizing effect (aggregation) on proteins, and this has become a major factor in limiting their use in multi-dose protein formulations (Roy S, et al., J Pharm ScL, 94(2): 382-96 (2005)).

To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market. Norditropin® (liquid, Novo Nordisk), Nutropin AQ® (liquid, Genentech) & Genotropin (lyophilized-dual chamber cartridge, Pharmacia & Upjohn) contain phenol while Somatrope® (Eli Lilly) is formulated with m-cresol.

Several aspects need to be considered during the formulation development of preserved dosage forms. The effective preservative concentration in the drug product must be optimized. This requires testing a given preservative in the dosage form with concentration ranges that confer antimicrobial effectiveness without compromising protein stability. For example, three preservatives were successfully screened in the development of a liquid formulation for interleukin-1 receptor (Type I), using differential scanning calorimetry (DSC). The preservatives were rank ordered based on their impact on stability at concentrations commonly used in marketed products (Remmele R L Jr., et al., Pharm Res., 15(2): 200-8 (1998)).

Development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein significantly minimizing the associated stability risks. With liquid formulations, preservative effectiveness and stability have to be maintained over the entire product shelf-life (−18-24 months). An important point to note is that preservative effectiveness has to be demonstrated in the final formulation containing the active drug and all excipient components.

Some preservatives can cause injection site reactions, which is another factor that needs consideration when choosing a preservative. In clinical trials that focused on the evaluation of preservatives and buffers in Norditropin, pain perception was observed to be lower in formulations containing phenol and benzyl alcohol as compared to a formulation containing m-cresol (Kappelgaard A. M., Horm Res. 62 Suppl 3:98-103 (2004)). Interestingly, among the commonly used preservative, benzyl alcohol possesses anesthetic properties (Minogue S C, and Sun D A., AnesthAnalg., 100(3): 683-6 (2005)). In various aspects the use of preservatives provide a benefit that outweighs any side effects.

x. Methods of Preparation of Pharmaceutical Formulations

The present invention further contemplates methods for the preparation of pharmaceutical formulations.

The present methods further comprise one or more of the following steps: adding a stabilizing agent as described herein to said mixture prior to lyophilizing, adding at least one agent selected from a bulking agent, an osmolality regulating agent, and a surfactant, each of which as described herein, to said mixture prior to lyophilization.

The standard reconstitution practice for lyophilized material is to add back a volume of pure water or sterile water for injection (WFI) (typically equivalent to the volume removed during lyophilization), although dilute solutions of antibacterial agents are sometimes used in the production of pharmaceuticals for parenteral administration (Chen, Drug Development and Industrial Pharmacy, 18:1311-1354 (1992)). Accordingly, methods are provided for preparation of reconstituted rVWF compositions comprising the step of adding a diluent to a lyophilized rVWF composition of the invention.

The lyophilized material may be reconstituted as an aqueous solution. A variety of aqueous carriers, e.g., sterile water for injection, water with preservatives for multi dose use, or water with appropriate amounts of surfactants (for example, an aqueous suspension that contains the active compound in admixture with excipients suitable for the manufacture of aqueous suspensions). In various aspects, such excipients are suspending agents, for example and without limitation, sodium carboxymethylcellulose, methylcellulose, hydroxypropylmethylcellulose, sodium alginate, polyvinylpyrrolidone, gum tragacanth and gum acacia; dispersing or wetting agents are a naturally-occurring phosphatide, for example and without limitation, lecithin, or condensation products of an alkylene oxide with fatty acids, for example and without limitation, polyoxyethylene stearate, or condensation products of ethylene oxide with long chain aliphatic alcohols, for example and without limitation, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example and without limitation, polyethylene sorbitan monooleate. In various aspects, the aqueous suspensions also contain one or more preservatives, for example and without limitation, ethyl, or n-propyl, p-hydroxybenzoate.

xi. Exemplary Mat-rVWF Formulation for Administration

In some embodiments, the present methods provide for an enhanced formulation that allows a final product with high potency (high mat-rVWF concentration and enhanced long term stability) in order to reduce the volume for the treatment (100 IU/ml to 10000 IU/ml). In some embodiments, the mat-rVWF concentration in the formulation for administration is about 100 IU/ml to 10000 IU/ml. In some embodiments, the mat-rVWF concentration in the formulation for administration is about 500 IU/ml to 10000 IU/ml. In some embodiments, the mat-rVWF concentration in the formulation for administration is about 1000 IU/ml to 10000 IU/ml. In some embodiments, the mat-rVWF concentration in the formulation for administration is about 2000 IU/ml to 10000 IU/ml. In some embodiments, the mat-rVWF concentration in the formulation for administration is about 3000 IU/ml to 10000 IU/ml. In some embodiments, the mat-rVWF concentration in the formulation for administration is about 4000 IU/ml to 10000 IU/ml. In some embodiments, the mat-rVWF concentration in the formulation for administration is about 5000 IU/ml to 10000 IU/ml. In some embodiments, the mat-rVWF concentration in the formulation for administration is about 6000 IU/ml to 10000 IU/ml. In some embodiments, the mat-rVWF concentration in the formulation for administration is about 7000 IU/ml to 10000 IU/ml. In some embodiments, the mat-rVWF concentration in the formulation for administration is about 8000 IU/ml to 10000 IU/ml. In some embodiments, the mat-rVWF concentration in the formulation for administration is about 9000 IU/ml to 10000 IU/ml. In some embodiments, the mat-rVWF is co-formulated with recombinant coagulation Factor VIII (rFVIII). In some embodiments, the rFVIII is full length FVIII. In some embodiments, the rFVIII is full-length and chemically modified. In some embodiments, the rFVIII comprises a FVIII fusion protein containing FIX-activation peptide instead of B-Domain. In some embodiments, the rFVIII is a FVIII hybrid containing truncated glycosylation rich B-Domain. In some embodiments, the FVIII is a FVIII B-domain-deleted variant. In some embodiments, the FVIII is a chemically modified variant of a FVIII B-domain-deleted variant. In some embodiments, the mat-rVWF with rFVIII co-formulation is made prior to a freeze drying or fill finish step and is stored by mixing the components in vitro or in an "on column" procedure (e.g., adding the FVIII during the purification method).

In some embodiments, the formulation for administration comprises one or more zwitterionic compounds, including for example, amino acids like Histidine, Glycine, Arginine. In some embodiments, the formulation for administration comprises a component with amphipathic characteristic having a minimum of one hydrophobic and one hydrophilic group, including for example polysorbate 80, octylpyranosid, dipeptides, and/or amphipathic peptides. In some embodiments, the formulation for administration comprises a non reducing sugar or sugar alcohol or disaccharides, including for example, sorbitol, mannitol, sucrose, or trehalose. In some embodiments, the formulation for administration comprises a nontoxic water soluble salt, including for example, sodium chloride, that results in a physiological osmolality. In some embodiments, the formulation for administration comprises a pH in a range from 6.0 to 8.0. In some embodiments, the formulation for administration comprises a pH of about 6.0, about 6.5, about 7, about 7.5 or about 8.0. In some embodiments, the formulation for administration comprises one or more bivalent cations that stabilize rVWF, including for example, Ca2+, Mg2+, Zn2+, Mn2+ and/or combinations thereof. In some embodiments, the formulation for administration comprises about 1 mM to about 50 mM Glycine, about 1 mM to about 50 mM Histidine, about zero to about 300 mM sodium chloride (e.g., less than 300 mM sodium), about 0.01% to about 0.05% polysorbate 20 (or polysorbate 80), and about 0.5% to about 20% (w/w) sucrose with a pH of about 7.0 and having a physiological osmolarity at the time point of administration.

In some embodiments, the formulation for administration can be freeze dried. In some embodiments, the formulation for administration is stable and can be stored in liquid state at about 2° C. to about 8° C., as well as at about 18° C. to about 25° C. In some embodiments, the formulation for administration is stable and can be stored in liquid state at about 2° C. to about 8° C. In some embodiments, the formulation for administration is stable and can be stored in liquid state at about 18° C. to about 25° C.

xii. Administration

To administer compositions to human or test animals, in one aspect, the compositions comprises one or more pharmaceutically acceptable carriers. The phrases "pharmaceutically" or "pharmacologically" acceptable refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

The pharmaceutical formulations are administered orally, topically, transdermally, parenterally, by inhalation spray, vaginally, rectally, or by intracranial injection. The term parenteral as used herein includes subcutaneous injections, intravenous, intramuscular, intracistemal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

Single or multiple administrations of the compositions are carried out with the dose levels and pattern being selected by the treating physician. For the prevention or treatment of disease, the appropriate dosage depends on the type of disease to be treated, as defined above, the severity and course of the disease, whether drug is administered for preventive or therapeutic purposes, previous therapy, the patient's clinical history and response to the drug, and the discretion of the attending physician.

xiii. Kits

As an additional aspect, the invention includes kits which comprise one or more lyophilized compositions packaged in a manner which facilitates their use for administration to subjects. In one embodiment, such a kit includes pharmaceutical formulation described herein (e.g., a composition comprising a therapeutic protein or peptide), packaged in a container such as a sealed bottle or vessel, with a label affixed to the container or included in the package that describes use of the compound or composition in practicing the method. In one embodiment, the pharmaceutical formulation is packaged in the container such that the amount of headspace in the container (e.g., the amount of air between the liquid formulation and the top of the container) is very small. Preferably, the amount of headspace is negligible (e.g., almost none). In one embodiment, the kit contains a first container having a therapeutic protein or peptide composition and a second container having a physiologically acceptable reconstitution solution for the composition. In one aspect, the pharmaceutical formulation is packaged in a unit dosage form. The kit may further include a device suitable for administering the pharmaceutical formulation according to a specific route of administration. Preferably, the kit contains a label that describes use of the pharmaceutical formulations.

xiv. Dosages

The dosage regimen involved in a method for treating a condition described herein will be determined by the attending physician, considering various factors which modify the action of drugs, e.g. the age, condition, body weight, sex and diet of the patient, the severity of any infection, time of administration and other clinical factors. By way of example, a typical dose of a recombinant VWF of the present invention is approximately 50 U/kg, equal to 500 µg/kg.

In one aspect, formulations of the invention are administered by an initial bolus followed by a continuous infusion to maintain therapeutic circulating levels of drug product. As another example, the inventive compound is administered as a one-time dose. Those of ordinary skill in the art will readily optimize effective dosages and administration regimens as determined by good medical practice and the clinical condition of the individual patient. The frequency of dosing depends on the pharmacokinetic parameters of the agents and the route of administration. The optimal pharmaceutical formulation is determined by one skilled in the art depending upon the route of administration and desired dosage. See for example, Remington's Pharmaceutical Sciences, 18th Ed. (1990, Mack Publishing Co., Easton, Pa. 18042) pages 1435-1712, the disclosure of which is hereby incorporated by reference. Such formulations influence the physical state, stability, rate of in vivo release, and rate of in vivo clearance of the administered agents. Depending on the route of administration, a suitable dose is calculated according to body weight, body surface area or organ size. Appropriate dosages may be ascertained through use of established assays for determining blood level dosages in conjunction with appropriate dose-response data. The final dosage regimen is determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. As studies are conducted, further information will emerge regarding the appropriate dosage levels and duration of treatment for various diseases and conditions.

EXAMPLES

The following non-limiting examples are provided for illustrative purposes only in order to facilitate a more complete understanding of representative embodiments.

These examples should not be construed to limit any of the embodiments described in the present specification including those pertaining to the methods of treating acquired and genetic von Willebrand disease.

Example 1: Purification of Maturated rVWF on a Cation Exchanger to Separate cVWF Propeptide from Mature rVWF Example 1 represents a purification of maturated rVWF on a cation exchanger (cation exchange (CEX) resin). The rVWF propeptide (rVWF-PP) remains bound to rVWF after furin maturation and was dissociated with sodium citrate as a chelating agent at a neutral pH prior to loading onto a CEX resin. The majority of rVWF propeptide passed through the cation exchange resin. And the remaining rVWF propeptide was depleted after a wash step. Sodium citrate was used as a component of the buffer substance and as a chelating agent.

Industrially, VWF, in particular recombinant VWF (rVWF), is synthesized and expressed together with rFVIII in a genetically engineered CHO cell line. The function of the co-expressed rVWF is to stabilize rFVIII in the cell culture process. rVWF is synthesized in the cell as the pro-form, containing a large pro-peptide attached to the N-terminus. Upon maturation in the endoplasmatic reticulum and Golgi apparatus, the rVWF-PP is cleaved off by the action of the cellular protease furin and is secreted as a homopolymer of identical subunits, consisting of dimers of the expressed protein. However, the maturation is incomplete, leading to a product comprising a mixture of rVWF-PP and mature VWF.

After a monoclonal antibody step to capture recombinant factor VIII, the flow-through containing rVWF (also referred to as the monoclonal antibody effluent) was loaded onto an anion exchanger (anion exchange (AEX) resin). rVWF was bound on the anion exchanger and was maturated with furin in presence of calcium. The rVWF was eluted from the anion exchanger with increasing conductivity. The product containing eluate was conditioned by a 1:2 dilution with 60 mM sodium citrate, pH 7.6 to a conductivity of 13.39 mS/cm and a pH of 7.39. The conditioned aqueous dilution was loaded onto a UNOsphere™ S Cation Exchange Media (Bio Rad, Cat. No.: 156-0115) cation exchanger column with an inner diameter of 15 mm, a bed height of 14.0 cm, and a volume of 24.74 ml with a flow rate of 100 cm/h, and then followed by a wash of 5 CV of 10 mM NaCl, 30 mM Na citrate, pH 7.6±0.2 to remove host cell proteins (HCP) and rVWF-PP. rVWF was eluted by increasing conductivity conducted by a linear gradient with a flow rate of 60 cm/h in 6 CV from 10 mM NaCl, 30 mM Na Citrate, pH 7.6±0.2 to buffer 500 mM NaCl, 30 mM Na Citrate, pH 7.6±0.2. The main eluate peak was split into two parts to separate low molecular weight rVWF multimers and high molecular weight rVWF multimers.

FIG. 1 shows purification of maturated r rVWF on a cation exchanger as represented in Example 1.

FIG. 2 provides a table of the purification results.

Figure 3:
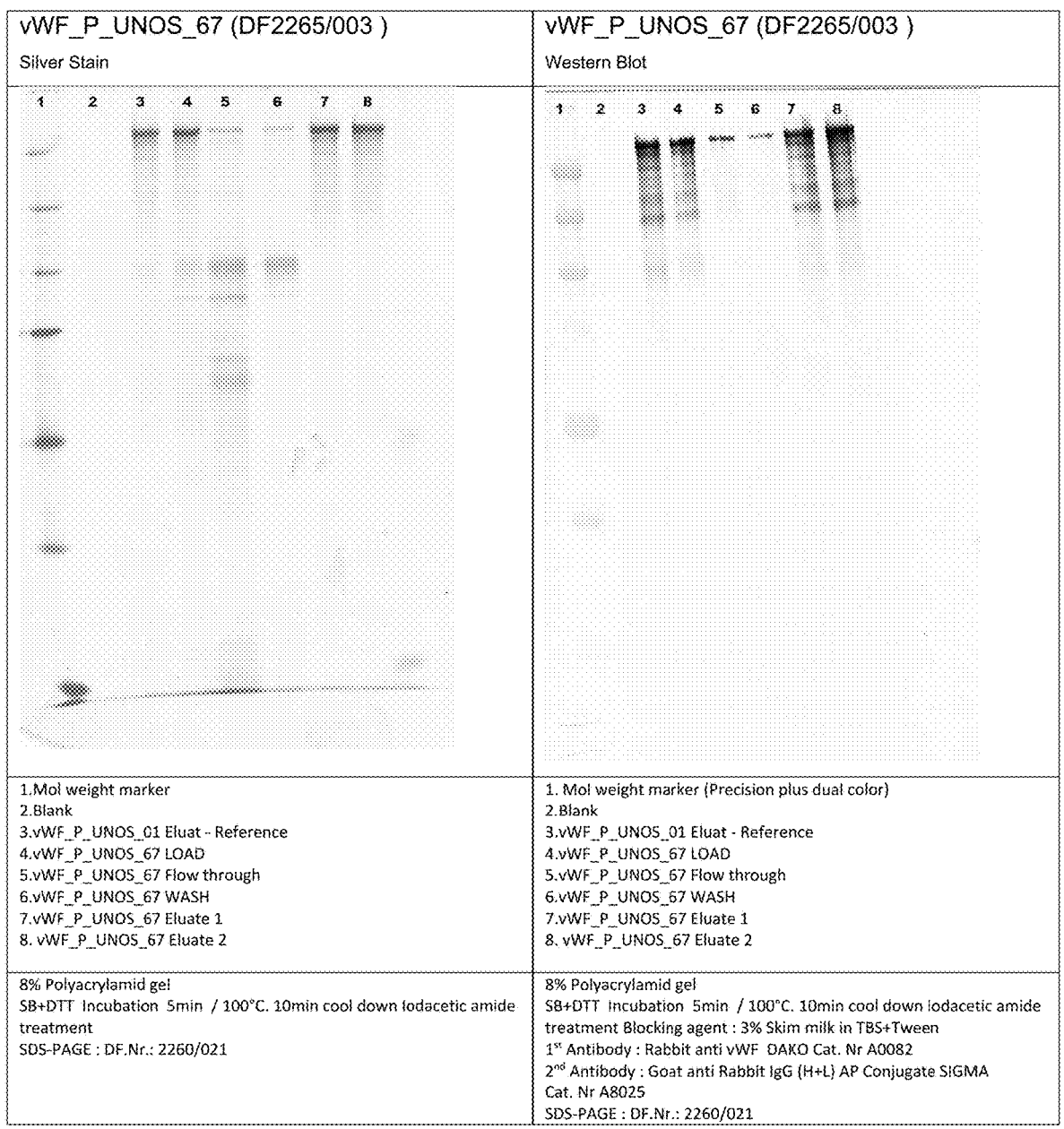
FIG. 3 shows a silver stained protein gel and a western blot illustrating the separation of mat-VWF and r-VWF propeptide (rVWF-PP) by the method of Example 1.

FIG. 3 shows a silver stained protein gel and a western blot illustrating the separation of rVWF and rVWF-PP by the method described in Example 1.

Examples 2 and 3: Optimized Method as Described in Example 1 for Commercial Manufacturing of rVWF Examples 2 and 3 represent an optimized method as described in Example 1 for commercial manufacturing of rVWF.

For Examples 2 and 3 an experimental setup for fermentation of rVWF and rFVIII was established. The method was used for a simplified purification method to obtain high pure rVWF for biochemical characterization.

The capture step was performed by tandem chromatography, which combined an affinity chromatography and an anion exchange chromatography in a single process step. rFVIII was bound on an anti FVIII-mAb column at a temperature of 2-8° C. based on immune affinity chromatography technique. This step can separate rFVIII from rVWF. The rVWF containing flow-through was online diluted in the same chromatography system with purified water and loaded directly on an AEX column. Recombinant furin maturation on the AEX column was carried out after increasing the temperature to +15° C. to 28° C. The furin maturated rVWF was eluted with a step elution by increasing conductivity. A polishing step was also performed. The rVWF containing AEX eluate was diluted with 10 mM Na citrate buffer, pH 7.6 and applied onto an UNOsphere™ S Cation Exchange Media (Bio Rad, Cat. No.: 156-0115) cation exchanger column having an inner diameter of 15 mm, a bed height of 14.0 cm, and a column volume of 25±0.5 ml with a flow rate of 100 cm/h. After a wash step with 10 mM NaCl, 30 mM Na citrate, 2 mM citric acid pH 7.6±0.2, rVWF was eluted with increasing conductivity using a linear gradient with a flow rate of 65 cm/h in 6CV from 10 mM NaCl, 30 mM Na citrate, pH 7.6±0.2 to a buffer of 500 mM NaCl, 30 mM Na citrate, pH 7.6±0.2. The main eluate peak was collected as eluate (pooled eluate) for analytical purposes.

In the final experimental design the last 30 to 40% of the peak was collected to obtain the rVWF with the highest specific activity.

Figure 4:
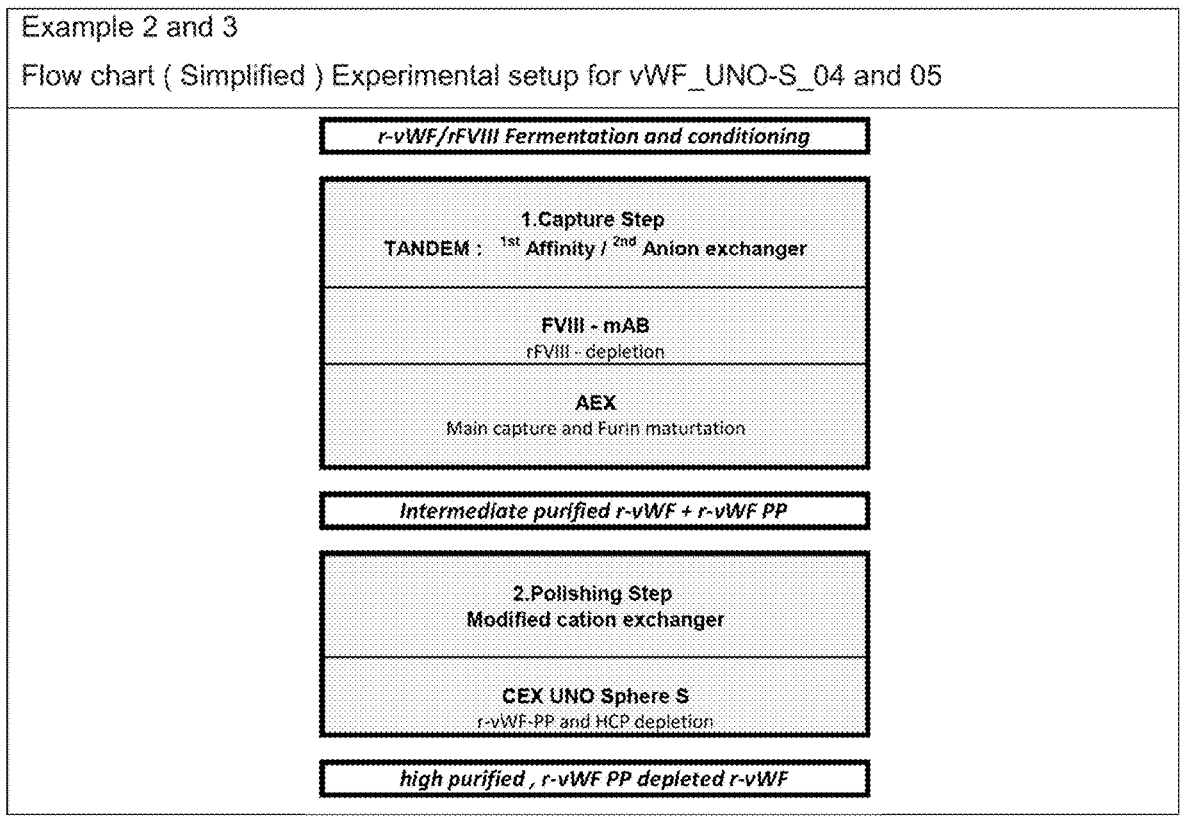
FIG. 4 shows a flow chart of the experimental set-up for Examples 2 and 3.

FIG. 4 shows a flow chart of the experimental set-up for Examples 2 and 3.

Figure 5:
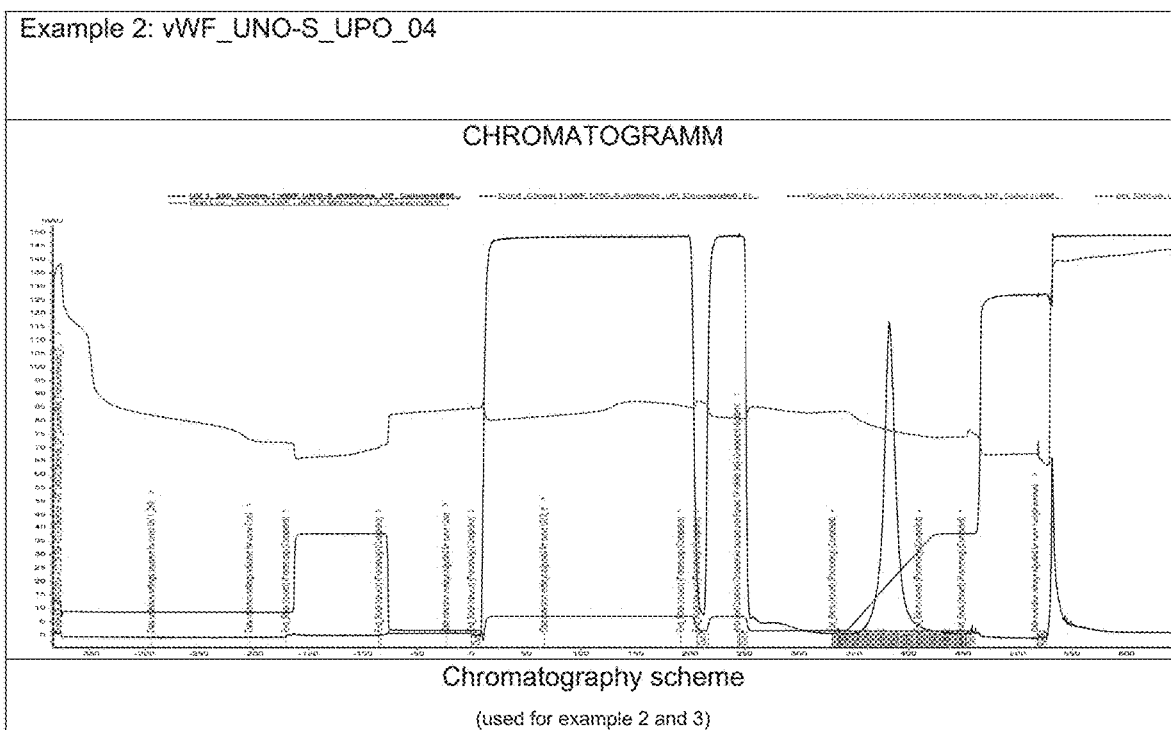
FIG. 5 shows a chromatogram for Example 2 and a chromatography scheme used for Examples 2 and 3

FIG. 5 shows a chromatogram for Example 2 and a chromatography scheme used for Examples 2 and 3.

FIG. 6 provides a table of the reagents used and a table of the results for Example 2.

Figure 7:
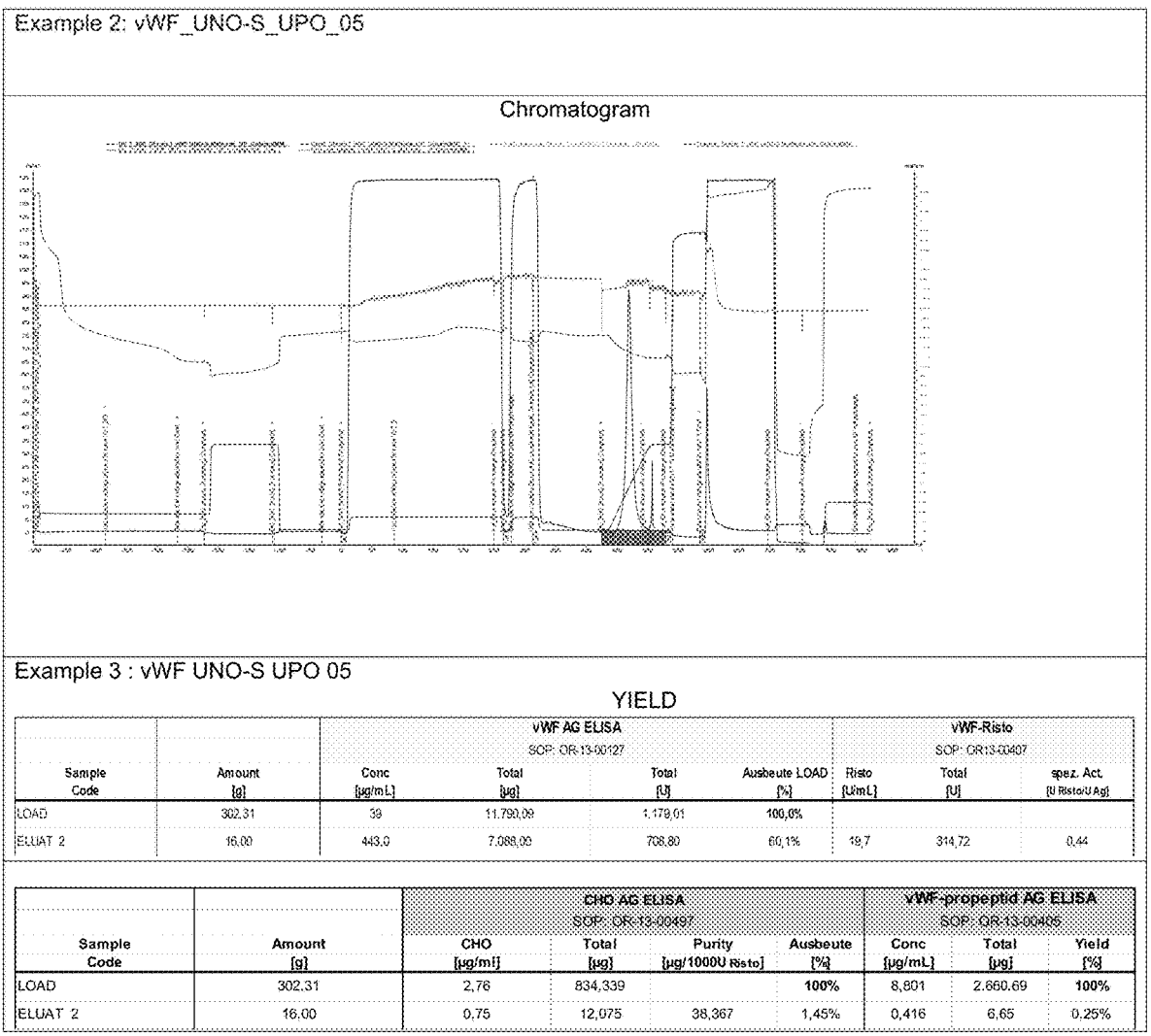
FIG. 7 shows another chromatogram for Example 2 and a table of the results for Example 3.

FIG. 7 shows another chromatogram for Example 2 and a table of the results for Example 3.

Figure 8:
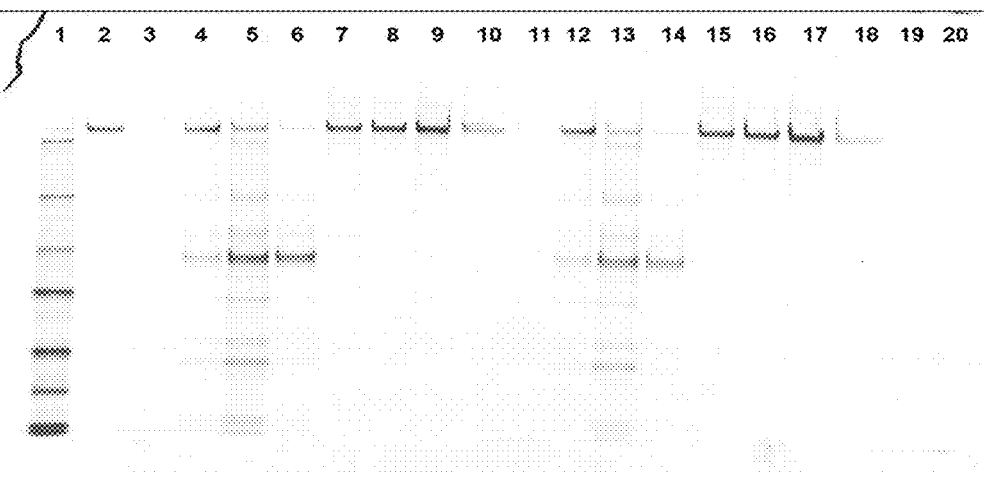
FIG. 8 shows a silver stained protein gel illustrating the separation of mat-rVWF and rVWF propeptide (rVWF-PP) by the method of Example 2 and Example 3.

FIG. 8 shows a silver stained protein gel illustrating the separation of rVWF and rVWF propeptide by the method of Example 2 and Example 3.

FIG. 9 shows a western blot illustrating the separation of rVWF and rVWF propeptide by the method of Example 2 and Example 3.

Example 4: Method for Commercial Manufacturing of rVWF by Separate rVWF and rVWF-PP by Size Exclusion Chromatography Example 4 represents an optimized method for commercial manufacturing of rVWF by separating rVWF and rVWF propeptide (rVWF-PP) via size exclusion chromatography. Sodium citrate is added to the SEC running buffer to provide an efficient split of rVWF and rVWF-PP.

A rVWF containing ultrafiltrated UNOsphere™ S-eluate was loaded directly onto an array of two Superose 6 prep grade SEC columns in series (GE Healthcare, Cat. No.: 28-9913-16), both with an inner diameter of 16 mm each, a bed height 82.0 cm (2×41 cm), and the volume of both columns was approximately 165 ml. The load was applied at a rate of 7 cm/h. The running buffer was 20 mM HEPES free acid, 150 mM NaCl, 15 mM Na citrate dihydrate pH 7.5±0.2. The size exclusion chromatography was carried out with isocratic conditions at a linear flow rate of 12 cm/h.

Figure 10:
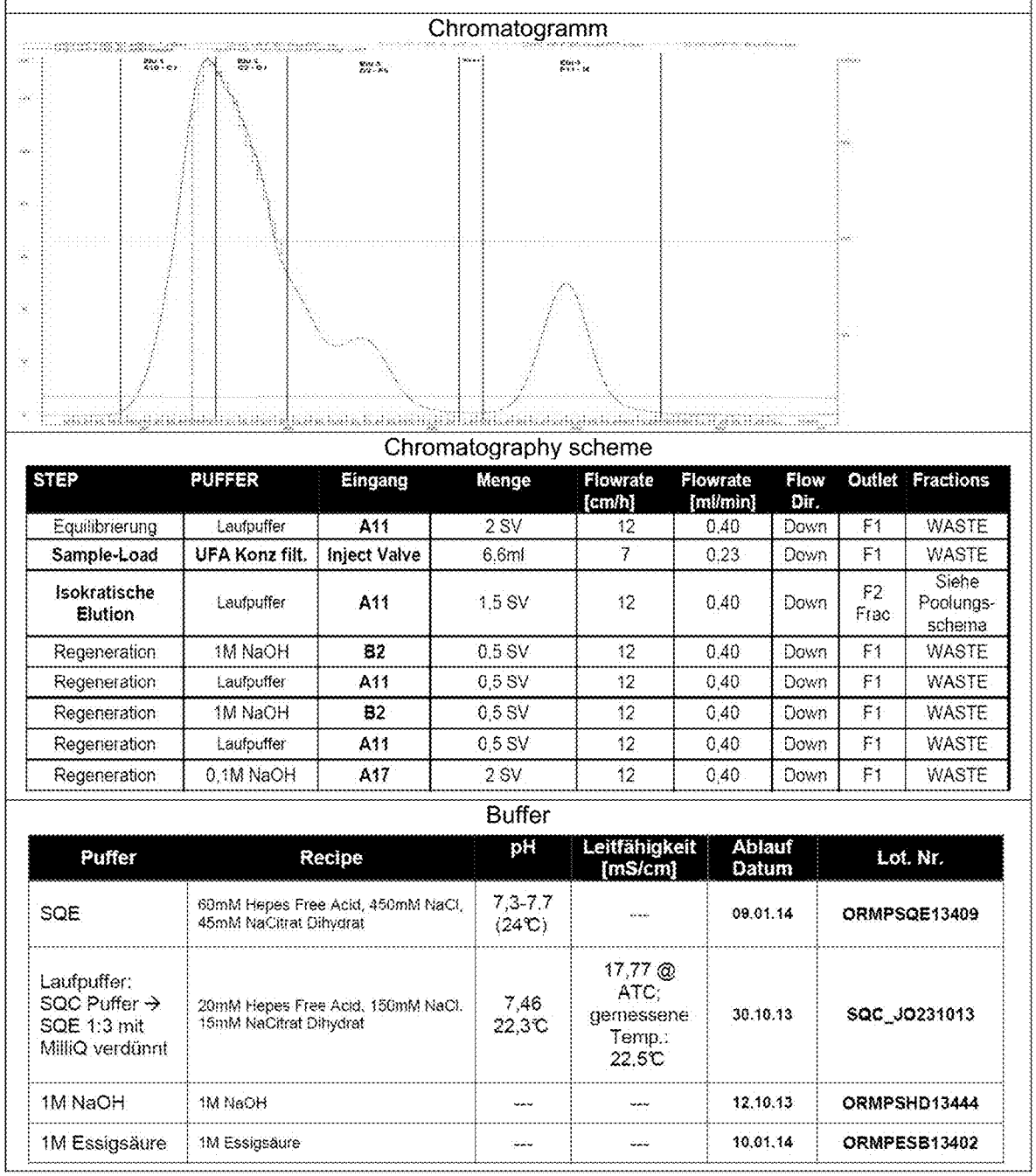
FIG. 10 shows a chromatogram, a chromatography scheme, and buffer compositions for Example 4.

FIG. 10 shows a chromatogram, a chromatography scheme, and buffer compositions for Example 4.

FIG. 11 provides a table of the results for Example 4.

FIG. 12 shows a silver stained protein gel and a western blot illustrating the separation of rVWF and rVWF propeptide by the method of Example 4.

Example 5: Optimized Method for Commercial Manufacturing of Mature rVWF by Separate rVWF and rVWF-PP by Size Exclusion Chromatography Example 5 represents a method for separating rVWF and rVWF-PP by size exclusion chromatography by applying a pH conditioned rVWF containing start material onto size exclusion chromatography.

A rVWF containing ultrafiltrated UNOsphere™ S-eluate was conditioned to a pH of 7.5±0.2 with 1 M glycine pH 9.0 prior loading onto the column. This solution was loaded onto an array of two Superose 6 prep grade SEC columns in series (GE Healthcare, Cat. No.: 28-9913-16), both with an inner diameter of 16 mm each, a bed height 82.0 cm (2×41 cm), and the volume of both columns was approximately 165 ml. The load was applied at a flow rate of 7 cm/h. The SEC running buffer comprised 20 mM HEPES free acid and 150 mM NaCl, pH 7.5±0.2. The size exclusion chromatography was carried out with isocratic conditions at a linear flow rate of 12 cm/h.

Figure 13:
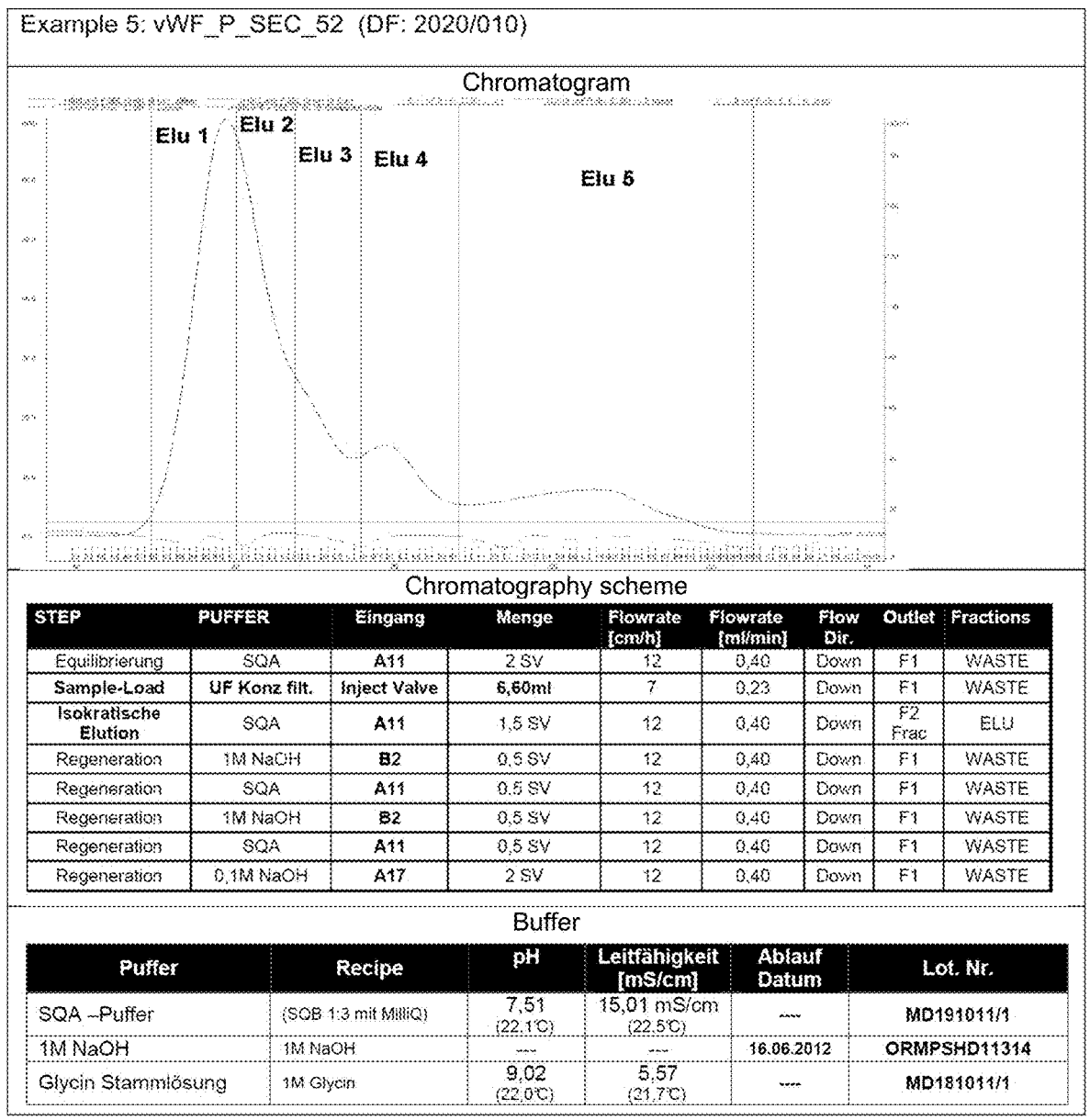
FIG. 13 shows a chromatogram, a chromatography scheme, and buffer compositions for Example 5.

FIG. 13 shows a chromatogram, a chromatography scheme, and buffer compositions for Example 5.

FIG. 14 provides a table of the results for Example 5.

Example 6: CEX Method for Purification of rVWF from rVWF Propeptide without Supplementation of Chelating Agents on a UNOsphere™ S Example 6 represents an CEX method without supplementation of chelating agents on ultrafiltrated UNOsphere™ S. This method is representative of a prior art method for purifying mature rVWF from rVWF propeptide. The method does not utilize a buffer comprising a chelating agent and/or a buffer having a pH of 7.0 or higher.

After a monoclonal antibody step to capture recombinant factor VIII, the flow-through, which contains rVWF, was loaded onto an anion exchanger. rVWF was bound on the anion exchanger and was maturated with furin in presence of calcium. The rVWF was eluted from the anion exchanger with increasing conductivity. The product containing eluate was then loaded onto a UNOsphere™ S Cation Exchange Media (Bio Rad, Cat. No.: 156-0115) cation exchanger column with an inner diameter of 15 mm, a bed height of 14.2 cm, and a volume of 25.09 ml at a flow rate of 100 cm/h followed by a wash of 10 CV of 10 mM Tris-HCl, 100 mM Na acetate, 85 mM NaCl, pH 6.5±0.2 to remove HCP and rVWF-propeptide. rVWF was eluted with a single step by applying 100 mM Na acetate, 500 mM NaCl, 100 mM glycine, 3 mM $CaCl_2$, pH 7.5±0.2 at flow rate of 65 cm/h. The main eluate peak was collected as product containing fraction.

Figure 15:
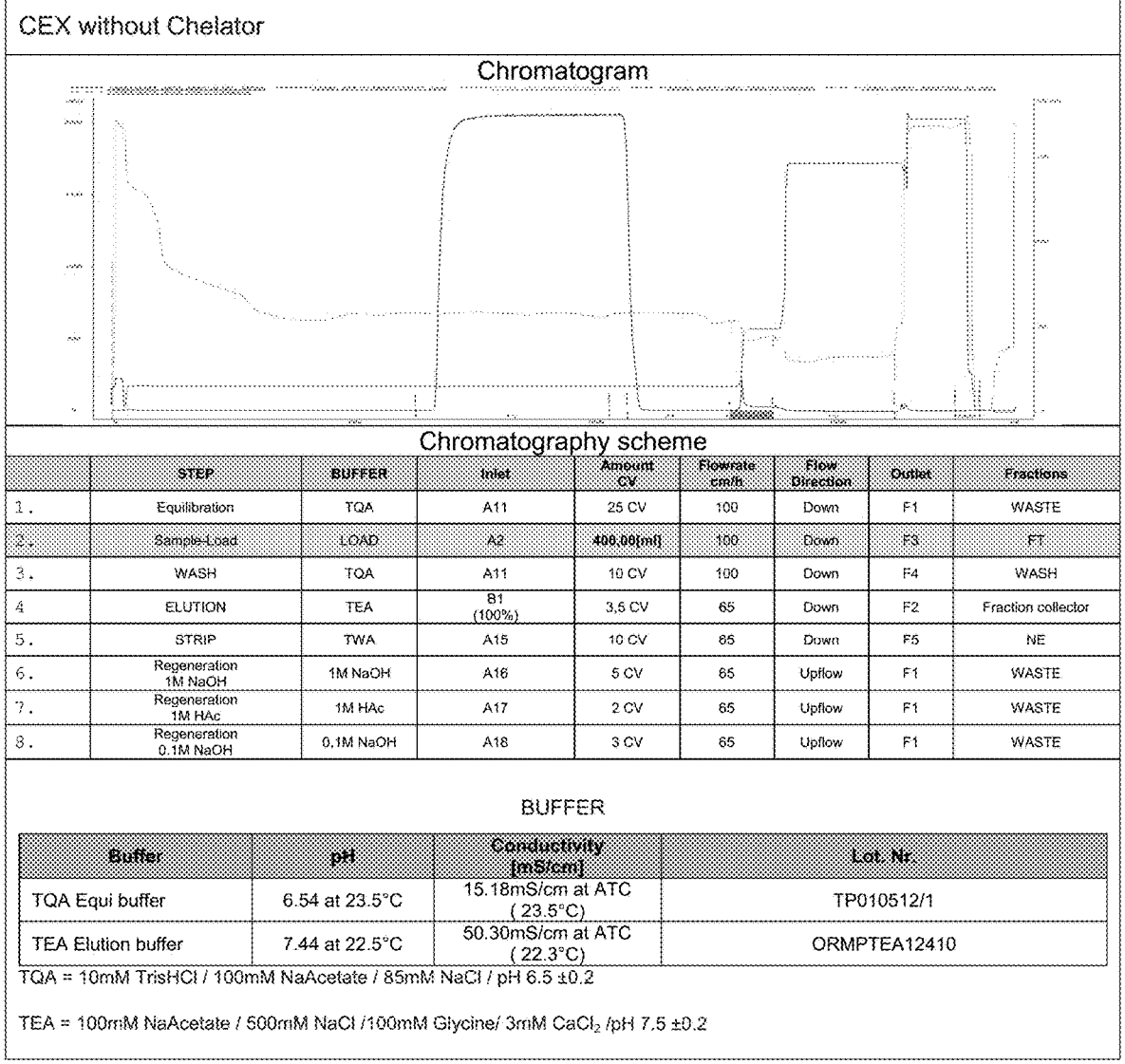
FIG. 15 shows a chromatogram, a chromatography scheme, and buffer compositions for Example 6.

FIG. 15 shows a chromatogram, a chromatography scheme, and buffer compositions and conditions for Example 6.

FIG. 16 provides a table of the results for Example 6.

Example 7: SEC Method for Purification of rVWF from rVWF Propeptide without Prior Supplementation of Chelating Agents or Elevated pH Example 7 represents SEC method without prior supplementation of chelating agents or elevated pH. This method is representative of a prior art method for purifying mature rVWF from rVWF propeptide. The SEC method does not include a buffer comprising a chelating agent and/or a buffer having a pH of 7.0 or higher which is used to condition the starting fraction (material) containing rVWF and residual rVWF propeptide.

A recombinant VWF containing ultrafiltrated UNOsphere™ S-eluate was loaded directly onto an array of two Superose 6 prep grade SEC columns in series (GE Healthcare, Cat. No.: 28-9913-16), both with an inner diameter of 16 mm each, a bed height of 82.0 cm (2×41 cm), and the volume of both columns was approximately 165 ml. The load was applied at a flow rate of 7 cm/h. The running buffer was 20 mM HEPES free acid, 150 mM NaCl, pH7.5±0.2. The size exclusion chromatography was carried out with isocratic conditions at a linear flow rate of 12 cm/h.

Figure 17:
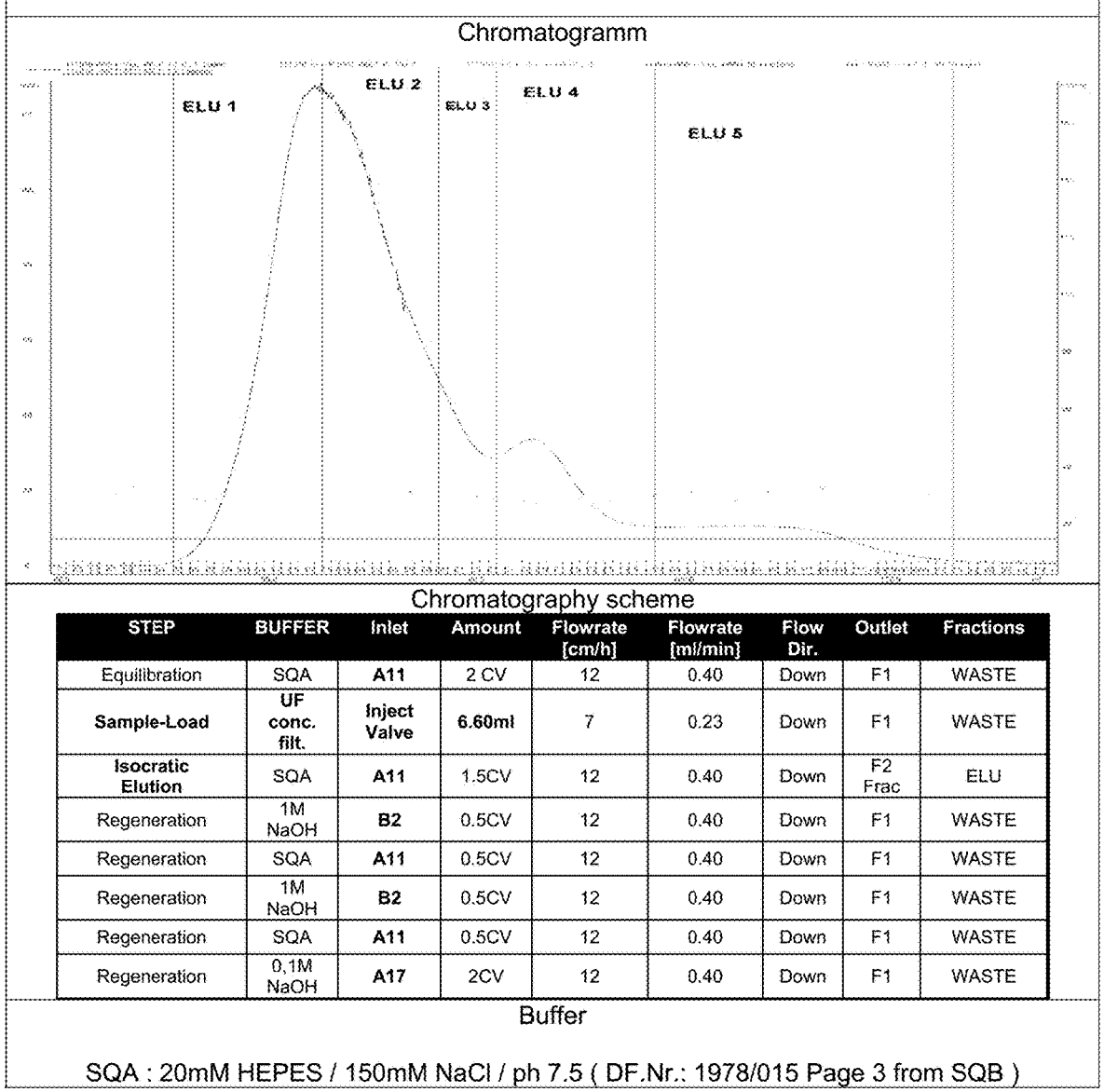
FIG. 17 shows a chromatogram, a chromatography scheme, and buffer compositions for Example 7.

FIG. 17 shows a chromatogram, a chromatography scheme, and buffer compositions for Example 7.

FIG. 18 provides a table of the results for Example 7.

Example 8: Separation of rVWF from rVWF Propeptide by Anion Exchange Chromatography and Cation Exchange Chromatography Example 8 represents a purification of maturated rVWF on a cation exchanger. The start material was obtained from the current rVWF manufacturing process after the AEX Mustang Q step. The rVWF containing Flow-Through from the AEX Mustang Q step was SD/VI treated and diluted with the chelating agent containing buffer to dissociate rVWF/rVWF-propeptide-complex. The diluted material was applied onto a CEX resin(Unosphere S). The majority of rVWF-PP, host cell proteins (HCPs) and low molecular weight rVWF multimers pass through the cation exchange resin. Remaining rVWF-PP was depleted after a wash step. The bound high molecular weight rVWF multimers were subsequently eluted by increasing the conductivity triggered by sodium ions.

Industrially, VWF, in particular recombinant VWF (rVWF), is synthesized and expressed together with rFVIII in a genetically engineered CHO cell line. The function of the co-expressed rVWF is to stabilize rFVIII in the cell culture process. rVWF is synthesized in the cell as the pro-form, containing a large pro-peptide attached to the N-terminus. Upon maturation in the endoplasmatic reticulum and Golgi apparatus, the pro-peptide is cleaved off by the action of the cellular protease furin and is secreted as a homopolymer of identical subunits, consisting of dimers of the expressed protein. However, the maturation is incomplete, leading to a product comprising a mixture of pro-peptide and mature VWF.

After a monoclonal antibody step to capture recombinant factor VIII, the flow-through, which contains rVWF, was loaded onto a Fractogel TMAE anion exchanger. rVWF is bound on the anion exchanger and was maturated with furin in presence of calcium. The rVWF was eluted from the anion exchanger with increasing conductivity. The TMAE-Eluate was filtrated through a Mustang Q (MUQ) filter unit to remove CHO-DNA and impurities that binds to the filter membrane. The loading material for the CEX step is the effluent of the Mustang Q filtration step (MUQ) that is treated with solvent and detergents to inactivate lipid enveloped viruses. For virus inactivation the MUQ effluent is incubated with a mix of the two detergents such as Triton-X-100 (1%) and polysorbate 80 (0.3%) and the organic solvent tri-n-butyl phosphate (0.3%) for one hour at room temperature. The product containing MUQ_flow-through was conditioned by a 1:2 dilution with 60 mM sodium citrate pH 7.6 to a conductivity of 21.9 mS/cm and a pH 7.16. The high conductivity was chosen to ensure the removal of rVWF propeptide (rVWF-PP) and low molecular weight rVWF multimers to utilize the capacity of the resin for the desired high molecular weight rVWF multimers. The conditioned dilution was loaded onto a UNOsphere™ S Cation Exchange Media (Bio Rad, Cat. No.: 156-0115) cation exchanger column with an inner diameter of 10 mm, a bed height of 14.3 cm, and volume of 11.23 ml with a flow rate of 100 cm/h. After loading, a first wash (Reequilibration) was performed using 5 CV of 10 mM NaCl, 30 mM Na Citrate, pH 7.6±0.2 to remove weakly bound HCP and rVWF-propeptide.

The second wash to deplete strong bound HCP and rVWF-propeptide was carried out with a step of 40% 500 mM NaCl, 30 mM Na citrate, pH 7.6±0.2 in 10 mM NaCl, 30 mM Na citrate, pH 7.6±0.2 (Wash 2).

The elution was carried out in two phases: (1) the first phase included a step of 45% 500 mM NaCl, 30 mM Na citrate, pH 7.6±0.2 in 10 mM NaCl, 30 mM Na citrate, pH 7.6±0.2 (Eluate 1 or E1), and (2) the second phase included a linear gradient from 45% to 100% of 500 mM NaCl, 30 mM Na citrate, pH 7.6±0.2 in 10 mM NaCl, 30 mM Na citrate, pH 7.6±0.2 (Eluate 2 or E2) in 6 column volumes. Wash 2 to the end of the gradient was performed at a flow rate of 65 cm/h.

Figure 19:
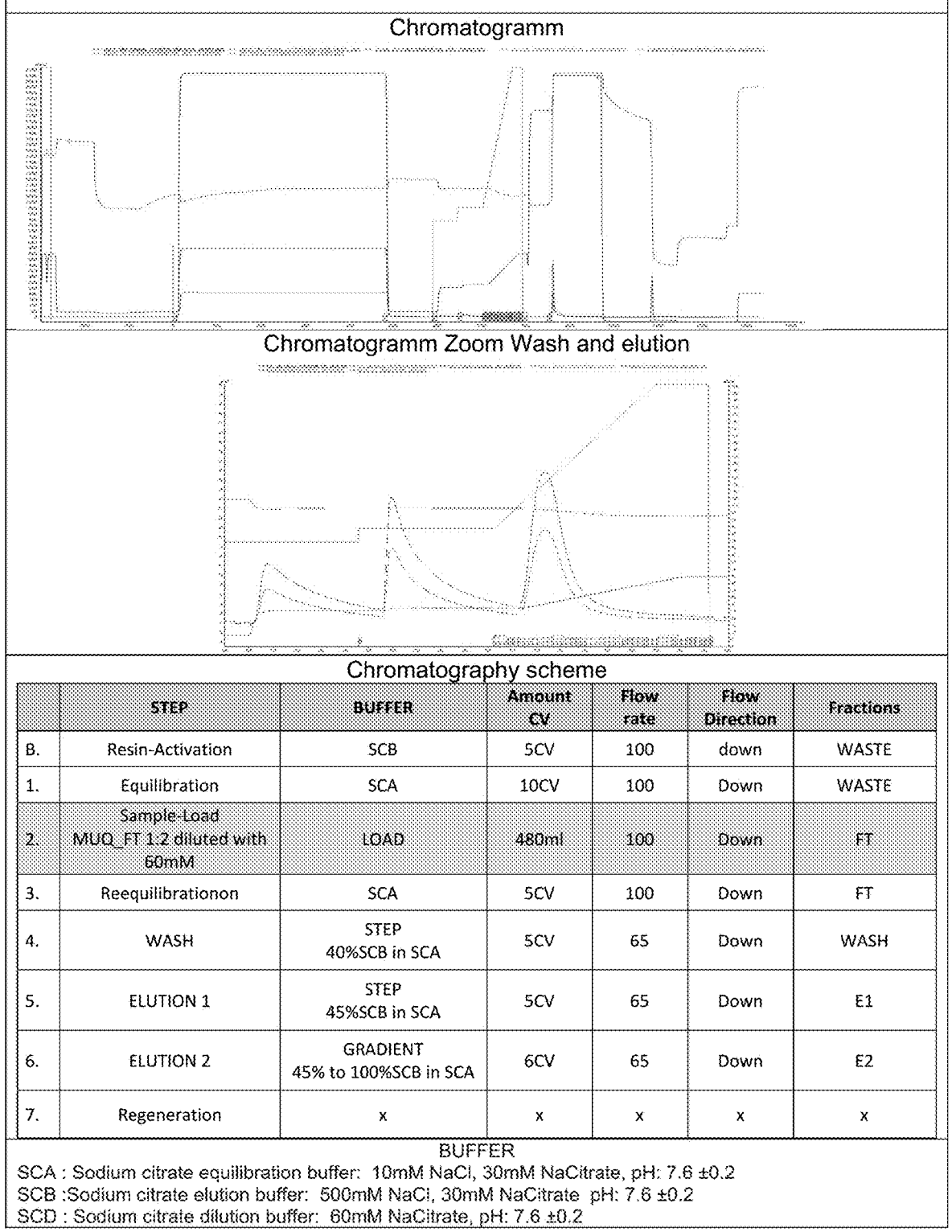
FIG. 19 shows a chromatogram, a chromatography scheme, and buffer compositions for Example 8.

FIG. 19 shows a chromatogram, a chromatography scheme, and buffer compositions for Example 8.

FIG. 20 provides a table of the results for Example 8.

FIG. 21 shows a silver stained protein gel illustrating the separation of rVWF and rVWF-propeptide by the method of Example 8.

FIG. 22 shows a western blot illustrating the separation of rVWF and rVWF-propeptide by the method of Example 8. The 1% agarose gel shows the multimeric pattern of the products.

Figure 23:
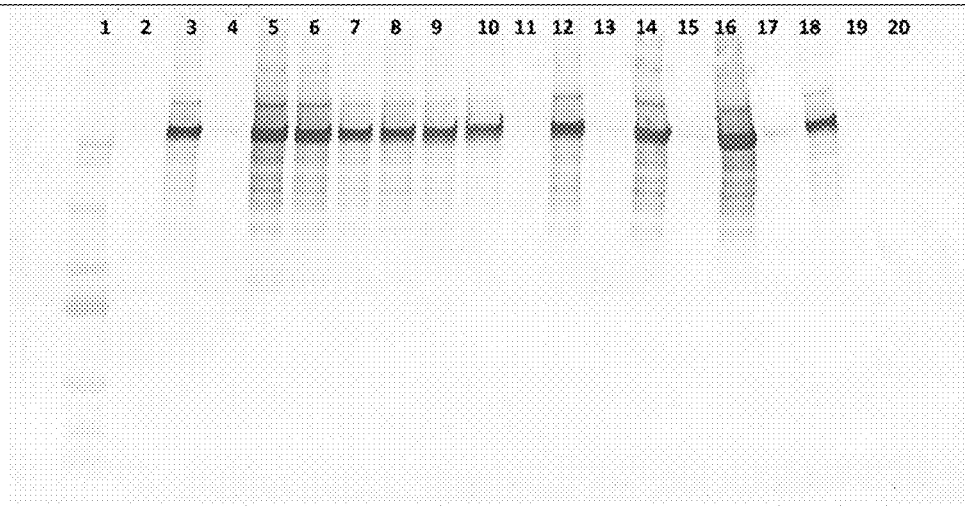
FIG. 23 shows a western blot illustrating the separation of mat-rVWF and rVWF propeptide (rVWF-PP) by the method of Example 8.

FIG. 23 shows a western blot illustrating the separation of rVWF and rVWF-propeptide by the method of Example 8.

Example 9: Separation of rVWF from rVWF Propeptide by Anion Exchange Chromatography and Cation Exchange Chromatography Example 9 represents an optimized purification of maturated rVWF on a cation exchanger. The start material was obtained from the current r-VWF manufacturing process after the AEX Mustang Q step. The rVWF containing Flow-Through from the AEX Mustang Q step was SD/VI treated and diluted with the chelating agent containing buffer to dissociate the rVWF/rVWF-Propeptide-complex. The diluted material was applied onto a CEX resin(Unosphere S). The majority of rVWF-PP, host cell proteins and low molecular weight rVWF multimers pass through the cation exchange resin. Remaining rVWF-PP was depleted after a wash step. The bound high molecular weight rVWF multimers were eluted by a gradient of increasing the conductivity triggered by sodium ions.

Industrially, VWF, in particular recombinant VWF (rVWF), is synthesized and expressed together with rFVIII in a genetically engineered CHO cell line. The function of the co-expressed rVWF is to stabilize rFVIII in the cell culture process. rVWF is synthesized in the cell as the pro-form, containing a large pro-peptide attached to the N-terminus. Upon maturation in the endoplasmatic reticulum and Golgi apparatus, the pro-peptide is cleaved off by the action of the cellular protease furin and is secreted as a homopolymer of identical subunits, consisting of dimers of the expressed protein. However, the maturation is incomplete, leading to a product comprising a mixture of pro-peptide and mature VWF.

After a monoclonal antibody step to capture recombinant factor VIII, the flow-through, which contains r-VWF, was loaded onto a Fractogel TMAE anion exchanger. rVWF was bound on the anion exchanger and was maturated with furin in presence of calcium. The rVWF was eluted from the anion exchanger with increasing conductivity. The TMAE-Eluate was filtrated trough a Mustang Q (MUQ) filter unit to remove CHO-DNA and impurities that binds to the filter membrane. The loading material for the CEX step is the effluent of the Mustang Q filtration step (MUQ) that is treated with solvent and detergents to inactivate lipid enveloped viruses.

For virus inactivation the MUQ effluent is incubated with a mix of the two detergents Triton-X-100 (1%) and polysorbate 80 (0.3%) and the organic solvent tri-n-butyl phosphate (0.3%) for one hour at room temperature. The product containing MUQ_flow through was conditioned by a 1:2 dilution with 60 mM sodium citrate pH 7.6 to a conductivity of 21.9 mS/cm and pH 7.16. The high conductivity is chosen to ensure the removal of rVWF-propeptide and low molecular weight rVWF to utilize the capacity of the resin for the desired high molecular weight r-VWF. The conditioned dilution was loaded onto a UNOsphere™ S Cation Exchange Media (Bio Rad, Cat. No.: 156-0115) cation exchanger column with an inner diameter of 10 mm, a bed height of 14.3 cm, and volume of 11.23 ml with a flow rate of 100 cm/h followed by a first wash (Reequilibration) of 5 CV of 10 mM NaCl, 30 mM Na citrate, pH 7.6±0.2 to remove weakly bound HCP and rVWF-propeptide.

The second wash (Wash 2) to deplete strong bound HCP and rVWF-propeptide was carried out with a step of 36% 500 mM NaCl, 30 mM Na citrate, pH 7.6±0.2 in 10 mM NaCl, 30 mM Na citrate, pH 7.6±0.2 in 5 column volumes.

The elution was carried out with a gradient from 36% 500 mM NaCl, 30 mM Na citrate, pH 7.6±0.2 in 10 mM NaCl, 30 mM Na citrate, pH 7.6±0.2 to 100% 500 mM NaCl, 30 mM Na citrate, pH 7.6±0.2 in 10 mM NaCl, 30 mM Na citrate, pH 7.6±0.2 in 8 column volumes. The eluate representing the desired product contains the pool of fractions beginning at >50% of 500 mM NaCl, 30 mM Na citrate, pH 7.6±0.2 in 10 mM NaCl, 30 mM Na citrate, pH 7.6±0.2 to 76% of 500 mM NaCl, 30 mM Na citrate, pH 7.6±0.2 in 10 mM NaCl, 30 mM Na citrate, pH 7.6±0.2. The wash and elution were performed with a flow rate of 50 cm/h.

Figure 24:
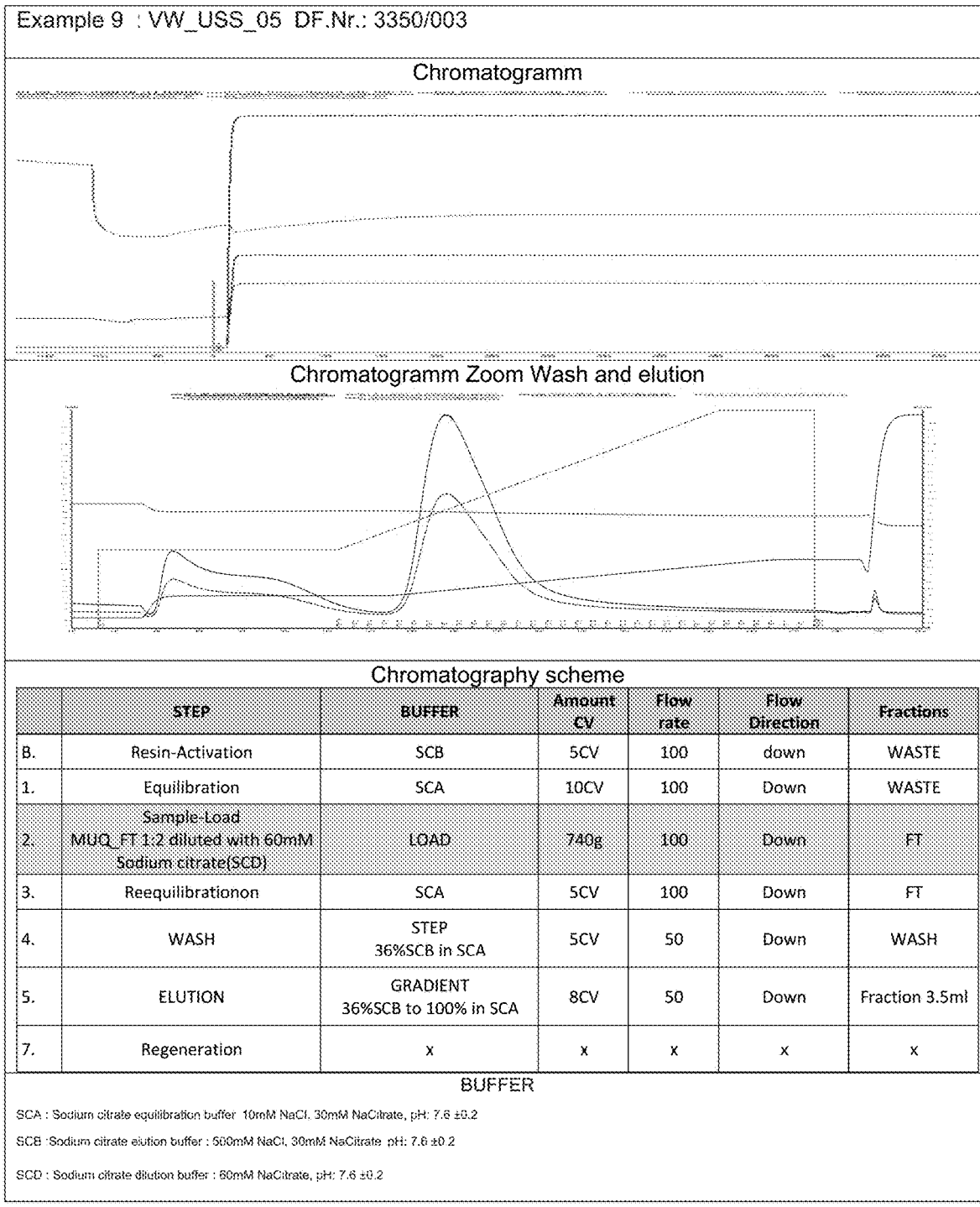
FIG. 24 shows a chromatogram, a chromatography scheme, and buffer compositions for Example 9.

FIG. 24 shows a chromatogram, a chromatography scheme, and buffer compositions for Example 9.

FIG. 25 provides a table of the results for Example 9.

FIG. 26 provides a table of the products for Example 9.

Figure 27:
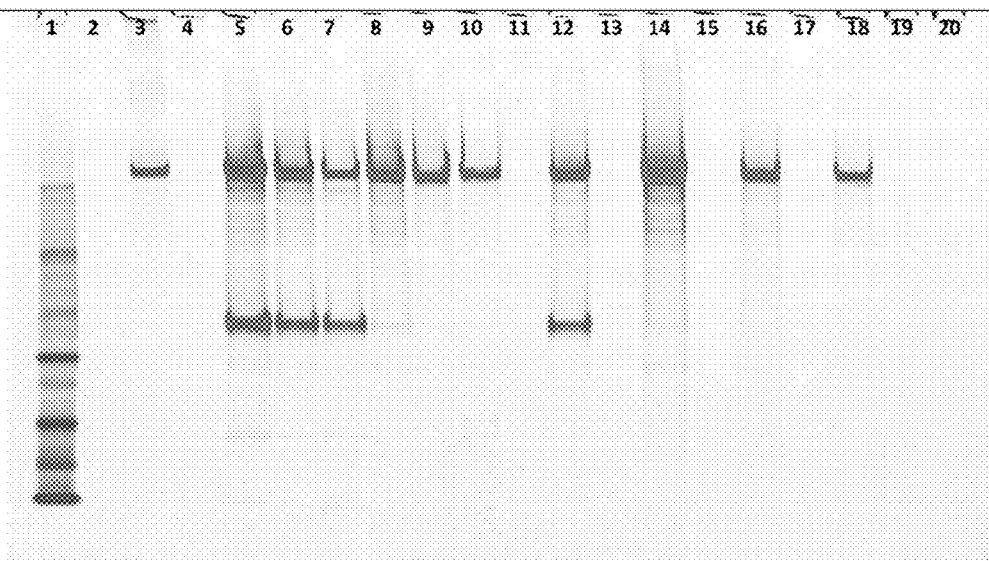
FIG. 27 shows a silver stained protein gel illustrating the separation of rVWF and rVWF propeptide by the method of Example 9.

FIG. 27 shows a silver stained protein gel illustrating the separation of rVWF and rVWF-propeptide by the method of Example 9.

FIG. 28 shows a western blot illustrating the separation of rVWF and rVWF propeptide by the method of Example 9. The 1% agarose gel shows the multimeric pattern of the products.

Figure 29:
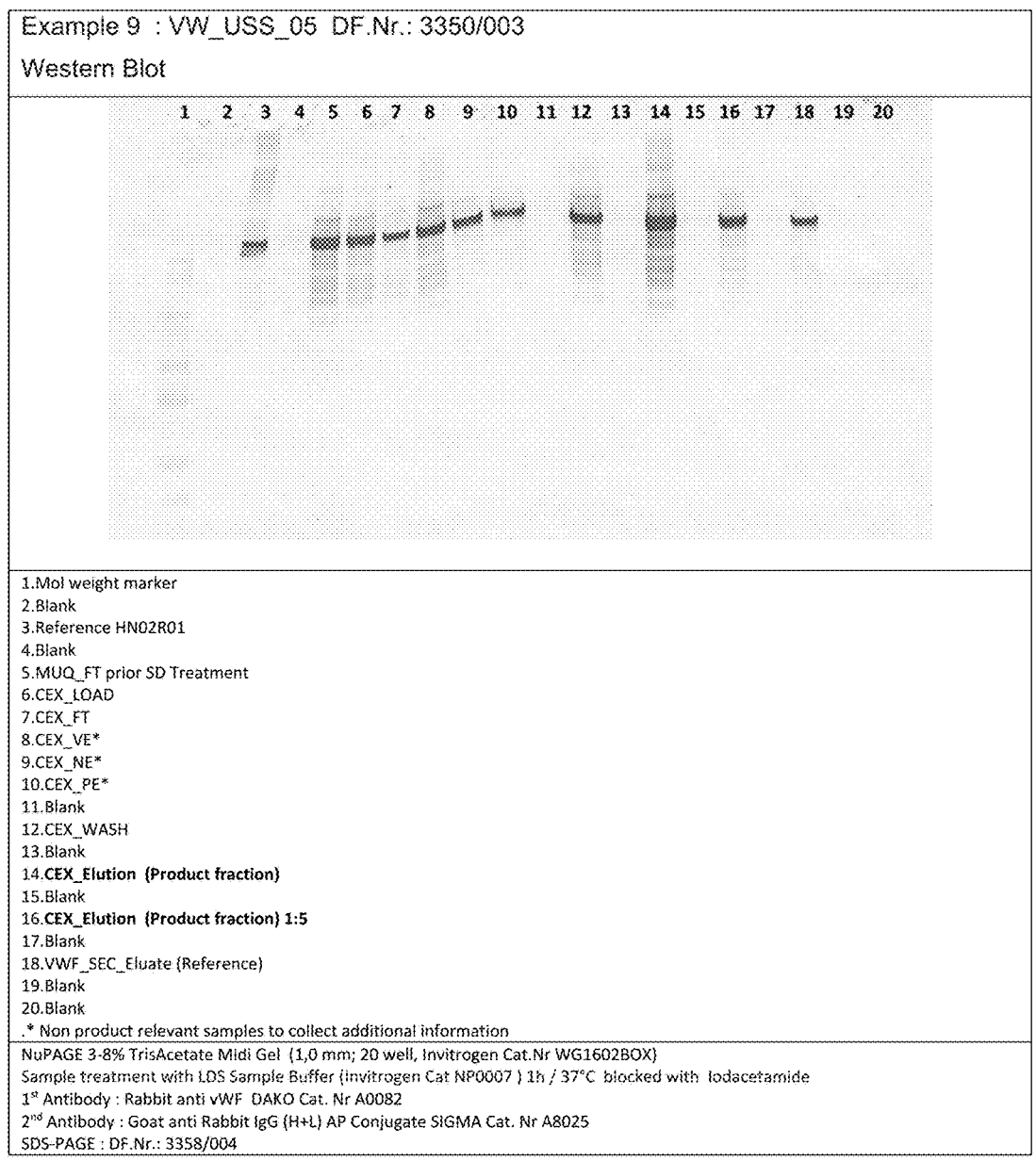
FIG. 29 shows a western blot illustrating the separation of rVWF and rVWF propeptide by the method of Example 9.

FIG. 29 shows a western blot illustrating the separation of rVWF and rVWF propeptide by the method of Example 9.

rVWF purification steps in presence of chelating agents and/or elevated pH showed a high depletion rate of r-VWF propeptide and host cell proteins. The depletion of r-VWF propeptide on cation exchanger is based on the fact that rVWF-PP does not bind onto a cation exchanger at condition in presence of chelating agents and/or elevated pH. The depletion of rVWF propeptide on size exclusion chromatography based on the fact of an efficient size separation in presence of chelating agents and/or elevated pH.

FIG. 30 shows the purity of the product containing fractions obtained for enhanced cation exchange chromatography (CEX) as used for Examples 1, 2, 3, 6, 8, and 9.

FIG. 31 shows the depletion factor of product related impurities for Examples 1, 2, 3, 6, 8, and 9.

FIG. 32 shows the purity of the product containing fractions obtained for enhanced size exclusion chromatography (SEC) as used for Examples 4 and 5.

FIG. 33 shows the depletion factor of product related impurities for Examples 4 and 5.

REFERENCES

U.S. Pat. No. 8,058,411; Method for producing mature VWF from VWF pro-peptide. Inventors: Wolfgang Mundt, Artur Mitterer, Meinhard Hasslacher, Christa Mayer.

U.S. Pat. No. 6,465,624; Purification of von Willebrand factor by cation exchange chromatography. Inventors: Bernhard Fischer, Oyvind L. Schonberger, Artur Mitterer, Christian Fiedler, Friedrich Dorner, Johann Eibl.

Example 10: Separation of rVWF from rVWF Propeptide by Anion Exchange Chromatography This study illustrates the dissociation (separation) of furin processed mature VWF/VWF-PP complex into mature VWF and VWF-PP using anion exchange chromatography and a elution buffer with an elevated pH (e.g., pH 8.5) and containing a chelating agent (EDTA). The separation was carried out on an anion exchanger (AEX), in particular, a Fractogel TMAE 650(M). A solvent-detergent treatment for viral inactivation was also performed on the column for about 1 hour. Details of the chromatography experiment are provided in FIGS. 34-36.

FIG. 34 shows the buffer formulations and materials used in the TMAE separation method.

FIG. 35 shows the loading conditions for the furin-processed mature VWF/VWF-propeptide complex.

FIG. 36 shows the details of the buffers, conditions, parameters, and flow rates of the chromatography method.

Figure 37:
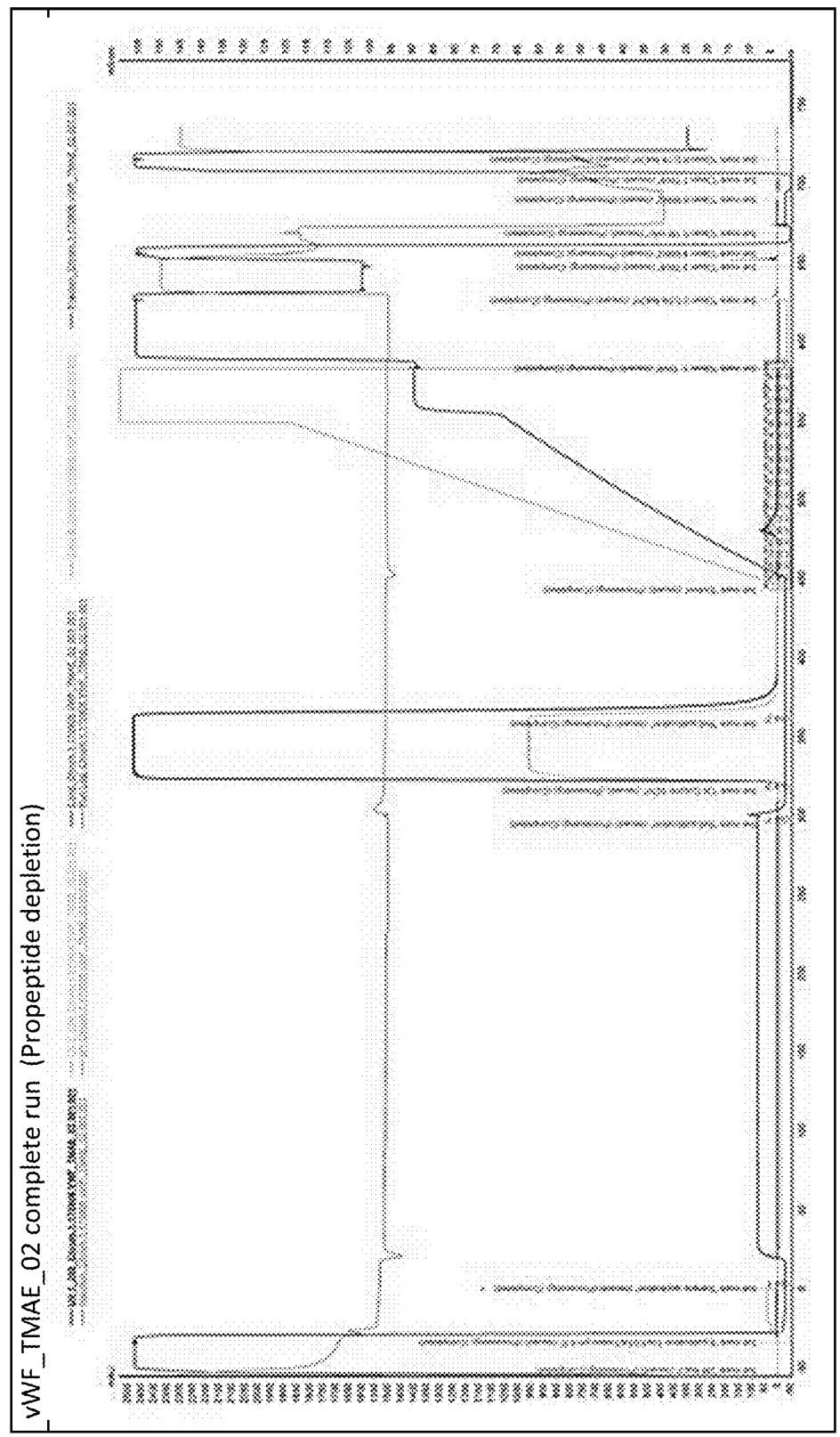
FIG. 37 shows a chromatogram of the dissociation of furin-processed mature VWF/VWF-propeptide complex into mature VWF and VWF-propeptide (VWF-PP). It shows depletion of VWF-PP from the fraction containing mature VWF.

FIG. 37 shows a chromatogram of the dissociation of furin-processed mature VWF/VWF-propeptide complex into mature VWF and VWF-propeptide (VWF-PP). It shows depletion of VWF-PP from the fraction containing mature VWF.

Figure 38:
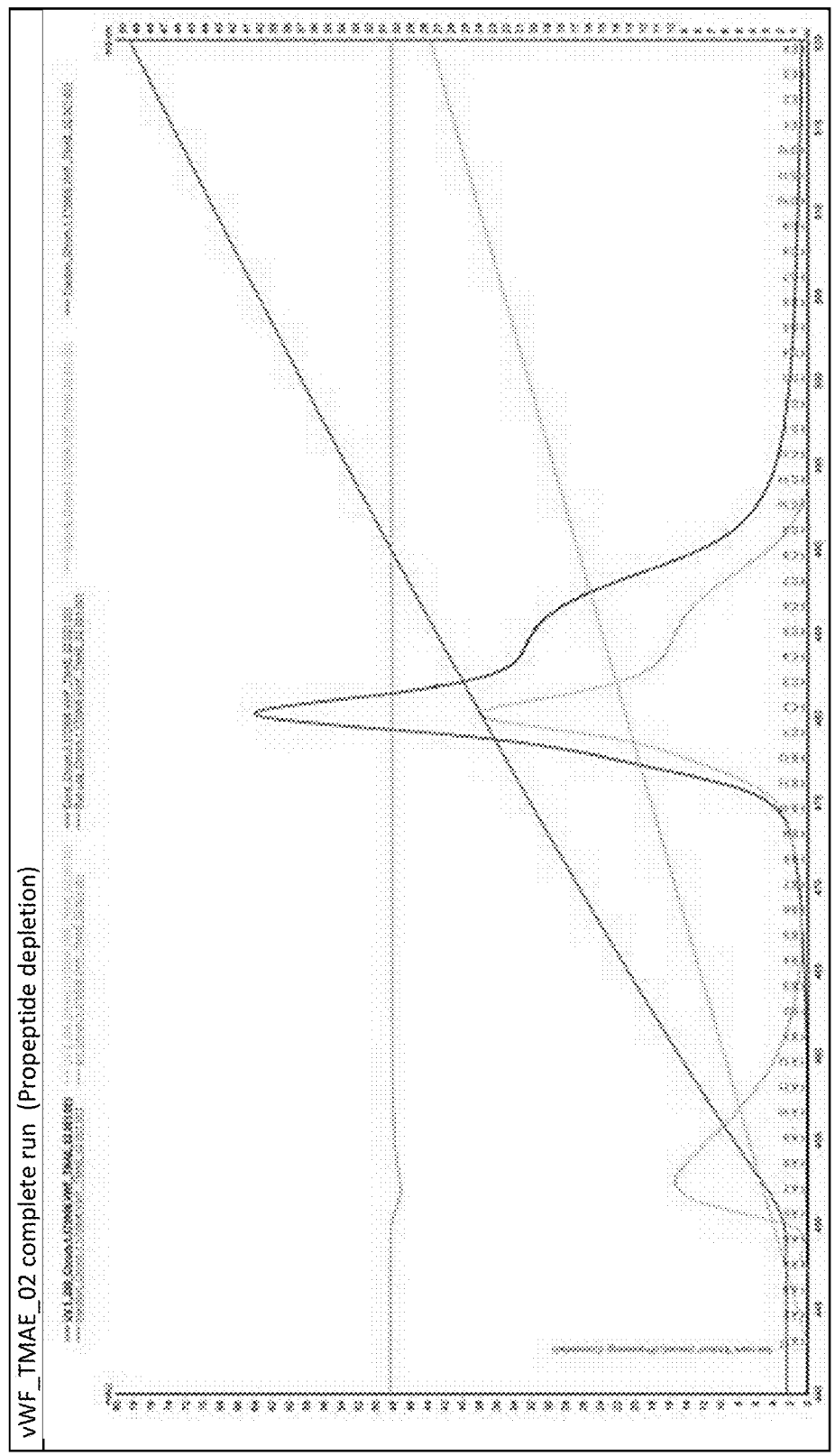
FIG. 38 shows another chromatogram of the separation of mature VWF and VWF-propeptide (VWF-PP). It shows depletion of VWF-PP from the fraction containing mature VWF.

FIG. 38 shows another chromatogram of the separation of mature VWF and VWF-propeptide (VWF-PP). It shows depletion of VWF-PP from the fraction containing mature VWF.

Example 11: Improvements in Different Chromatography Methods for the Separation of Mature VWF (matVWF) and VWF Propeptide (VWF-PP)

In the first study, two methods for purifying recombinant mature VWF were compared.

Figure 39A:
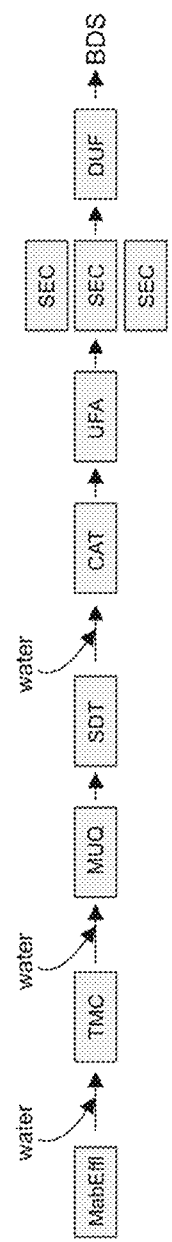
FIG. 39A and FIG. 39B provide schematic diagrams of exemplary methods for the purification of mature VWF including separation of mature VWF and VWF-PP.
Figure 39B:
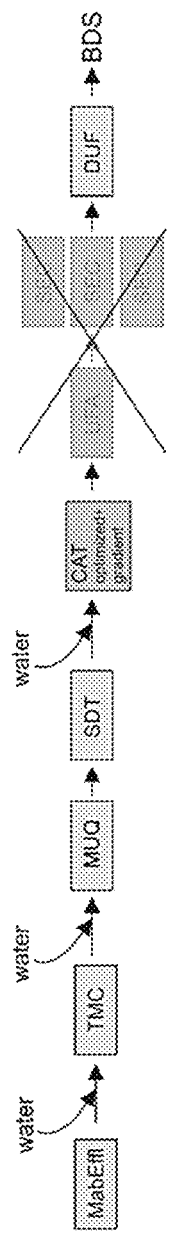

FIG. 39 provides a schematic of the two methods for isolating mature VWF. In one method the downstream processing steps, such as those after obtaining the mAb effluent (MABEffl), the capture step of TMAE anion exchange chromatography and on-column maturation (TMC), and the Mustang Q negative anion exchange chromatography step (MUQ) include solvent-detergent treatment (SDT) for viral inactivation, cation exchange chromatography (CAT), ultrafiltration concentration (UFA), size exclusion chromatography (SEC), and dialysis-ultrafiltration concentration (DUF) to produce a bulk drug substance (mature VWF). In the other method, the downstream processing steps include an improved cation exchange chromatography (CAT) step followed by a dialysis-ultrafiltration (DUF) concentration step to produce a bulk drug substance, and do not include SEC.

FIG. 40 provides a table highlighting some of the advantages of the improved cation exchange chromatography method (CAT 2.0) described herein and shown in FIG. 39. The improved CAT method can remove: host cell impurities by a reduction factor of greater than 1000, VWF-PP by a reduction factor of greater than 2000, and residual FVIII by a reduction factor of less than 10. The CAT method can be used to separate and pool VWF multimers. In addition, the method can replace size exclusion chromatography as a polishing step to isolate the active fraction of VWF and to remove remaining host cell derived impurities and VWF-PP.

In the second study, the conditions of the SEC process were varied to improve the separation mature VWF and VWF-PP. In other words, it was determined that a modified buffer for SEC could increase the purity of mature VWF by reducing the amount of VWF-PP.

Figure 41:
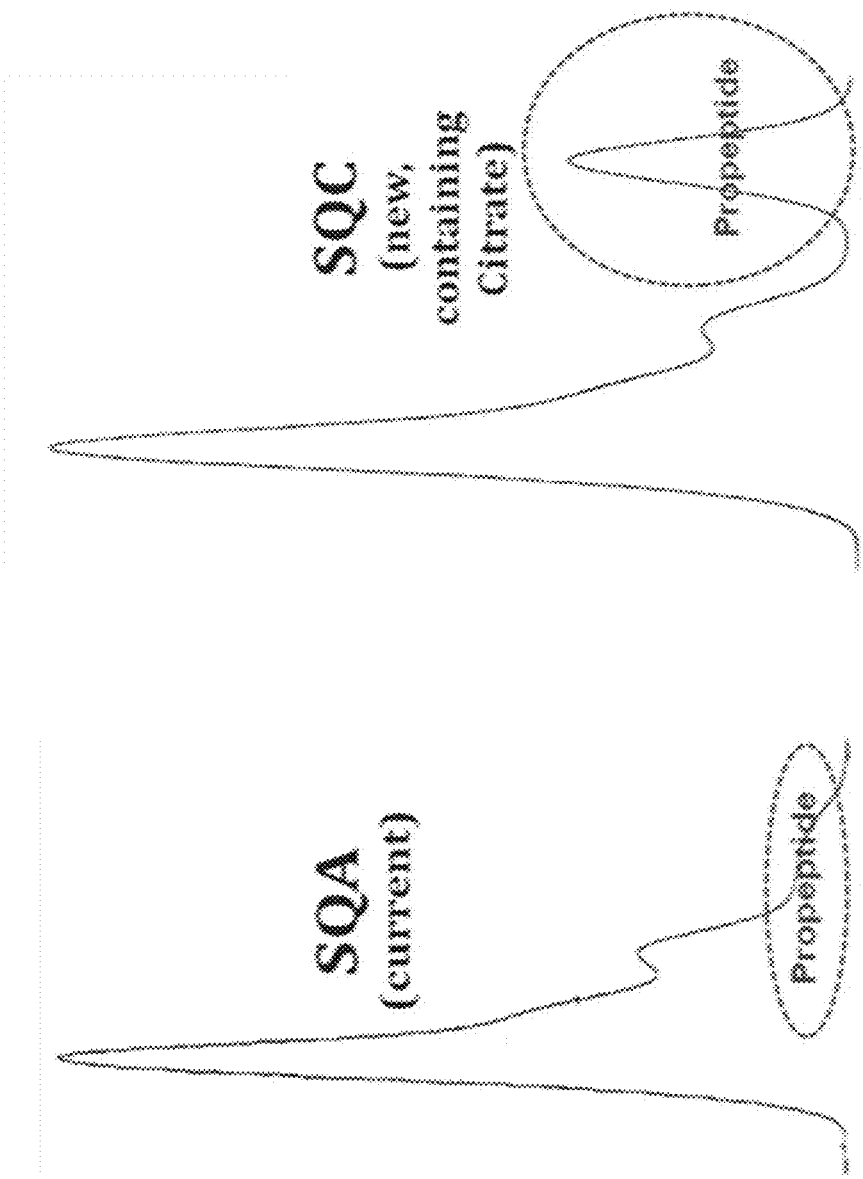
FIG. 41 shows a schematic of two chromatograms showing the separation of rVWF propeptide using the size exclusion chromatography described herein using either a SQA running buffer or a SQC running buffer that contains citrate. The change in SEC parameters (SEC buffers) did not result in a change in the purification of mature VWF besides increased removal/separation of residual VWF-PP.

FIG. 41 shows a schematic of two chromatograms showing the separation of r-VWF propeptide using size exclusion chromatography with a standard SEC buffer (SQA buffer) or with a modified SEC buffer (SQC buffer). FIG. 42 provides a table highlighting some of the advantages of using the SQC buffer. For instance, the method using the SQC buffer can remove host cell impurities by a reduction factor of greater than about 100 and residual FVIII by a reduction factor of less than 10. Surprisingly, it can remove VWF-PP such that the impurity levels are less than 2 µg/1000 units.

As such, described in this example are methods of improving the separation of mature VWF from VWF-PP.

Example 12: Development of an Improved CAT (UNO_S) Step

The downstream process of recombinant von Willebrand factor (rVWF) 1st generation starting from monoclonal antibody (MAB) flow through includes a polishing step by cation exchange chromatography (CAT) on UNO_Sphere S (UNO_S) resin. The UNO_S Eluate is thereafter concentrated by ultrafiltration and further processed by Size-Exclusion-Chromatography (SEC) to separate high and low molecular weight rVWF multimers and to remove free rVWF pro-peptide, a product related impurity generated in course of the downstream process. The high molecular weight rVWF sub-fraction represents bulk drug substance (BDS) that is finally formulated to obtain final drug product (FDP).

For the downstream process of 2nd generation rVWF, it was suggested to replace the SEC step by an improved cation exchange chromatography method and to separate high and low and molecular weight rVWF multimers as well as rVWF pro-peptides by an alternative cation exchange (CAT) elution procedure (gradient elution, instead of step elution). In this example the experiments for the 2nd generation rVWF polishing purification step CAT are outlined. New process parameters like the CAT loading pH and conductivity, the conductivity and length of the column washing steps and the eluate pooling criteria were explored on small scale to obtain a scalable and robust process downstream unit operation step.

1. Objective

The downstream process of 1st generation rVWF (VON-VENDI®) starts with a capture step on TMAE Sepharose (TMC step) using ADVATE® MAB flow through as feed, followed by a Mustang Q filtration step to remove CHO host cell DNA. Next, a Solvent/Detergent (S/D) step is perform to inactivate potential lipid enveloped viruses, followed by a polishing step on UNO_Sphere S (UNO_S) resin a weak cation exchanger (CAT step). The CAT step is dedicated to remove the S/D chemicals introduced during for virus inactivation step. The UNO_S Eluate is thereafter concentrated by ultrafiltration and further processed by Size-Exclusion-Chromatography (SEC) to separate high and low molecular weight rVWF multimers and to remove free rVWF pro-peptide, a product related impurity generated in course of the downstream process. The high molecular weight rVWF sub-fraction represents BDS that is finally formulated to obtain FDP.

For the downstream process of $2^{nd}$ generation rVWF it was suggested to cancel the SEC step and to replace it by an improved cation exchange chromatography method.

In a series of five experiments, the separation of high from low molecular weight rVWF multimers as well as the removal of rVWF pro-peptides was achieved by a gradient CAT elution procedure. The new gradient elution mode was able to replace the step elution procedure that is applied in the $1^{st}$ generation downstream process. In this example the five experiments for the $2^{nd}$ generation rVWF polishing purification step CAT are outlined in detail. All experiments were performed according to study plan described herein.

2. Introduction and Background

Figure 43A:
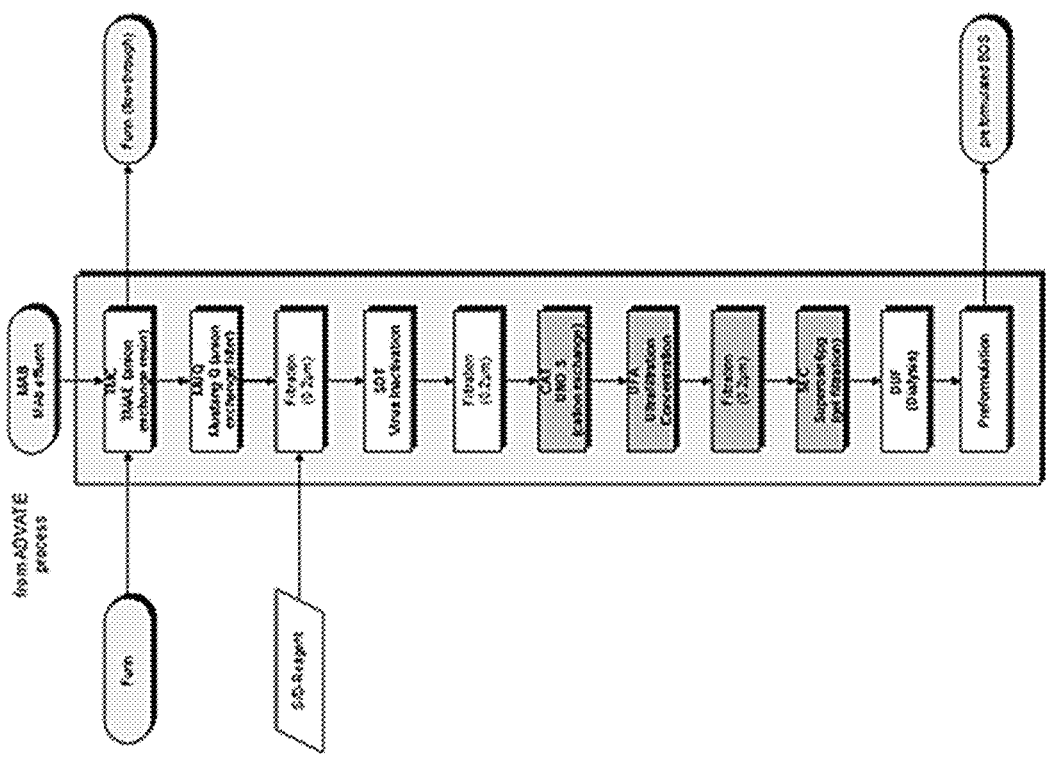
FIG. 43A and FIG. 43B provide flowcharts of downstream processing protocols for rVWF.

The current report describes the development of a 2nd generation (Gen 2) T process, by combining two VWF downstream unit operation steps CAT and SEC as currently applied in the 1st generation (Gen 1) procedure. In a series of experiments, process parameters were explored that had been identified in a risk assessment and that were considered as important for the performance of the chromatographic step CAT. The current study was based on a scale down model from the current rVWF manufacturing process. This process was stablished in Orth for the production of Clinical Phase III material and transferred to manufacturing (MFG) scale for commercial production (FIG. 43A). To facilitate an understanding of the introduced changes in the CAT Unit operation step described in the this report, a brief process description of the currently used 1st generation rVWF downstream unit operation steps S/D, CAT and SEC is given below.

As used in the Gen 1 process, the rVWF polishing step CAT is a chromatographic cation exchange process on UNO_Sphere S, a macroporous acrylamido based media with a "strong" sulfonic cation exchange ligand. The loading material for the polishing step is the effluent of the anion exchange filtration step MUQ that is treated with solvent and detergents to inactivate lipid enveloped viruses. For virus inactivation the MUQ effluent is incubated with a mix of the two detergents Triton-X-100 (1%) and Polysorbate 80 (0.3%) and the organic solvent tri-n-butyl phosphate (0.3%) for one hour at room temperature. Prior treatment the product solution is filtered through a 0.2° µm membrane filter to remove potentially present particulates. After virus inactivation, the product solution is diluted with approximately one volume of water to reduce the concentration of the S/D reagents adjust the conductivity for the loading step onto the CAT Column. The pH is not adjusted. The CAT chromatographic step has the main objective to remove the S/D reagents and further reduce process related impurities including media components like soy peptone and other impurities like rFurin, rFVIII polypeptides and CHO derived proteins and DNA. Following the unit operation step CAT, the obtained product fraction (CAT-E) is further processed by Size Exclusion chromatography (SEC) on Superose 6 resin. The loading material for the polishing step SEC is the eluate pool of the Cation Exchange polishing step CAT on UNO_Sphere S. As the loading volume for a SEC column is limited to achieve a reasonable resolution the CAT eluate pool is concentrated by a factor of approximately 15 by ultrafiltration using a cellulose based membrane cassette with a cut-off of 30° kDa (step UFA). At clinical phase III production scale the ultrafiltration concentration (UFA) concentrate is divided in two fractions that are processed separately on the SEC column. This measure was implemented to keep the SEC column volume and column diameters low. The buffer matrix as well as conductivity and pH of the loading material corresponds to the CAT eluate pool and is not adjusted after the concentration step UFA before loading onto the SEC column. The objective of the step SEC is the final impurity removal for CHO host cell proteins and serves as the major removal step for the product related impurity rVWF pro-peptide generated during the initial capture the step on TMAE Sepharose (TMC step). In addition, the step SEC resolves rVWF multimers based on their size allowing a pooling schema for enrichment of high molecular weight rVWF multimers that contribute to Ristocetin Cofactor activity of the product.

Figure 43B:
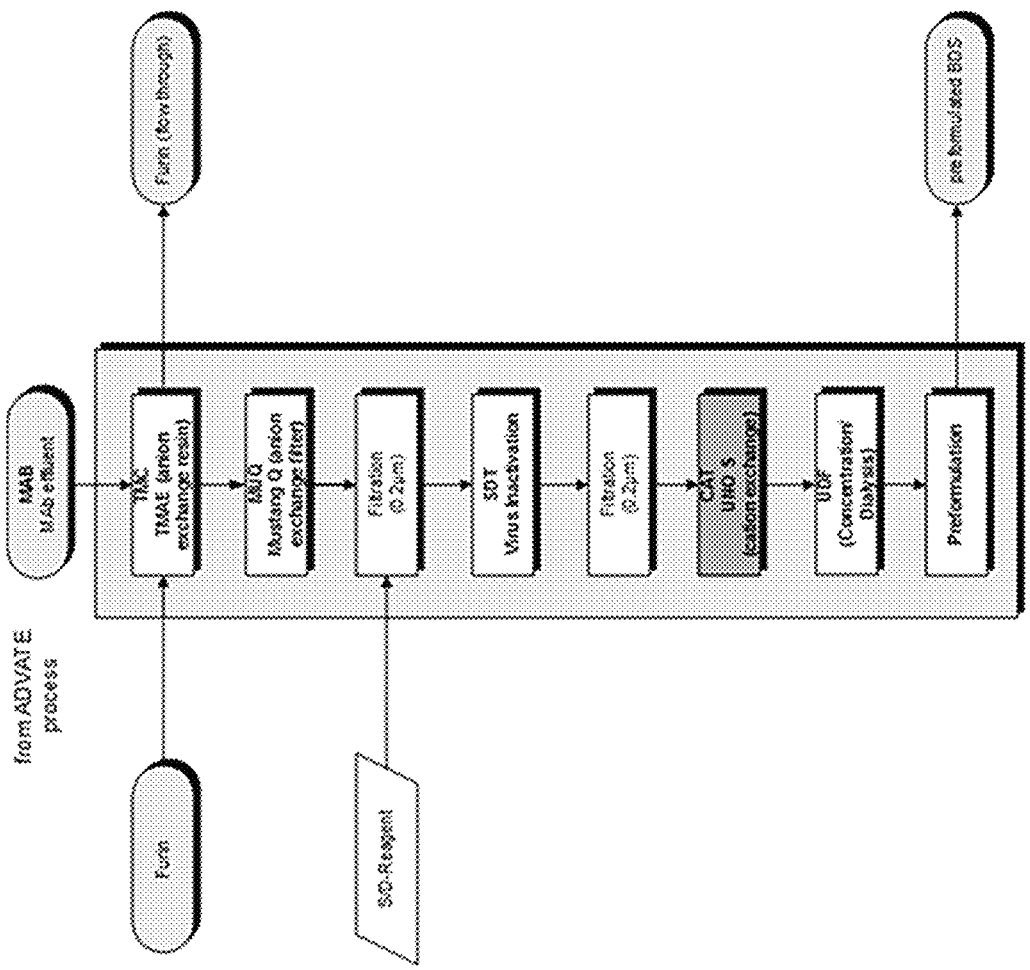

This report describes the replacement of the current unit operation steps performed in the MFG (FIG. 43A) scale by an improved CAT (UNO_S) step (FIG. 43B). The CAT step improvement was investigated on a small scale. The UDF (concentration/dialysis) step following the CAT step might have to be optimized as well.

3. Materials and Methods

The materials and the methods as well as the sampling plan are described herein.

3.1 rVWF Load Materials

For all experiments, frozen MUQ-E product was used. The material was stored frozen at ≤−60° C. in 130° mL aliquots and was thawed overnight at a range from +2 to +8° C. on demand. Once the MUQ-Eluate was thawed, S/D regents were added and the mixture was filtered through a 0.2 μm filter KA02EAVP2S® from Pall. Thereafter, the filtered material was incubated under moderate steering for 60 min at ambient room temperature (about +25° C.) to inactivate/dissolve potential lipid enveloped viruses. The S/D reaction was stopped by 1:2 dilution with 60 mM Na-Citrate buffer, pH 7.5. Diluted material was used as feed for the following CAT step.

3.2 Chromatography Hardware

For the experiments described in the current report, the small scale chromatography system AKTA pure 25 (GE Healthcare) was used. The system was equipped with probes for on-line monitoring UV absorption, conductivity, pressure, temperature and pH with electronic recording. The system was controlled by Unicorn 7.0 operated software. All runs were performed at ambient room temperature.

The ÄKTA system tubings were PEEK which is different to the large scale where a Millipore process system with stainless steel piping is used. The hardware components are all qualified R&D equipment.

The lab-scale column that was used for all five experiments was equipped with 10 μm PP frits; the particle size of the UNO_Sphere S resin was about 80 μm in diameter. At large scale stainless steel frits with a mesh size of 20 μm are used. All columns are qualified items designed for R&D purposes.

A hardware comparison between the current GEN 1 MGF equipment in NE and the small scale GEN 2 equipment used in the current study is shown in FIG. 44.

3.3 Buffers

The buffers used for the small scale purification runs were made in the laboratory area or were received from the manufacturing area. For the preparation of buffers, qualified chemicals that were also used for the production of buffers for pilot scale clinical production were used. Buffers were 0.2°μm filtered and stored in bags or glass bottles at room temperature before use. A description of the buffer composition is given in FIG. 48.

3.4 Analytical Methods

The rVWF biochemical characterization, potency and impurity assays performed include those to analyze VWF: RistoCo activity, VWF antigen, VWF-propeptide antigen content, FVIII activity chromogenic method, UV absorption profile (280 nm, 254 nm), polypeptide pattern such as degradation, multimer pattern, and CHO HCP content. In some cases, other analytical test can be performed to determine, such as but not limited to, pro-VWF antigen content, FVIII antigen content, furin activity, furin antigen, total protein (BCA), free sulfhydryl, CHO BIP WB, CHO DNA, murine monoclonal antibody, soy peptone, Triton X-100, polysorbate 80, tri-n-butylphosphate, dynamic light scattering (DLS) (hydrodynamic radius), sialic acids, n-glycan content, VWF collagen binding, and VWF oxidation.

4 Alterations in the CAT Process rVWF 2nd Generation (GEN 2)

In order to replace the SEC step in a $2^{nd}$ generation rVWF downstream process the parameters listed below were explored. Most of the changes introduced are based on R&D feasibility studies. The chromatography resin type (UNO_Sphere S resin by BioRad) and the composition (not the pH) of the applied buffer was not altered. The $2^{nd}$ generation CAT process included the following changes: S/D treatment, loading concentration and flow rates, and wash and elution steps.

4.1 S/D Treatment

The S/D treatment was performed in the same way as in the GEN 1 process, except the S/D inactivation was stopped by a 1:2 dilution of the virus inactivated material with 60° mM Na-citrate buffer that set the CAT feed to a preferred pH of 7.5-8.0 (pH testing range 6.0-9.0) and to a preferred conductivity of 10-30° mS/cm$^2$ at +25° C. (conductivity testing rage 5-40° mS/cm$^2$ at +25° C.). In the GEN 1 rVWF CAT step that was performed, the CAT load was set to a pH of 8.9-9.2. In the GEN 2 set-up, conductivity and pH were set to a point that minimized the CHO-HCP, CHO-DNA and rVWF pro-peptide binding to the matrix. Similarly low molecular weight (LMW) rVWF molecules were hindered to bind to the column matrix, whereas preferably only high molecular weight (HMW) rVWF molecules were captured. One aim of the present study was to increase the conductivity during the loading phase and to deplete as much LMW rVWF, CHO-HCP, CHO-DNA and rVWF pro-peptide from the feed as possible.

4.2 Loading Concentrations and Flowrates

The loading concentration (RU rVWF/mL resin) was increased in course of the study to enable a higher product load without increasing the column volume. At the manufacturing scale (MFG) a loading concentration of 60-140 RU/ml resin is generally applied, in contrast, in the current small scale study 90-270 IU/ml resin were loaded. The equilibration, loading and re-equilibration flow rates of the $2^{nd}$ generation CAT procedure were the same as in the $1^{st}$ generation process (100 cm/h). Washing and elution flow-rates were altered as shown in FIG. 45.

4.3 Loading Concentrations and Flowrates

The washing step preceding the elution phase was altered to optimize the removal of process and product related impurities. The step elution as applied in the 1st generation process was changed to a gradient elution. The gradient length was explored in course of the study. The change of the elution procedure was based on the observation that low molecular weight rVWF molecules elute in early gradient fractions where as high molecular weight rVWF molecules elute in late gradient fractions (see, e.g., U.S. Pat. No. 6,465,624).

5. Comparison of the CAT Gen 1 and Gen 2 Process

In both procedures the CAT process includes the following steps: column activation (loading of the anionic ligand with the cationic counter ion sodium) and equilibration (preparing the column for loading in terms of a stable pH and conductivity, monitored at the column outlet), followed by the product loading of the S/D treated and diluted MUQ eluate.

During loading on MFG scale, the eluate was filtered online through a 0.2°μm filter to protect the column against particulate matter that could have been formed during the S/D treatment. In the small scale process, this step was omitted. After pumping the product containing solution onto the column, the loading was completed and loosely bound impurities were removed by applying a wash step which removes low molecular weight S/D reagents that were pumped onto the column. The pH and the conductivity of the wash step correspond to the parameters of the equilibration and loading steps. After washing, bound proteins were eluted from the column by applying a step elution using an elution buffer with increased conductivity and counter ion concentration. A product pool of ≤3.6° C.V was collected.

In the small scale Gen 2 process, an alternative gradient elution procedure was used to remove rVWF pro-peptide, small molecular weight rVWF molecules and high molecular weight molecules from the column (FIG. 45). The washing steps preceding the elution were performed as step wash with the same pH and conductivity as the starting point of the gradient elution. Four wash scenarios were tested: 0% B (10 CV), 55% B (10 CV), 40% B (5 CV) & 45% B (5 CV) and 36% B (5 CV). The corresponding gradient elution steps were 0-100% B (12 CV), 55-100% B (6 CV), 45-100% B (6CV) and 36-100% B (6 CV). The elution was completed by a 2-3 CV wash with 100% B.

The eluates were pooled according to the eluting product related impurities and product sub-species. After elution of the product the column was cleaned and sanitized with basic and acidic solutions. The main objective of this polishing step was the further removal of process related impurities including CHO host cell protein, human rFurin, media compounds like soy peptone), product related impurities (rVWF pro-peptide) and low molecular weight S/D reagents. Only a minor contribution was expected in the removal of rFVIII. Following the improved CAT (UNO_S) step, a protein concentration and buffer exchange step (ultra/diafiltration) can be required. However this ultra/diafiltration step was not part of the study described herein. The differences in the chromatographic procedure between the $1^{st}$ GEN MFG scale process and the $2^{nd}$ generation small scale process are outlined in FIGS. 46-48.

6. Results

In the following section, the results of the current study are presented. The five experiments conducted at small scale clearly show that the replacement of the SEC unit operation step and the preceding ultrafiltration (buffer exchange) step is possible by the introduction of a modified UNOs (CAT) procedure.

6.1 Chromatograms

Figure 49A:
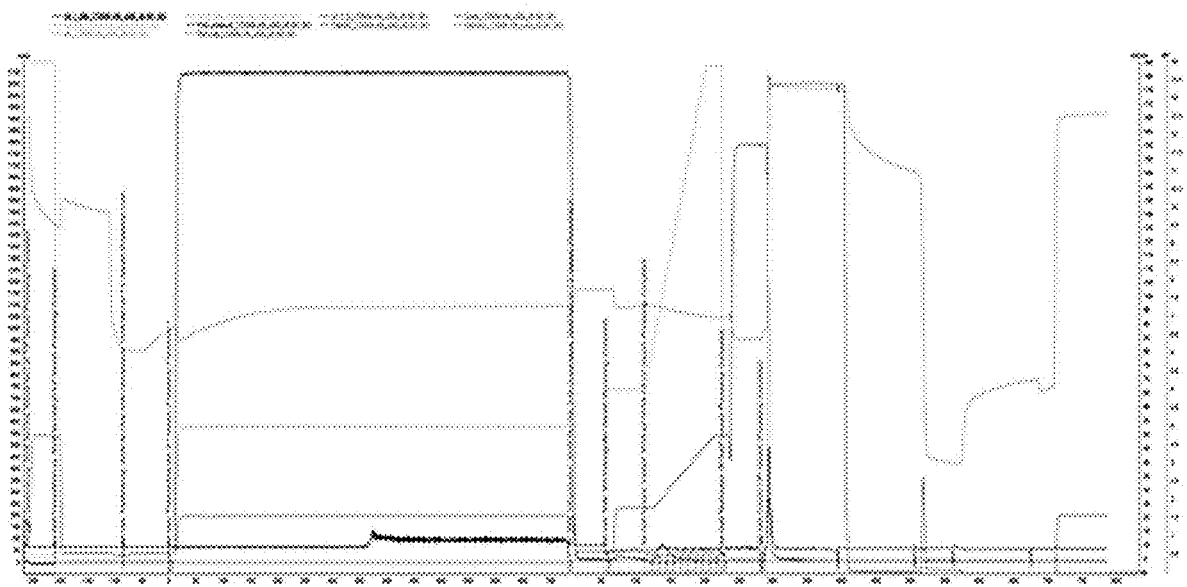
FIG. 49A and FIG. 49B show chromatograms of run VW_USS_05.
Figure 49B:
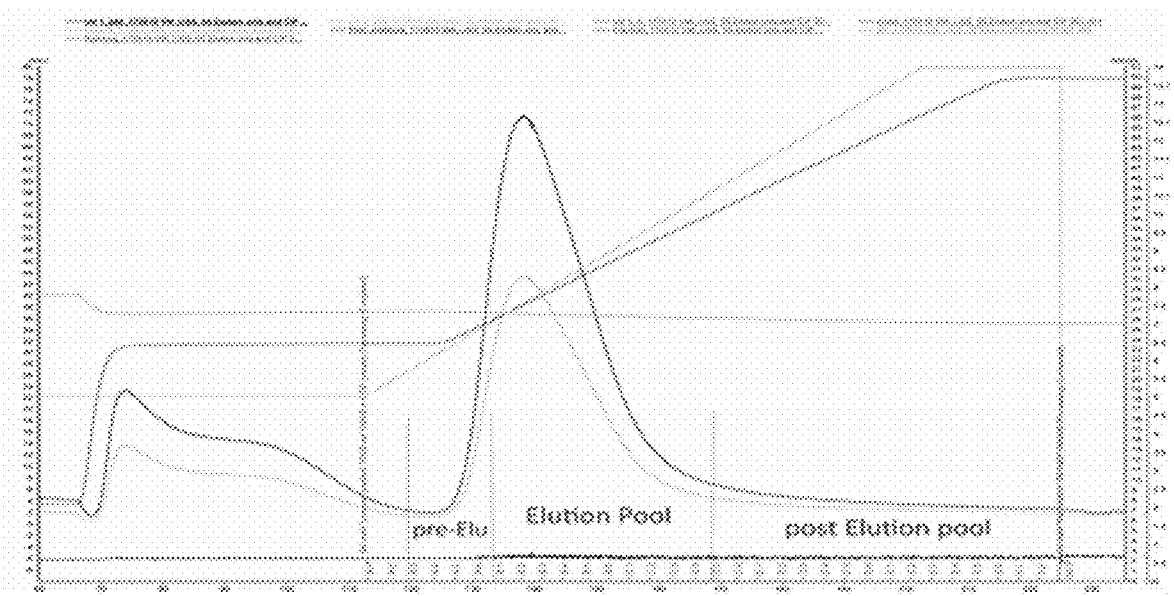

As outlined above, five experiments with different wash and gradient elution procedure were performed. The intention of the UNO S step was to find an optimal method for the removal of product and process related impurities on the one hand and to achieve an optimal yield in terms of VWF Ag and Activity. FIG. 49 shows two chromatograms of the final ($5^{th}$) run VW_USS_05 are presented. The upper panel of FIG. 49 depicts the total run, including column activation, loading phase (the high UV280 nm absorption is caused by the S/D chemicals contained in the feed), re-equilibration, wash, gradient elution, 2M NaCl wash and the CIP procedure. The chromatogram is fused from 2 result files which explains the scale of the x-axis (result file 1: activation until end of load; result file 2: start of re-equilibration, 36% B wash, gradient elution, CIP). The lower panel of FIG. 49 depicts the elution phase in detail (step wash to 36% elution-buffer B, followed by the gradient elution 36% B to 100% B and a 100% elution-buffer B phase).

6.2 SDS-PAGE

Figure 50:
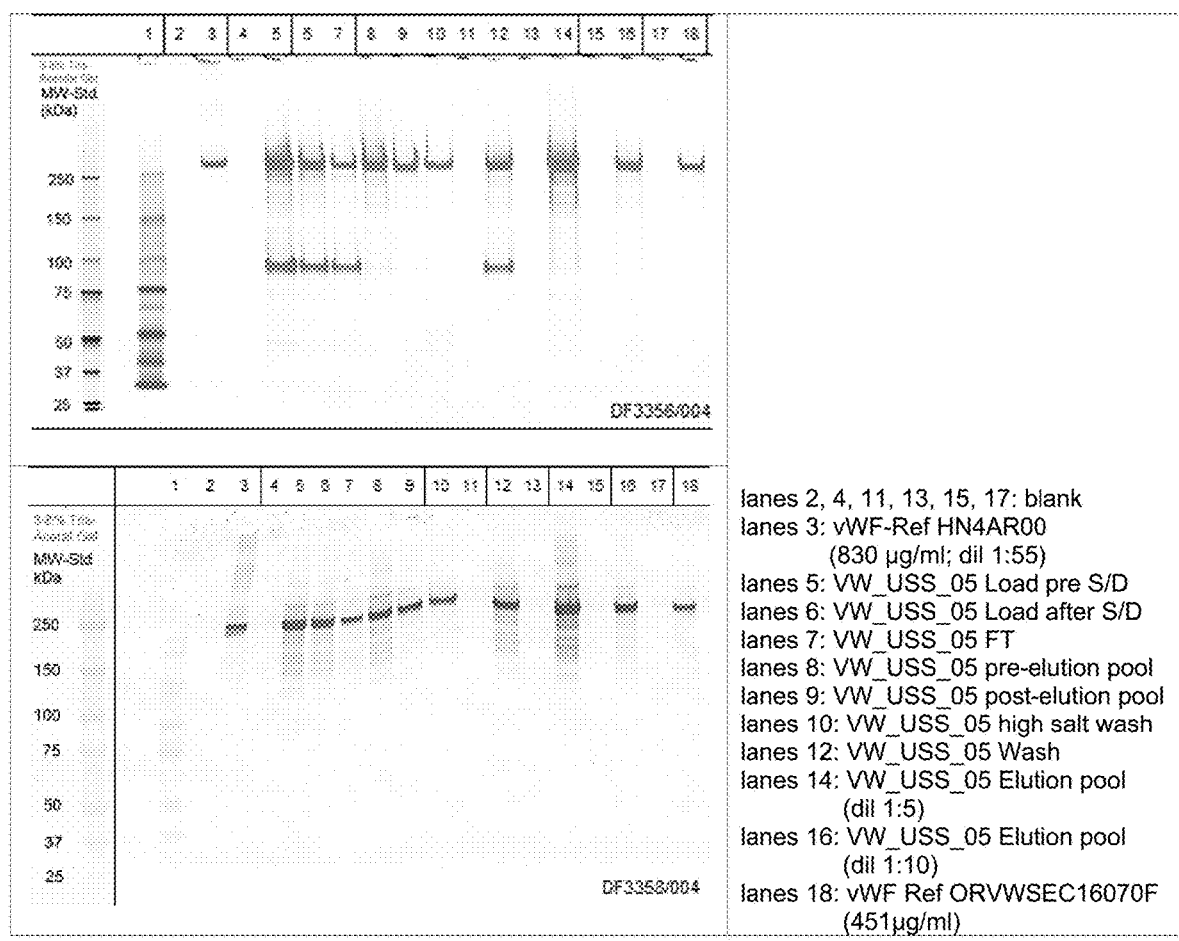
FIG. 50 depicts SDS-PAGE silver stain gel and Western blot of run VW_UUS_05.

With the variation and optimization of the chromatography conditions applied (e.g., conductivity of washes, start of gradient elution), the separation of pro-peptide and mature rVWF was refined. In addition, the removal of process related impurities and the yield of mature rVWF Ag and activity was improved. SDS-PAGE results (silver stain and anti rvwf western blot) of the last ($5^{th}$) run in the series of experiments is presented in FIG. 50.

The SDS-PAGE was performed on 3-8% Tris-Acetate gels under reducing conditions. The separated polypeptides were visualized by silver staining (top) and Western blot (bottom). Prior to loading, samples were reduced with DTT, thereafter free sulfhydryl groups were blocked with iodo acetamide. For the Western blot, the $1^{st}$ antibody was a polyclonal rabbit anti-human-VWF antibody (from Dako; order number A0082; diluted 1:1000), the $2^{nd}$ antibody was a polyclonal, AP-conjugated goat anti-rabbit-IgG anti body (from Sigma; order number A-8025; diluted 1:2000). The rVWF band runs at above 250 kDa; the VWF pro-peptide runs at about 90 kDa. The pro-peptide is not detected by the antibody used for Western blotting.

Results of run VWF_USS_05 show a clear separation of pro-peptide and mature rVWF. The eluate sample (lane 16) and a reference sample purified according to the generation 1 procedure (lane 18) are highly comparable.

6.3 Multimer Analysis

Figure 51:
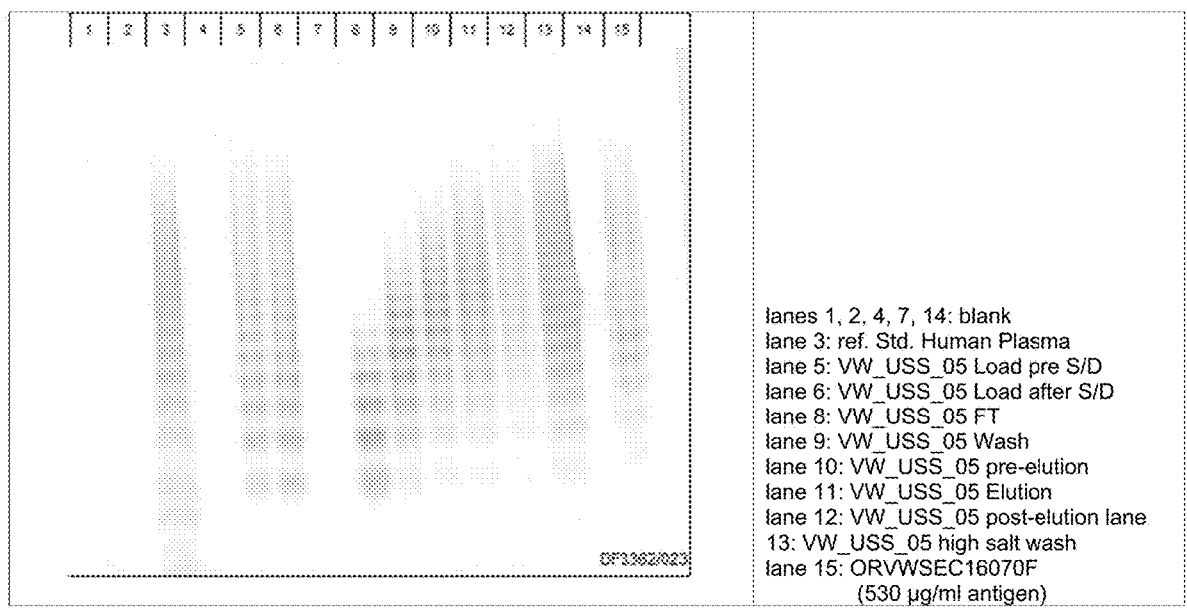
FIG. 51 depicts a multimer agarose gel of run VW_UUS_05.

To assess the distribution of high and low molecular weight rVWF sub-species multimer analysis by agarose gel and Western blot was performed. Samples from Load, flowthrough (FT), Wash, Elution and high salt wash were tested (FIG. 51) LMW rVWF subspecies are contained in the flow through (FT; effluent fraction) (lane 8) and wash/pre-elution (lanes 9 and 10). The Elution and post-elution pools (lanes 11 and 12) show a band pattern comparable to the reference sample SEC-F (lane 15). The reference sample was purified according to the generation 1 (Gen 1) process and corresponds roughly to the ascending peak of the SEC eluate pool. The high salt wash (lane 13) contains ultra-large rVWF molecules which is seen by the smear in the upper region of the lane.

The multimer analyses were performed on 1% agarose gels according a standard protocol. Approximately 50 ng of rVWF was applied per lane and separated under non-reducing conditions in the presence of urea. The separated polypeptides were visualized by Western Blot using a rabbit anti-human VWF antibody (Dako) as $1^{st}$ antibody (diluted 1:1000) and an AP-conjugated goat anti-rabbit IgG antibody (Sigma) as $2^{nd}$ antibody (diluted 1:2000).

Comparing the rVWF multimer distribution between UNO_S (Gen 2) and SEC (Gen 1) runs, a reverse separation effect can be clearly seen. In the SEC procedure ultra-large and large molecules elute first (void volume), followed by the target molecules and the pro-peptide. In Gen 2 the order of separation is just the opposite (small to large). However, both methods resulted in the same rVWF multimer distribution in the eluate pool. Following the UNO_S step, a UDF (concentration/dialysis) unit operation was required to concentrate the target molecule and to transfer it into formulation buffer.

6.4 Analytical Results

A summary of analytical results is given in FIG. 52-FIG. 55. Each table shows results of one specific analytical assay and contains data of all 5 runs performed in course of the study. A comparative overview of Eluate results is also presented in FIG. 56. Besides of the percentage of rVWF:Ag and Risto Co activity Eluate yields, the table contains calculated rations to allow a direct comparison between different run setup.

6.5 Match of Analytical Data to Success Criteria

The targeted parameters of the eluate (product fraction) resulting from the modified CAT (UNO_S) unit operation step partly comply with selected BDS product specifications. As the CAT-E product pool needs to be concentrated and dialyzed to obtain BDS material, the development targets (FIG. 57) are mainly (calculated) ratios that are independent of absolute parameter concentrations.

The fact that most of the development targets were met or nearly reached demonstrates the feasibility of the suggested procedure described herein. Not all analytical assays were performed, yet key results such as rVWF:Ag and Risto yield, CHO HCP and pro-peptide impurity removal, as well as the distribution of rVWF multimers show a comparable performance of the suggested new CAT procedure and the previously applied UNO_S/SEC combination.

7. Discussion

Five UNO_S runs were performed in the course of the present study to investigate a $2^{nd}$ generation CAT procedure. The results of the optimized (last) run show a separation of high from low molecular weight rVWF multimers as well as the removal of rVWF pro-peptides and CHO-HCP impurities from the target protein that is comparable to the results achieved with the Gen 1 procedure (e.g., UNO_S in step elution mode+SEC step). The introduced wash step with a conductivity of about 24 mS/cm (36% Elution Buffer B) followed by a gradient elution step to about 50 mS/cm (100% Elution Buffer B) resulted in a CAT Eluate pool of comparable quality to the previously yielded Gen 1 SEC F pool. Although an additional UDF step to concentrate and dialyze the CAT eluate may be used, the Gen 2 CAT procedure described herein shows great potential to replace the UDF and SEC unit operation steps applied in the Gen 1 downstream process to obtain BDS material.

Example 13: Evaluation Multimers of DF3338/042 and DF3362/023 Westernblot Anti-VWF The mat-rVWF obtained from this method was analyzed for the multimeric content. Advantages of the desceibed cation exhcnage (CEX) methods includes:

Reduction of unit operations—1 CEX replaces 3-unit operation of the current process.

Depletion of r-vWF-Propeptide and depletion of host cell proteins are similar to an affinity step.

By including the SD-treatment "On colum" on cation exchanger—4-unit operations are included in one step.

By including the SD-treatment "On colum" and the furin maturation on cation exchanger—5 unit operations are included in one step.

Reduced shear stress that lowers the risk of the generation of thrombotic rVWF (due to less unit operations, filtrations and significant reduced hold times).

For this analys, western blots were run. The westernblot images were imported into Corel Photo Paint Software and converted into 16 Bit grey scale images. The 16 bit grey scale format is a requirement for the evaluation. The evaluation was made with Image Quant 1D Software.

The images were vertical flipped to simplify the evaluation (Lane numbers remain the same):

Band 1-6=Low molecular weight

Band 7-12=Intermediate molecular weight

Band>12=High molecularweight

Densitometric evaluation of vWF multimers of the product obtained from enhanced CEX as described herein as compared to the product obtained from the 3-unit operation process.

TABLE 11

Densitometric evaluation summary.

| | | Benchmark | VW_USS_04 E | VW_USS_05 E |
|---|---|---|---|---|
| % Low MW | SUM Band 1-6 | 40.86 | 34.91 | 38.39 |
| % Medium MW | SUM Band 7-12 | 40.27 | 39 | 36.87 |
| % High MW | SUM Band >12 | 18.87 | 26.08 | 24.74 |

The raw data showing the multimer percentages is provided in FIGS. 61-63.

Example 14: Variant vWF Purification Process

I. Background r-vWF pro-peptide is a product related impurity of CHO Cell derived r-VWF product. The production cell line generates r-VWF which contains about 60% of pro-r-vWF. The r-VWF propeptide is attached to the r-vWF polypeptide covalent by peptide amide bond and additionally non-covalently by divalent cations. The covalent peptide amide bond is cleaved by in-vitro incubation with rFurin. However, the cleaved r-VWF propeptide remains attached to the VWF molecule and a method for separation of these two polypeptides is described in this example. It was discovered that the rvWF/rvWF_PP complex is stabilized by divalent cations and low pH. By applying chelator of divalent cations or high pH in combination with a proper separation method the two molecules can be separated with high efficency and in a robust manner. As chelator low concentrations of EDTA or citrate were found to be effective and pH greater or equal pH 7 were also be seen effective when applied on cation exchange resin as wash procedure or on size exclusion chromatography when applied in the separation buffer. The same principle should be applyable to all separation technologies including ion exchange or size separation either by resins or membrane technology. In the current production process for rVWF the step SEC is performed with a running buffer containing citrate to support the separation of rVWF and rVWF-PP.

1. Description of Example Scope—VW_USS_07
    1. Depletion of r-vWF-Propeptide
    2. Example for alternative "SD_VI on column" treatment
    3. Generating rFVIII/r-vWF complex "on column"
    4. On column pre-formulation during elution of the rFVIII/r-vWF complex in an alternative formulation buffer system Process Details:

After a monoclonal antibody step to capture recombinant factor VIII the Flow-through, which contains r-vWF, was loaded onto an Fractogel TMAE anion exchanger. r-vWF was bound on the anion exchanger and was maturated with Furin in presence of Calcium. The r-vWF was eluted from the anion exchanger with increasing conductivity. The TMAE-Eluate was filtrated trough a Mustang Q (Mustang Q, Pall Part Number XT5000MSTGQP1) filter unit to remove CHO-DNA and impurities that binds to the filter membrane. The product containing MUQ_Flow through was conditioned by a 1:2 dilution with [60 mM sodiumcitrate pH 7.6] to a conductivity of 21.9 mS/cm and pH 7.16. The high conductivity was chosen to ensure the removal of r-vWF propeptide and low mol weight r-vWF to utilize the capacity of the resin for the desired high mol weight r-vWF. The conditioned load was loaded onto a UNOsphere™ S Cation Exchange Media (Bio Rad, Art.Nr.: 156-0115) inner diameter=10 mm bed height 8.8 cm volume 6.91 ml with a flow rate of 100 cm/h followed by a first wash (Reequilibration) of 2CV with [30 mM Na-Citrate, 180 mM NaCl, pH 7.5] to deplete strong bound HCP and r-vWF-Propeptide.

A potential "On column treatment" (WSD) was carried out with [30 mM Na-Citrate, 180 mM NaCl, pH 7.5 containing 25 g/Kg of a mix of 18.0 g Polysorbate 80, 3.5 g Dimethylsulfoxide DMSO, 3.5 g TnBP] in 12 column volumes and a contact time of approx. 1 hour to inactivate lipid enveloped viruses. The components of the "On column treatment" were washed out with Wash 2 in 10 column volumes of [30 mM Na-Citrate, 180 mM NaCl, pH 7.5]. By applying Wash 3 the buffer was changed from the Sodiumcitrate buffer system to a Glycine/Taurine system by applying [50 mM Glycine, 10 mM Taurine, 10% Sucrose, 0.1% Polysorbate 80, pH 5.5] in 4 column volumes. At step "FVIII-Con" recombinant human coagulation factor VIII derived from the ADVATE process was loaded onto the bound r-vWF in 10 column volumes.

The FVIII-Con-buffer consists of [1.57 g rFVIII S2 ADV S17B010901B2 diluted in 218.67 g of 50 mM Glycine, 10 mM Taurine, 5% (w/w) Sucrose, 5% (w/w) D-Mannitol, 0.1% Polysorbate 80, 2 mM CaCl$_2$), 150 mM NaCl, and a pH 7.4]. Wash 4 was applied to wash out unbound rFVIII and to prepare the buffer matrix for the pre-formulation by applying 5 column volumes of [50 mM Glycine, 10 mM Taurine, 5% (w/w) Sucrose, 5% (w/w) D-Mannitol, 0.1% Polysorbate 80, 2 mM CaCl$_2$), 150 mM NaCl, pH 7.4]. Both the r-vWF and the rFVIII was eluted with [50 mM Glycine, 10 mM Taurine, 5% (w/w) Sucrose, 5% (w/w) D-Mannitol, 0.1% Polysorbate 80, 2 mM CaCl$_2$, 600 mM NaCl, pH 7.4±0.2] from the column to form an eluate. The eluate was diluted to adjust the Sodiumchloride content to approx. 150 mM NaCl with [50 mM Glycine, 10 mM Taurine, 5% (w/w) Sucrose, 5% (w/w) D-Mannitol, 0.1% Polysorbate 80, 2 mM CaCl$_2$, pH 7.4].

Figure 67:
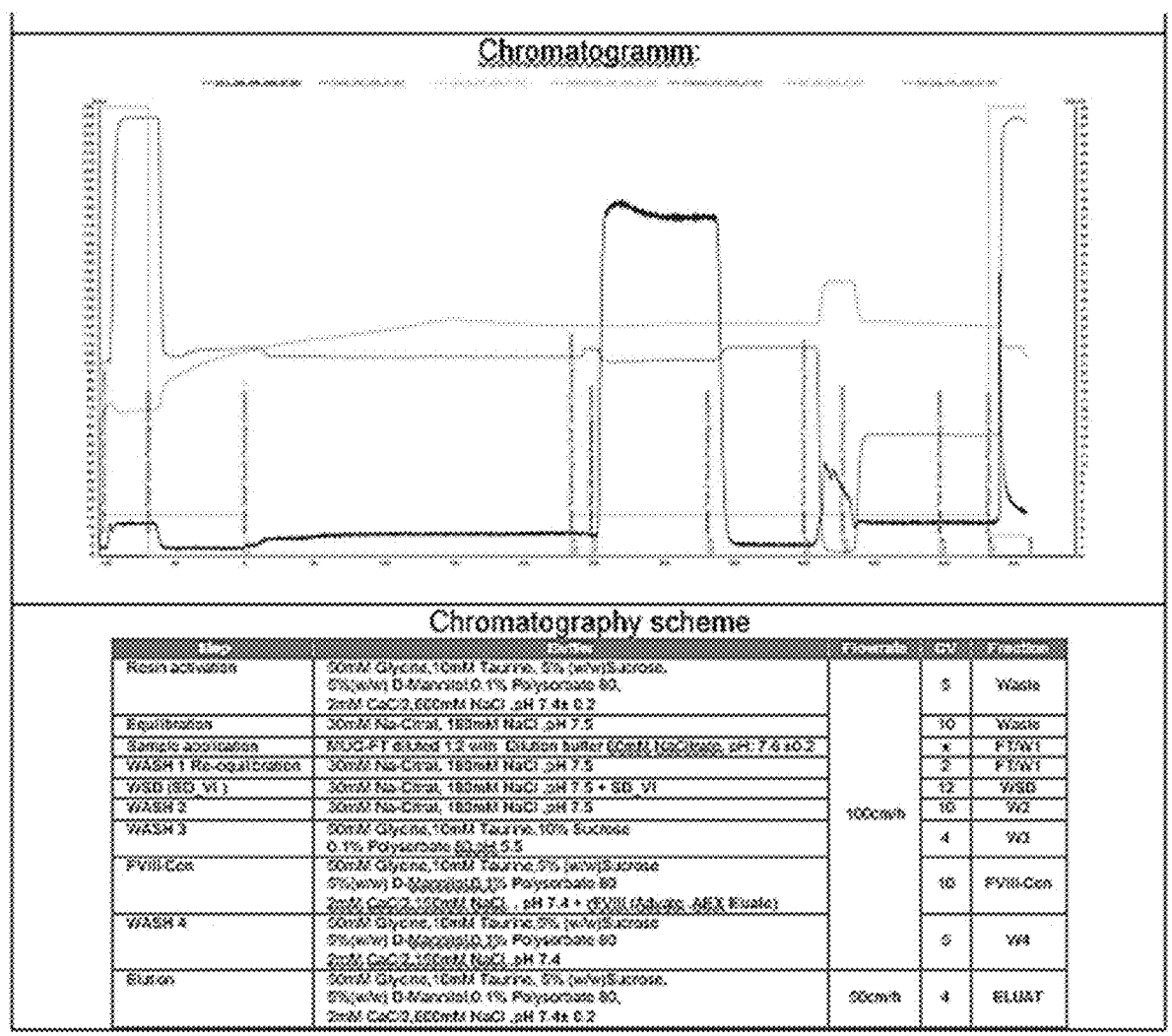
FIG. 67 shows a chromatogram and chromatogram scheme of the run VW_USS_07.

Process Sequence:

The sequence of the key steps of this example consists of the following steps (See, also the bottom of FIG. 67 for the chromatography scheme.)

1. Mab FVIII capture (FT is the r-vWF containing fraction)
2. Fractogel TMAE capture+maturation
3. Mustang Q in FT mode
4. CEX as described (VW_USS_07)

Figure 69:
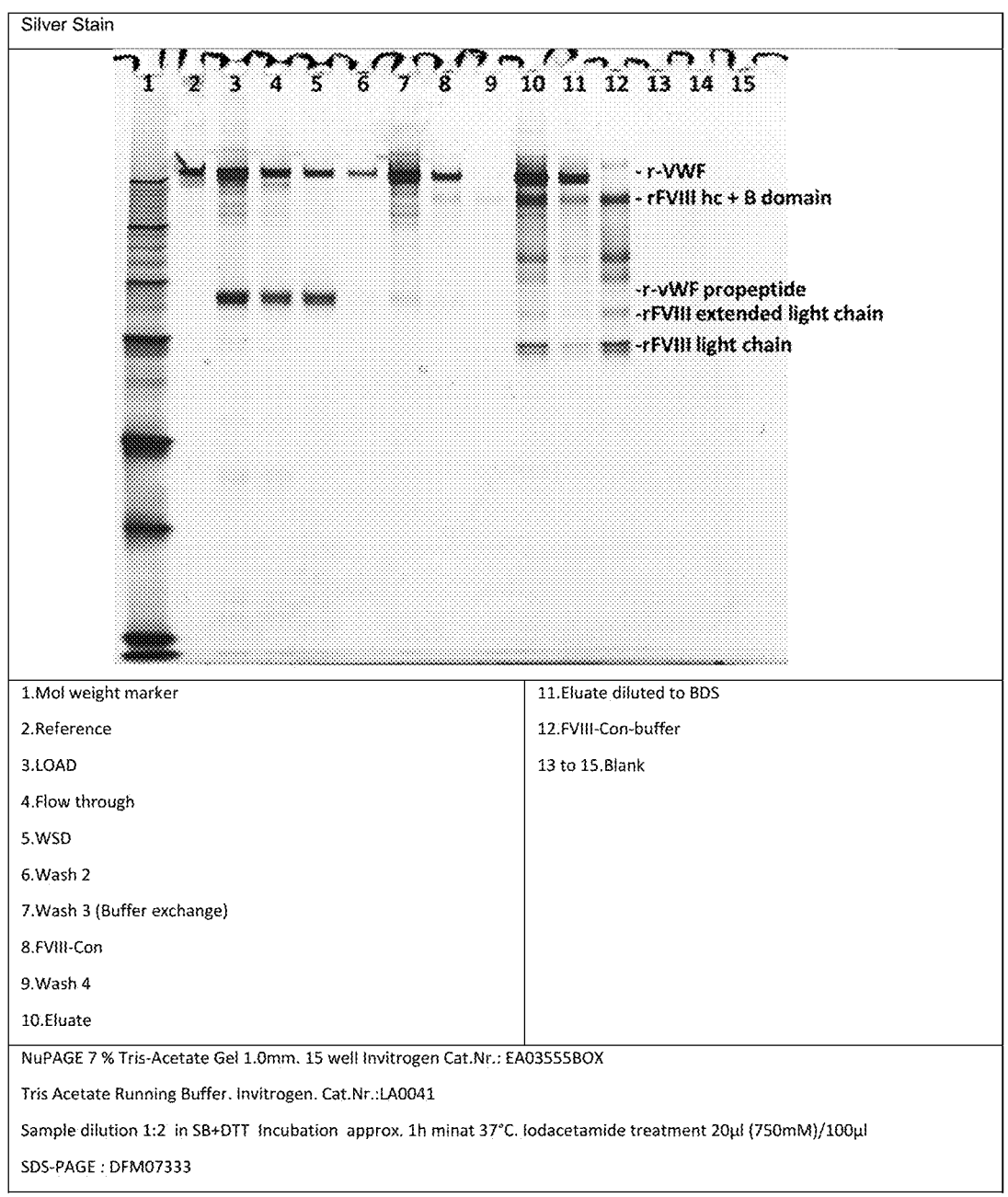
FIG. 69 shows SDS-PAGE silver stain gel of the representative run. Dep version. In some embodiments, the methods described herein apply to recombinant VWF (rVWF).
Figure 71:
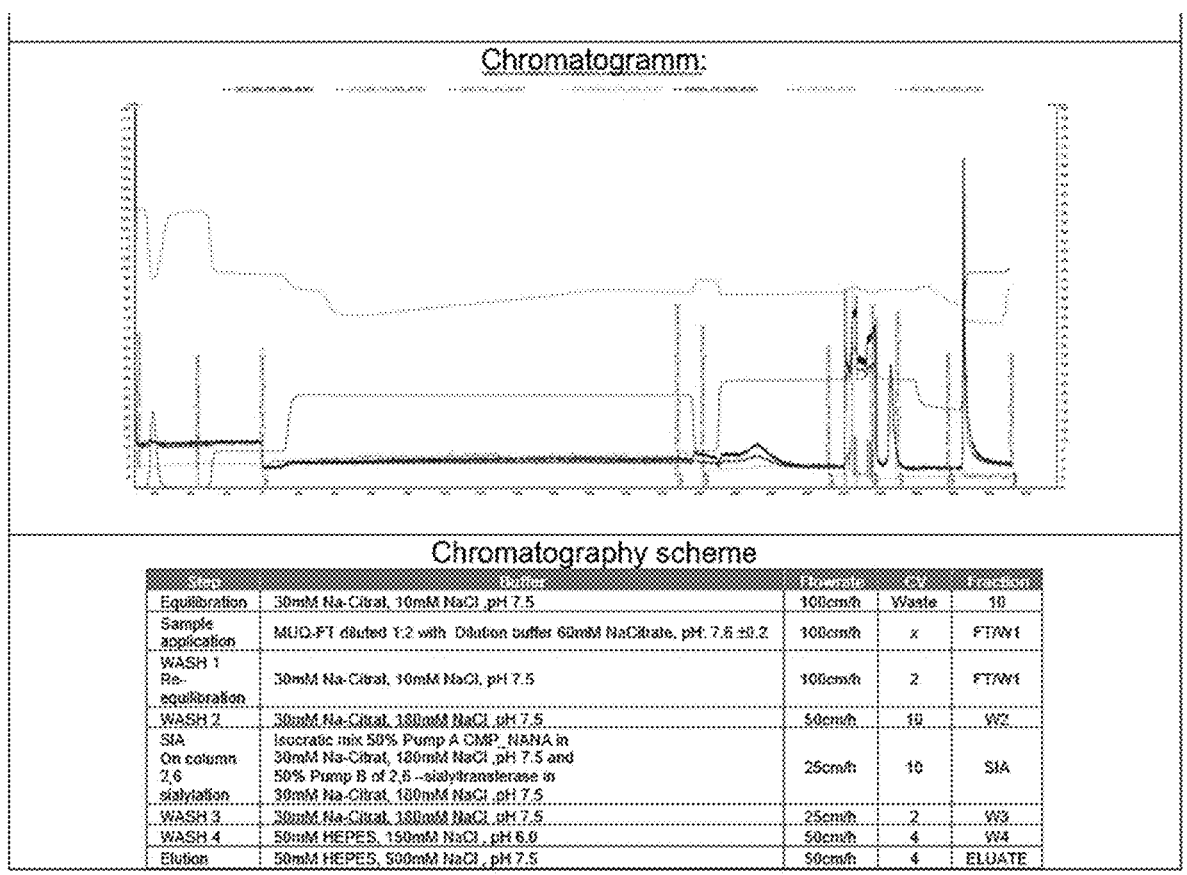
Figure 73:
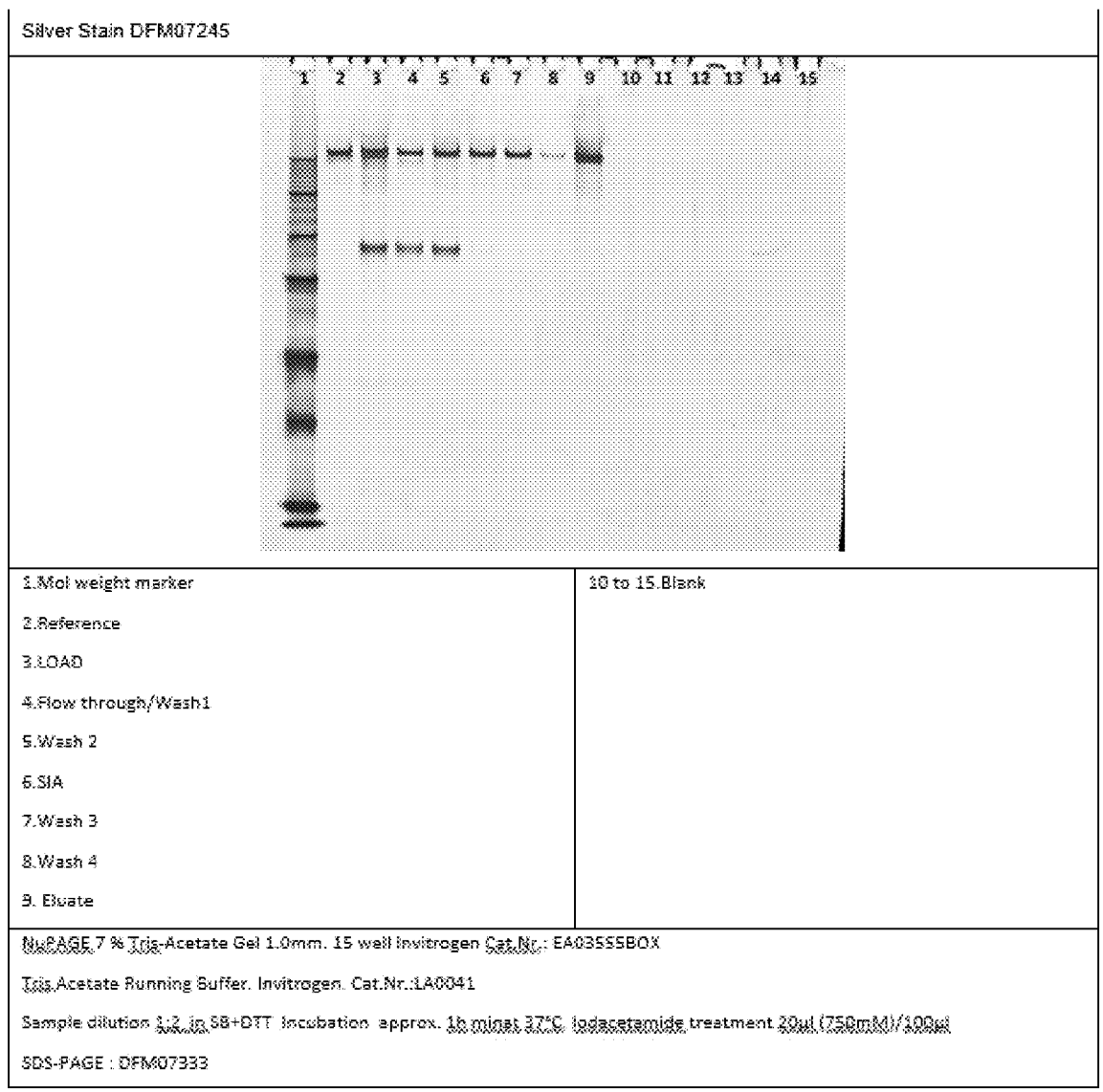
Figure 75:
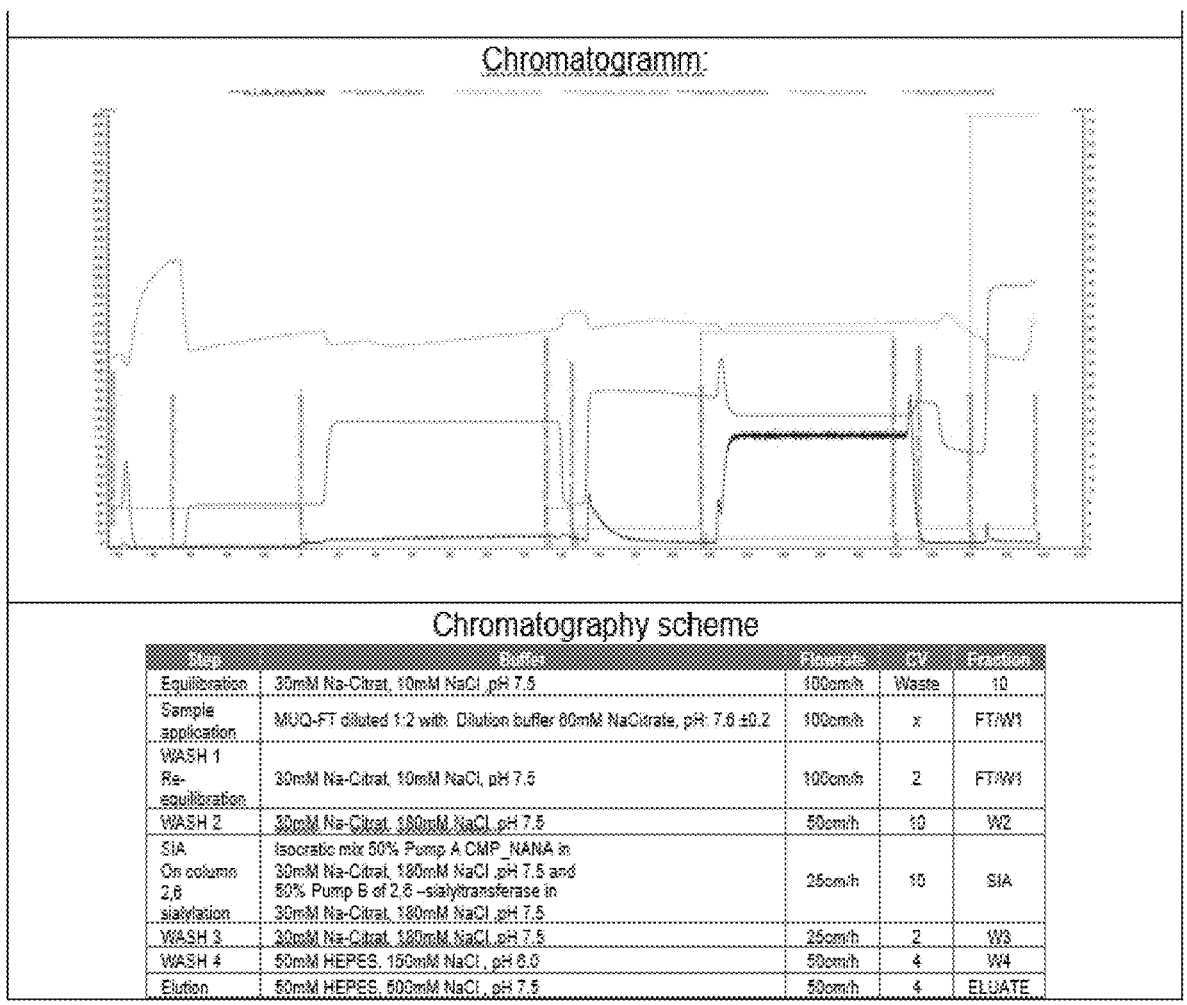
Figure 77:
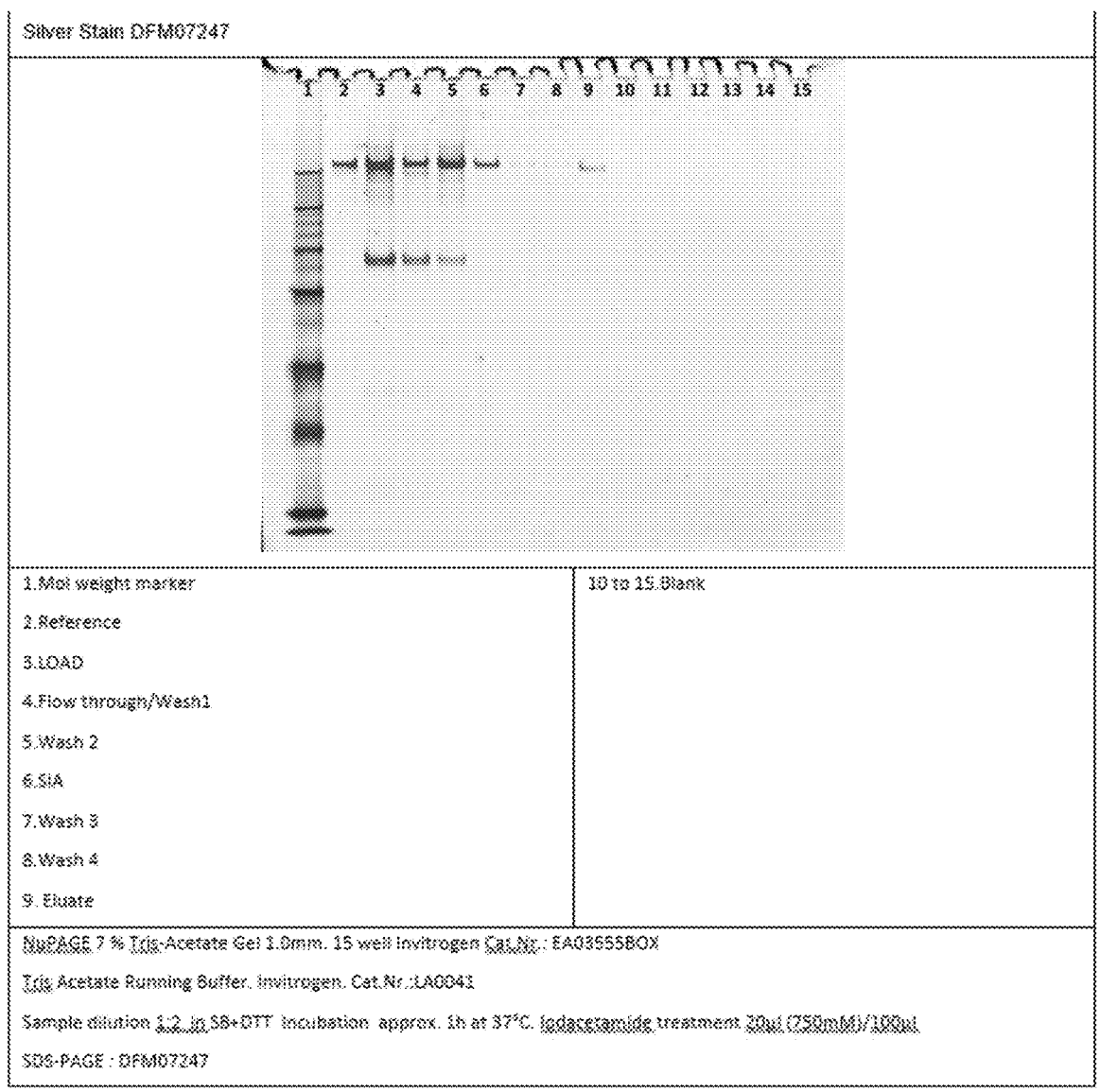

Result:

The experiment was successfully carried out in all 4 points:

1. Depletion of r-vWF-Propeptide occurred—during the wash steps Wash 1, WSD ((W)ash with (S)olvent (D)detergent) and Wash 2 (see, FIGS. 67, 68, and 69.)
2. Example for alternative "SD_VI on column treatment" at step WSD.
3. Generating rFVIII/r-vWF complex "on column"—step FVIII-Con.
4. On column pre-formulation during elution of the rFVIII/r-vWF complex in an alternative formulation buffer system (see, FIG. 66, last row).

Example 15: Variant vWF Purification Process—Testing for Sialylation

I. Background r-vWF pro-peptide is a product related impurity of CHO Cell derived r-VWF product. The production cell line generates r-vWF which contains about 60% of pro-r-vWF. The r-vWF propeptide is attached to the r-vWF polypeptide covalent by peptide amide bond and additionally non-covalently by divalent cations. The covalent peptide amide bond is cleaved by in-vitro incubation with rFurin. However, the cleaved r-VWF propeptide remains attached to the VWF molecule and a method for separation of these two polypeptides is described in this example. The present example provides an alternate, variant embodiment for separation of the r-vWF propeptide from the r-VWF polypeptide after furin cleavage in order to test for additional sialylation. Additional details and results of the purification process are depicted in FIGS. 70-73 and 78.

1. Experiment Nr.: VW_USS_06
    1. Depletion of r-vWF-Propeptide
    2. Generate additional 2,6 Sialylation on column on r-vWF
2. Experiment Nr.: VW_USS_06

After a monoclonal antibody step to capture recombinant factor VIII the Flow-through, which contains r-vWF, was loaded onto an Fractogel TMAE anion exchanger. r-vWF was bound on the anion exchanger and was maturated with Furin in presence of Calcium, the r-vWF was eluted from the anion exchanger with increasing conductivity. The TMAE-Eluate was filtrated trough a Mustang Q (Mustang Q, Pall Part Number XT5000MSTGQP1) filter unit to remove CHO-DNA and impurities that binds to the filter membrane. The product containing MUQ_Flow through was conditioned by a 1:2 dilution with [60 mM sodiumcitrate pH 7.6] to a conductivity of 18.39 mS/cm and pH 7.33. The high conductivity was chosen to ensure the removal of r-vWF propeptide and low molecular weight r-vWF to utilize the capacity of the resin for the desired high mol weight r-vWF. The conditioned load was loaded onto a UNOsphere™ S Cation Exchange Media (Bio Rad, Art. Nr.: 156-0115) inner diameter=10 mm bed height 8.8 cm volume 6.91 ml with a flow rate of 100 cm/h followed by a first wash (Reequilibration) of 2CV with [30 mM Na-Citrate, 180 mM NaCl, pH 7.5] to deplete strong bound HCP and r-vWF-Propeptide. To introduce additional 2,6 Sialylation a mixture of 50% (v/v) CMP-NANA Solution based on [30 mM Na-Citrat, 180 mM NaCl, pH 7.5] and 50% (v/v) of alpha 2,6 Sialyltransferase based on [30 mM Na-Citrat, 180 mM NaCl, pH 7.5] was applied onto the column in 10 column volumes and a flow rate of 25 cm/h by online mixing. The composition of the CMP-NANA Solution was 11 mg CMP_NANA C8271-25 mg Lot.Nr.: SLBV 7777 dissolved in 154.29 g [30 mM Na-Citrate, 180 mM NaCl, pH 7.5]. The composition of the alpha 2,6 Sialyltransferase buffer was alpha 2,6 Sialyltransferase S2076-1UN SIGMA, Lot.Nr. SLBV0552 from Photobacterium Damsela dissolved in 1 ml purified water-0.5 g of the dissolved alpha 2,6 Sialyltransferase was diluted with 152.10 g [30 mM Na-Citrat, 180 mM NaCl, pH 7.5]. A further wash with 2 column volumes of [30 mM Na-Citrate, 180 mM NaCl, pH 7.5] was applied to remove excess of CMP_NANA and alpha 2,6 Sialyltransferase. A buffer exchange was provided by applying 4 column volumes of [50 mM HEPES, 150 mM NaCl pH 6.0]. The Elution was performed with [50 mM HEPES, 500 mM NaCl, pH 7.5] in 4 column volumes.

3. Complete Purification Sequence VW_USS_06

The sequence of the key steps of this example consists of the following steps:
1. Mab FVIII capture (FT is the r-vWF containing fraction)
2. Fractogel TMAE capture+maturation
3. Mustang Q in FT mode
4. CEX as described (VW_USS_06)

Result:
No additional 2,6 sialylation detected in using the method in the present example. However, 2,3 sialylation was found which is the usual sialylation pattern for r-vWF.

Example 16: Variant vWF Purification Process—Testing for Sialylation

I. Background r-vWF pro-peptide is a product related impurity of CHO Cell derived r-VWF product. The production cell line generates r-VWF which contains about 60% of pro-r-vWF. The r-vWF propeptide is attached to the r-VWF polypeptide covalent by peptide amide bond and additionally non-covalently by divalent cations. The covalent peptide amide bond is cleaved by in-vitro incubation with rFurin. However, the cleaved r-VWF propeptide remains attached to the VWF molecule and a method for separation of these two polypeptides is described in this example. The present example provides an alternate, variant embodiment for separation of the r-VWF propeptide from the r-VWF polypeptide after furin cleavage in order to test for additional sialylation. Additional details and results of the purification process are depicted in FIGS. 74-78.

1. Experiment Nr.: VW_USS_08
   1. Depletion of r-vWF-Propeptide
   2. Generate additional 2,6 Sialylation on column on r-vWF
2. Experiment Nr.: VW_USS_08

After a monoclonal antibody step to capture recombinant factor VIII the Flow-through, which contains r-vWF, was loaded onto an Fractogel TMAE anion exchanger. r-vWF was bound on the anion exchanger and was maturated with Furin in presence of Calcium, the r-vWF was eluted from the anion exchanger with increasing conductivity. The TMAE-Eluate was filtrated trough a Mustang Q (Mustang Q, Pall Part Number XT5000MSTGQP1) filter unit to remove CHO-DNA and impurities that binds to the filter membrane. The product containing MUQ_Flow through was conditioned by a 1:2 dilution with [60 mM sodium citrate pH 7.6] to a conductivity of 19.97 mS/cm and pH 7.33. The high conductivity was chosen to ensure the removal of r-vWF propeptide and low mol weight r-vWF to utilize the capacity of the resin for the desired high mol weight r-vWF. The conditioned load was loaded onto a UNOsphere™ S Cation Exchange Media (Bio Rad, Art.Nr.: 156-0115) inner diameter=10 mm bed height 8.8 cm volume 6.91 ml with a flow rate of 100 cm/h followed by a first wash (Reequilibration) of 2CV with [30 mM Na-Citrate, 180 mM NaCl, pH 7.5] to deplete strong bound HCP and r-vWF-Propeptide. To introduce additional 2,6 Sialylation a mixture of 50% (v/v) CMP-NANA Solution based on [30 mM Na-Citrat, 180 mM NaCl, pH 7.5] and 50% (v/v) of alpha 2,6 Sialyltransferase based on [30 mM Na-Citrat, 180 mM NaCl, pH 7.5] was applied onto the column in 10 column volumes and a flow rate of 25 cm/h by online mixing. The composition of the CMP-NANA Solution was 14 mg CMP_NANA C8271-25 mg Lot. Nr.: SLBV 7777 dissolved in 121.57 g [30 mM Na-Citrat, 180 mM NaCl, pH 7.5]. The composition of the alpha 2,6 Sialyltransferase buffer was alpha 2,6 Sialyltransferase S2076-1UN SIGMA, Lot.Nr. SLBV0552 from Photobacterium Damsela dissolved in 121.10 g [30 mM Na-Citrat, 180 mM NaCl, pH 7.5]. A further wash with 2 column volumes of [30 mM Na-Citrate, 180 mM NaCl, pH 7.5] was applied to remove excess of CMP_NANA andalpha 2,6 Sialyltransferase. A buffer exchange was provided by applying 4 column volumes of [50 mM HEPES, 150 mM NaCl pH 6.0]. The Elution was performed with [50 mM HEPES, 500 mM NaCl, pH 7.5] in 4 column volumes.

3. Complete Purification Sequence VW_USS_08

The sequence of the key steps of this example consists of the following steps:
1. Mab FVIII capture (FT is the r-vWF containing fraction)
2. Fractogel TMAE capture+maturation
3. Mustang Q in FT mode
4. CEX as described (VW_USS_08)

Result:
No additional 2,6 sialylation detected using the method in the present example. However, 2,3 sialylation was found which is the usual sialylation pattern for r-vWF.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A method for obtaining a composition comprising a high purity, propeptide depleted mature recombinant rVWF (mat-rVWF), said method comprising the steps of:
   a) loading a solution comprising mat-rVWF/rVWF-PP complex, mat-rVWF, and rVWF propeptide (rVWF-PP) onto a size exclusion column;
   b) washing said size exclusion column with a buffer, thereby dissociating said mat-rVWF/rVWF-PP complex in said solution in a) into mat-rVWF and rVWF-PP, wherein said dissociation occurs by disruption of the non-covalently associated mat-rVWF and rVWF-PP, wherein said buffer comprises at least one chelating agent and exhibits a pH of at least 7; and
   c) collecting said mat-rVWF to obtain a high purity, mat-rVWF composition, wherein said high purity, mat-rVWF composition comprises at least 95% mature rVWF and less than 5% rVWF-PP.

2. The method of claim 1, wherein said high purity, mat-rVWF composition comprises at least 96% mat-rVWF and less than 4% rVWF-PP, at least 97% mat-rVWF and less than 3% rVWF-PP, at least 98% mat-rVWF and less than 2% rVWF-PP, at least 99% mat-rVWF and less than 1% rVWF-PP, or at least 99.5% mat-rVWF and less than 0.5% rVWF-PP, or 99.9% mat-rVWF and less than 0.1% rVWF-PP.

3. The method according to claim 1, wherein said solution is selected from the group consisting of a cell culture medium, an antibody column flow-through solution, and a buffered solution.

4. The method according to claim 1, wherein said solution has been treated with furin prior to step a).

5. The method according to claim 1, wherein said solution is an antibody column flow-through solution.

6. The method according to claim 1, wherein said at least one chelating agent is a divalent cation chelating agent.

7. The method according to claim 6, wherein said divalent cation chelating agent is selected from the group consisting of EDTA, EGTA, CDTA, and citrate.

8. The method according to claim 1, wherein said pH is at least 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0.

9. The method according to claim 1, wherein said pH is at least about 7.2 to about 7.8.

10. The method according to claim 9, wherein said pH is at least about 7.6.

11. The method according to claim 1, wherein said pH is increased by the addition of basic amino acids, Tris, NaOH, Tricine, or ethanolamine.

12. The method according to claim 1, wherein said buffer comprises a buffering agent selected from the group consisting of glycine, HEPES (4-(2-hydroxyethyl)-1-piperazineethanesulfonic acid), TrisHCl (Tris(hydroxymethyl)-aminomethane), histidine, imidazole, acetate citrate, MES, and 2-(N-morpholino)ethanesulfonic acid.

13. The method according to claim 1, wherein said buffer further comprises one or more monovalent cations.

14. The method according to claim 13, wherein said one or more monovalent cations are selected from the group consisting of Na+, K+, Li+, and Cs+.

15. The method according to claim 13, wherein said monovalent cation is Na+.

16. The method according to claim 1, wherein said buffer further comprises one or more monovalent, divalent and/or trivalent anions.

17. The method according to claim 16, wherein said one or more monovalent, divalent and/or trivalent anions are selected from the group consisting of Cl⁻, acetate⁻, $SO_4^{2-}$, Br⁻, and citrate³⁻.

18. The method according to claim 1, wherein said buffer comprises at least one buffer exhibiting a conductivity of >0.5 mS/cm at 25° C.

19. The method according to claim 1, wherein said high purity mat-rVWF composition comprises a host cell (HC) impurity level of <2.0%.

20. The method according to claim 1, wherein said high purity, mat-rVWF composition comprises a host cell (HC) impurity level of <0.6%.

21. The method according to claim 1, wherein said solution comprising mat-rVWF/rVWF-PP complex, mat-rVWF, and rVWF-PP is derived from a capture step for rVWF.

22. The method according to claim 1, wherein said solution comprising mat-rVWF/rVWF-PP complex, mat-rVWF, and rVWF-PP is derived from a method comprising a FVIII immunoaffinity step and anion exchange chromatography step.

23. The method of claim 12, wherein said buffering agent is HEPES.

24. The method of claim 1, wherein said buffer comprises Na citrate.

25. The method of claim 1, wherein said buffer comprises NaCl.

26. The method of claim 1, wherein said buffer comprises HEPES, Na citrate, and NaCl.

27. The method of claim 1, wherein said buffer comprises 20 mM HEPES, 15 mM Na citrate, and 150 mM NaCl.

28. The method of claim 1, further comprising lyophilizing said high purity, mat-rVWF composition after step (c).

\* \* \* \* \*